(12) United States Patent
Yamamoto et al.

(10) Patent No.: US 6,906,072 B1
(45) Date of Patent: Jun. 14, 2005

(54) PIPERAZINE COMPOUND AND PHARMACEUTICAL COMPOSITION CONTAINING THE COMPOUND

(75) Inventors: Noboru Yamamoto, Ibaraki (JP); Yuichi Suzuki, Ibaraki (JP); Manami Kimura, Chiba (JP); Tetsuhiro Niidome, Ibaraki (JP); Yoichi Iimura, Ibaraki (JP); Tetsuyuki Teramoto, Brookline, MA (US); Yoshihisa Kaneda, Ibaraki (JP); Toshihiko Kaneko, Ibaraki (JP); Nobuyuki Kurusu, Ibaraki (JP); Daisuke Shinmyo, Ibaraki (JP); Yukie Yoshikawa, Ibaraki (JP); Shinji Hatakeyama, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/169,837

(22) PCT Filed: Jan. 18, 2001

(86) PCT No.: PCT/JP01/00288

§ 371 (c)(1),
(2), (4) Date: Jul. 10, 2002

(87) PCT Pub. No.: WO01/53258

PCT Pub. Date: Jul. 26, 2001

(30) Foreign Application Priority Data

Jan. 20, 2000 (JP) ........................................ 2000-012176

(51) Int. Cl.[7] .................... C07D 409/06; A61K 31/496; A61P 25/00; A61P 25/04
(52) U.S. Cl. .................... 514/252.13; 544/379
(58) Field of Search ........................ 514/252.12, 252.13, 514/253.01, 253.02, 253.11, 254.02, 254.03, 254.04, 254.06, 254.07, 254.11, 255, 2.3; 544/359, 360, 363, 364, 367, 368, 369, 366, 370, 37, 376, 377, 379, 391, 392, 402

(56) References Cited

U.S. PATENT DOCUMENTS

| | | | |
|---|---|---|---|
| 4,994,460 A * | 2/1991 | Dextraze et al. | ....... 514/252.14 |
| 5,231,105 A | 7/1993 | Shoji | .......................... 514/325 |
| 5,281,601 A | 1/1994 | Cross | .......................... 514/320 |
| 5,420,131 A | 5/1995 | Carceller et al. | ............ 514/253 |
| 6,117,875 A | 9/2000 | Shimazaki et al. | ..... 514/255.01 |
| 6,426,345 B1 | 7/2002 | Shimazaki et al. | ....... 514/234.2 |

FOREIGN PATENT DOCUMENTS

| | | |
|---|---|---|
| EP | 0 393 574 A2 | 10/1990 |
| EP | 393574 A | 10/1990 |
| EP | 400661 A | 12/1990 |
| EP | 0 400 661 A1 | 12/1990 |
| EP | 0 441 226 A1 | 8/1991 |
| EP | 441226 A | 8/1991 |
| EP | 0 458 459 A2 | 11/1991 |
| EP | 458459 A | 11/1991 |
| FR | 2676225 A | 11/1992 |
| FR | 2676225 | 11/1992 |
| GB | 1305458 A | 1/1973 |
| GB | 1305458 | 1/1973 |
| JP | 47-38984 | 12/1972 |
| JP | 47-38984 A | 12/1972 |
| JP | 62-286980 A | 12/1987 |
| JP | 62-286980 A2 * | 12/1987 |
| JP | 62-286980 | 12/1987 |
| JP | 63-35562 A | 2/1988 |
| JP | 63-35562 | 2/1988 |
| JP | 64-3182 A | 1/1989 |
| JP | 64-3182 | 1/1989 |
| JP | 64-61468 A | 3/1989 |
| JP | 64-61468 | 3/1989 |
| JP | 2-83375 A | 3/1990 |
| JP | 2-83375 | 3/1990 |

(Continued)

OTHER PUBLICATIONS

Jain KK., Expert Opin Investig Drugs. Oct. 2000;9(10):2403–10, Medline abstract PMID: 11060815.*

Gilmore, J. et al, Ann. Report Med. Chem., vol. 30, 1995, p 51–60.*

(Continued)

Primary Examiner—Thomas McKenzie
(74) Attorney, Agent, or Firm—Birch, Stewart, Kolasch & Birch, LLP

(57) ABSTRACT

The present invention provides a novel compound having a superior calcium antagonism, in particular, a neuron-selective calcium antagonism. Namely, it provides a compound represented by the following formula, a salt thereof or a hydrate of them.

(I)

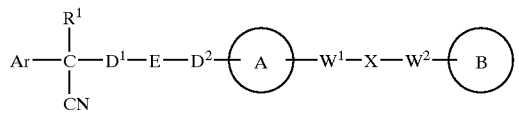

In the formula, Ar indicates an optionally substituted 5- to 14-membered aromatic ring etc.; the ring A indicates any one ring selected from a piperazine, a homopiperazine, a piperidine and the like; the ring B indicates an optionally substituted $C_{3-14}$ on hydrocarbon ring etc.; E indicates a single bond, a group represented by the formula —CO—, etc.; X indicates a single bond, an oxygen atom etc.; $R^1$ indicates a hydrogen atom, a halogen atom, a hydroxyl group etc.; and $D^1$, $D^2$, $W^1$ and $W^2$ are the same as or different from each other and each represents a single bond or an optionally substituted $C_{1-6}$ alkylene chain.

16 Claims, 3 Drawing Sheets

FOREIGN PATENT DOCUMENTS

| | | | |
|---|---|---|---|
| JP | 5-97673 A | 4/1993 | |
| JP | 5-97673 | 4/1993 | |
| JP | 11-80155 A | 3/1999 | |
| JP | 11-80155 | 3/1999 | |
| WO | 91/09015 A | 6/1991 | |
| WO | WO 91/09015 | 6/1991 | |
| WO | 441226 A1 | * | 8/1991 |
| WO | WO 91/18899 | 12/1991 | |
| WO | 91/18899 A | 12/1991 | |
| WO | 96/26196 A | 8/1996 | |
| WO | WO 96/26196 | 8/1996 | |
| WO | 97/26258 | 7/1997 | |
| WO | WO 97/26258 | 7/1997 | |
| WO | WO 99/06383 | 2/1999 | |
| WO | 99/06383 A | 2/1999 | |
| WO | WO 00/05210 A1 | * | 2/2000 |
| WO | 00/05210 A | 2/2000 | |

OTHER PUBLICATIONS

Moehrle et al., Arch. Pharm., vol. 326(6), pp. 565–568, Compound No. 4 (1995).

Butora et al., Collect. ,Czech. Chem. Comm., Compound vol. 57 (9), pp. 1967–1981, No. 7 (1992).

Carceller et al., J. Med. Chem., vol. 35(22), pp. 4118–4134 (1992).

Laguere et al., Eur. J. Med., vol. 25(4), pp. 351–359, (1990).

Vartanyan et al., Khim.–Farm. Zh., vol. 23(5), pp. 562–565, Compound. No. 7 (1989).

Lachowicz et al., Life Sci., vol. 64(6/7), pp. 535–539 (1999).

Yevich et al., J. Med. Chem., vol. 35(24), pp. 4516–4525, No. 4,31 (1992).

Butora et al., Collect. Czech. Chem. Comm., vol. 57, No. 9, pp. 1967–1981, (1992).

Carceller et al., J. Med. Chem., vol. 35, No. 22, pp. 4118–4134, (1992).

Laguerre et al., Eur. J. Med. Chem., vol. 25, No. 4, pp. 351–359, (1990).

Vartanyan et al., Khim. –Farm. Zh., vol. 23, No. 5, pp. 562–565, (1989).

Lachowicz et al., Life Sci., vol. 64, No. 6/7, pp. 535–539, (1999).

Yevich et al., J. Med. Chem., vol. 35, No. 24, pp. 4516–4525, (1992).

Laurie et al., Naunyn–Schmiedeberg's Arch. Pharmacol., vol. 351, No. 6, pp. 565–568, (1995).

Tani, M., Annu. Rev. Physiol., vol. 52, pp. 543–559, (1990).

Scrip, No. 2203, vol. 24, (1997).

Lipton, S., Advances in Pharmacology, vol. 22, pp. 271–297, (1991).

Mattson et al., TINS, vol. 16, No. 10, pp. 409–414, (1993).

Nichiyakurishi, Folia. Pharmacol. Japon., vol. 86, pp. 323–328, (1985).

Drugs of the Future, vol. 23, No. 2, pp. 152–160, (1998).

Dobrovsky et al., Casopis Lekaru Ceskych, vol. 130, No. 22–23, pp. 625–630, (1991).

Jimenes–Jimenez et al., Rev. Neurol., vol. 24, No. 134, pp. 1199–1209, (1996).

Asakura et al., Brain Research, vol. 776, pp. 140–145, (1997).

Jyunkanseigyo, Circulation Control, vol. 14, No. 2, pp. 139–145, (1993).

Shinkeinaika, Neurological Medicine, vol. 50, pp. 423–428, (1999).

Terwindt et al., Neurology, vol. 50, No. 4, pp. 1105–1110, (1998).

* cited by examiner

PIPERAZINE COMPOUND AND PHARMACEUTICAL COMPOSITION CONTAINING THE COMPOUND

This application is the national phase under 35 U.S.C. § 371 of PCT International Application No. PCT/JP01-00288 which has an International filing date of Jan. 18, 2001, which designated the United States of America.

TECHNICAL FIELD

The present invention relates to a novel compound useful as a calcium antagonist, a salt thereof, a hydrate of them, a production process thereof, and a pharmaceutical composition thereof; and specifically relates to a neuron-selective calcium antagonist, in particular a novel compound having a P/Q-type calcium channel and/or an N-type calcium channel inhibiting activity, etc.

PRIOR ART

In Japan, the number of patients with cerebral apoplexy is about 1.4 million or more per year, and the medical expenses therefor are estimated to be about two billion yen. Cerebral apoplexy is the second cause of death next to malignant tumor and is the biggest cause for bedridden man often suffering from severe secondary diseases. A key to the treatment of cerebral apoplexy is to deal with the acute stage, and the treatment at the acute stage influences the life and function prognosis of the patient and significantly influences secondary diseases.

For the purpose of improving blood stream, several drugs such as ozagrel sodium (thromboxane synthase inhibitor), argatroban (anti-thrombin agent) as an agent for treatment of chronic arterial occlusion, t-PA (alteplase: tissue plasminogen activator which should be used within 3 hours after the onset) as thrombolytic agent etc. are now approved of, or in off lavel use. However, the therapy according to a conventional medicine is the complicate procedures as described in (1) to (6), and cautious judgment by a specialist on the basis of enough knowledge and experience has been required. Namely, (1) in the case of thrombus-type cerebral infarction, respiratory control, blood pressure control and blood transfusion control are first conducted. (2) Blood gas and blood pressure are periodically measured. (3) At the acute stage, reactive high blood pressure is observed, but if complications in the heart and kidney are not observed, treatment for decreasing blood pressure is not conducted. (4) Then, in the early-acute stage case with no low absorption range observed in CT, the thrombus-lytic agent "urokinase" is used. (5) In the case where these agents are not applicable or in the case where 24 hours or more has elapsed after the onset, "ozagrel sodium" is administered. Or "argatroban" is administered. However, argatroban is not applicable to lacuna infarction.

(6) To prevent the development of cerebral edema, "glycerin" or "mannitol" is administered at a suitable dosage.

Further, the therapeutic effects of the drugs used heretofore are not satisfactory and further there is the danger that bleeding is often accompanied by their pharmacological effect. Accordingly, there is the problem that it is difficult for those except of skilled medical specialists to use these drugs.

On the other hand, the following literatures describe that compounds having an inhibitory action on N type or P/Q type calcium channels can serve as an agent for inhibiting the death of neural cells or for protecting cerebral neural cells, an agent for treating or improving nervous diseases, an agent for treating or improving acute ischemic stroke, head trauma, death of neural cells, Alzheimer disease, cerebral circulatory metabolism disturbance, cerebral function disturbance or pain, an anti-spasm agent, an agent for treating or improving schizophrenia and an agent for preventing, treating or improving migraine, epilepsy, maniac-depressive psychosis, neural degenerative diseases (Parkinson disease, Alzheimer disease, amyotrophic lateral sclerosis, Huntington disease), cerebral ischemia, epilepsy, head trauma, AIDS dementia complications, edema, anxiety disorder (generalized anxiety disorder) and diabetic neuropathy, and as an agent for preventing, treating or improving edema, anxiety disorder, schizophrenia, diabetic neuropathy and migraine.

(1) Acute ischemia stroke: Annj. Rev. Physiol., 52 543-559, 1990.
(2) Head trauma: SCRIP, No. 2203, 24, 1997.
(3) Ischemia—death of cerebral neural cells: Advances in Pharmacology, 2, 271–297, 1991.
(4) Alzheimer disease: Trends in Neuroscience, 16, 409, 1993.
(5) Cerebral circulatory metabolism disturbance: Nichiyakurishi, 85, 323–328, 1985.
(6) Cerebral function disturbance: Acta Neurol. Scand., 7:2, 14–200, 1998.
(7) Analgesic: Drug of the Future, 23(2), 152–160, 1998.
(8) Cerebral ischemia, migraine, epilepsy, maniac-depressive psychosis: Casopis Lekau Ceskych., 130 (22–23), 625–630, 1991.
(9) Neural degenerative diseases (Parkinson disease, Alzheimer disease, amyotrophic lateral sclerosis, Huntington disease), cerebral ischemia, epilepsy, head trauma, and AIDS dementia complications: Revista de Neurologia., 24(134), 1199–1209, 1996.
(10) Edema: Brain Research, 776, 140–145,1997.
(11) Anxiety disorder (generalized anxiety disorder), schizophrenia: Jyunkanseigyo (Circulation Control), 14(2), 139–145,1993.
(12) Diabetic neuropathy: Shinkeinaika (Neurological Medicine), 50, 423–428,1999.
(13) Migraine: Neurology, 50(4), 1105–1110,1998.

DISCLOSURE OF THE INVENTION

In light of this, the present inventors have intensively studied for investigating a preparation which has a superior effect of treatment and amelioration for cerebral acute ischemic stroke for which no useful preparation is not found and has high safety which does not cause bloodshed tendency, focusing on a neuron-selective, potential-dependent calcium channel antagonist which directly effects on neural cell and inhibits the progression of infarction nidus. As a result, the present inventors have succeeded in synthesizing a novel nitrogen-containing compound which is represented by the formula (I), a salt thereof and a hydrate thereof, and further surprisingly have found that these compounds, a salt thereof or a hydrate thereof have the superior suppression action of neural cell death and protective action of cerebral neuron based on the P/Q type or N-type calcium channel antagonism, that cell infarction property and toxicity are remarkably reduced in comparison with a conventional calcium antagonist and that the compound and the like are superior in safety, and have completed the present invention.

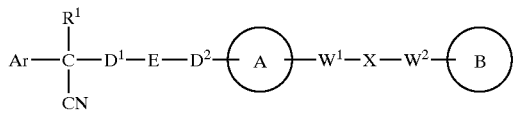

(I)

In the formula, Ar is (1) a $C_{6-14}$ aromatic hydrocarbon cyclic group which may be substituted, (2) a 5- to 14-memberedaromatic heterocyclic group which may be substituted, (3) a $C_{1-6}$ alkyl group substituted with a $C_{1-6}$ aromatic hydrocarbon cyclic group which may be substituted or (4) a $C_{1-6}$ alkyl group substituted with a 5- to 14-membered aromatic heterocyclic group which may be substituted; the ring A indicates a piperazine ring, homopiperazine ring, piperidine ring, homopiperidine ring, pyrrolidine ring or diazabicyclo[2,2,1]heptane ring which may be substituted, respectively; the ring B indicates (1) a $C_{3-14}$ hydrocarbon ring which may be substituted or (2) a 5- to 14-membered heterocyclic ring which may be substituted; E indicates (1) a single bond, a group represented by the formula (2) —CO— or (3) —CH(OH)—; X indicates (1) a single bond, (2) an oxygen atom, (3) a sulfur atom, (4) a $C_{1-6}$ alkylene chain which may be substituted, a group represented by (5) the formula —$NR^2$— (wherein $R^2$ indicates a hydrogen atom, or a $C_{1-6}$ alkyl group, a $C_{3-8}$ cycloalkyl group, a lower acyl group or a $C_{1-6}$ alkylsulfonyl group which may be substituted), (6) —CO—, (7) —COO—, (8) —OCO—, (9) —$CONR^3$— (wherein $R^3$ indicates a hydrogen atom or a $C_{1-6}$ alkyl group which may be substituted), (10) —$NR^4CO$— (wherein $R^4$ indicates a hydrogen atom or a $C_{1-6}$ alkyl group which may be substituted), (11) —SO—, (12) —$SO_3$—, (13) —$SONR^5$— (wherein $R^5$ indicates a hydrogen atom or a $C_{1-6}$ alkyl group which may be substituted), (14) —$NR^6SO$— (wherein $R^6$ indicates a hydrogen atom or a $C_{1-6}$ alkyl group which may be substituted), (15) —$SO_2NR^7$— (wherein $R^7$ indicates a hydrogen atom or a $C_{1-6}$ alkyl group which may be substituted), (16) —$NR^8SO_2$— (wherein $R^8$ indicates a hydrogen atom or a $C_{1-6}$ alkyl group which may be substituted), (17)>C=N—$OR^9$ (wherein $R^9$ indicates a hydrogen atom or a $C_{1-6}$ alkyl group which may be substituted), (18) —$NR^{10}$—$W^3$—O— (wherein $R^{10}$ indicates a hydrogen atom or a $C_{1-6}$ alkyl group, a $C_{1-6}$ cycloalkyl group, a lower acyl group or a $C_{1-6}$ alkylsulfonyl group which may be substituted; and $W^3$ indicates a $C_{1-6}$ alkylene group which may be substituted), (19) —NH—CO—NH—, (20) —NH—CS—NH—, (21) —C(=$NR^{15}$)$NR^{16}$— (wherein $R^{15}$ and $R^{16}$ are the same as or different from each other and each indicates a hydrogen atom, nitrile group, a $C_{1-5}$, alkyl group, a $C_{3-6}$ alkenyl group, a $C_{3-8}$ cycloalkyl group or a $C_{3-8}$, cycloalkenyl group), (22) —NHC(=NH)—, (23) —O—CO—S—, (24) —S—CO—O—, (25) —OCOO—, (26) —NHCOO—, (27) —OCONH—, (28) —CO($CH_2$)$_m$O— (wherein m indicates 0 or an integer of 1 to 6), (29) —CHOH— or (30) —CHOH($CH_2$)$_n$O— (wherein n indicates 0 or an integer of 1 to 6); $R^1$ indicates (1) a: hydrogen atom, (2) a halogen atom, (3) hydroxyl group, (4) a $C_{1-6}$ alkyl group which may be substituted with one or more groups selected from hydroxyl group, a halogen atom and nitrile group, (5) a $C_{2-6}$ alkenyl group which may be substituted with one or more groups selected from hydroxyl group, a halogen atom and nitrile group, (6) a $c_{2-6}$ alkynyl group which may be substituted with one or more groups selected from hydroxyl group, a halogen atom and nitrile group, (7) a $C_{3-8}$ cycloalkyl group which may be substituted with one or more groups selected from hydroxyl group, a halogen atom and nitrile group, (9) a $C_{1-6}$ alkoxy-$C_{1-6}$ alkyl group, (10) an amino-$C_{1-6}$ alkyl group in which the nitrogen may be substituted, (11) a group represented by the formula —$N(R^{11})R^{12}$— (wherein $R^{11}$ and $R^{12}$ are the same as or different from each other and each indicates a hydrogen atom or a $C_{1-6}$ alkyl group), (12) an aralkyl group, (13) morpholinyl group, (14) thiomorpholinyl group, (15) piperidyl group, (16) a pyrrolidinyl group or (17) a piperazinyl group; and $D^1$, $D^2$, $W^1$ and $W^2$ are the same as or different from each other and each indicates (1) a single bond or (2) a $C_{1-6}$ alkylene chain which may be substituted, provided that, in the above definition, 1-[4-cyano-5-methyl-4-(2-cyano-5-thienyl)hexyl]-4-[2-(4-fluorophenoxy)ethyl]piperazine; 1-[4-cyano-5-methyl-4-(2-cyano-5-thienyl)hexyl]-4-[2-(3-fluorophenoxy)ethyl]piperazine; and 1-[4-cyano-5-methyl-4-(2-thienyl)hexyl]-4-[2-(3-fluorophenoxy)ethyl]piperazine are excluded.

Namely, the first aspect of the present invention is 1) a compound represented by the above formula (I), a salt thereof or a hydrate of them, and further, 2) in the above-mentioned 1), Ar may be a $C_{6-14}$, aromatic hydrocarbon ring or 5- to 14-membered aromatic heterocyclic ring, which may be substituted, 3) in the above-mentioned 1), Ar may be a thiophene ring or benzene ring, which may be substituted, 4) in the above 1), Ar may be a $C_{6-14}$ aromatic hydrocarbon ring or 5- to 14-membered aromatic heterocyclic ring, which may be substituted with any one or more groups selected from nitrile group and a halogen atom, 5) in the above-mentioned 1), Ar may be a thiophene ring or a benzene ring which may be substituted with any one or more groups selected from nitrile group and a halogen atom, respectively, 6) in the above-mentioned 1), the ring A may be piperazine ring, homopiperazine ring or piperidine ring, 7) in the above-mentioned 1), the ring A may be a piperazine ring, 8) in the above-mentioned 1), the ring A may be a piperazine ring, a homopiperazine ring or a piperidine ring which may be substituted with any one or more groups selected from hydroxyl group, a halogen atom, cyano group, a $C_{1-6}$ alkyl group which may be substituted, a $C_{2-6}$ alkenyl group which may be substituted, a $C_{2-6}$ alkynyl group which may be substituted, a $C_{2-6}$ alkoxy group which may be substituted, a $C_{2-6}$ alkenyloxy group which may be substituted, a $C_{1-6}$ alkylcarbonyl group which may be substituted, a $C_{2-6}$ alkenylcarbonyl group which may be substituted, a $C_{1-6}$ alkoxycarbonyl group which may be substituted and a $C_{2-6}$ alkenyloxycarbonyl group which may be substituted, 9) in the above-mentioned 1), the ring B maybe a $C$, aromatic hydrocarbon ring or a 5- to 14-membered aromatic heterocyclic ring which may be substituted, respectively, 10) in the above-mentioned 1), the ring B may be a benzene, a thiophene, a pyridine, a 1,4-benzodioxane, an indole, a benzothiazole, a benzoxazole, a benzimidazole, a 2-keto-1-benzimidazole, a thiazole, an oxazole, an isoxazole, a 1,2,4-oxadiazole, an indanone, a benzofuran, a quinoline, a 1,2,3,4-tetrahydroquinoline, a naphthalene or a 1,2,3,4-tetrahydronaphthalene which may be substituted, respectively, 11) in the above-mentioned 1), the ring B may be a $C_{6-14}$ aromatic hydrocarbon ring or a 5- to 14-membered aromatic heterocyclic ring which may be substituted with any one or more groups selected from a halogen atom, nitrile group, a $C_{1-6}$ alkyl group, a lower acyl group, a $C_{1-6}$ alkylsulfonyl group and an aralkyl group, respectively, 12) in the above-mentioned 1), $D^1$ and $D^2$ may be the same as or different from each other and each may be (1) a single bond or (2) a $C_{1-6}$ alkylene chain which may be substituted with any one or more groups selected from hydroxyl group, a halogen atom, nitrile group, a $C_{1-6}$ alkyl group, a $C_{1-6}$ alkenyl group and a $C_{1-6}$ alkoxy group, 13) in the above-mentioned 1), E may be a single bond, 14) in the above-mentioned $D^1$ and $D^2$ may be a $C_{1-6}$ alkylene chain; and E may be a single bond, 15) in the above-mentioned 1), the partial structure -$D^1$-E-$D^2$- may be a $C_{1-6}$ alkylene group, 16) in the above-mentioned 1), $W^1$ and $W^2$ may be the same as or different from each other and each may be (1) a single bond or (2) a $C_{1-6}$ alkylene chain which may be substituted with any one or more groups selected from hydroxyl group, a halogen atom, nitrile group, a $C_{1-6}$ alkyoxy group and a $C_{2-6}$ alkenyloxy group, 17) in the above-mentioned 1), $W^1$ may be (1) a single bond or (2) a $C_{1-6}$ alkylene chain which may be substituted with any one or more groups selected from (i) nitrile group, (ii) a $C_{1-6}$ alkyl group which may be substituted with any one or more groups selected from a $C_{1-6}$ alkoxy group and a $C_{2-6}$ alkenyloxy group and (iii) a $C_{2-6}$ alkenyl group; and $W^2$ may be a single bond, 18) in the above-mentioned 1), $W^1$ and $W^2$ may be the same as or different from each other and each may be a $C_{1-6}$ alkylene chain substituted with any one or more groups selected from a $C_{1-6}$ alkyl group and a $C_{2-6}$ alkenyl group, and further the above-mentioned $C_{1-6}$ alkyl group and/or $C_{2-6}$ alkenyl group may be bound together to form a ring or the above-mentioned $C_{1-6}$ alkyl group or $C_{2-6}$ alkenyl group is bound to the ring B or X to form a ring, 19) in the above-mentioned 1), X may be (1) a single bond, (2) oxygen atom, a group represented by (3) the formula —$NR^2$— (wherein $R^2$ indicates a hydrogen atom, or a $C_{1-6}$ alkyl group, a $C_{3-8}$ cycloalkyl group, a lower acyl group or a $C_{1-6}$ alkylsulfonyl group which may be substituted), (4) —$NR^{10}$—$W^3$—O— (wherein $R^{10}$ indicates a hydrogen atom, or a $C_{2-6}$ alkyl group, a $C_{3-8}$ cycloalkyl group, a lower acyl group or a $C_{1-6}$ alkylsulfonyl group which may be substituted; and $W^3$ is a $C_{1-6}$ alkylene group which may be substituted) or (5) —NH—$SO_2$—, 20) in the above-mentioned 1), X may be (1) oxygen atom, a group represented by (2) the formula —$NR^2$— (wherein $R^2$ indicates a hydrogen atom, or a $C_{1-6}$ alkyl group, a $C_{3-8}$ cycloalkyl group, a lower acyl group or a $C_{1-6}$ alkylsulfonyl group which may be substituted) or (3) —NH—$SO_2$—, 21) in the above-mentioned 1), the partial structure —$W^1$—X—$W^2$— may be a $C_{1-6}$ alkylene group which may be substituted, 22) in the above-mentioned 1), $W^1$ may be a $C_{1-6}$ alkylene chain which may be substituted; $W^2$ is a single bond; and X may be oxygen or a group represented by the formula —$NR^2$— (wherein $R^2$ has the same meaning as the above-mentioned definition), 23) in the above-mentioned 22), the substituent of $W^1$ may be any one or more groups selected from (1) nitrile group, (2) a $C_{1-6}$ alkyl group which may be substituted with a $C_{1-6}$ alkyoxy group or a $C_{2-6}$ alkenyloxy group and (3) a $C_{2-6}$ alkenyl group; and $R^2$ may be a $C_{1-6}$ alkyl group which may be substituted, 24) in the above-mentioned 1), $R^1$ may be a $C_{1-6}$ alkyl group, 25) in the above-mentioned 1), $R^1$ may be methyl group, ethyl group, n-propyl group or isopropyl group, 26) the compound in the above-mentioned 1) maybe a compound represented by the formula:

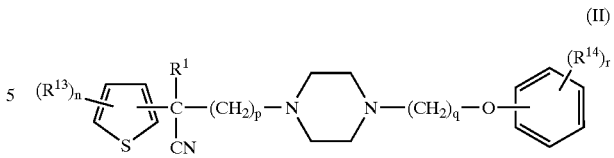

in the formula, $R^1$ has the same meaning as in the above definition; $R^{13}$ and $R^{14}$ are the same as or different from each other and each indicates (1) a hydrogen atom, (2) a halogen atom, (3) hydroxyl group, (4) mercapto group, (5) a $C_{1-6}$ alkyl group which may be substituted with any one or more groups selected from hydroxyl group and a halogen atom, (6) a $C_{1-6}$ alkoxy group which may be substituted with any one or more groups selected from hydroxyl group, a halogen atom and a $C_{1-6}$ alkoxycarbonyl group, (7) a nitro group, (8) an amino group which may be substituted, (9) cyano group, (10) carboxyl group, (11) a $c_{1-6}$ alkoxycarbonyl group, (12) a $C_{1-6}$ thioalkoxy group, (13) a $C_{1-6}$ alkylsulfonyl group, (14) a lower acyl group, (15) a $C_{6-14}$ aromatic hydrocarbon cyclic group which may be substituted, (16) a 5- to 14-membered aromatic heterocyclic group which may be optionally substituted, (17) an aryloxy group or (18) an aralkyloxy group, or (19) $R^{13}$s themselves or $R^{14}$s themselves may be bound together to form (i) an aliphatic ring which may be substituted, (ii) a heterocyclic ring which may be substituted or (iii) an alkylenedioxy group; n indicates 0 or an integer of 1 to 3; p indicates an integer of 1 to 6; q indicates an integer of 1 to 6; and r indicates 0 or an integer of 1 to 5, provided that, in the above definition, 1-[4-cyano-5-methyl-4-(2-cyano-5-thienyl)hexyl]-4-[2-(4-fluorophenoxy)ethyl]piperazine; 1-[4-cyano-5-methyl-4-(2-cyano-5-thienyl)hexyl]-4-[2-(3-fluorophenoxy)ethyl]piperazine; and 1-[4-cyano-5-methyl-4-(2-thienyl)hexyl]-4-[2-(3-fluorophenoxy)ethyl]piperazine are excluded and 27) the compound in the above-mentioned 1) may be a compound represented by the formula:

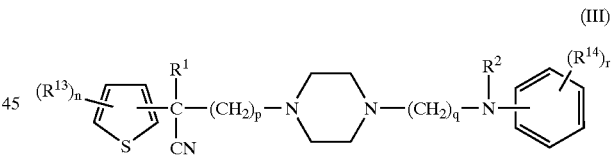

in the formula; $R^1$ and $R^2$ have the same meanings as defined above; $R^{13}$ and $R^{14}$ are the same as or different from each other and each indicates (1) a hydrogen atom, (2) a halogen atom, (3) hydroxyl group, (4) mercapto group, (5) a $C_{1-6}$ alkyl group which may be substituted with any one or more groups selected from hydroxyl group and a halogen atom, (6) a $C_{1-6}$ alkoxy group which may be substituted with any one or more groups selected from hydroxyl group, a halogen atom and a $C_{1-6}$ alkoxycarbonyl group, (7) nitro group, (8) an amino group which may be substituted, (9) cyano group, (10) carboxyl group, (11) a $C_{1-6}$ alkoxycarbonyl group, (12) a $C_{1-6}$ thioalkoxy group, (13) a $C_{1-6}$ alkylsulfonyl group, (14) a lower acyl group, (15) a $C_{6-14}$ aromatic hydrocarbon cyclic group which may be substituted, (16) a 5- to 14-membered aromatic heterocyclic group which may be substituted, (17) an aryloxy group or (18) an aralkyloxy group, or (19) $R^{13}$s themselves or $R^{14}$S themselves may be bound together to form (i) an aliphatic ring which may be substituted, (ii) a heterocyclic ring which may be substituted or (iii) an alkylenedioxy group; n indicates 0 or an integer of 1 to 3; p indicates an integer of 1 to 6; q indicates an integer of 1 to 6; r indicates 0 or an integer of 1 to 5, and 28) in the above-mentioned 1), the compound may be any one selected from 4-[(4-cyano-5-methyl-4-phenyl)hexyl]-N-(4-fluorophenyl)-N'-(2-methylpropyl)-1(2H)-pyrazinecarboxyimidamide; 1-isopropyl-4-[4-(1-isobutyl-1H-benzo[d]imidazol-2-yl)piperazino]-1-phenylbutyl cyanide; 1-[4-cyano-5-methyl-4-(5-cyano-2-thienyl)hexyl]-4-[2-(3-cyanophenoxy)ethyl]piperazine; 1-[4-cyano-5-methyl-4-(2-thienyl)hexyl]-4-[2-(3-cyanophenoxy)ethyl] piperazine; 1-[4-cyano-5-methyl-4-(5-cyano-2-thienyl) hexyl]-4-[3-(5-cyano-2-thienyl)propyl]piperazine; 1-[4-cyano-5-methyl-4-(3-thienyl)hexyl]-4-[2-(3-cyanophenoxy) ethyl]piperazine; 1-(4-cyano-5-methyl-4-[4-(2-cyano)-thienyl]hexyl)-4-[2-(3-cyanophenoxy)ethyl]piperazine; 1-[(4-cyano-5-methyl-4-phenyl)hexyl]-4-[(2-benzoxazolyl) amino]piperidine; 1-[4-cyano-4-(5-cyano-2-thienyl)-5-methylhexyl]-(3S)-3-[N-(2-cyanoethyl)-N-benzylamino] pyrrolidine; 1-[4-cyano-4-(5-cyano-2-thienyl)-5-methylhexyl]-(3R)-3-[N-(2-cyanoethyl)-N-benzylamino] pyrrolidine; 1-[(4-cyano-5-methyl-4-phenyl)hexyl]-4-(benzothiazolyl]piperazine; 1-[(4-cyano-5-methyl-4-phenyl)hexyl]-4-[2-(6-methoxy)benzothiazolyl]piperazine; 1-[(4-cyano-5-methyl-4-phenyl)hexyl]-4-(2-benzoxazolyl] piperazine; 1-[(4-cyano-5-methyl-4-phenyl)hexyl]-4-(2-quinolinyl]piperazine; 4-[4-(1-methyl-1H-benzo[d] imidazol-2-yl)-1,4-diazepan-1-yl]-1-isopropyl-1-phenylbutyl cyanide; 4-[4-(1-ethyl-1H-benzo[d]imidazol-2-yl)-1,4-diazepan-1-yl]-1-isopropyl-1-phenylbutyl cyanide; ethyl 4-(4-cyano-5-methyl-4-phenylhexyl)-1-[2-(4-fluorophenoxy)ethyl]-2-piperazinecarboxylate; 1-[(2-oxo-1,2-dihydro-3-quinolyl)methyl]-4-[(4-cyano-5-methyl-4-phenyl)hexyl]piperidine; 4-[(4-cyano-5-methyl-4-phenyl) hexyl]-1-{[2-(methanesulfonylamino)phenyl]methyl} piperazine; 4-[(4-cyano-5-methyl-4-phenyl)hexyl]-1-[(2-(methanesulfonylamino)phenyl]methyl]piperidine; (S)-3-phenyl-2-amino-propanoic acid {1-[4-cyano-5-methyl-5-(2-thionyl)hexyl]piperazinyl}amide; 4-[4-(4-phenylpiperidinyl)piperidinyl]-1-isopropyl-1-phenylbutyl cyanide; 4-[4-(4-cyano-4-phenylpiperidinyl)piperidinyl)-1-isopropyl-1-phenylbutyl cyanide; and 4-(4-(4-benzylpiperidinyl)piperidinyl]-1-isopropyl-1-phenylbutyl cyanide.

Further, the second characteristic of the present invention is 29) a pharmaceutical composition containing the compound represented by the formula:

(I)

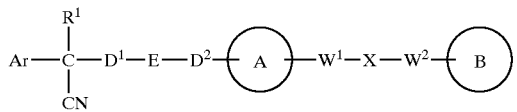

(in the formula, Ar is (1) a $C_{6-14}$, aromatic hydrocarbon cyclic group which may be substituted, (2) a 5- to 14-membered aromatic heterocyclic group which may be substituted, (3) a $C_{1-6}$ alkyl group substituted with a $C_{6-14}$ aromatic hydrocarbon cyclic group which may be substituted or (4) a $C_{1-6}$ alkyl group substituted with a 5- to 14-membered aromatic heterocyclic group which may be substituted; the ring A indicates a piperazine ring, a homopiperazine ring, a piperidine ring, a homopiperidine ring, a pyrrolidine ring, adiazabicyclo[2,2,1]heptane ring which may be substituted, respectively; the ring B indicates (1) a $C_{3-14}$ hydrocarbon ring which may be substituted or (2) a 5- to 14-membered heterocyclic ring which may be substituted; E indicates (1) a single bond, a group represented by (2) the formula —CO— or (3) —CH(OH)—; X indicates (1) a single bond, (2) oxygen atom, (3) sulfur atom, (4) a $C_{1-6}$ alkylene chain which may be substituted, a group represented by (5) the formula —$NR^2$— (wherein $R^2$ indicates a hydrogen atom, or a $C_{1-6}$ alkyl group, a $C_{3-8}$ cycloalkyl group, a lower acyl group or a $C_{1-6}$ alkylsulfonyl group which may be substituted.), (6) —CO—, (7) —COO—, (8) —OOC—, (9) —$CONR^3$— (wherein $R^3$ indicates a hydrogen atom or a $C_{1-6}$ alkyl group which may be substituted), (10) —$NR^4$ CO— (wherein $R^4$ indicates a hydrogen atom or a $C_{1-6}$ alkyl group which may be substituted), (11) —SO—, (12) —$SO_2$—, (13): —$SONR^5$— (wherein $R^5$ indicates a hydrogen atom or a $C_{1-6}$ alkyl group which may be substituted). (14) —$NR^6$ SO— (wherein $R^6$ indicates a hydrogen atom or a $C_{1-6}$ alkyl group which may be substituted), (15) —$SO_2NR^7$— (wherein $R^7$ indicates a hydrogen atom or a $C_{1-6}$ alkyl group which may be substituted), (16) —$NR^8SO_2$— (wherein $R^8$ indicates a hydrogen atom or a $C_{1-6}$ alkyl group which may be substituted) (17)>C=N—$OR^9$ (wherein $R^9$ indicates a hydrogen atom or a $C_{1-6}$ alkyl group which may be substituted), (18) —$NR^{10}$—$W^3$—O— (wherein $R^{10}$ indicates a hydrogen atom, or a $C_{1-6}$ alkyl group, a $C_{3-6}$ cycloalkyl group, a lower acyl group or a $C_{1-6}$ alkylsulfonyl group which may be substituted; and $W^3$ indicates a $C_{1-6}$ alkylene group which may be substituted), (19) —NH—CO—NH—, (20) —NH—CS—NH—, (21) —C(—$NR^{15}$) $NR^{16}$— (wherein $R^{15}$ and $R^{16}$ are the same as or different from each other and each indicates a hydrogen atom, nitrile group, a $C_{1-6}$ alkyl group, a $C_{2-6}$ alkenyl group, a $C_{3-8}$ cycloalkyl group or a $C^{3-8}$ cycloalkenyl group), (22) —NHC (—NH)—, (23) —O—CO—S—, (24) —S—CO—O—, (25) —OCOO—, (26) —NHCOO—, (27) —OCONH—, (28) —$CO(CH_2)_mO$— (wherein m indicates 0 or an integer of 1 to 6), (29) —CHOH— or (30) —$CHOH(CH_2)_nO$— (wherein n indicates 0 or an integer of 1 to 6.); $R^1$ indicates (1) a hydrogen atom, (2) a halogen atom, (3) hydroxyl group, (4) a $C_{2-6}$ alkyl group which may be substituted with one or more groups selected from hydroxyl group, a halogen atom and nitrile group, (5) a $C_{2-6}$ alkenyl group which may be substituted with one or more groups selected from hydroxyl group, a halogen atom and nitrile group, (6) a $C_{2-6}$ alkynyl group which may be substituted with one or more groups selected from hydroxyl group, a halogen atom and nitrile group, (7) a $C_{3-8}$ cycloalkyl group which may be substituted with one or more groups selected from hydroxyl group, a halogen atom and nitrile group, (9) a $C_{1-6}$ alkoxy-$C_{1-6}$ alkyl group, (10) an amino-$C_{1-6}$ alkyl group in which the nitrogen atom may be substituted, (11) a group represented by the formula —$N(R^{11})R^{12}$— (wherein $R^{11}$ and $R^{12}$ are the same as or different from each other and each indicates a hydrogen atom or a $C_{1-6}$ alkyl group), (12) an aralkyl group, (13) morpholinyl group, (14) thiomorpholinyl group, (15) piperidyl group, (16) pyrrolidinyl group or (17) piperazinyl group; and $D^1$, $D^2$, $W^1$ and $W^2$ are the same as or different from each other and each indicates (1) a single bond or (2) a $C_{1-6}$ alkylene chain which may be substituted, provided that, in the above definition, 1-[4-cyano-5-methyl-4-(2-cyano-5-thienyl)hexyl]-4-[2-(4-fluorophenoxy)ethyl]piperazine; 1-[4-cyano-5-methyl-4-(2-cyano-5-thienyl)hexyl]-4-[2-(3-fluorophenoxy) ethyl]piperazine; and 1-[4'-cyano-5-methyl-4-(2-thienyl)hexyl]-4-[2-(3-fluorophenoxy)ethyl]piperazine are excluded), a salt thereof or a hydrate of them, and further, 30) the composition in the above-mentioned 29) may be a calcium antagonist, 31) the composition in the above-mentioned 29) may be a neuron-selective calcium antagonist, 32) the composition in the above-mentioned 29) may be a P/Q-type calcium channel and/or an N-type calcium channel inhibitor, 33) the composition in the above-mentioned 29) may be an agent for treating, preventing or improving a disease against which the inhibitory action of at least one of P/Q-type calcium channel and N-type calcium channel is efficacious, 34) the composition in the above-mentioned 29) may be an agent for inhibiting the death of neural cell or for protecting cerebral neural cells, 35) the composition in the above-mentioned 29) may be an agent for treating, preventing or improving neural disease, 36) the neural disease in the above-mentioned 35) may be acute ischemic stroke, cerebral apoplexy, cerebral infarction, head trauma, cerebral neural cell death, Alzheimer disease, Parkinson disease, amyotrophic lateral sclerosis, Huntington disease, cerebral circulatory metabolism disturbance, cerebral function disturbance, pain, spasm, schizophrenia, migraine, epilepsy, manic-depression, neural degenerative diseases, cerebral ischemia, AIDS dementia complications, edema, anxiety disorder, diabetic neuropathy, cerebral vascular dementia and multiple sclerosis and 37) the composition in the above-mentioned 29) may be an analgesic.

The present invention provides a method for preventing, treating or improving a disease against which a calcium antagonism is effective, a disease against which a neuron-selective calcium antagonism is effective or a disease against which a P/Q-type calcium channel inhibitory action and/or an N-type calcium channel inhibitory action is effective, by administering a pharmacologically effective amount of the compound represetend by the above formula (I), a salt thereof or a hydrate of them to a patient.

The present invention provides a method for preventing, treating or improving neural disease or pain.

Further, the present invention provides use of the compound represented by the above formula (I), a salt thereof or ahydrate of them for producing a calcium antagonist, a neuron-selective calcium antagonist, a P/Q-type calcium channel and/or an N-type calcium channel inhibitor, an agentifor treating, preventing or improving a disease against which a P/Q-type calcium channel and/or an N-type calcium channel inhibitory action is efficacious, an agent for inhibiting the death of neural cells or for protecting cerebral neural cells.

Additionally, the present invention provides use of the compound represented by the above formula (I), a salt thereof or a hydrate of them for producing an agent for treating, preventing or improving neural diseases or an analgesic.

The neural disease is any one of disease selected from acute ischemic stroke, cerebral apoplexy, cerebral infarction, head trauma, cerebral neural cell death, Alzheimer's disease, Parkinson's disease, amyotrophic lateral sclerosis, Huntington's disease, cerebral circulation metabolic affection, cerebral dysfunction, pain, spasm, schizophrenia, migraine, epilepsy, manic-depression, neural degenerative diseases, cerebral ischemia, AIDS dementia complications, edema, anxiety disorder, diabetic neuropathy, cerebral vascular dementia and multiple sclerosis.

The meanings of the symbols, terms and the like described in the specification of the present application are illustrated below, and the present invention is illustrated in detail.

The structural formula of a compound happens to represent a fixed isomer for convenience in the specification of the present application, but the present invention includes all of geometrical isomers which occur in the structure of the compound, optical isomers based on an asymmetric carbon, stereo-isomers, the isomers of tautomers and the like, and a mixture of the isomer. The present invention is not limited to the indication of the formulae for convenience, and may be one of the isomers and a mixture thereof. Accordingly, in the compounds of the present invention, there may exist an optically active body and a racemic body which have an asymmetric carbon atom in the molecule, but they are not limited in the present invention, and both of them are included therein. Further, crystal polymorphism happens to exist, but is not similarly limited, and the crystal form may be either single or a mixture of crystal forms and may be a hydrate in addition to an anhydride. A so-called metabolite which occurs due to decomposition of the compounds according to the present invention in vivo is also included in the scope of claim for patent of the present invention.

The term "and/or" in the specification of the present application is used for the meanings which contain both the case of "and" and the case of "or". Accordingly, for example, "A and/or B" includes both the case of "A and B" and the case of "A or B", and indicates that it may be either of the cases.

The "neural disease" in the specification of the present application mainly indicates acute ischemic stroke, cerebral apoplexy, cerebral infarction, head trauma, cerebral neural cell death, Alzheimer's disease, Parkinson's disease, amyotrophic lateral sclerosis, Huntington's disease, cerebral circulation metabolic affection, cerebral dysfunction, pain, spasm, schizophrenia, migraine, epilepsy, manic-depression, neural degenerative diseases, cerebral ischemia, AIDS dementia complications, edema, anxiety disorder, diabetic neuropathy, cerebral vascular dementia and multiple sclerosis.

The "analgesic" in the specification of the present application means a medicine which mitigates or removes pain by changing the perception of stimulation of a nociceptor without causing narcoticism and unconsciousness.

The "halogen atom" used in the specification of the present application means atoms such as fluorine atom, chlorine atom, bromine atom and iodine atom, preferably fluorine atom, chlorine atom and bromine atom, and more preferably fluorine atom and chlorine atom.

The "$C_{1-6}$ alkyl group" used in the specification of the present application means an alkyl group having 1 to 6 carbon atoms, and the preferable examples thereof include linear or branched alkyl groups such as methyl group, ethyl group, n-propyl group, isopropyl group, n-butyl group, isobutyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group and 3-methylpentyl group.

The "$C_{2-6}$ alkenyl group" used in the specification of the present application means an alkenyl group having 2 to 6 carbon atoms, and is preferably a linear or branched alkenyl group such as vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexanedienyl group and 1,6-hexanedienyl group.

The "$C_{2-6}$ alkynyl group" used in the specification of the present application means an alkynyl group having 2 to 6 carbon atoms, and is preferably a linear or branched alkynyl group such as ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexanediynyl group and 1,6-hexanediynyl group.

The "$C_{1-6}$ alkoxy group" used in the specification of the present application means a "$C_{1-6}$ alkyloxy group" in which an oxygen atom is bonded with a group having the same meaning as the $C_{1-6}$ alkyl group in the fore-mentioned definition, and the preferable examples thereof include methoxy group, ethoxy group, n-propoxy group, isopropoxy group, sec-propoxy group, n-butoxy group, isobutoxy group, sec-butoxy group, tert-butoxy group, n-pentyloxy group, isopentyloxy group, sec-pentyloxy group, n-hexoxy group, isohexoxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 1,2-dimethylbutoxy group, 2,2-dimethylbutoxy group, 2,3-dimethylbutyloxy group, 1,3-dimethylbutyloxy group, 2-ethylbutoxy group, 1,3-dimethylbutoxy group, 2-methylpentoxy group, 3-methylpentoxy group, hexyloxy group etc.

The "$C_{3-6}$ alkenyloxy group" used in the specification of the present application means a group in which oxygen atom is bound to a group having the same meaning as the $C_{1-6}$ alkenyl group defined above, and the preferable examples thereof include vinyloxy group, allyloxy group, 1-propenyloxy group, 2-propenyloxy group, isopropenyloxy group, 2-methyl-1-propenyloxy group, 3-methyl-1-propenyloxy group, 2-methyl-2-propenyloxy group, 3-methyl-2-propenyloxy group, 1-butenyloxy group, 2-butenyloxy group, 3-butenyloxy group, 1-pentenyloxy group, 1-hexenyloxy group, 1,3-hexanedienyloxy group, 1,6-hexanedienyloxy group etc.

The "$C_{3-8}$ cycloalkyl group" used in the specification of the present application means a cycloalkyl group in which the ring is formed by 3 to 8 carbon atoms, and the preferable group includes cyclopropyl group, cyclobutyl group, cyclopentyl group, cyclohexyl group, cycloheptyl group, cyclooctyl group etc. Further, the "$C_{3-8}$ cycloalkane" used in the specification of the present application means a ring corresponding to the above-mentioned $C_{3-8}$ cycloalkyl group.

The "$C_{3-8}$ cycloalkenyl group" used in the specification of the present application means a $C_{3-8}$ cycloalkenyl group in which a ring is formed by 3 to 8 carbon atoms, and the examples thereof include a group represented by the formula:

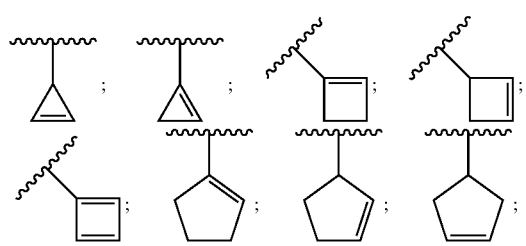

-continued

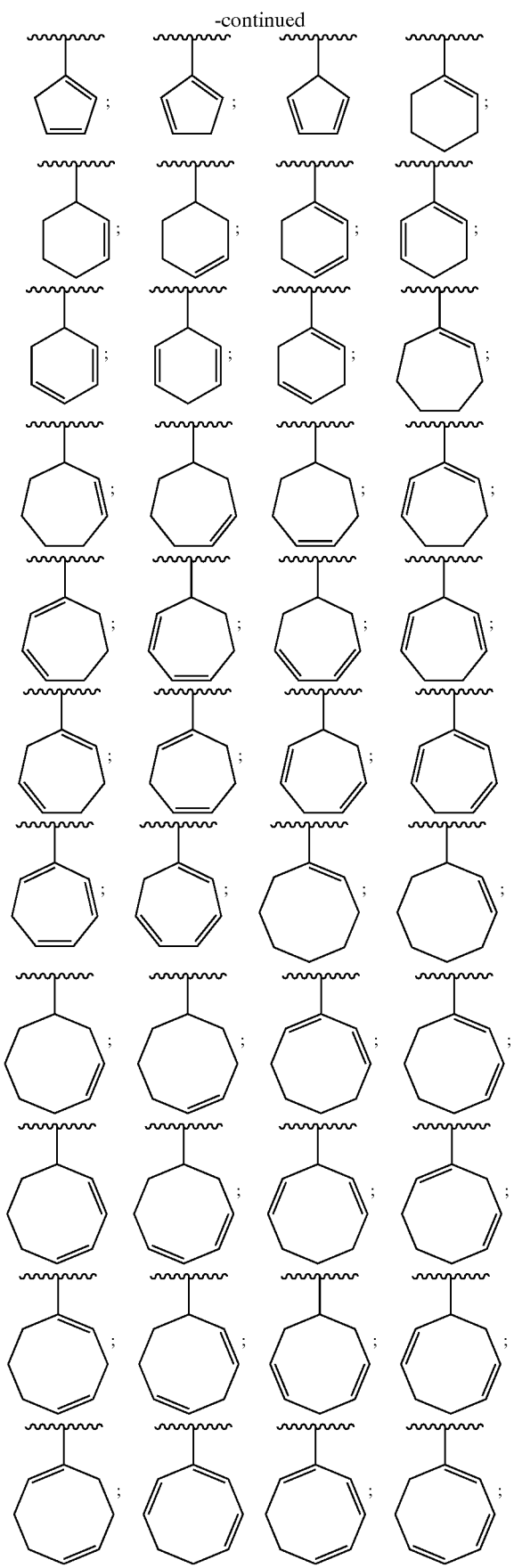

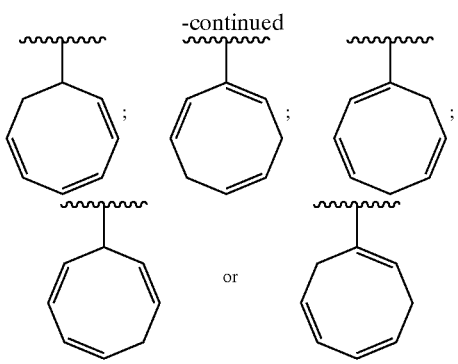

The "aromatic cyclic group" used in the specification of the present application is a term meaning a $C_{6-14}$ aromatic hydrocarbon cyclic group or a 5- to 14-membered aromatic heterocyclic group.

(1) Examples of the above-mentioned "$C_{6-14}$ aromatic hydrocarbon cyclic group" include mono-cyclic, di-cyclic or tri-cyclic $C_{6-14}$ aromatic hydrocarbon groups such as phenyl group, indenyl group, 1-naphthyl group, 2-naphthyl group, azulenyl group, hepthalenyl group, biphenyl group, indathenyl group, acenaphthyl group, fluorenyl group, phenalenyl group, phenanthrenyl group, anthracenyl group, cyclopentacyclooctenyl group, benzocyclooctenyl group, and the like.

(2) Examples of the "5- to 14-membered aromatic heterocyclic group" include a mono-cyclic, di-cyclic or tri-cyclic 5- to 14-membered aromatic heterocyclic ring which contains any one or more of hetero atoms selected from nitrogen atom, sulfur atom and oxygen atom, and for example:

(i) aromatic heterocyclic rings containing nitrogen such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizyl group, phthalazyl group, naphthylidinyl group, quinoxalyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenacinyl group, pimidazopyridinyl group, imidazopyrimidinyl group and pyrazolopyridinyl group;

(ii) aromatic heterocyclic rings containing sulfur such as thienyl group and benzothienyl group;

(iii) aromatic heterocyclic rings containing oxygen such as furyl group, pyranyl group, cyclopentapyranyldgroup, benzofuranyl group and isobenzofuranyl group; and (iv) aromatic hetero cyclic rings containing 2 or more different kinds of hetero atoms selected from nitrogen atom, sulfur atom and oxygen atom, such as bhiazolyl group, isothiazolyl group, benzothiazolyl group, benzthiazolyl group, phenothiazinyl group, isoxazolyl group, bfurazanyl group, phenoxazinyl group, oxazolyl group, benzoxazolyl group, oxadiazolyl group, pyrazolooxazolyl group, imidazothiazolyl group, thienofuranyl group, furopyrrolyl group, pyridoxazinyl group may be proposed.

The "$C_{3-14}$ hydrocarbon ring" used in the specification of the present application means a $C_{3-8}$ cycloalkane, a $C_{3-8}$ cycloalkene or a $C_{6-14}$ aromatic hydrocarbon ring, and the meanings of these rings refer to the same meaning as a $C_{3-8}$ cycloalkane, a $C_{3-8}$ cycloalkene and a $C_{6-14}$ aromatic hydrocarbon ring defined above.

The "5- to 14-membered heterocyclic ring" used in the specification of the present application means a 5- to 14-membered heterocyclic ring containing any one or more of hetero atoms selected from nitrogen atom, sulfur atom and oxygen atom, and an aromatic heterocyclic ring and a non-aromatic heterocyclic ring are included in the ring. Here, (1) the above-mentioned "5- to 14-memberedaromatic heterocyclic ring" have the same meaning as a 5- to 14-membered aromatic heterocyclic ring defined above. Further, (2) the preferable ring as the "5- to 14-membered non-aromatic heterocyclic ring" includes 5- to 14-membered non-aromatic heterocyclic rings such as pyrrolidine ring, pyrroline ring, piperidine ring, piperazine ring, imidazoline ring, pyrazolidine ring, imidazolidine ring, morpholine ring, tetrahydrofuran ring, tetrahydropyran ring, aziridine ring, oxirane ring, oxathiorane ring, pyridone ring etc., and condensed rings such as phthalimide ring, succinimide ring etc.

The "hydrocarbon group" used in the specification of the present application specifically means a $C_{1-6}$ alkyl group, a $c_{2-6}$ alkenyl group, a $C_{2-6}$ alkynyl group, a $C_{3-8}$ cycloalkyl, a $C_{3-8}$ cycloalkenyl group or a $C_{6-14}$ aromatic hydrocarbon cyclic group, and the respective meanings are the same as defined above.

Meaning of Ar

In the compound represented by the above formula (I) according to the present invention, Ar indicates (1) a $C_{6-14}$ aromatic hydrocarbon cyclic group which may be substituted, (2) a 5- to 14-membered aromatic heterocyclic group which may be substituted, (3) a $C_{1-6}$ alkyl group substituted with a $C_{6-14}$ aromatic hydrocarbon cyclic group which may be substituted or (4) a $C_{1-6}$ alkyl group substituted with a 5- to 14-membered aromatic heterocyclic group which may be substituted.

Examples of the above-mentioned "$C_{6-14}$ aromatic hydrocarbon cyclic group" preferably include phenyl group, pentalenyl group, indenyl group, naphthyl group, 1,2,3,4-tetrahydronaphthyl group, azulenyl group, hepthalenyl group, benzocyclooctenyl group, tetranyl group, phenanthrenyl group etc., and more preferably phenyl group, naphthyl group etc.

Further, the preferable examples of the "5- to 14-membered aromatic heterocyclic group" include pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizyl group, phthalazyl group, naphthylidinyl group, quinoxalyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenacinyl group, imidazopyridinyl group, imidazopyrimidinyl group, pyrazolopyridinyl group, thienyl group, benzothienyl group, furyl group, pyranyl group, cyclopentapyranyl group, benzofuranyl group, isobenzofuranyl group, thiazolyl group, isothiazolyl group, benzothiazolyl group, benzthiazolyl group, phenothiazinyl group, isoxazolyl group, furazanyl group, phenoxazinyl group, oxazolyl group, benzoxazolyl group, oxadiazolyl group, pyrazolooxazolyl group, imidazothiazolyl group, thienofuranyl group, phlopyrrolyl group, pyridoxazinyl group etc., more preferably thienyl group, pyridyl group etc., and further preferably thienyl group.

When Ar is the "$C_{6-14}$ aromatic hydrocarbon cyclic group optionally substituted" or the "5- to 14-membered aromatic heterocyclic group optionally substituted", examples of the "substituent" include (i) hydroxyl group, (ii) a halogen atom (for example, fluorine atom, chlorine atom, bromine atom and an iodine atom), (iii) nitrile group, (iv) a $C_{1-6}$ alkyl group (preferably, methyl group, ethyl group, n-propyl group, isopropyl group, n-butyl group, isobutyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group etc.), (v) a $C_{2-6}$ alkenyl group (preferably, vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexanedienyl group, 1,6-hexanedienyl group etc.), (vi) a$C_{2-6}$alkynyl group (preferably, ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexanediynyl group, 1,6-hexanediynyl group etc.), (vii) a $C_{1-6}$alkoxy group (preferably, methoxy group, ethoxy group, n-propoxy group, isopropoxy group, sec-propoxy group, n-butoxy group, isobutoxy group, sec-butoxy group, tert-butoxygroup, n-pentyloxy group, isopentyloxy group, sec-pentyloxy group, n-hexoxy group, isohexoxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 1,2-dimethylbutoxy group, 2,2-dimethylbutoxy group, 2,3-dimethylbutyloxy group, 1,3-dimethylbutyloxy group, 2-ethylbutoxy group, 1,3-dimethylbutoxy group, 2-methylpentoxy group, 3-methylpentoxy group, hexyloxy group etc.), (viii) $C_{1-6}$ alkylthio group (preferably, methylthio group, ethylthio group, n-propylthio group, isopropylthio group, n-butylthio group, isobutylthio group, sec-butylthio group, tert-butylthiogroup, n-pentylthio group, 1,1-dimethylpropylthio group, 1,2-dimethylpropylthio group, 2,2-dimethylprbpylthio group, 1-ethylpropylthio group, 2-ethylpropylthio group, n-hexylthio group, 1-methyl-2-ethylpropylthio group, 1-ethyl-2-methylpropylthio group, 1,1,2-trimethylpropylthio group, 1-propylpropylthio group, 1-methylbutylthio group, 2-methylbutylthio group, 1,1-dimethylbutylthio group, 1,2-dimethylbutylthio group, 2,2-dimethylbutylthio group, 1,3-dimethylbutylthio group, 2,3-dimethylbutylthio group, 2-ethylbutylthio group, 2-methylpentylthio group, 3-methylpentylthio group etc.), (ix) a $C_{1-6}$ alkoxycarbonyl group, (x) a hydroxyl $C_{1-6}$ alkyl group, (xi) a halogenated $C_{1-6}$ alkyl group, (xii) a hydroxy-imino $C_{1-6}$alkyl group, (xiii): nitro group, (xiv) an amino group in which the nitrogen atom may be substituted, (xv) a carbamoyl group in which the nitrogen atom may be substituted, (xvi) a sulfamoyl group in which the nitrogen atom may be substituted, (xvii) a lower acyl group, (xviii) an aromatic acyl group, (xix) a $C_{1-6}$alkylsulfonyl group such as methylsulfonyl group, etc., and the "substituent" is preferably (a) hydroxyl group, (b) a halogen atom, (c) nitrile group, (d) a $C_6$ alkyl group, (e) a $C_{1-6}$alkylsulfonyl group, (f) a $C_{1-6}$ alkoxy group, (g) a $C_{1-6}$ alkylthio group etc., and, more preferably, nitrile group or a halogen atom (for example, fluorine atom etc.).

Further, examples of the more preferable "$C_{6-14}$ aromatic hydrocarbon cyclic group which may be substituted" or "5- to 14-membered aromatic heterocyclic group which may be substituted" in the definition of Ar include a thiophene, a pyridine, a benzene or a naphthalene ring which may be substituted with any one or more groups selected from a halogen atom and cyano group. The most preferable example includes a thiophene ring which may be substituted with any one or more groups selected from a halogen atom and cyano group, and namely, a ring represented by the formula:

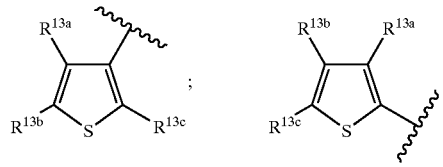

wherein $R^{13a}$, $R^{13b}$ and $R^{13c}$ are the same as or different from each other, and each indicates a hydrogen atom, a halogen atom or cyano group.

In the compound represented by the above formula (I) according to the present invention, when Ar is the "$C_{1-6}$ alkyl group substituted with a $C_{1-6}$ aromatic hydrocarbon cyclic group which may be substituted" or the "$C_{1-6}$ alkyl group substituted with 5- to 14-membered aromatic heterocyclic group which may be substituted", the "$C_{6-14}$ aromatic hydrocarbon cyclic group which may be substituted" or the "5- to 14-membered aromatic heterocyclic group which may be substituted" has the same meaning as the $C_{6-14}$ aromatic hydrocarbon cyclic group which may be substituted or the 5- to 14-membered aromatic heterocyclic group which may be substituted in the above-mentioned definition, respectively. The $C_{1-6}$alkyl group substituted with those groups means a $C_{1-6}$alkyl group substitutedwith such groups. Here, preferable examples of the "$C_{1-6}$ alkyl group" include methyl group, ethyl group, n-propyl group, isopropyl group, n-butyl group, isobutyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl, group, 1-ethyl-2-methylpropyl group, 1,1,2-trimethylpropyl group, 1-prop ylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group etc. Preferable examples of the "$C_{1-6}$ alkyl group substituted with an aromatic group which may be substituted" include a benzyl group, a phenethyl group, a phenylpropyl group, a naphthylmethyl group, a naphthylethyl group, a naphthylpropyl group, a pyridylmethyl group, a pyrazinylmethyl group, a pyrimidinylmethyl group, a pyrrolylmethyl group, an imidazolylmethyl group, a pyrazolylmethyl group, a quinolylmethyl group, an isoquinolylmethyl group, furfuryl group, thienylmethyl group, thiazolylmethyl group etc., which maybeoptionally substituted respectively with one ore more groups selected from nitrile group, ahalogenatom (for example, fluorineatom, chlorineatom, bromine atom, iodine atom etc.) etc.

Further, preferable examples of the "$C_{1-6}$ alkoxycarbonyl group" in the definition of Ar include methoxycarbonyl group, ethoxycarbonyl group, n-propoxycarbonyl group, isopropoxycarbonyl group, sec-propoxycarbonyl group, n-butoxycarbonyl group, isobutoxycarbonyl group, sec-butoxycarbonylcarbonyl group, tert-butoxycarbonylcarbonyl group, n-pentoxycarbonyl group, isopentoxycarbonyl group, sec-pentoxycarbonyl group, tert-pentoxycarbonyl group, n-hexoxycarbonyl group, isohexoxycarbonyl group, 1,2-dimethylpropoxycarbonyl group, 2-ethylpropoxycarbonyl group, a 1-methyl-2-ethylpropoxycarbonyl group, 1-ethyl-2-ethylpropoxycarbonyl group, 1,1,2-trimethylpropoxycarbonyl group, 1,1-dimethylbutoxycarbonyl group, 2,2-dimethylbutoxycarbonyl group, 2-ethylbutoxycarbonyl group, 1,3-dimethylbutoxycarbonyl group, 2-methylpentoxycarbonyl group, 3-methylpentoxycarbonyl group etc.

Preferable examples of the above-mentioned "hydroxy $C_{2-6}$ alkyl group" include linear or branched $C_{1-6}$ alkyl groups such as hydroxymethyl group, 1-hydroxyethyl group, 2-hydroxyethyl group, 3-hydroxy-n-propyl group, hydroxy-isopropyl group, hydroxy-sec-propyl group, hydroxy-n-butyl group, hydroxy-isobutyl group, hydroxy-sec-butyl group, hydroxy-tert-butyl group, hydroxy-n-pentyl group, hydroxy-iso-pentyl group, hydroxy-n-hexyl group and hydroxy-iso-hexyl group.

The above-mentioned "halogenated $C_{1-6}$ alkyl group" means a group in which one or more of the same or different halogen atoms are bound to the "$C_{1-6}$ alkyl group" having the same meaning as the $C_{1-6}$ alkyl group defined above, and preferable examples thereof include fluoromethyl group, difluoromethyl group, trifluoromethyl group, chloromethyl group, 1-fluoroethyl group, 2-fluoroethyl group, 1,1-difluoroethyl group, 1,2-difluoroethyl group, 2,2-difluoroethyl group, 2,2,2-trifluoroethyl group etc.

The above-mentioned "hydroxyimino $C_{1-6}$ alkyl group" means a group in which hydroxyimino group is bound to a group having the same meaning as the $C_{1-6}$ alkyl group defined above.

The "amino group in which a nitrogen atom may be optionally substituted" means an amino group which is represented by the formula —N($R^{15}$)$R^{16}$— (wherein $R^{15}$ and $R^{16}$ are the same as or different from each other and each indicates (1) a hydrogen atom, (2) a $C_{1-6}$alkyl group, a $C_{1-6}$ alkenyl group or a $C_{1-6}$ alkynyl group which may be substituted respectively with one or more groups selected from a halogen atom, a $C_{3-8}$ cycloalkyl group, a $C_{3-8}$ cycloalkenyl group and a $C_{1-6}$ alkoxy group, (3) a $C_{3-8}$ cycloalkyl group or a $C_{3-8}$ cycloalkenyl group which may be substituted with a halogen atom, (4) a carbonyl group substituted with any one of groups selected from a $C_{1-6}$alkyl group, a $C_{1-6}$ alkenyl group, a $C_{1-6}$alkynyl group, a $C_{3-8}$ cycloalkyl group, a $C_{3-8}$ cycloalkenyl group, a $C_{1-6}$ alkoxy group, a $C_{6-14}$ aromatic hydrocarbon cyclic group, a 5-to 14-membered aromatic heterocyclic group and a 5- to 14-membered non-aromatic heterocyclic group which may be substituted with a halogen atom, respectively, (5) a carbamoyl group substituted with any one of groups selected from a $C_{1-6}$ alkyl group, a $C_{1-6}$ alkenyl group, a $C_{1-6}$ alkynyl group, a $C_{6-}$, aromatic hydrocarbon cyclic group and a 5- to 14-membered aromatic heterocyclic group or (6) a sulfonyl group substituted with any one of groups selected from a $C_{1-6}$ alkyl group, a $C_{1-6}$ alkenyl group and a $C_{1-6}$ alkynyl group, or (7) $R^{15}$ and $R^{16}$ may be bound together to form a 3- to 10-membered non-aromatic heterocyclic group containing the nitrogen atom to which they are bound, and the heterocyclic group may be substituted with one or more of groups selected from hydroxyl group, a halogen atom, a $C_{1-6}$ alkoxy group etc.).

Examples of the preferable amino group include unsubstituted amino group, methylamino group, dimethylamino group, ethylamino group, diethylamino group, methylethylamino group, acetamide ($CH_3CONH$—) group, propionamide group, methanesulfonamide group, ethanesulfonamide group, pyrrolidinyi group, pyrazolinyl group, piperidinyl group, piperazinyl group, 4-morpholinyl group, 4-thiomorpholinyl etc. The more preferable examples of the "amino group which may be substituted" include an amino group which may be substituted with one or two groups selected from a $C_{1-6}$alkyl group, a $C_{2-6}$ alkenyl group, a $C_{2-6}$ alkynyl group, a $C_{3-8}$ cycloalkyl group and a $C_{3-8}$ cycloalkenyl group.

The above-mentioned "carbamoyl group in which the nitrogen atom may be substituted" means a carbamoyl group in which the nitrogen atom may be substituted with a group selected from a $C_{1-6}$ alkyl group, a $C_{2-6}$ alkenyl group, a $C_{2-6}$ alkynyl group, a $C_{3-8}$ cycloalkyl group and a $C_{3-8}$ cycloalkenyl group. Further, the carbamoyl group naturally includes a case in which the nitrogen atom of the carbamoyl group is a portion of a cyclic amine. The preferable examples of the "carbamoyl group in which the nitrogen atom may be substituted" includes unsubstituted carbamoyl group, N-methylcarbamoyl group, N,N-dimethylcarbamoyl group, N-ethylcarbamoyl group, N,N-diethylcarbamoyl group, N-niethyl-N-ethylcarbamoyl group, 1-pyrrolidinylcarbonyl group, 1-pyrazolinylcarbonyl group, 1-piperidylcarbonyl group, 1-piperazinylcarbonyl group, 4-morpholinylcarbonyl group, 4-thiomorpholinylcarbonyl group etc.

The above-mentioned "sulfamoyl group in which the nitrogen atom may be substituted" means a sulfamoyl group in which the nitrogen atom may be optionally substituted with a group selected from a $C_{1-6}$ alkyl group, a $C_{2-6}$ alkenyl group, a $C_{2-6}$ alkynyl group, a $C_{3-8}$ cycloalkyl group, a $C_{3-8}$ cycloalkenyl group etc. Further, the sulfamoyl group naturally includes a case in which the nitrogen atom of the sulfamoyl group is a portion of a cyclic amine. The preferable examples of the "sulfamoyl group in which the nitrogen atom may be substituted" include unsubstituted sulfamoyl group (—$SO_2NH_2$), N-methylsulfamoyl group (—$SO_2NHCH_2$), N,N-dimethylsulfamoyl group (—$SO_2NH(CH_3)_2$), N-ethylsulfamoyl group (—$SO_2NHC_2H_5$), N,N-diethylsulfamoyl group (—$SO_2NH(C_2H_5)_2$), N-methyl-N-ethylsulfamoyl group (—$SO_2N(CH_3)C_2H_5$), 1-pyrrolidinylsulfonyl group, 1-pyrazolinylsulfonyl group, 1-piperidylsulfonyl group, 1-piperazinylsulfonyl group, 4-morpholinylsulfonyl group, 4-thiomorpholinylsulfonyl group etc.

The above-mentioned "lower acyl group" means a linear or molecular chain acyl group derived from a fatty acid having 1 to 6 carbons, and the preferable examples of the group include formyl group, acetyl group, propionyl group, butyryl group, isobutyryl group, valeryl group, isovaleryl group, pivaloyl group, hexanoyl group etc.

Meaning of the Ring A

In the compound represented by the above formula (I) according to the present invention, the ring A indicates any one ring selected from piperazine ring, homopiperazine ring, piperidine ring, homopiperidine ring, pyrrolidine ring and diazabicyclo[2,2,1]heptane ring. Examples of the ring A preferably include a piperazine ring, a homopiperazine ring, a piperidine ring, a homopiperidine ring, a pyrrolidine ring, more preferably a piperidine ring, a piperazine ring, and further more preferably a piperazine ring. When the ring A is piperazine ring, piperidine ring, pyrrolidine ring or diazabicyclo[2,2,1]heptane ring, an aspect represented by the formula:

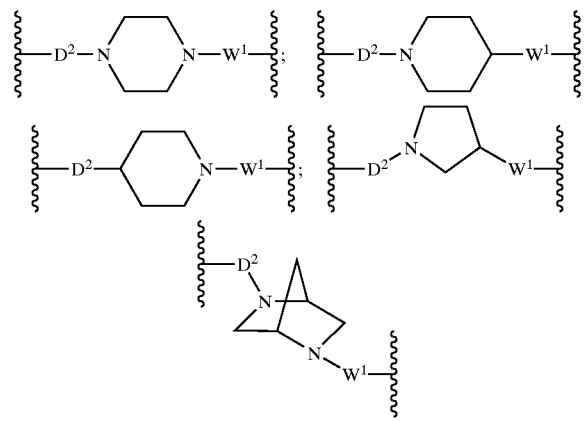

is listed as the preferable aspect in which the bonding chains $D^2$ and $W^1$ are bound to the ring A, and as more preferable one, listed is the formula:

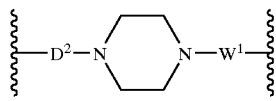

Meaning of Ring B

In the compound represented by the above formula (I) according to the present invention, the ring B indicates (1) a $C_{3-14}$ hydrocarbon ring which may be substituted, or (2) a 5-to 14-memberedheterocyclic ring which may be substituted.

(1) The "$C_{3-14}$ hydrocarbon ring" in the definition of the ring B means a $C_{3-8}$ cycloalkane, a $C_{3-8}$ cycloalkene or a $C_{6-14}$ aromatic hydrocarbon ring. When the ring B is "a $C_{3-8}$ cycloalkane", examples of the ring preferably include 3- to 8-membered cycloalkanes such as cyclopropane, cyclobutane, cyclopentane, cyclohexane, cycloheptane etc., and more: preferably cyclopropane, cyclobutane, cyclopentane, cyclohexane etc. When the ring B is "a $C_{3-8}$ cycloalkene", examples of the ring preferable include 3- to 8-membered cycloalkenes such as cyclopropene, cyclobutene, cyclopentene, cyclohexene and cycloheptene, and further, a non-aromatic unsaturated hydrocarbon ring in which a carbon—carbon double bond in an aromatic hydrocarbon ring is partially saturated. Cyclopropene, cyclobutene, cyclopentene, cyclohexene etc. are more preferred. When the ring B is a "$C_{6-14}$ aromatic hydrocarbon ring", the ring preferably includes benzene ring, pentalene ring, indene ring, naphthalene ring, 1,2,3,4-tetrahydronaphthalene ring, azulene ring, heptalene ring, benzocyclooctene ring, phenanthrene ring etc., and the condensed ring of a $C_{3-8}$ cycloalkane with an aromatic hydrocarbon ring and the condensed ring of a $C_{3-8}$ cycloalkene with an aromatic hydrocarbon ring are also included in the "$C_{6-14}$ aromatic hydrocarbon ring".

(2) The "5- to 14-membered heterocyclic ring" in the definition of the ring B indicates a 5- to 14-membered non-aromatic heterocyclic ring or a 5- to 14-membered aromatic heterocyclic ring. When the ring B is the "5- to 14-membered non-aromatic heterocyclic ring", the ring preferably includes pyrrolidine ring, pyrroline ring, piperazine ring, imidazoline ring, pyrazolidine ring, imidazolidine ring, morpholine ring, tetrahydropyran ring, aziridine ring, oxirane ring, phthalimide ring, succinimide ring etc. When the ring B is a "5- to 14-membered aromatic heterocyclic ring", the preferable ring includes pyrrole ring, pyridine ring, pyridazine ring, pyrimidine ring, pyrazine ring, pyrazole ring, imidazole ring, indole ring, isoindolyl ring, indolizine ring, purine ring, indazole ring, quinoline ring, isoquinoline ring, quinolizine ring, phthalazine ring, naphthylidine ring, quinoxaline ring, quinazoline ring, benzimidazole ring, cinnoline ring, pteridine ring, imidazotriazine ring, pyrazinopyridazine ring, acridine ring, phenanthridine ring, carbazole ring, carbazoline ring, perimidine ring, phenanthroline ring, phenacine ring, thiophene ring, benzothiophene ring, furan ring, pyran ring, cyclopentapyran ring, benzofuran ring, isobenzofuran ring, thiazole ring, isothiazole ring, benzthiazole ring, benzothiazole ring, phenothiazine ring, isoxazole ring, furazane ring, phenoxazine ring, pyrazolooxazole ring, imidazothiazole ring, thienofuran ring, furopyrrole ring, pyridoxazine ring, 1,4-benzodioxane ring, benzoxazole ring, 2-keto-1-imidazole ring, oxazole ring, 1,2,4-oxadiazole ring, indanone ring, 1,2,3,4-tetrahydroquinoline ring etc.

Examples of the "substituent" in the "$C_{3-14}$ hydrocarbon ring which may be substituted" or the "5- to 14-membered heterocyclic ring which may be substituted" in the ring B include one or more groups selscted from (1) hydroxyl group, (2) a halogen atom (for example, fluorine atom, chlorine atom, bromine atom, iodine atom etc.), (3) nitrile group, (4) a $C_{1-6}$ alkyl group which may be substituted (for example, a $C_{1-6}$ alkyl group which may be substitutedwith one or more groups selectedfrom hydroxyl group, a halogen atom, nitrile group, hydroxyimino group etc.), (5) a $C_{2-6}$ alkenyl group which may be substituted (for example, a $C_{2-6}$ alkenyl group which may be substituted with one or more groups selected from hydroxyl group, a halogen atom, nitrile group, hydroxyimino group etc.), (6) a $C_{1-6}$alkoxy group which may be substituted (for example, a $C_{1-6}$ alkenyl group which may be substituted with one or more groups selected from hydroxyl group, a halogen atom, nitrile group, hydroxyimino group etc.), (7) a $C_{1-6}$ alkylthio group which may be substituted, (8) a $C_{1-6}$ alkoxycarbonyl group, (9) nitro group, (10) an amino group in which the nitrogen atom may be substituted, (11) a carbamoyl group in which the nitrogen atom may be substituted, (12) a sulfamoyl group in which the nitrogen atom may be substituted, (13) a lower acyl group, (14) an aromatic acyl group, (15) a $C_{1-6}$ alkylsulfonyl group (for example, methylsulfonyl group, ethylsulfonyl group etc.), (16) a $C_{6-14}$ aromatic hydrocarbon cyclic group, (17) a 5- to 14-membered aromatic heterocyclic group, and (18) an aralkyl group (for example, benzyl group, phenethyl group etc.), and it is preferably (i) hydroxyl group, (ii) a halogen atom (for example, fluorine atom, chlorine atom, bromine atom etc.), (iii) nitrile group, (iv) a $C_{1-6}$alkyl group (for example, methyl group, ethyl group, n-propyl group, isopropyl group, n-butyl group, isobutyl group, tert-butyl group etc.), (v) a $C_{6-14}$ aromatic hydrocarbon cyclic group, (vi) a 5- to 14-membered aromatic heterocyclic group, etc., and more preferably, nitrile group, fluorine atom, chlorine atom etc.

The most preferable aspect of the ring B is a $C_{6-14}$ aromatic hydrocarbon ring or a 5- to 14-memberedaromatic heterocyclic ring which may be substituted, respectively. Specific examples include a benzene ring, a thiophene ring, a pyridine ring, a 1,4-benzodioxane ring, an indole ring, a benzothiazole ring, a benzoxazole ring, a benzimidazole ring, a 2-keto-1-imidazole ring, a thiazole ring, a oxazole ring, an isoxazole ring, a 1,2,4-oxadiazole ring, an indanone ring, a benzofurane ring, a quinoline ring, a 1,2,3,4- tetrahydroquinoline ring, a naphthalene ring, a 1,2,3,4-tetrahydronaphthalene ring etc., which may be substituted with one or more groups selected from nitrile group, a halogen atom (for example, fluorine atom, chlorine atom, bromine atom etc.), a $C_{6-14}$ aromatic hydrocarbon cyclic group (for example, phenyl group, naphthyl group etc.), a 5- to 14-membered aromatic heterocyclic group (for example, pyridyl group, thienyl group, furyl group etc.), a $C_{1-6}$ alkyl group (for example, methyl group, ethyl group, n-propyl group, isopropyl group, isobutyl group etc.), a lower acyl group and a $C_{1-6}$ alkylsulfonyl group (for example, methylsulfonyl group, ethylsulfonyl group etc.), respectively.

Meaning of E

In the compound represented by the above formula (I) according to the present invention, the bonding chain E indicates a single bond, a group represented by the formula —CO— or —CH(OH)—. The most preferable aspect in E is a single bond.

Meaning of X

In the compound represented by the above formula (I) according to the present invention, the bonding chain X indicates (1) a single bond, (2) oxygen atom, (3) sulfur atom, (4) a $C_{1-6}$ alkylene chain which may be substituted, a group represented by (5) the formula —$NR^2$— (wherein $R^2$ indicates a hydrogen atom, or a $C_{1-6}$ alkyl group, a $C_{3-8}$ cycloalkyl group, a lower acyl group or a $C_{1-6}$ alkylsulfonyl group which may be substituted), (6) —CO—, (7) —COO—, (8) —OOC—, (9) —$CONR^3$—(wherein $R^3$ indicates a hydrogen atom or a $C_{1-6}$ alkyl group which may be substituted), (10) —$NR^4CO$— (wherein $R^4$ indicates a hydrogen atom, or a $C_{1-6}$ alkyl group which may be optionally substituted), (11) —SO—, (12) —$SO_2$—, (13) —$SONR^5$— (wherein $R^5$ indicates a hydrogen atom, or a $C_{1-6}$ alkyl group which may be substituted), (14) —$NR^6SO$— (wherein $R^6$ indicates ahydrogen atom, or a $C_{1-6}$alkyl group which may be substituted), (15) —$SO_2NR^7$— (wherein $R^7$ indicates a hydrogen atom, or a $C_{1-6}$ alkyl group which may be substituted), (16) —$NR^8SO_2$— (wherein $R^8$ indicates a hydrogen atom, or a $C_{1-6}$ alkyl group which may be substituted), (17)>C=N—$OR^9$ (wherein $R^9$ indicates a hydrogen atom, or a $C_{1-6}$ alkyl group which may be substituted), (18) —$NR^{10}$—$W^3$—O— (wherein $R^{10}$ indicates a hydrogen atom, or a $C_{1-6}$ alkyl group, a $C_{3-8}$ cycloalkyl group, a lower acyl group or a $C_{1-6}$ alkylsulfonyl group which may be substituted; and $W^3$ indicates a $C_{1-6}$ alkylene group which may be substituted), (19) —NH—CO—NH—, (20) —NH—CS—NH—, (21) —C(—$NR^{15}$)$NR^{16}$— (wherein $R^{15}$ and $R^{16}$ are the same as or different from each other and indicates a hydrogen atom, nitrile group, a $C_{1-6}$alkyl group, a $C_{2-6}$ alkenyl group, a $C_{2-6}$ cycloalkyl group or a $C_{3-8}$ cycloalkenyl group), (22) —NHC(=NH)—, (23) —O—CO—S—, (24) —S—CO—O—, (25) —OCOO—, (26) —NHCOO—, (27) —OCONH—, (28) —CO(CH$_2$)$_m$O— (wherein m indicates 0 or an integer of 1 to 6), (29) —CHOH—, or (30) —CHOH(CH$_2$)$_n$O— (wherein n indicates 0 or an integer of 1 to 6).

When X is the "$C_{1-6}$ alkylene chain which may be substituted", the "$C_{1-6}$ alkylene chain" indicates a chain derived from a linear or branched $C_{1-6}$ alkane, and the examples thereof include methylene, ethylene, ethylidene, trimethylene, isopropylidene, propylene, tetramethylene, 1,2-butylene, 1,3-butylene, 2,3-butylene, isobutylene etc.

In the definition of X, the most preferable examples of the "C, alkyl group which may be substituted" indicated by $R^2$ to R''' include a $C_{1-6}$alkyl group (for example, methyl group, ethyl group, n-propyl group, isopropyl group etc.) which may be substituted with one or more groups selected from hydroxyl group, a halogen atom (for example, fluorine atom, chlorine atom, bromine atom, iodine atom etc.), nitrile group, nitro group, a $C_{1-6}$ alkoxy group (for example, methoxy group, ethoxy group, n-propoxy group, isopropoxy group etc.). etc.

In the definition of X, the preferable examples of the "$C_{3-8}$ cycloalkyl group" indicated by $R^2$ and $R^{10}$ includes cyclopropanyl group, cyclobutanyl group, cyclopentanyl group, cyclohexanyl group, cycloheptanyl group etc., and the group is more preferably cyclopropanyl group, cyclobutanyl group, cyclopentanyl group, cyclohexanyl group etc.

In the definition of X, the preferable examples of the "lower acyl group" indicated by $R^2$ and $R^{10}$ include formyl group, acetyl group, propionyl group, butyryl group, isobutyryl group, valeryl group, isovaleryl group, pivaloyl group, hexanoyl group etc.

In the definition of X, the preferable examples of the "$C_{1-6}$ alkylsulfonyl group" indicated by $R^2$ and $R^{10}$ include methylsulfonyl group, ethylsulfonyl group, n-propylsulfonyl group, isopropylsulfonyl group, sec-propylsulfonyl group, n-butylsulfonyl group, isobutylsulfonyl group, sec-butylsulfonyl group, tert-butylsulfonyl group, n-pentylsulfonyl group, isopentylsulfonyl group, sec-pentylsulfonyl group, tert-pentylsulfonyl group, n-hexylsulfonyl group, isohexylsulfonyl group, 1,2-dimethylpropylsulfonyl group, 2-ethylpropylsulfonyl group, 1-methyl-2-ethylpropylsulfonyl group, 1-ethyl-2-methylpropylsulfonyl group, 1,1,2-trimethylpropylsulfonyl group, 1,1,2-trimethylpropylsulfonyl group, 1,1-dimethylbutylsulfonyl group, 2,2-dimethylbutylsulfonyl group, 2-ethylbutylsulfonyl group, 1,3-dimethylbutylsulfonyl group, 2-methylpentylsulfonyl group, 3-methylpentylaulfonyl group etc.

In the definition of X, $R^{15}$ and $R^{\approx}$are the same as or different from each other and each indicates a hydrogen atom, nitrile group, a $C_{1-6}$ alkyl group, a $C_{2-6}$ alkenyl group, a $C_{3-8}$ cycloalkyl group or a $C_{3-8}$ cycloalkylene group. The preferable groups of both of them are the same as or different from each other and each means a hydrogen atom, nitrile group, methyl group, ethyl group, n-propyl group, isopropyl group, cyclopropyl group, cyclopentyl group, cyclohexyl group etc. It is more preferable that $R^{15}$ is nitrile group, ethyl group, n-propyl group, isopropyl group or cyclohexyl group, and $R^{16}$ is a hydrogen atom. Further, the most preferable aspect of the formula —C(=$NR^{15}$)$NR^{16}$— is a chain represented by the formula —C(=NCN)NH—.

The meanings of the respective groups listed in the definition of X are described above. (1) The preferable aspect of X is a single bond, oxygen atom, sulfur atom, a $C_{1-6}$ alkylene chain which may be substituted, a group represented by the formula —$NR^2$— (wherein $R^2$ indicates a hydrogen atom, or a $Cl_{1-6}$ alkyl group, a $C_{3-8}$ cycloalkyl group, a lower acyl group or a $C_{2-6}$ alkylsulfonyl group which may be substituted), —CO—, —$NR^{10}$—$W^3$—O— (wherein $R^{10}$ indicates a hydrogen atom, or a $C_{2-6}$ alkyl group, a $C_{3-8}$ cycloalkyl group, a lower acyl group or a $C_{1-6}$ alkylsulfonyl group which may be substituted; and $W^1$ indicates a $C_{1-6}$ alkylene group which may be substituted) and —NH—$SO_2$—. (2) The more preferable aspect is oxygen atom, a $C_{1-6}$ alkylene chain which may be substituted, a group represented by the formula —$NR^2$— (wherein $R^2$ indicates a hydrogen atom, or a $C_{1-6}$alkyl group, a $C_{3-8}$ cycloalkyl group, a lower acyl group or a $C_{1-6}$ alkylsulfonyl group which may be substituted), —CO—, —$NR^{10}$—$W^3$-O— (wherein $R^{10}$ indicates a hydrogen atom, or a $C_{1-6}$ alkyl group, a $C_{3-8}$ cycloalkyl group, a lower acyl group or a $C_{1-6}$ alkylsulfonyl group which may be substituted; and $W^3$ indicates a $C_{1-6}$ alkylene group which may be substituted) and —NH—SO$_2$—. (3) The further more preferable aspect is oxygen atom, a $C_{1-6}$ alkylene chain which may be substituted, a group represented by the formula —NR$^2$— (wherein R$^2$ indicates a hydrogen atom, or a $C_{1-6}$ alkyl group, a $C_{3-8}$ cycloalkyl group, a lower acyl group or a $C_{1-6}$ alkylsulfonyl group which may be substituted), —CO—, and —NH—SO$_2$—. (4) The most preferable aspect is oxygen atom or a group represented by the formula —NR$^2$— (wherein R$^2$ indicates a hydrogen atom, or a $C_{1-6}$ alkyl group, a $C_{3-8}$ cycloalkyl group, a lower acyl group or a $C_{1-6}$ alkylsulfonyl group which may be substituted).

Meaning of R$^1$

The group represented by R$^1$ in the above formula (I) indicates (1) a hydrogen atom, (2) a halogen atom, (3) hydroxyl group, (4) a $C_{1-6}$ alkyl group which may be substituted with one or more groups selected from hydroxyl group, a halogen atom and nitrile group, (5) a $C_{2-6}$ alkenyl group which may be substituted with one or more groups selected from hydroxyl group, a halogen atom and nitrile group, (6) a $C_{2-6}$ alkynyl group which may be substituted with one or more groups selected from hydroxyl group, a halogen atom and nitrile group, (7) a $C_{3-7}$ cycloalkyl group which may be substituted with one or more groups selected from hydroxyl group, a halogen atom and nitrile group, (9) a $C_{1-6}$ alkoxy-$C_{1-6}$ alkyl group, (10) an amino-$C_{1-6}$ alkyl group in which the nitrogen atom may be substituted, (11) the formula —N(R$^{11}$)R$^{12}$— (wherein R$^{12}$ and R$^{12}$ are the same as or different from each other and each indicates a hydrogen atom or a $C_{1-6}$ alkyl group), (12) an aralkyl group, (13) morpholinyl group, (14) thiomorpholinyl group, (15) piperidyl group, (16) pyrrolidinyl group or (17) piperazinyl group.

The preferable atom as the above-mentioned "halogen atom" includes fluorine atom, chlorine atom and bromine atom, and more preferably includes fluorine atom and chlorine atom.

The "$C_{1-6}$ alkyl group" in R$^1$ preferably includes methyl group, ethyl group, n-propyl group, isopropyl group, n-butyl group, isobutyl group, sec-butyl group tert-butyl group etc., more preferably methyl group, ethyl group, n-propyl group and isopropyl group, further preferably n-propyl group and isopropyl group, and most preferably isopropyl group.

The "$C_{2-6}$ alkenyl group" in R$^1$ preferably includes vinyl group, allyl group, 1-propenyl group, isopropenyl group, 1-buten-1-yl group, 1-buten-2-yl group, 1-buten-3-yl group, 2-buten-1-yl group, 2-buten-2-yl group etc., and more preferablyvinylgroup, allyl group, isopropenyl group etc.

The preferable examples of the "$C_{2-6}$ alkynyl group" in R$^1$ include ethynyl group, 1-propynyl group, 2-propynyl group, butynyl group, pentynyl group, hexynyl group etc.

The preferable examples of the "$C_{3-8}$ cycloalkyl group" in R$^1$ include cyclopropanyl group, cyclobutanyl group, cyclopentanyl group, cyclohexanyl group etc.

The preferable examples of the "$C_{1-6}$ alkoxy-$C_{3-6}$ alkyl group in R$^1$ indicate a $C_{1-6}$ alkyl group substituted with a group having the same meaning as the $C_{1-6}$ alkoxy group defined above, and the preferable group includes methoxymethyl group, ethoxymethyl group, 1-methoxyethyl group, 2-methoxyethyl group, 1-ethoxyethyl group, 2-methoxy-n-propyl group, 3-methoxy-n-propyl group, 2-(n-propoxy) ethyl group etc.

The preferable examples as the "$C_{1-6}$alkyl group substituted with nitrile group" in R$^1$ includes cyanomethyl group, 2-cyanoethyl group, 3-cyano-n-propyl group, 2-cyanoisopropyl group, 2-cyano-n-butyl group, 2-cyano-sec-butyl group, 2-cyano-tert-butyl group, 2-cyano-n-pentyl group, 3-cyano-n-hexyl group etc.

The preferable examples as the "amino-$C_{1-6}$ alkyl group in which the nitrogen atom may be substituted" in R$^1$ includes aminomethyl group, methylaminomethyl group, dimethylaminomethyl group, ethylaminomethyl group, diethylaminomethyl group, methylethylaminomethyl group, acetamidomethyl group, pyrrolidinylmethyl group, 2-pyrazolinylethyl group, 1-piperidylethyl group, piperazinylmethyl group etc.

The preferable examples as the "aralkyl group" in R$^1$ includes benzyl group, phenethyl group, phenylpropyl group, naphthylmethyl group, naphthylethyl group, naphthylpropyl group etc.

The meanings of the respective groups listed in the definition of R$^1$ are described above, and the preferable aspect of R$^1$ includes a hydrogen atom, a halogen atom, hydroxyl group, a $C_{1-6}$ alkyl group, a $c_{2-6}$ alkenyl group, a $C_{2-6}$ alkynyl group, a $C_{3-8}$ cycloalkyl group, a hydroxyl $C_{1-6}$ alkyl group, a $C_{1-6}$alkoxy-$C_{1-6}$ alkyl group, a cyano-$C_{1-6}$ alkyl group and a $C_{1-6}$ alkyl group substituted with a halogen atom. The more preferable aspect thereof includes a halogen atom, hydroxyl group, a $C_{1-6}$ alkyl group, a $C_{2-6}$ alkenyl group and a $C_{2-6}$ alkynyl group, and the further preferable aspect includes a $C_{1-6}$ alkyl group (particularly, methyl group, ethyl group, n-propyl group, isopropyl group).

Meanings of D$^1$, D$^2$, W$^1$ and W$^2$

In the compound represented by the above formula (I) according to the present invention, D$^1$, D$^2$, W$^1$ and are the same as or different from each other and each respectively indicates (1) a single bond or (2) an optionally substituted $C_{1-6}$ alkylene chain.

The preferable aspect of the "$C_{1-6}$ alkylene chain" in the above-mentioned "$C_{1-6}$ alkylene chain which may be substituted" includes methylene chain, ethylene chain, ethylidene chain, trimethylene chain, isoproylidene chain, propylene chain, tetramethylene chain, 1,2-butylene chain, 1,3-butylene chain, 2,3-butylene chain, isobutylene chain etc.

Further, a chain being asymmetric in left and right is included in these $C_{1-6}$alkylene chains, but in this case, the binding direction is not limited, and both of the binding directions are also included in the $C_{1-6}$alkylene chain".

The preferable aspect of the "substituent" in the above-mentioned "$C_{1-6}$ alkylene chain which may be substituted" includes (i) a hydroxy group, (ii) a halogen atom (for example, fluorine atom, chlorine atom, bromine atom, iodine atom etc.), (iii) nitrile group, (iv) a $C_{1-6}$alkyl group (for example, methyl group, ethyl group, n-propyl group, isopropyl group, n-butyl group, tert-butyl group etc.), (v) a $C_{2-6}$alkenyl group (for example, vinyl group, allyl group, 1-propenyl group, 2-propenyl group, isopropenyl group, 2-methyl-1-propenyl group, 3-methyl-1-propenyl group, 2-methyl-2-propenyl group etc.), (vi) a $C_1$, alkoxy group (for example, methoxy group, ethoxy group, n-propoxy group, isopropoxy group, n-butoxy group, tert-butoxy group etc.), etc.

Further, when the "substituent" is a $C_{1-6}$ alkyl group and/or a $C_{2-6}$ alkenyl group, these substituents can be bound together to form a 5- to 14-membered ring, and in the case of W$^1$ and W$^2$, these substituents can be bonded with the ring B or X to form a 5- to 14-membered ring.

As the preferable aspect, D$^1$, D$^2$, W$^1$ and W$^2$ are the same as or different from each other and each include (1) a single bond or (2) a methylene chain, ethylene chain, ethylidene chain, trimethylene chain, isopropylidene chain, propylene chain, tetramethylene chain, 1,2-butylene chain, 1,3-butylene chain, 2,3-butylene chain, isobutylene chain etc., which may be substituted respectively with one or more groups selected from hydrbxyl group, a halogen atom and nitrile group.

The respective meanings of E, X, $D^1$, $D^2$, $W^1$ and $W^2$ are described above. Here, the preferable aspect of the partial structure -$D^1$-E-$D^2$- includes ethylene chain (—$CH_2$—$CH_2$—), ethylidene chain (—CH($CH_3$)—), trimethylene chain (—($CH_2$)$_3$—), isopropylidene chain (—CH($CH_3$)$_2$—), propylene chain (—CH($CH_3$)$CH_2$—), tetramethylene chain (—($CH_2$)$_4$)—), 1,2-butylene chain (—CH($C_2H_5$)$CH_2$—), 1,3-butylene chain (—CH($CH_3$)$CH_2CH_2$—), 2,3-butylene chain (—CH($CH_3$)CH($CH_3$)—), isobutylene chain (—CH($CH_3$)$_2CH_2$—) etc. The more preferable aspect includes trimethylene chain (—($CH_2$)$_3$—), isopropylidene chain (—CH($CH_3$)$_2$—), propylene chain (—CH($CH_3$)$CH_2$—), tetramethylene chain (—($CH_2$)$_4$—), 1,2-butylene chain (—CH($C_2H_5$)$CH_2$—) etc., and the further preferable aspect includes tetramethylene chain (—($CH_2$)$_3$—) etc. Further, the preferable aspect of the partial structure —$W^1$—X—$W^2$— includes a single bond, a chain represented by the formula —$CH_2$—$CH_2$—O—, —$CH_2$—$CH_2$—$NR^2$—, —($CH_2$)$_3$—O— or —($CH_2$)$_3$—$NR^2$—.

The aspects of the compound represented by the above formula (I) according to the present invention are not specifically limited, and those skilled in the art can freely combine the groups listed in the above definitions concerning each of Ar, the ring A, the ring B, E, X, $R^1$, $D^1$, $D^2$, $W^1$ and $W^2$, and carry out all compounds within the scope. The more preferable aspects among them include the case where Ar is an optionally substituted 5- to 14-memberedaromatic heterocyclic group; the ring A is piperazine ring, piperidine ring or pyrrolidine ring; and the ring B is a $C_{6-14}$ aromatic hydrocarbon group or 5- to 14-membered aromatic heterocyclic group which may be substituted; E is a single bond; and X is a single bond, oxygen atom, an optionally substituted $C_{1-6}$ alkylene group or a group represented by the formula —$NR^2$— (wherein $R^2$ has the same meaning as defined above). As the further preferable aspect, a compound represented by the formula:

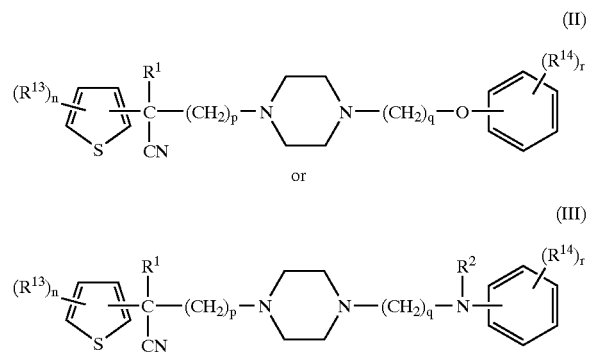

(wherein the respective symbols in the formulae have the same meanings as defined above), a salt thereof or a hydrate of them.

Compounds obtained in Examples described later are naturally included in the preferable aspects of the compound according to the present invention, and typical compounds are mentioned below.

4-[(4-Cyano-5-methyl-4-phenyl)hexyl]-N-(4-fluorophenyl)-N'-(2-methylpropyl)-1(2H)-pyrazinecarboxyimidamide;
1-isopropyl-4-[4-(1-isobutyl-1N-benzo[d]imidazol-2-yl)piperazino]-1-phenylbutyl cyanide;
1-[4-cyano-5-methyl-4-(5-cyano-2-thienyl)hexyl)-4-[2-(3-cyanophenoxy)ethyl)piperazine;
1-[4-cyano-5-methyl-4-(2-thienyl)hexyl]-4-[2-(3-cyanophenoxy)ethyl]piperazine;
1-[4-cyano-5-methyl-4-(5-cyano-2-thienyl)hexyl]-4-[3-(5-cyano-2-thienyl)propyl]piperazine;
1-[4-cyano-5-methyl-4-(3-thienyl)hexyl]-4-[2-(3-cyanophenoxy)ethyl]piperazine;
1-(4-cyano-5-methyl-4-[4-(2-cyano)thienyl]hexyl)-4-(2-(3-cyanophenoxy)ethyl]piperazine;
1-[(4-cyano-5-methyl-4-phenyl)hexyl]-4-[(2-benzoxazolyl)amino)piperidine;
1-[4-cyano-4-(5-cyano-2-thienyl)-5-methylhexyl]-(3S)-3-[N-(2-cyanoethyl)-N-benzylamino]pyrrolidine;
1-[4-cyano-4-(5-cyano-2-thienyl)-5-methylhexyl]-(3R)-3-[N-(2-cyanoethyl)-N-benzylamino]pyrrolidine;
1-[(4-cyano-5-methyl-4-phenyl)hexyl]-4-(benzothiazolyl)piperazine;
1-((4-cyano-5-methyl-4-phenyl)hexyl]-4-(2-(6-methoxy)benzothiazolyl]piperazine;
1-((4-cyano-5-methyl-4-phenyl)hexyl]-4-(2-benzoxazolyl)piperazine;
1-[(4-cyano-5-methyl-4-phenyl)hexyl]-4-(2-quinolinyl]piperazine;
4-[4-(1-methyl-1H-benzo[d]imidazol-2-yl)-1,4-diazepan-1-yl]-1-isopropyl-1-phenylbutyl cyanide;
4-[4-(1-ethyl-1H-benzo[d]imidazol-2-yl)-1,4-diazepan-1-yl]-1-isopropyl-1-phenylbutyl cyanide;
ethyl 4-(4-cyano-5-methyl-4-phenylhexyl)-1-[2-(4-fluorophenoxy)ethyl]-2-piperazinecarboxylate;
1-[(2-oxo-1,2-dihydro-3-quinolyl)methyl]-4-[(4-cyano-5-methyl-4-phenyl)hexyl]piperidine;
4-[(4-cyano-5-methyl-4-phenyl)hexyl)-1-1-[2-methanesulfonylamino]phenyl]methyl)piperazine;
4-((4-cyano-5-methyl-4-phenyl)hexyl]1-1-{[2-methanesulfonylamino]phenyl]methyl)piperidine;
(S)-3-phenyl-2-aminopropanoic acid(1-[4-cyano-5-methyl-5-(2-thionyl)hexyl]piperazinyl)amide;
4-[4-(4-phenylpiperidinyl)piperidinyl]-1-isopropyl-1-phenylbutyl cyanide;
4-[4-(4-cyano-4-phenylpiperidinyl)piperidinyl]-1-isopropyl-1-phenylbutyl cyanide; and
4-[4-(4-benzylpiperidinyl)piperidinyl]-1-isopropyl-1-phenylbutyl cyanide.

The compound represented by the above formula (I) according to the present invention, a salt thereof or a hydrate of them can be produced by known production processes or processess according to the processes. As the known production processes, for example, a production process described in JP-A 2000-169462 (a production process described in paragraphs "0054" to "0065" in the Publication), and production processes described in JP-A 2000-12207, 2000-12208 and 2000-12209 are listed.

Further, the raw material compound in the production of the compound (I) may form a salt or a hydrate, and is not specifically limited so far as it does not inhibit the reaction. When the compound (I) according to the present invention is obtained as a free body, it can be converted to a salt which the above compound (I) may form, according to a conventional process. When the compound according to the present invention is prepared as a free body, it can be converted to a salt according to a conventional process. Various isomers (for example, geometrical isomer, optical isomers based on an asymmetric carbon, stereo-isomers, the isomers of tautomers and the like) which are obtained for the compound (I) according to the present invention can be purified and isolated by conventional separation procedures (for example, recrystallization, a diastereomer salt method, an enzyme division method, various chromatography and the like).

The "salt" in the specification of the present application is not specifically limited so far as it forms a salt with the compound according to the present invention and is pharmacologically accepted, and is preferably a salt of hydrogen halide acid (for example, hydrofluorate, hydrochloride, hydrobromate, hydroiodate and the like), a salt of an inorganic acid (for example, sulfate, nitrate, perchlorate, phosphate, carbonate, bicarbonate and the like), a salt of an organocarboxylic acid (for example, a salt of acetic acid, a salt of trifluoroacetic acid, a salt of oxalic acid, a salt of maleic acid, a salt of tartaric acid, a salt of fumaric acid, a salt of citric acid, and the like), a salt of an organosulfonic acid (for example, methanesulfonate, trifluoromethanesulfonate, ethanesulfonate, benzenesulfonate, toluenesulfonate, camphorsulfonate, and the like), a salt of an amino acid (for example, a salt of aspartic acid, a salt of glutamic acid, and the like), a quaternary ammonium salt, an alkali metal salt (for example, sodium salt, potassium salt and the like), an alkali earth metal salt (for example, magnesium salt, calcium salt and the like), and the like. Hydrochloride, a salt of oxalic acid, a salt of trifluoroacetic acid, and the like are more preferable.

The compound represented by the fore-mentioned formula (I) or a salt thereof, or a hydrate thereof can be formulated by an ordinary method, and preferable preparations include tablets, powders, granules, parvules, coated tablets, capsules, syrups, troches, inhalants, suppositorium, injections, paste medicines, eye ointments, eye drops, nasal drops, eardrops, poultices, lotions and the like. Forpreparations, excipients, binders, disintegrants, lubricants, colorants, and flavoring agents which are conventionally used, if necessary, stabilizers, emulsifiers, absorption accelerators, surfactants, pH regulators, antiseptics, antioxidants and the like can be used. Ingredients which are conventionally used for the raw materials of pharmaceutical preparations can be formulated by a normal method. As these ingredients, for example, there are listed animal and vegetable oils such as soy bean flexure, tallow and synthetic glyceride; hydrocarbons such as liquid paraffin, squalane and solid paraffin; ester oils such as octyldodecyl myristate and isopropyl myristate; higher alcohols such as cetostearyl alcohol and behenic alcohol; silicone resins; silicone oils; surfactants such as polyoxyethylene fatty acid ester, sorbitan fatty acid ester, glycerin fatty acid ester, polyoxyethylene sorbitan fatty acid ester, polyoxyethylene-hardened castor oil and polyoxyethylene-polyoxypropylene block copolymer; water-soluble polymers such as hydroxy ethyl cellulose, polyacrylic acid, carboxyvinyl polymer, polyethylene glycol, polyvinyl pyrrolidone) and methyl cellulose; lower alcohol such as ethanol and isopropanol; polyvalent alcohols such as glycerin, propylene glycol, dipropylene glycol and sorbitol; sugars such as glucose and dextrose; inorganic powders such as silicic anhydride, aluminum magnesium silicate and aluminum silicate; purified water and the like. Specifically, as excipients used are: lactose, corn starch, white sugar, dextrose, mannitol, sorbit, crystal cellulose, silicon dioxide and the like; as binders used are: polyvinyl alcohol, polyvinyl ether, methyl cellulose, ethyl cellulose, gum arabic, gum tragacanth, gelatin, shellac, hydroxypropyl cellulose, hydroxypropylmethyl cellulose, polyvinyl pyrrolidone, polypropylene glycol-polyoxyethylene block copolymer, meglumine, calcium citrate, dextrin, pectin and the like; as disintegrants used are: starch, agar, gelatin powder, crystalline cellulose, calcium carbonate, sodium bicarbonate, calcium citrate, dextrin, pectin, carboxymethyl cellulose calcium and the like; as lubricants used are: magnesium stearate, talc, polyethylene glycol, silica, hardened vegetable oil and the like; as colorants used is: any colorant which is approved to be added to pharmaceuticals; as flavoring agents used are: cocoa powder, menthol, aroma powder, peppermint oil, borneol, cinnamon powder and the like; as antioxidants used are: ascorbic acid, α-tocopherol and the like which are approved to be added to pharmaceuticals.

For example, (1) oral preparations are made as powders, fine granules, granules, tablets, coated tablets, capsules etc. according to a conventional method after adding the compound according to the present invention, a salt thereof or a hydrate of them, fillers, and further, if necessary, binders, disintegrants, lubricants, colorants, flavoring agents etc. (2) In case of tablets and granules, sugar coating and gelatin coating and additionally, if necessary, appropriate coating are allowed to be carried out. (3) In case of syrups, preparations for injection, eye drops and the like, pH regulators, resolving aids, isotonizing agents and the like, and if necessary, dissolution assistants, stabilizers, buffers, suspending agents, antioxidants and the like are added and formulated according to a conventional method. In case of the preparations, a freeze-dry product can be also made, and injections can be administered in vein, subcutis and a muscle. Preferable examples of the suspending agent include methyl cellulose, polysorbate 80, hydroxyethyl cellulose, gum arabic, tragacanth powder, carboxymethyl cellulose sodium, polyoxyethylene sorbitan monolaurate and the like; preferable examples of the resolving aids include polyoxyethylene hardened castor oil, polysorbate 80, nicotinamide, polyoxyethylene sorbitan monolaurate and the like; preferable examples of the stabilizer include sodium sulfite, meta sodium sulfite, diethyl ether and the like; Preferable examples in the preservative include methyl p-oxybenzoate, ethyl p-oxybenzoate, sorbic acid, phenol, cresol, chlorocresol and the like. (4) Further, in the case of external preparations, the preparation process is not specifically limited, and the external preparations can be produced by a conventional method. As the raw material of a base drug used, various raw materials which are conventionally used for pharmaceuticals, quasi drug, cosmetics and the like can be used. For example, raw materials such as animal and vegetable oils, a mineral oil, an ester oil, waxes, higher alcohols, fatty acids, a silicone oil, a surfactant, phosphatides, alcohols, polyvalent alcohols, water-soluble polymers, clay minerals, purified water and the like are listed. According to requirement, a pH regulator, an antioxidant, a chelating agent, antiseptic and fungicide, a coloring agent, flavors and the like can be added. Further, if necessary, ingredients having differential derivation action, blood flow accelerator, antibacterial, antiphlogistine, cell activator, vitamins, amino acids, a humectant, keratolysis medicine and the like can be formulated. The dose of the pharmaceuticals according to the present invention is different depending on the extent of symptom, age, sexuality, body weight, administration form, modality of salt, the difference of sensitiveness formedicine, thespecificmodalityof affection, but in the case of an adult, for oral administration, approximately 30 $\mu$g to 1000 mg per day in general, preferably 100 $\mu$g to 500 mg, and more preferably 100 $\mu$g to 100 mg of the pharmaceutical is administered at one time or several times. For injection administration, approximately 1 to 3000 $\mu$g/kg in general, and preferably 3 to 1000 $\mu$g/kg of the pharmaceutical is administered at one time or several times.

The compound represented by the above formula (I) according to the present invention, a salt thereof or a hydrate of them is useful as a calcium antagonist and specifically, a neuron-selective calcium antagonist. The compound according to the present invention has a novel compound having a P/Q-type calcium channel and an N-type calcium channel inhibiting activity, and is useful as an agent for treating or preventing a disease against which a P/Q-type calcium channel inhibitory action and an N-type calcium channel inhibitory action are effective. Further, the compound represented by the above formula (I) according to the present invention, a salt thereof or a hydrate of them has a remarkably low extent of cell affection in comparison with a conventional antagonist, and is a safe calcium antagonist whose toxicity is reduced. Accordingly, the compound according to the present invention, a salt thereof or a hydrate of them is useful as a neural cell death depressor, a cerebral neural cell demulcent, an agent for treating or preventing neural disease and an analgesic. In particular, it is useful as an agent for treating, preventing or improving acute ischemic stroke, cerebral apoplexy, cerebral infarction, head trauma, cerebral neural cell death, Alzheimer's disease, Parkinson's disease, amyotrophic lateral sclerosis, Huntington's disease, cerebral circulationmetabolic affection, cerebral dysfunction, pain, spasm, schizophrenia, migraine, epilepsy, manic-depression, neural degenerative diseases, cerebral ischemia, AIDS dementia complications, edema, anxiety disorder, diabetic neuropathy, cerebral vascular dementia, multiple sclerosis etc.

EXAMPLES

Figure 1:
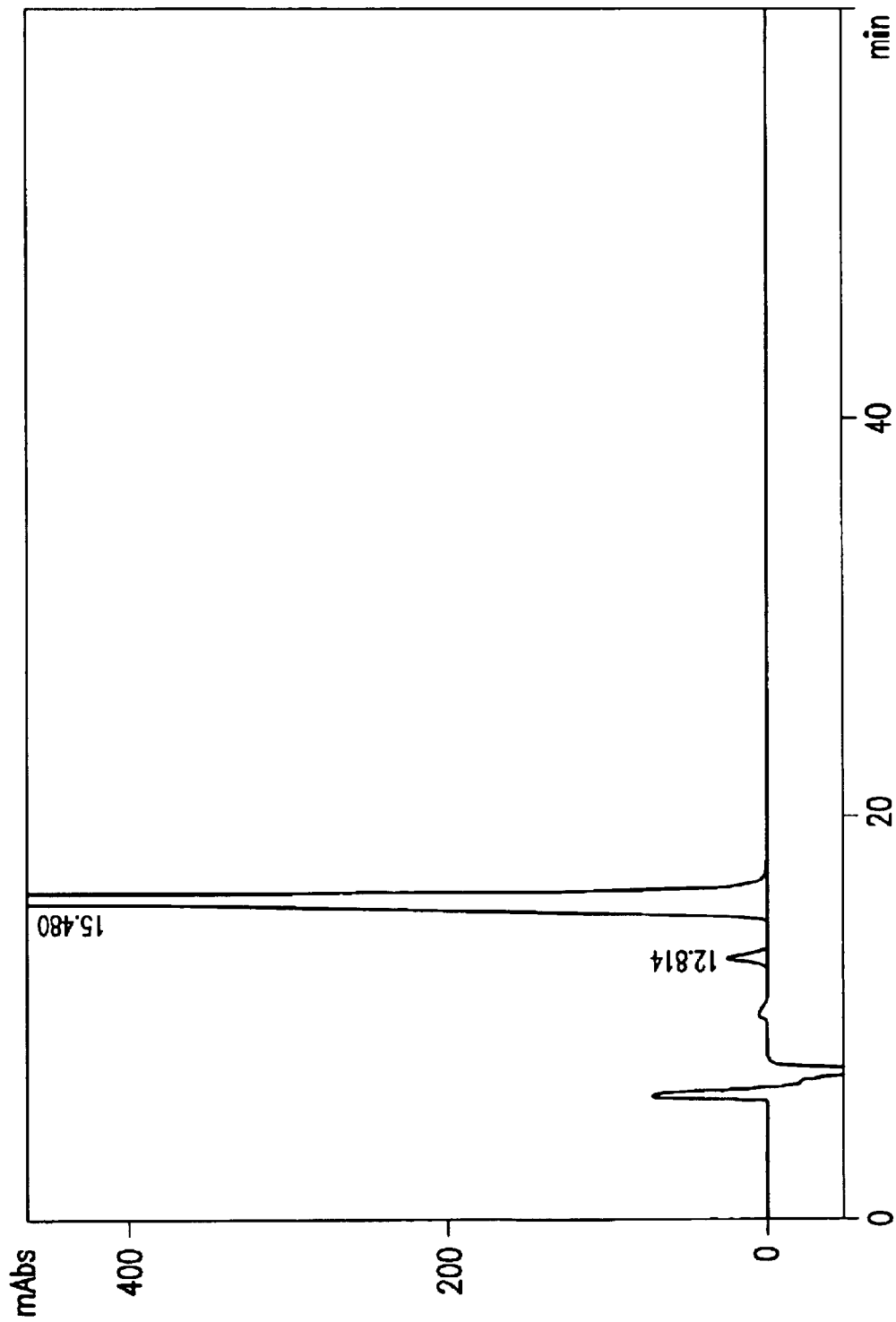
FIG. 1 shows a HPLC chart in Reference Example 97.

Examples are shown below as the best modes for carrying out the present invention, but those Reference Examples, Examples (further, a pharmacologically acceptable salt thereof or a hydrate of them, and the pharmaceutical containing thereof) and Test Examples are only illustrative, and the compound according to the present invention is not limited to specific examples below at any case. Those skilled in the art can add various variations to not only Examples shown below, but also the Scope of claim for Patent in the specification of the present application to carry out the present invention to a maximum extent, and such variations are included in the Scope of claim for Patent in the specification of the present application.

Further, the symbol "Z" used in Reference Examples or Examples below means benzyloxycarbonyl group, and "HPLC" means high performance liquid chromatography, respectively.

Reference Example 1 2-((4-Cyano-5-methyl-4-phenyl)hexyl]-5-benzyl-2,5-diazabicyclo[2.2.1]heptane

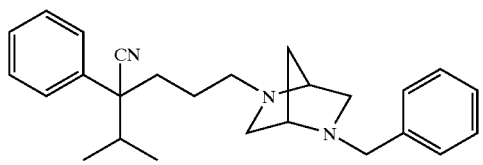

The title compound was obtained as a pale brown oil in accordance with the method described in Example 15 (15%).

$^1$H-NMR (400 MHz, CDCl$_3$) δ 0.78 (d, J=6.8 Hz, 3H), 1.04–1.16 (m, 1H), 1.20 (d, J=6.8 Hz, 3H), 1.45–1.57 (m, 1H), 1.64 (dd, J=9.6 Hz, J=33.6 Hz, 2H), 1.94 (dt, J=4.4 Hz, J=12.4 Hz, 1H), 2.07–2.23 (m, 2H), 2.30–2.38 (m, 1H), 2.50–2.71 (m, 5H), 3.19 (d, J=14 Hz, 2H), 3.66 (q, J=14 Hz, 2H), 7.19–7.40 (m, 10H).

Reference Example 2 3-methyl-2-(2-naphthyl)butyronitrile

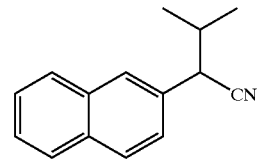

3.00 g (17.9 mmol) of 2-naphthylacetonitrile was dissolved in 10 ml of dimethyl sulfoxide, and 2.43 g (19.7 mmol) of 2-bromopropane, 330 mg (0.90 mmol, cat) of tetra-n-butylammonium iodide and 10 ml of 50% potassium hydroxide were successively added thereto. After completion of the reaction, brine was added, and the mixture was extracted with ether. The organic layer was washed with brine, dried over magnesium sulfate and evaporated, to give a crude product. The crude product was subjected to 150 g of silica gel (ethyl acetate:hexane=1:10), to give 2.42 g (11.6 mmol, 64.6%) of the title compound as a yellow oil.

$^1$H-NMR (400 MHz, CDCl$_3$) δ 1.07 (d, J=6.8 Hz, 3H), 1.11 (d, J=6.8 Hz, 3H), 2.10–2.30 (m, 1H), 3.84 (d, J=3.84 Hz, 1H), 7.38 (dd, J=1.8 Hz, 8.6 Hz, 1H) 7.48–7.55 (m, 2H), 7.79–7.88 (m, 4H)

Reference Example 3 4-cyano-5-methyl-4-(2-naphthyl) Hexanol

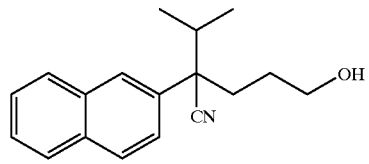

1.00 g (4.78 mmol) of 3-methyl-2-(2-naphthyl)butyronitrile was dissolved in 20 ml of dimethylformamide, 191 mg (4.78 mmol, 60% by weight) of sodium hydride was added thereto, and the mixture was heated. After 30 minutes; it was cooled to a room temperature, 0.93 ml (4.00 mmol) of (3-bromopropoxy)-tert-butyldimethylsilane was added thereto. After completion of the reaction, brine was added thereto, and the mixture was extracted with ethyl acetate. The organic layer was washed with brine, dried over magnesium sulfate and evaporated, to give a crude product. The crude product was subjected to 50 g of silica gel (ethyl acetate:hexane=1:18), to give 1.40 g of a mixture of the objective product, a raw material and an impurity. The mixture was used for the following reaction without purification. Namely, 1.40 g of the abve-mentioned crude 4-cyano-5-methyl-5-(2-naphthyl)hexanoxy-tert-butyldimethylsilane was dissolved in 20 ml of tetrahydrofuran, and 5 ml (5 mmol) of tetraammonium fluoride was added thereto. After completion of the reaction, brine was added thereto, and the mixture was extracted withethyl acetate. Theorganiclayerwaswashedwith an aqueous saturated ammonium chloride and brine, dried over magnesium sulfate and evaporated, to give a crude product. The crude product was subjected to 50 g of silica gel (ethyl acetate:hexane=1:4), to give 590 mg (2.21 mmol, 46.2%, 2 steps) of the title compound as a yellow oil.
¹H-NMR (400 MHz, CDCl₃) δ 0.80 (d, J=6.8 Hz, 3H) 1.10–1.30 (m, 1H), 1.27 (d, J=6.8 Hz, 3H), 1.57–1.69 (m, 1H), 2.02–2.12 (m, 1H), 2.20–2.37 (m, 2H), 3.58 (t, J=6.2 Hz, 2H), 7.38 (dd, J=2.0 Hz, 8.4 Hz, 1H), 7.48–7.56 (m, 2H), 7.84–7.91 (m, 3H), 7.95 (brd-s, 1H)

Reference Example 4 1-[(4-cyano-5-methyl-4-phenyl)hexyl]-3-tert-butoxycarbanylaminopyrrolidine

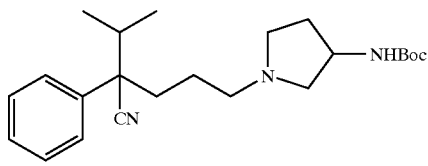

2.76 g (8.44 mmol) of 4-cyano-5-methyl-4-phenylhexyl iodide was dissolved in 50.0 ml of acetonitrile, 1.29 ml (9.28 mmol) of triethylamine and 1.88 g (10.1 mmol) of 3-tert-butoxycarbonylaminopyrrolidine were added thereto, and the mixture was heated to 60° C. After completion of the reaction, the mixture was partitioned between ethyl acetate and brine. The organic layer was dried over magnesium sulfate, and then evaporated, to give a crude product. The crude product was subjected to 50 g of Cromatorex NH silica gel (ethyl acetate:hexane=2:1), to give 2.97 g (7.76 mmol, 91.3%) of the title compound as a pale yellow syrup.
¹H-NMR (400 MHz, CDCl₃) δ 0.78 (d, J=6.8 Hz, 3H), 1.21 (d, J=6.8 Hz, 3H), 1.05–1.25 (m, 1H), 1.43 (s, 9H), 1.50–1.65 (m, 2H), 1.88–2.00 (m, 1H), 2.00–2.28 (m, 4H), 2.28–2.60 (m, 4H), 2.65–2.70 (m, 1H), 4.05–4.20 (brd-s, 1H), 4.82–4.95 (brd-s, 1H), 7.26–7.59 (m, 5H)

Reference Example 5 1-[(4-cyano-5-methyl-4-phenyl)hexyl]-3-aminopyrrolidine

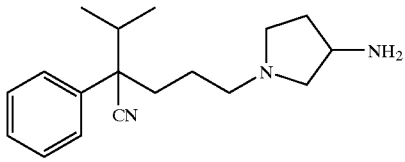

2.36 g (6.12 mmol) of 1-[(4-cyano-5-methyl-4-phenyl)hexyl]-3-tert-butoxycarbonylaminopyrrolidine was dissolved in a mixed solution of 5 ml of tetrahydrofuran and 10 ml of methanol, and a 4N hydrogen chloride-ethyl acetate solution was added thereto. After completion of the reaction, the mixture was adjusted to basic with a 2N aqueous sodium hydroxide, and extracted with chloroform. The organic layer was dried over magnesium sulfate, and then evaporated, to give 1.66 g (5.82 mmol, 95.1%, an orange syrup) of a crude product.
¹H-NMR (400 MHz, CDCl₃) δ 0.77 (d, J=6.4, 3H), 1.20 (d, J=6.8, 3H), 1.08–1.24 (m, 1H), 1.42–1.62 (m, 2H), 1.84–2.00 (m, 3H), 2.08–2.28 (m, 4H), 2.32–2.48 (m, 3H), 2.58–2.67 (m, 2H), 3.42–3.51 (m, 1H), 7.26–7.40 (m, 5H)

Reference Example 6 1-[(4-cyano-5-methyl-4-phenylvhexyl]-3-(N-(2-cyanoethyl)aminolpyrrolidine

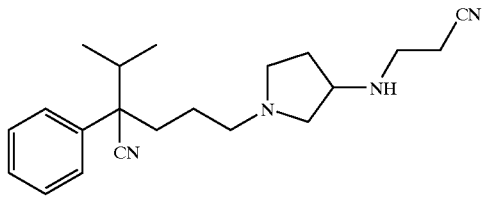

700 mg (2.45 mmol) of 1-[(4-cyano-5-methyl-4-phenyl)hexyl]-3-aminopyrrolidine was dissolved in 15 ml of methanol, 0.19 ml (2.85 mmol) of acrylonitrilewasadded thereto, and the mixture was heated under reflux. After completion of the reaction, the mixture was evaporated, to give a crude product. The crude product was subjected to 20 g of Cromatorex NH silica gel (ethyl acetate 100%), to give 775 mg (2.29 mmol, 93.5%) of the title compound as an orange syrup.
¹H-NMR (400 MHz, CDCl₃) δ 0.77 (d, J=6.8 Hz, 3H), 1.07–1.24 (m, 1H), 1.20 (d, J=6.4 Hz, 3H), 1.08–1.24 (m, 1H), 1.46–1.62 (m, 2H), 1.86–1.96 (m, 1H), 2.04–2.24 (m, 4H), 2.28–2.46 (m, 4H), 2.46–2.62 (m, 2H), 2.49 (t, J=6.8 Hz, 2H), 2.85 (t, J=6.8 Hz, 2H), 3.22–3.30 (mx 1H), 7.26–7.40 (m, 5H)

Reference Example 7 3-Fluorophenoxyacetaldehyde

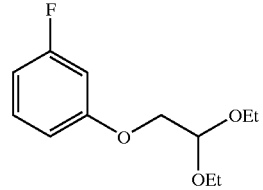

2.00 g (17.8 mmol) of m-fluorophenol was dissolved in 50 ml of dimethylformamide, 785 mg (19.6 mmol, 60% by weight, mineral) of sodium hydride and 3.21 ml (21.3 mmol) of bromoacetaldehydediethylacetal were successively added thereto, and the mixture was heated to 60° C. After completion of the reaction, brine was added thereto and the mixture was extractedwith ethyl acetate. Theorganiclayerwaswashedwith brine, dried over magnesium sulfate and then evaporated, to give a crude product. The crude product was subjected to 105 g of Cromatorex NH silica gel (ethyl acetate:hexane=1:40), to give 3.17 g (13.9 mmol, 78.1%) of the title compound as a yellow oil.
¹H-NMR (400 MHz, CDCl₃) δ 1.25 (t, J=7.0 Hz, 6H), 3.55–3.82 (m, 4H), 3.99 (d, J=5.0 Hz, 2H), 4.82 (t, J=5.0 Hz, 1H), 6.61–6.72 (m, 3H), 7.17–7.25 (m, 1H)

1.68 g (7.38 mmol) of the above acetal was dissolved in 30 ml of acetone and 20 mL of a 2.5N hydrochloric acid, and the mixture was heated. After completion of the reaction, the mixture was extracted with ethyl acetate. The organic layer was washed with brine, dried over magnesium sulfate and then evaporated, to give 800 mg of a crude product which contains the objective compound below. The crude product was subjected to the above-mentioned reaction without purification.

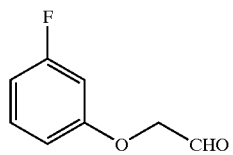

Reference Example 8 1-benzyl-3-[N-(2-cyanoethyl)amino]pyrrolidine

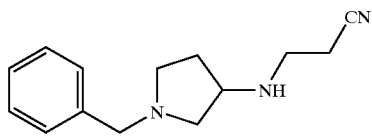

4.00 g (22.7 mmol) of 1-benzyl-3-aminopyrrolidine was dissolved in 70 ml of methanol, 1.49 ml (22.7 mmol) of acrylonitrile was added thereto, and the mixture was heated to 70° C. After completion of the reaction, the reaction solution was evaporated, and the resulting crude product was subjected to 100 g of Cromatorex NH silica gel (ethyl acetate 100%), to give 4.60 g (20.1 mmol, 88.4%) of the title compound as a yellow oil.

$^1$H-NMR (400 MHz, CDCl$_3$) δ 1.54–1.66 (m, 1H), 2.10–2.22 (m, 1H), 2.40–2.60 (m, 2H), 2.49 (t, J=6.8 Hz, 2H), 2; 67–2.78 (m, 2H), 2.86 (t, J=6.8 Hz, 2H) 3.30–3.38 (m, 1H), 3.57–3.73 (m, 2H), 7.22–7.36 (m, 5H)

Reference Example 9 1-benzyl-3-[N-(2-cyanoethyl)-N-[2-(4-cyanophenoxy)ethyl]Amino]pyrrolidine

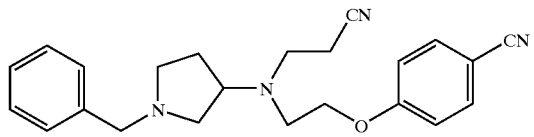

2.03 g (8.87 mmol) of 1-benzyl-3-[(N-(2-cyanoethyl)amino)pyrrolidine was dissolved in 50 ml of dichloroethane, and 1.30 g (8.06 mmol) of 4-cyanophenoxyacetaldehyde separately synthesized, 1.02 ml (17.7 mmol) of acetic acid and 2.56 g (12.1 mmol) of sodium triacetoxyborohydride were successively added thereto. After completion of the reaction, the mixture was adjusted to basic with a 2N aqueous sodium hydroxide, and extracted with ethyl acetate. The organic layer was washed with brine, dried over magnesium sulfate and evaporated, to give a crude product. The crude product was subjected to 250 g of Cromatorex NH silica gel (ethyl acetate:hexane=2:3), to give 2.39 g (6.38 mmol, 79.2%) of the title compound as a yellow syrup.

$^1$H-NMR (400 MHz, CDCl$_3$) δ 1.70–1.84 (m, 1H), 2.03–2.14 (m, 1H), 2.40–2.54 (m, 1H), 2.47 (t, J=6.8 Hz, 2H), 2.55–2.68 (m, 2H), 2.76–2.88 (m, 1H), 2.91–3.09. (m, 4H), 3.48–3.68 (m, 2H), 3.64–3.74 (m, 1H), 4.03 (t, J=5.6 Hz, 2H), 6.9 (t, J=9.2 Hz, 2H), 7.24–7.40 (m, 5H), 7.57 (t, J=9.2 Hz, 2H)

Reference Example 10 3-[(N-(2-cyanoethyl)-N-[2-(4-cyanophenoxy)ethyl]Amino]pyrrolidine

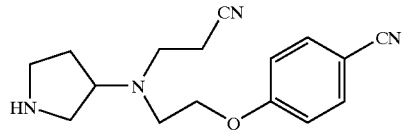

1-Benzyl-3-[(N-(2-cyanoethyl)-N-{2-(4-cyanophenoxy)ethyl)amino)pyrrolidine was dissolved in dichloroethane, AceCl (0.84 ml, 7.66 mmol) was addedthereto, and the mixture was heated under reflux. After about one hour, AceCl (0.12 ml) was added thereto, and the mixture was continued to be heated. After completion of the reaction, the mixture was evaporated. To the residue was added 30 ml of methanol was added thereto, followed byheatingunderreflux. Afterone hour, the reaction solution was evaporated. The residue was extracted with 2N hydrochloric acid, washed with ether, and then adjusted to pH 11–12 with a 2N aqueous sodium hydroxide. The mixture was extracted with ethyl acetate, dried over magnesium sulfate evaporated, to give a crude product. The crude product was subjected to 50 g of Cromatorex NH silica gel (ethyl acetate:methanol= 1:0–3:1), to give 1.12 g (3.93 mmol, 61.6%) of the title compound as a yellow oil.

$^1$H-NMR (400 MHz, CDCl$_3$) δ 1.64–1.76 (m, 1H), 1.94–2.06 (m, 1H), 2.52 (t, J=6.8 Hz, 2H), 2.56–2.70 (m, 2H), 2.77–2.86 (m, 1H), 2.91–3.20 (m, 5H), 3.36–3.51 (m, 1H), 4.08 (t, J=5.6 Hz, 2H), 6.96 (t, J=9.2 Hz, 2H), 7.60 (t, J=9.2 Hz, 2H)

Reference Example 11 1-[(4-cyano-5-methyl-4-phenyl)hexyl]-4-[(methoxycarbonyl)methyl]piperazine

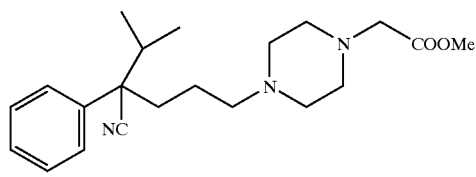

1.00 g (3.50 mmol) of 1-((4-cyano-5-methyl-4-phenyl)hexyl]piperazine and 0.54 ml (3.85 mmol) of triethylamine were dissolved in 25 ml of tetrahydrofuran. Under ice-cooling, 0.35 ml (3.85 mmol) of methyl bromoacetate was added drop wise thereinto. After completion of the reaction, brine was added, and the mixture was extracted with ethyl acetate. The organic layer was washed with brine, dried over magnesium sulfate and evaporated, to give a crude product. The crude product was subjected to 50 g of Cromatorex NH silica gel (ethyl acetate:hexane=2), to give 1.22 g (3.41 mmol, 97.5%) of the title compound as an orange oil.

$^1$H-NMR (400 MHz, CDCl$_3$) δ 0.77 (d, J=6.8 Hz, 3H), 1.05–1.20 (m, 1H), 1.20 (d, J=6.4 Hz, 3H), 1.48–1.64 (m, 1H), 1.84–1.93 (m, 1H), 2.06–2.18 (m, 2H), 2.24–2.31 (m, 2H), 2.31–2.46 (m, 4H), 2.46–2.60 (m, 4H), 3.19 (s, 2H), 3.71 (s, 3H), 7.24–7.39 (m, 5H)

Reference Example 12 3-fluorobenzamidpoxime

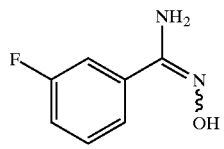

To 200 ml of an ethanol solution of 10.0 g (82.6 mmol) of 3-fluorobenzcyanide were added 8.61 g (124 mmol) of hydroxylamine hydrochloride and 22.8 g (165 mmol) of potassium carbonate, followed by heating under reflux. After completion of the reaction, the mixture evaporated. To the residue was added brine, and the mixture was extracted with ethyl acetate. The organic layer was washed with brine, dried over magnesium sulfate and evaporated, to give a crude product. The crude product was subjected to 100 g of silica gel (ethyl acetate:hexane=1:2–1:4), to give 8.00 g (51.9 mmol, 62.8%) of the title compound as a yellow solid.
$^1$H-NMR (400 MHz, CDCl$_3$) δ 4.75–4.85 (m, 2H), 7.09–7.59 (m, 4H)

Reference Example 13 N-Z-4-piperidineethanol

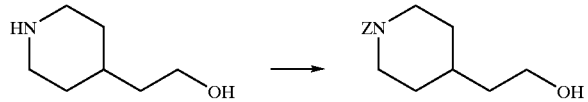

4.70 g (36.4 mmol) of 4-piperidineethanol and 10.0 g (72.8 mmol) of potassium carbonate were dissolved in ether (50 ml) and water (50 ml). Under ice-cooling, ZCl (4.44 ml, 25.0 mmol) was dissolved in 30 ml of ether, and the solution was added dropwise thereinto. The physical property of the resulting title compound is described below. After completion of the reaction, brine was added and the mixture was extracted with ether. The organic layer was washed with brine and an aqueous saturated ammonium chloride, dried over magensium sulfate and evaporated, to give a crude product. The crude product was subjected to 100 g of silica gel (ethyl acetate:hexane=1:2), to give 5.48 g (20.8 mmol, 57.2%) of the title compound as a colorless oil.
$^1$H-NMR (400 MHz, CDCl$_3$) δ 1.05–1.25 (m, 2H), 1.40–1.75 (m, 5H), 2.70–2.85(m, 2H), 3.71 (t, J=6.59 Hz, 2H), 4.10–4.25 (m, 2H), 5.12 (s, 2H), 7.28–7.39 (m, 5H)

Reference Example 14 1-benzyloxycarbonyl-4-[2-(4- fluorophenoxy)ethyl]piperidine

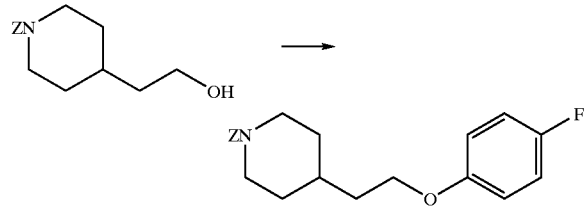

2.00 g (7.60 mmol) of N-Z-4-piperidineethanol, 1.70 g (15.2 mmol) of 4-fluorophenol and 2.39 g (9.12 mmol) of triphenylphosphine were dissolved in 50 ml of tetrahydrofuran, and the mixture was ice-cooled. After 10 minutes, 1.44 ml (9.12 mmol) of diethylazocarboxylate was added dropwise thereinto, and then the mixture was stirred at room temperature. After completion of the reaction, brine was added and the mixture was extractedwithethyl acetate. Theorganiclayerwaswashedwith brine, dried over magnesium sulfate and evaporated, to give a crude product. The crude product was subjected to 100 g of silica gel (ethyl acetate:hexane=1:3), togive2.19 g (6.12 mmol, 80.6%) of the title compound as a colorless oil.
$^1$H-NMR (400 MHz, CDCl$_3$) δ 1.10–1.30 (m, 2H), 1.65–1.80 (m, 5H), 2.70–2.90 (m, 2H), 3.96 (t, J=6.0 HZ, 2H), 4.10–4.28 (m, 2H), 5.13 (s. 2H), 6.79–6.84 (m, 2H), 6.93–6.99 (m, 2H), 7.28–7.38 (m, 5H)

Reference Example 15 4-[2-(4-fluarophenoxy)ethyl] piperidine

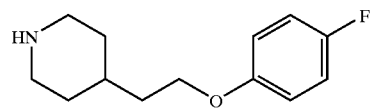

2.19 g (6.12 mmol) of 1-benzyloxycarbonyl-4-[2-(4-fluorophenoxy)ethyl]piperidine was dissolved in 40 ml of methanol, 300 mg of 10% palladium-carbon was added, and replacement with hydrogen was carried out. After completion of the reaction, the mixture was filtered, and the filtrate was evaporated, to give a crude product. The crude product was subjected to 50 g of Cromatorex NH silica gel (ethyl acetate:hexane=1:3-ethyl acetate:methanol=6:1), to give 1.30 g (5.82 mmol, 95.1%) of the title compound as a yellow oil.
$^1$H-NMR (400 MHz, CDCl$_3$) δ 1.10–1.23 (m, 2H), 1.60–1.77 (m, 5H), 2.59 (dt, J=2.4 Hz, 12.2 Hz, 2H), 3.96 (t, J=6.0 HZ, 2H), 4.10–4.28 (m, 2H), 5.13 (s, 2H), 6.79–6.85 (m, 2H), 6.92–6.99 (m, 2H)

Reference Example 16 1-benzyl-4-hydroxypropyl-1,2,5,6-tetrahydropyridine

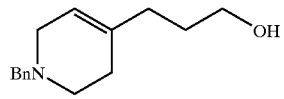

5.00 g (36.4 mmol) of 3-pyridinepropanol was dissolved in 150 ml of acetonitrile, 4.55 ml (38.3 mmol) of benzylbromide was added, and the mixture was heated at 70° C. After 2 hours, heating was stopped, and the mixture was evaporated. Then, the residue was dissolved in 100 ml of methanol, and the mixture was cooled to 0° C. 4.12 g (109 mmol) of sodium borohydride was added thereto. After completion of the reaction, 50 ml of water was added thereto, and the mixture was evaporated. Then, the residue waspartitionedbetween ethylacetateand brine. After drying the organic layer over magnesium sulfate, the mixture was evaporated, to give a crude product. The crude product was subjected to 150 g of Cromatorex NH silica gel (ethyl acetate:hexane=1:6–1:1), to give 6.48 g (28.0 mmol, 77.0%) of the title compound as a yellow oil.
$^1$H-NMR (400 MHz, CDCl$_3$) δ 1.65–1.74 (m, 2H), 2.02–2.13 (m, 4H), 2.55 (t, J=6.0 Hz, 2H), 2.93–2.98 (m, 2H), 3.57 (s. 2H), 3.64 (t, J=6.4 Hz, 2H), 5.38–5.42 (m 1H), 7.22–7.37 (m, 5H)

Reference Example 17 1-benzyl-4-hydroxypropylpiperidine

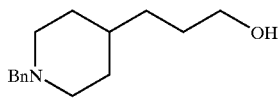

6.48 g of 1-benzyl-4-hydroxypropyl-1,2,5,6-tetrahydropyridine was dissolved in 60 ml of methanol, 88 mg of PtO$_2$ was added, and atmosphere was replaced with hydrogen. After completion of the reaction, the mixture was filtered, and the filtrate was evaporated, to give 4.50 g (19.3 mmol, 68.9%) of the title compound as a yellow oil.
$^1$H-NMR (400 MHz, CDCl$_3$) δ 1.16–1.33 (m, 5H), 1.33–1.41 (brd-s, 1H), 1.53–1.74 (m, 4H), 1.87–1.98 (m, 2H), 2.83–2.90. (m, 2H), 3.48 (s, 2H), 3.62 (t, J=6.4 Hz, 2H), 7.16–7.27 (m, 5H)

Reference Example 18 1-benzyl-4-methanesulfonyloxypropylpiperidine

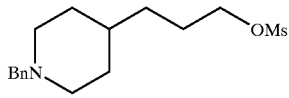

2.58 g (11.1 mmol) of 1-benzyl-4-hydroxypropylpiperidine and 3.26 ml (23.4 mmol) of triethylamine were dissolved in 50 ml of tetrahydrofuran, and 1.67 ml (21.6 mmol) of methanesulfonyl chloride wasaddeddropwise. After completion of the reaction, the mixture was partitioned between ethyl acetate and brine. The organic layer was dried over magnesium sulfate, and then evaporated, to give a crude product. The crude product was subjected to 50 g of Cromatorex NH silica gel (ethyl acetate:hexane=1:1), to give 2.90 g (9.31 mmol, 83.9%) the title compound as a yellow oil. The physico-chemical data of the target compound was as indicated below.
$^1$H-NMR (400 MHz, CDCl$_3$) δ 1.18–1.37 (m, 5H), 1.58–1.68 (m, 2H), 1.71–1.80 (m, 2H), 1.88–1.97 (m, 2H), 2.84–2.90 (m, 2H), 3.00 (s, 3H), 3.48 (s, 21H), 4.21 (t, J=6.8 Hz, 2H), 7.13–7.32 (m, 5H)

Reference Example 19 4-[(4-cyano-5-methyl-4-phenyl)hexyl]piperidine

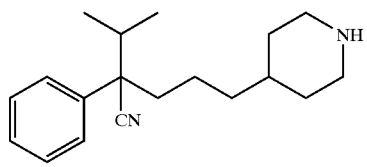

2.43 g (6.49 mmol) of 1-benzyl-4-[(4-cyano-5-methyl-4-phenyl)hexyl]piperidine was dissolved in 30 ml of 1,2-dichloroethane, 0.85 ml (7.79 mmol) of AceCl was added thereto, and the mixture was heated under reflux. After 45 minutes, the mixture was evaporated. Then, 30 ml of methanol was added thereto, and the mixture was heated under reflux again. After completion of the reaction, the mixture was evaporated, extracted with water and washed with ether. The resulting aqueous layer was adjusted to basic, and then the mixture was partitioned between ethyl acetateandbrine. The organiclayer was dried over magnesium sulfate, and then evaporated, to give 1.62 g (5.69 mmol, 87.7%) a yellow crude product. The physico-chemical data of the title compound was as indicated below.
$^1$H-NMR (400 MHz, CDCl$_3$) δ 0.77 (d, J=6.8 Hz, 3H), 0.86–1.04 (m, 3H), 1.07–1.28 (m, 3H), 1.19 (d, J=6.4 Hz, 3H), 1.29–1.44 (m, 1H), 1.48–1.58 (m, 21H) 1.74–1.85 (m, 1H), 2.04–2.14 (m, 2H), 2.49 (dt, J=2.4 Hz, 12.0 Hz, 2H), 2.95–3.02 (m, 2H), 7.26–7.40 (m, 5H)

Reference Example 20 3-cyano-3-(2-thienyl)propanol

Under a nitrogen atmosphere, sodium borohydride (650 mg)

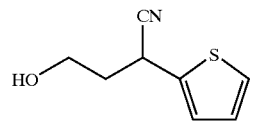

was added in an ice bath to a DMF solution (25 ml) of thiophene-2-acetonitrile (1 g) and (3-bromopropoxy)-tert-butyldimethylsilane (2.06 g). After 20 minutes, the organic layer was separated by adding an aqueous saturated ammonium chloride and ethyl acetate were added thereto. The resulting organic layer was washed with water and brine, and dried over anhydrous magnesium sulfate. After filtering off the drying agent, the mixture was evaporated. The resulting residue was dissolved in acetonitrile (20 mL), a 1 M tetrabutylammonium fluoride/tetrahydrofuran solution (9.7 ml) was added thereto, and the mixture was stirred at a room temperature. After 18 hours, the organic layer was separated by adding water and ethyl acetate. The resulting organic layer was rinsed with water and brine, and dried over magnesium sulfate. After filtering off the drying agent, the mixture was evaporated. The resulting residue was purified by silica gel column chromatography (hexane:ethyl acetate system), to give the title compound as a red oil (637 mg, 43%).
$^1$H-NMR (400 MHz, CDCl$_3$) δ 2.08–2.16 (m, 1H), 3.08 (t, J=7.0 Hz, 2H), 3.75 (t, J=7.0 Hz, 2H), 4.15–4.20 (m, 1H), 7.14 (dd, J=3.8 Hz, 4.8 Hz, 1H), 7.65 (dd, J=0.8 Hz, 4.8 Hz, 1H), 7.75 (dd, J=0.8 Hz, 3.8 Hz, 1H).

Reference Example 21 2-[(3-cyano-3-phenyl)propyl]-1,3-dioxolane

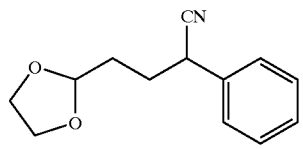

Under a nitrogen atmosphere, sodium amide (1.11 g) was added to a tetrahydrofuran solution (25 ml) of phenylacetonitrile (3 g). After 30 minutes, a tetrahydrofuran solution (25 ml) of 2-(2-bromoethyl)-1,3-dioxolane (4.64 g) was added to the reaction solutionthrough adroppingfunnel. After stirring 2 hours, an aqueous saturated ammonium chloride and ethyl acetate were added thereto, to separate the organic layer. The resulting organic layer was washed with water and brine, and dried over anhydrous magnesium sulfate. After filtering off thedrying agent, themixturewas evaporated. The resulting residue was purified by silica gel column chromatography (hexane:ethyl acetate system), to give the title compound (3.47 g, 62%).

¹H-NMR (400 MHz, CDCl₃) δ 1.75–1.90 (m, 2H), 1.95–2.10 (m, 2H), 3.80–4.00 (m, 5H),4.91 (t, J=4.4 Hz, 1H), 7.30–7.42 (m, 5H).

Reference Example 22 Ethyl 4-methyl-3-phenylpentanoate

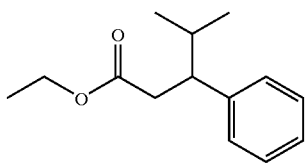

Under a nitrogen atmosphere, ethyl trimethylsilylethylacetate (5.19 g) was added at −78° C. to a solution of a lithium diisopropylamide/tetrahydrofuran solution (1.5 M, 21.6 mL) added to tetrahydrofuran solution (100 mL). After 20 minutes, a tetrahydrofuran solution (10 ml) of isobutyrophenone (4.0 g) was added thereto, and the temperature of the mixture was naturally returned to room temperature. After stirring 18 hours, sodium bisulfate monohydrate (0.6 g) was added and the mixture was stirred. Further, after 10 minutes, the organic layer was separated by adding a 0.2N hydrochloric acid solution (250 mL) and ethyl acetate (200 mL) thereto. The resulting organic layer was washed with water and brine, and dried over anhydrous magnesium sulfate. After filtering off the drying agent, the mixture was evaporated. 756 Mg among the resulting crude product (7.9 g) was dissolved in methanol (5 mL), a catalytic amount of 10% palladium carbon (9.5 mg) was added, and the mixture was stirred under hydrogen atmosphere. After 4 hours, the catalyst was filtered off, and the filtrate was concentrated. The resulting residue was purified by silica gel column chromatography (hexane:ethyl acetate system), to give the title compound as a colorless oil (350 mg).
¹H-NMR (400 MHz, CDCl₃) δ 0.75 (d, J=6.4 Hz, 3H), 0.95 (d, J=6.8 Hz, 3H), 1.06 (t, J=7.2 Hz, 3H), 1.80–1.90 (m, 1H), 2.58 (dd, J=10 Hz, 15.2 Hz, 1H), 2.77 (dd, J=5.6 Hz, 15.2 Hz, 1H), 2.84–2.91 ([, 1H), 7.12–7.29 (m, 5H).

Reference Example 23 4-methyl-3-phenylpentanol

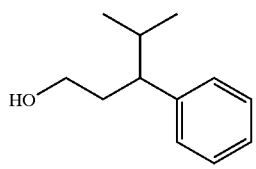

Under a nitrogen atmosphere, ethyl 4-methylpentanoate (350 mg) was dissolved in tetrahydrofuran (10 mL) at −78° C., a lithium aluminum hydride/tetrahydrofuran solution (1.0 M, 1.58 mL) was added, and the mixture was stirred. While the temperature of the mixture was naturally returned to room temperature, the mixture was stirred, and after 1.5 hours, water (0.05 mL), a 2N aqueous sodium hydroxide (0.05 mL) and water (0.15 mL) were successively added thereto, and the mixture was stirred. Further, diethyl ether was added thereto, and then the resulting insoluble matters were filtered off and the filtrate was evaporated. The resulting residue was purified by silica gel column chromatography (hexane:ethyl acetate system), to give the title compound as a colorless oil (257 mg, 42%: 2 steps).
¹H-NMR (400 MHz, CDCl₃) δ 0.73 (d, J=6.8 Hz, 3H), 0.97 (d, J=6.4 Hz, 3H), 1.78–1.88 (m, 2H), 2.04–2.14 (m, 1H), 2.36–2.46 (m, 1H), 3.34–3.54 (m, 2H), 7.20–7.16 (m, 2H), 7.17–7.22 (m, 1H), 7.25–7.31 (m, 2H).

Reference Example 24 4-methyl-3-phenylpentanoic Acid

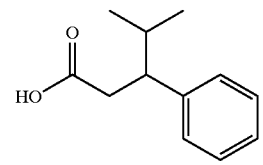

Under a nitrogen atmosphere, sodium hydride (60%, 1.2 g) was added at 0° C. to a tetrahydrofuran solution (30 mL) of tert-butyldiethylphosphonoacetate (4.9 g). After 10 minutes, the temperature of the mixture was naturally returned to room temperature, and the mixture was stirred. After 1 hour, a tetrahydrofuran solution (10 mL) of isobutyrophenone (4.0 g) was added. After stirring for 13 hours, the organic layer was separated by adding water and ethyl acetate thereto. The resulting organic layer was washed with water and brine, and dried over anhydrous magnesium sulfate. After filtering off the drying agent, the mixture was evaporated. 5.48 g among the resulting crude product (6.1 g) was dissolved in methanol (30 mL), a catalytic amount of 10% palladium carbon (250 mg) was added, and the mixture was reacted under pressuring by hydrogen (3.9 kg/cm²). After 1.3 hours, the catalyst was filtered off, and then the filtrate was concentrated. The resulting residue was purified by silica gel column chromatography (hexane:ethyl acetate system). The resulting product (3.0 g) was dissolved in acetone (50 mL) and 5N hydrochloric acid (20 mL), and the mixture was stirred for 3 hours under reflux conditions. The solution was evaporated, to give the title compound as a reddish yellow oil (1.96 g, 58%: 3 steps).
¹H-NMR (400 MHz, CDCl₃) δ 0.75 (d, J=6.8 Hz, 3H), 0.94 (d, J=6.8 Hz, 3H). 1.80–1.91 (m, 1H), 2.62 (dd, J=10.0 Hz, 15.6 Hz, 1H), 2.80 (dd, J=5.6 Hz, 15.6 Hz, 1H), 2.82–2.91 (m, 1H), 7.11–7.16 (m, 2H), 7.13–7.22 (m, 1H), 7.23–7.29 (m, 2H).

Reference Example 25 N-methyl-N-methoxy-4-methyl-3-phenylpentaneamide

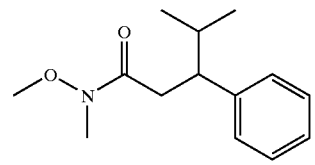

Under a nitrogen atmosphere, a dimethylformamide solution of diethyl cyanophosphonate (1.97 g) and triethylamine (1.63 mL) was added to a tetrahydrofuran solution (24 mL) of 4-methyl-3-phenyl-pentanoic acid (1.96 g), N, O—dimethylhydroxyamine hydrochloride (1.18 g) and triethylamine (1.63 mL) at 0° C. After 19 hours, the organic layer was separated by adding diethyl ether and an aqueous saturated ammonium chloride thereto. The resulting organic layer was washed with water and brine, and dried over anhydrous magnesium sulfate. After filtering off the drying agent, the mixture was evaporated. The resulting residue was purified by silica gel column chromatography (hexane:ethyl acetate system), to give the title compound (1.13 g, 47%).

¹H-NMR (400 MHz, CDCl₃) δ 0.76 (d, J=6.6 Hz, 3I), 0.97 (d, J=6.6 Hz, 3H), 1.84–1.96 (m, 1H), 2.74–2.86 (m, 2H), 2.97–3.05 (m, 1H), 3.06 (s, 3H), 3.57 (s, 3H), 7.15–7.21 (m, 3H), 7.24–7.29 (m, 2H).

Reference Example 26 4-methyl-3-phenylpentanal

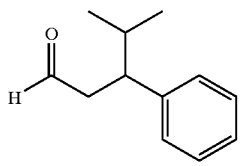

Under a nitrogen atmosphere, N-methyl-N-methoxy-4-methyl-3-phenyl-pentaneamide (215 mg) was dissolved in tetrahydrofuran (9.1 mL) at −78° C., and a diisobutylaluminum hydride/toluene solution (1.5 M, 1.2 mL) was added. After one hour, methanol (3 mL) was added to the reaction system, the temperature of the mixture was returned to room temperature after termination of foaming, and the mixture was continuously stirred. The organic layer was separated by adding diethyl ether, water and a 1N aqueous hydrochloric acid thereto. The resulting organic layer was washed with water and brine, and dried over anhydrous magnesium sulfate. After filtering off the drying agent, the mixture was evaporated, to give the title compound as a colorless oil (200 mg). The resulting compound was used for the next reaction without purification.
¹H-NMR (400 MHz, CDCl₃) δ 0.77 (d, J=6.6 Hz, 3H), 0.95 (d, J=6.8 HZ, 3H). 1.82–1.92 (m, 1H), 2.70–2.84 (m, 2H), 2.90–2.98 (m, 1H), 7.13–7.32 (m, 5H), 9.59–9.61 (m, 1H).

Reference Example 27 4-methyl-3-phenylhexanal

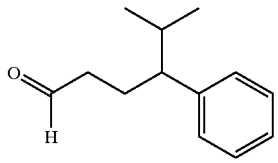

Under a nitrogen atmosphere, a n-butyllithium/tetrahydrofuran solution (1.53 M, 1.2 mL) was added to a tetrahydrofuran solution of (methoxymethyl) triphenylphosphonium chloride (627 mg) at −78° C., and then the temperature of the mixture was raised to 0° C. After 20 minutes, the outer temperature was lowered to −78° C., and then 4-methyl-3-phenyl-pentanal (200 mg) was added thereto together with tetrahydrofuran (4 mL). After 45 minutes, the temperature of the mixture was returned to room temperature, and the mixture was further stirred for 20 minutes. The organic layer was separated by adding diethyl ether and an aqueous saturated ammonium chloride thereto. The resulting organic layer was washed with water and brine, and dried over anhydrous magnesium sulfate. After filtering off the drying agent, the mixture was evaporated, to give the title compound as a colorless oil (200 mg). The resulting compound was dissolved in isopropanol (2 mL)/water (2 mL), p-toluenesulfonic acid (6 mg) was added thereto, and then the reaction was carried outfor 8.5 hours under refluxing. The organic layer was separated by adding diethyl ether and an aqueous saturated ammonium chloride thereto. The resulting organic layer was washed with water and brine, and dried over anhydrous magnesium sulfate.

After filteringoff thedryingagent, themixturewasevaporated. The residue was purified by NH silica gel column chromatography (hexane:ethyl acetate system), to give the title compound as a colorless oil (103 mg, 59%, 3 steps).
¹H-NMR (400 MHz, CDCl₃) δ 0.72 (d, J=6.8 Hz 3H), 0.99 (d, J=6.6 Hz, 3H), 1.76–1.90 (m, 2H), 2.12–2.28 (m, 4H), 7.07–7.10 (m, 2H), 7.18–7.22 (m, 1H), 7.26–7.35 (m, 2H), 9.63–9.65 (m, 1H).

Reference Example 28 1-[(2-vinyl-2-(4-fluoronhenoxy)ethyl]piperazine

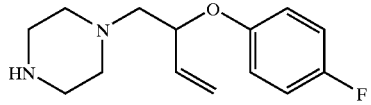

The title compound was synthesized in accordance with the method of Example 104 described in JP-A 11-206862.
¹H-NMR (400 MHz, CDCl₃) δ 2.50–2.60 (m, 4H), 2.59 (dd, J=4.0 Hz, 13.6 Hz, 1H), 2.77 (dd, J 7.5 Hz, 13.6 Hz, 1H), 2.86–2.90. (m, 4H), 4.70–4.76 (m, 1H), 5.22 (brd, J=10.6 Hz, 1H), 5.27 (brd, J=17.2 Hz, 1H), 5.87 (ddd, J=5.7 Hz, 10.6 Hz, 17.2 Hz, 1H), 6.82–6.89 (m, 2H), 6.89–6.97 (m, 2H).

Reference Example 29 4-bromo-2-thionhenecarboaldehyde Dimethylacetal

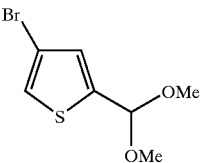

(90%) 4-Bromo-2-thiophenecarboaldehyde (10.0 g) was dissolved in methanol (50 ml), and an ion-exchange resin, Amberlite IR120B (5 g) was added thereto. After heating under reflux for 10 hours, the mixture was cooled as it was to room temperature, and the ion-exchange resin was filtered off. The filtrate was evaporated, and the resulting residue was purified by (NH) silica gel column chromatography (hexane), to give the title compound as a pale yellow oil (8.93 g, 72%).
¹H-NMR (400 MHz, CDCl₃) δ 3.36 (s, 6H), 5.59 (d, J=0.8 Hz, 1H), 7.00 (dd, J=0.8 Hz, J=1.6 Hz, 1H), 7.20 (d, J=1.6 Hz, 1H).

Reference Example 30 3-cyano-5-thiophenecarboaldehyde

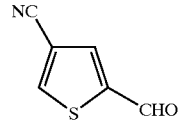

Method 1)
4-Bromo-2-thiophenecarboaldehyde dimethylacetal (6.82 g) was dissolved in DMF (50 ml), and copper cyanide (4.29 g) was added thereto. After heating under reflux for 3 hours, the mixture was cooled as it was to room temperature and ethyl acetate was added thereto. The mixture was washed with an aqueous ammonia, water, 0.1N aqueous hydrochloric acid and brine, dried over anhydrous magnesium sulfate and then evaporated, to give an oil. The residue was dissolved in an 80% aqueous acetic acid (100 ml), and the mixture was stirred at 0° C. for one hour. The mixture was washed with brine. After cooling as it was to room temperature, ethyl acetate was added thereto. The mixture was washed with an aqueous saturated sodium bicarbonate and brine, dried over anhydrous magnesium sulfate and then evaporated. The resulting residue was purified by silica gel column chromatography (hexane/ethyl acetate system), and then recrystallized from ethyl acetate-hexane, to give the title compound as pale yellowish white crystals (2.44 g, 62%).

Method 2)

4-Bromo-2-thiophenecarboaldehyde (5.00 g) was dissolved in DMF (40 ml), and copper cyanide (3.52 g) was added thereto. After heating under reflux for 3 hours, the mixture was cooled as it was to room temperature and ethyl acetate was added thereto. The mixture was washed with an aqueous ammonia, water, 0.1N aqueous hydrochloric acid and further brine, dried over anhydrous magnesium sulfate and then evaporated. The resulting residue was purified by silica gel column chromatography (hexane/ethyl acetate system), and then recrystallized from ethyl acetate-hexane, to give the title compound as pale yellowish white crystals (2.30 g, 71%).

The physico-chemical data of the title compound was as indicated below.

$^1$H-NMR (400 MHz, CDCl$_3$) δ 7.94 (d, J=1.2 Hz, 1H), 8.27 (d, J=1.2 Hz, 1H), 9.95 (d, J=1.2 Hz, 1H).

Reference Example 31 3-cyano-5-(1-hydroxy-2-methylpropyl)Thiophene

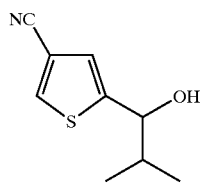

3-Cyano-5-thiophenecarboaldehyde (2.00 g) was dissolved in anhydrous ether (100 ml) and anhydrous tetrahydrofuran (THF) (20 ml), and an ether solution (10.9 ml) of (2.0 M) isopropylmagnesium chloride was added thereto. After stirring at 0° C. for 2 hours, ethyl acetate was added thereto. The mixture was washed with an aqueous saturated ammonium chloride and further brine, dried over anhydrous magnesium sulfate and then evaporated. The resulting residue was purified by silica gel column chromatography (hexane/ethyl acetate system), to give the title compound as a pale yellow oil (1.25 g, 47%).

$^1$H-NMR (400 MHz, CDCl$_3$) δ 0.91 (d, J=6.8 Hz, 3H), 1.00 (d, J=6.8 Hz, 3H), 1.99 (sext, J=6.8 Hz, 1H), 2.42 (d, J=4 Hz, 1H), 4.68 (dd, J=4 Hz, J=6 Hz, 1H), 7.08–7.10 (m, 1H), 7.85 (d, J=1.6 Hz, 1H).

Reference Example 32 3-cyano-5-(1-oxo-2-methylpropyl)Thiophene

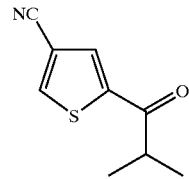

Oxalyl chloride (0.70 ml) was dissolved in methylene chloride (10 ml), and then the mixture was cooled to −60 to −50° C. Dimethyl sulfoxide (0.57 ml) was added thereto, and the mixture was stirred for 2 minutes. Further, a methylene chloride solution (6 ml) of 3-cyano-5-(1-hydroxy-2-methylpropyl)thiophene (1.21 g) was added thereto at −60 to −50° C., and the mixture was stirred for 15 minutes. Then, triethylamine (4.65 ml) was added, and the temperature of the mixture was raised to a room temperature. Ethyl acetate was added, and the mixture was washed with water and further brine, dried over anhydrous magnesium sulfate and then evaporated. The resulting residue was recrystallized from ethanol, to give the title compound as pale yellowish white crystals (0.59 g) Further, the filtrate was purified by silica gel column chromatography (hexane/ethyl acetate system), to give the title compound (0.41 g, total yield: 1.00 g, 84%).

$^1$H-NMR (400 MHz, CDCl$_3$) δ 1.27 (d, J=6.8 Hz, 6H), 3.36 (qui, J=6.8 Hz, 1H), 7.86 (d, J=1.2 Hz, 1H), 8.18 (d, J=0.8 Hz, 1H).

Reference Example 33 [1-cyano-1-(3-cyano-5-thienyl)-2-methylpropyl]Diethylphosphate

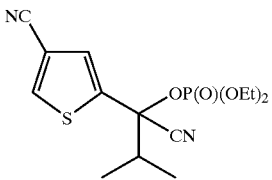

3-Cyano-5-(1-oxo-2-methylpropyl)thiophene (0.90 g) was dissolved in THF (50 ml), and a DMF solution (30.1 ml) of (0.5 M) lithium cyanide and (90%) diethylcyanophosphonate (2.29 ml) were added thereto. After stirring at room temperature for 30 minutes, ethyl acetate and hexane were added thereto. The mixture was washed with water and further brine, dried over anhydrous magnesium sulfate and then evaporated. The resulting residue was purified by silica gel column chromatography (hexane/ethyl acetate system), to give the title compound as a pale yellow oil (1.72 g, quantitatively).

$^1$H-NMR (400 MHz, CDCl$_3$) δ 0.96 (d, J=6.8 Hz, 3H), 1.27–1.34 (m, 9H), 2.49 (qui, J=6.8 Hz, 1H), 4.00–4.21 (m, 4H), 7.56 (d, J=1.2 Hz, 1H), 8.04 (d, J=1.6 Hz, 1H).

Reference Example 34 3-cyano-5-(1-cyano-2-methylpropyl) Thiophene

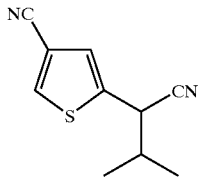

(1-Cyano-1-(3-cyano-5-thienyl)-2-methylpropyl] diethylphosphate (45 mg) was dissolved in ethyl acetate (5 ml), (10%) palladium-carbon (20 mg) was added, and hydrogenation was carried out at room temperature and a normal pressure for 2 hours. The catalyst was filtered off, and the filtrate was evaporated. The resulting residue was purified by preparative thin layer silica gel column chromatography (hexane/ethyl acetate system), to give the title compound as a pale yellow oil (22 mg, 88%).
$^1$H-NMR (400 MHz, CDCl$_3$) δ 1.09 (d, J=6.8 Hz, 3H), 1.14 (d, J=6.8 Hz, 3H), 2.20 (sext, J=6.8 Hz, 1H), 3.96 (d, J=6.8 Hz, 1H), 7.26 (s, 1H), 7.91 (d, J=1.6 Hz, 1H).

Reference Example 35 Ethyl 4-cyano-4-(3-cyano-5-thienyl)-5-methylhexanate

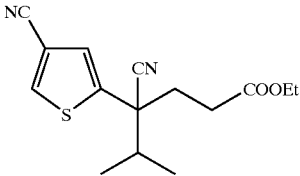

Potassium tert-butoxide (35 mg) was suspended in DMF (5 ml), and a DMF solution (5 ml) of 3-cyano-5-(1-cyano-2-methylpropyl]thiophene (0.60 g) was added thereto. After stirring at room temperature for 3.5 hours, ethyl acetate was added. The mixture was washed with an aqueous saturated ammonium chloride and further brine, dried over anhydrous magnesium sulfate and then evaporated. The resulting residue was purified by silica gel column chromatography (hexane/ethyl acetate system) to give the title compound as a pale yellow oil (0.55 g, 60%).
$^1$H-NMR (400 MHz, CDCl$_3$) δ 0.94 (d, J=6.8 Hz, 3H), 1.23 (d, J=6.8 Hz, 3H), 1.24 (t, J=6.8 Hz, 3H), 2.04–2.15 (m, 3H), 2.45–2.60 (t, 2H), 4.04–4.17 (m, 2H), 7.30 (d, J=1.2 Hz, 1H), 7.93 (d, J=1.6 Hz, 1H).

Reference Example 36 4-cyano-4-(3-cyano-5-thienyl)-5-methylhexanol

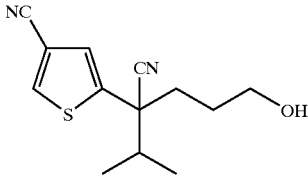

Ethyl 4-cyano-4-(3-cyano-5-thienyl)-5-methylhexanate (0.55 g) was dissolved in THF (10 ml), lithium borohydride (46 mg) was added, and the mixture was heated under reflux for 1.5 hours. After cooling as it was to room temperature, 1N aqueous hydrochloric acid and water were added at 0° C., and the mixture was extracted with ethyl acetate. The mixture was further washed with brine, dried over anhydrous magnesium sulfate and then evaporated. The resulting residue was purified by silica gel column chromatography (hexane/ethyl acetate system), to give the title compound pale as a yellow oil (1.25 g, 47%). Further, the catalyst was filtered off, and the filtrate was evaporated. The resulting residue was purified by preparative thin layer silica gel column chromatography (hexane/ethyl acetate system), to give the title compound as a pale yellow oil (0.39 g, 83%).
$^1$H-NMR (400 MHz, CDCl$_3$) δ 0.93 (d, J=6.8 Hz, 3H), 1:21 (d, J=6.8 Hz, 3H). 1.19–1.41 (m, 1H), 1.45–1.70 (m, 1H), 1.65–1.77 (m, 1H), 1.88 (dt, J=4 Hz, J=13.2 Hz, 1H), 2.09 (qui, J=6.8 Hz, 1H), 2.30 (dt, J=4 Hz, J=12.4 Hz, 1H), 3.66 (t, J=6.4 Hz, 2H), 7.30 (d, J=1.2 Hz, 1H), 7.92 (s, 1H).

Reference Example 37 N-(2-Cyanoethyl)-N-(0.2-iodoethyl)aniline

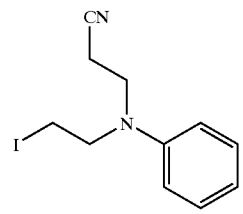

2.00 g (10.5 mmol) of N-(2-cyanoethyl)-N-(2-hydroxyethyl) aniline was dissolved in 60.0 ml of acetonitrile, and 2.20 ml (15.8 mmol) of triethylamine and 0.90 ml (11.6 mmol) of mesyl chloride were successively added thereto. After completion of the reaction, brine was added thereto, and the objective product was extracted with ether. The organic layer was washed with brine, and then dried over anhydrous magnesium sulfate. The solvent was evaporated, to give a crude product. The crude product was dissolved in acetone, and 12.0 g (80.1 mmol) of sodium iodide was added. After completion of the reaction, brine was added thereto, and the objective product was extracted with ethyl acetate. The organic layer was washed with brine, and then dried over anhydrous magnesium sulfate. The solvent was evaporated, to give a crude product. The crude product was subjected to silica gel (eluted with ethyl acetate:hexane=1:3), to give 2.78 g (9.26 mmol, 88.2%) of the title compound as a yellow syrup.
$^1$H-NMR (400 MHz, CDCl$_3$) δ 2.62 (t, J=7.0 Hz, 2H), 3.26 (t, J=8.0 Hz, 2H), 3.71–3.81 (m, 4H), 6.66–6.72 (m, 2H), 6.81–6.86 (m, 1H), 7.25–7.32 (m, 2H)

Reference Example 38 1-[2-[N-(2 Cyanoethyl) anilino]ethyl]piperazine

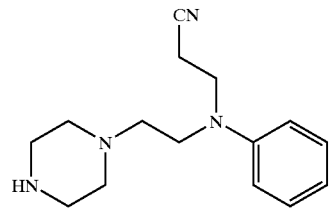

2.78 g (9.26 mmol) of the above-mentioned iodide was dissolved in 50.0 ml of acetonitrile, and 2.5 g (13.4 mmol) of 1-tert-butoxycarbonylpiperazine and 1.29 ml (13.4 mmol)

of triethylamine were successively added, and the mixture was heated to 60° C. After completion of the reaction, brine was added thereto, and the objective product was extracted with ethyl acetate. The organic layer was washed with brine, and then dried over anhydrous magnesium sulfate. The solvent was evaporated, to give a crude product. The crude product was dissolved in 40 ml of methanol, and 30 ml of a 4N hydrogen chloride-ethyl acetate solution was added. After completion of the reaction, water and 10 ml of 5N HCl were added, and the mixture was washed with ethyl acetate. Then the aqueous layer was adjusted to pH 11 with a 5N aqueous sodium hydroxide, and then the objective product was extracted with ethyl acetate. The organic layer was dried over anhydrous magnesium sulfate and the solvent was evaporated, to give 1.81 g. (7.01 mmol, 75.7%) of the title compound as a yellow syrup, as a crude product.
$^1$H-NMR (400 MHz, CDCl$_3$) δ 2.00–2.10 (brd-s, 1H), 2.45–2.58 (m, 4H), 2.54 (t, J=6.8 Hz, 2H), 2.69 (t, J=7.2 Hz, 2H), 2.92 (t, J=5.0 Hz, 4H), 3.51 (t, J=6.8 Hz, 2H), 3.71 (t, J=7.2 Hz, 2H), 6.65–6.72 (m, 2H), 6.73–6.79 (m, 1H), 7.22–7.29 (m, 2H)

Reference Example 39 3-(1,3-dioxolan-2-yl) Thiophene

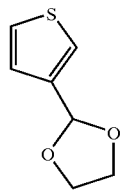

20.3 g (181 mmol) of 3-thiophenealdehyde, 50 ml of ethylene glycol and 2.00 g (7.96 mmol) of PPTS were dissolved in 230 ml of toluene, and dehydration was carried out using Dean-stark. After completion of the reaction, the mixture was extracted with ethyl acetate. The extract was washed with brine, and then dried over anhydrous magnesium sulfate. The solvent was evaporated, to give a crude product. The crude product was subjected to silica gel (ethyl acetate:hexane=1:10), to give 12.1 g (77.3 mmol, 86.7%) of the title compound as a yellow oil.
$^1$H-NMR (4001 MHz, CDCl$_3$) δ 3.97–4.15 (m, 4H), 5.91 (s, 2H), 7.16 (ddd, J=0.4 Hz, 1.2 Hz, 5.2 Hz, 1H), 7.32 (dd, I=2.8 Hz, 5.2 Hz, 1H), 7.42 (ddd, J=0.4 Hz, 1.2 Hz, 2.8 Hz, 1H)

Reference Example 40 3-(1.3-dioxolan-2-yl)-2-thiophenecarboaldehyde

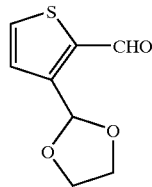

5.00 g (32.0 mmol) of 3-(1,3-dioxolan-2-yl)thiophene was dissolved in 100 ml of THF. 24.5 ml (1.5 mol/l) of n-butyllithium was added dropwise thereinto. After stirring for 0.5 hour, the mixture was cooled to −70° C., 3.10 ml (40.0 mmol) of DMF was added, and then the mixture was transferred to an ice bath. After stirring for about 2 hours, an aqueous saturated ammonium chloride was added, and the mixture was extracted with ethyl acetate. The extract was washed with brine, and then dried over anhydrous magnesium sulfate. The solvent was evaporated, to give a crude product. The crude product was subjected to silica gel (ethyl acetate:hexane=1:2), to give 3.68 g (20.0 mmol, 62.4%) of the title compound as a yellow oil.
$^1$H-NMR (400 MHz, CDCl$_3$) δ 3.97–4.15 (m, 4H), 5.91 (s, 2H), 7.16 (ddd, J=0.4 Hz, 1.2 Hz, 5.2 Hz, 1H), 7.32 (dd, J=2.8 Hz, 5.2 Hz, 1H), 7.42 (ddd, J=0.4 Hz, 1.2 Hz, 2.8 Hz, 1H)

Reference Example 41 3-(1,3-dioxolan-2-yl)-2-thiopheneacetonitrile

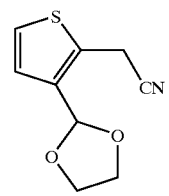

20 ml of a THF solution of 4.49 g (40.0 mmol) of potassium tert-butoxide was cooled to −45 to −30° C., and 20 ml of a THF solution of 3.90 g (20.0 mmol) of TOSmic and 20 ml of a THF solution of 3.68 g (20.0 mmol) of 3-(1,3-dioxolan-2-yl)-2-thiophenecarboaldehyde were successively added thereto. After 40 minutes, 60 ml of methanol was added at −15° C. After heating under reflux for 15 minutes, an aqueous saturated ammonium chloride was added, and the mixture was extracted with ethyl acetate. The extract was washed with brine, and then dried over anhydrous magnesium sulfate. The solvent was evaporated, to give a crude product. The crude product was subjected to Cromatorex NH silica gel (ethyl acetate:hexane=1:4), to give 1.43 g (7.32 mmol, 36.6%) of the title compound as a yellow oil.
$^1$H-NMR (400 MHz, CDCl$_3$) δ 4.00–4.15 (m, 4H), 4.04 (s, 2H), 5.91 (s, 1H), 7.06 (d, J=5.6 Hz, 2H), 7.21 (d, J=5.6 Hz, 2H)

Reference Example 42 2-[3-(1,3-dioxolan-2-yl)-2Thienyl)-4-methylbutyronitrile

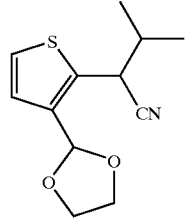

1.43 g (7.32 mmol) of 3-(1,3-dioxolan-2-yl)-2-thiopheneacetonitrile was dissolved in 2 ml of dimethyl sulfoxide, and 1.08 g (8.78 mmol) of 2-bromopropane, 100 mg (cat) of tetra-n-butylammonium iodide and 3 ml of 50% potassium hydroxide were successively added. After 25 minutes, 300 mg of 2-bromopropane, further after 50 minutes, 1 ml of 50% potassium hydroxide and 2 ml of DMSO were added. After completion of the reaction, brine was added, and the mixture was extracted with ethyl acetate. The organic layer was washed with brine, dried over anhydrous magnesium sulfate and evaporated, to obtain a crude product. The crude product was subjected to 100 g of silica gel (ethyl acetate:hexane=1:8), to give 853 mg (3.59 mmol, 49.1%) of the title compound as a yellow oil.
¹H-NMR (400 MHz, CDCl₃) δ 1.03 (d, J=6.8 Hz, 3H), 1.19 (d, J=6.4 Hz, 3H), 2.17–2.27 (m, 1H), 3.97–4.13 (m, 4H), 4.31 (d, J=8.0 Hz, 1H), 7.06 (d, J=5.2 Hz, 2H), 7.24 (d, J=5.2 Hz, 2H)

Reference Example 43 2-(3-formyl-2-thienyl)-4-methylbutyronitrile

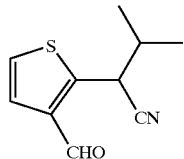

2.16 g (9.10 mmol) of 2-[3-(1,3-dioxolan-2-yl)-2-thienyl]-4-methylbutyronitrile was dissolved in 40 ml of acetone, 115 ml of 5N HCl was added, and the mixture was heated at 70° C. for 3 minutes. After completion of the reaction, brine was added, and the mixture was extracted with ethyl acetate. The organic layer was washed with brine, dried over magnesium sulfate and evaporated, to give a crude product. The crude product was subjected to 75 g of silica gel (ethyl acetate:hexane=1:2), to give 1.66 g (8.58 mmol, 94.3%) of the title compound as a brown oil.
¹H-NMR (400 MHz, CDCl₃) δ 1.12 (d, J=6.8 Hz, 3H), 1.14 (d, J=6.8 Hz, 3H), 2.18–2.29 (m, 1H), 4.97 (d, J=6.4 Hz, 1H) 7.34 (d, J=5.2 Hz, 2H), 7.44 (d, J=5.2 Hz, 2H), 10.01 (s, 1H)

Reference Example 44 2-(3-cyano-2-thienyl]-4-methylbutyranitrile

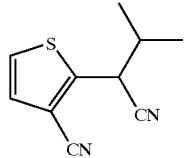

1.66 g (8.58 mmol) of 2-(3-formyl-2-thienyl)-4-methylbutyronitrile was dissolved in 40 ml of ethanol, 10 ml of an aqueous solution containing 894 mg (12.9 mmol) of hydroxylamine hydrochloride and 1.41 g (17.2 mmol) of sodium acetate was added thereto, and then the mixture was heated at 80° C. After completion of the reaction, brine was added, and the objective product was extracted with ethyl acetate. The organic layer was washed with brine, and then dried over anhydrous magnesium sulfate. The solvent was evaporated, to give a crude oxime. The oxime was dissolved in 50 ml of dimethylformamide, and 5.56 g (34.3 mmol) of carbodiimidazole was added. Then, the mixture was heated at 60° C., and further after 50 minutes, 2.40 ml (17.2 ml) of triethylamine was added thereto. After completion of the reaction, brine was added under cooling, and the objective product was extracted with ethyl acetate. The organic layer was washed with brine, and then dried over anhydrous magnesium sulfate. The solvent was evaporated, to give a crude product. The crude product was subjected to silica gel (eluted with ethyl acetate:hexane=1:9), to give 1.07 mg (5.47 mmol, 63.7%) of the title compound as an orange oil.
¹H-NMR (400 MHz, CDCl₃) δ 1.10 (d, J=6.8 Hz, 3H), 1.19 (d, J=6.8 Hz, 3H), 2.27–2.38((m, 1H), 4.20 (d, J=7.2 Hz, 1H), 7.22 (d, J=5.6 Hz, 2H), 7.40 (d, J=5.6 Hz, 2H)

Reference Example 45 Ethyl 4-cyano-5-methyl-4-(3-cyano-2-thienyl)hexanolate

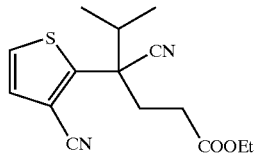

1.07 g (5.47 mmol) of 2-(3cyano-2-thienyl)-4-methylbutyronitrile and 0.71 ml (6.56 mmol) of ethyl acrylate were dissolved in 30 ml of tetrahydrofuran. 123 mg (1.09 mmol, cat.) of potassium tert-butoxide was added little by little to the solution at room temperature. After completion of the reaction, brine, an aqueous saturated ammonium chloride and 2N HCl were successively added, and the objective product was extracted with ethyl acetate. The organic layer was successively washed with brine and brine, and then dried over anhydrous magnesium sulfate. The solvent was evaporated, to give a crude product. The crude product was subjected to silica gel (eluted with ethyl acetate:hexane=1:9), to give 904 mg (3.11 mmol, 56.9%) of the title compound as a yellow oil.

¹H-NMR (400 MHz, CDCl₃) δ 0.94 (d, J=6.8 Hz, 3H), 1.24 (t, J=7.2 Hz, 3H), 1.29 (d, J=6.4 Hz, 3H), 2.04–2.26 (m, 1H), 2.46–2.74 (m, 4H), 4.07–4.16 (m, 2H), 7.29 (d, J=5.3 Hz, 2H), 7.31 (d, J=5.3 Hz, 2H)

Reference Example 46 4-cyano-5-methyl-4-(3-cyano-2-thienyl)hexanol

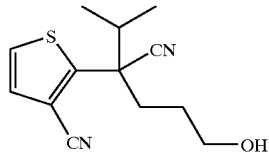

500 mg (1.72 mmol) of ethyl 4-cyano-5-methyl-4-(3-cyano-2-thienyl)hexanolate was dissolved in 10 ml of THF, 37.5 mg (1.72 mmol) of lithium borohydride was added, and the mixture was heated under reflux. After one hour 20 minutes, heating was stopped, and 2N HCl was added under ice-cooling. The mixture was extracted with ethyl acetate, and the extract was successively washed with brine and water, and then dried over anhydrous magnesium sulfate. The solvent was evaporated, to obtain a crude product. The crude product was subjected to silica gel (eluted with ethyl acetate:hexane=35:65), to give 244 mg (0.98 mmol, 57.1%) of the title compound as a colorless oil.

¹H-NMR (400 MHz, CDCl₃) δ 0.94 (d, J=6.4 Hz, 3H), 1.26 (d, J=6.8 Hz, 3H). 1.24–1.39 (m, 1H), 1.68–1.82 (m, 1H), 2.28–2.48 (m, 2H), 2.59–2.70 (m, 1H), 3.64–3.72 (m, 2H), 7.28–7.29. (m, 2H)

Reference Example 47 4-cyano-5-methyl-4-(3-cyano-2-thienyl) Hexyl Iodide

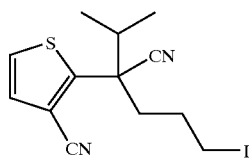

244 mg (0.98 mmol) of 4-cyano-5-methyl-4-(3-cyano-2-thienyl)hexanol was dissolved in 10 ml of acetonitrile and 0.16 ml (1.18 mmol) of triethylamine, and 83.6 µl (108 mmol) of mesyl chloride was added thereto. After about 5 minutes, 1.47 g (9.80 mmol) of sodium iodide was added. After completion of the reaction, brine and ethyl acetate were added, and the ethyl acetate layer was washed with an aqueous sodium thiosulfate aqueous solution and brine, dried over anhydrous magnesium sulfate and evaporated, to give a crude product. The crude product was subjected to silica gel (eluted at ethyl acetate:hexane=1:10), to give 334 mg (0.93 mmol, 95.1%) of the title compound as a yellow oil.

$^1$H-NMR (400 MHz, CDCl$_3$) δ 0.93 (d, 1=6.8 Hz, 3H), 1.27 (d, J=6.8 Hz, 3H), 1.49–1.62 (m, 1H), 1.98–2.10 (m, 1H), 2.27–2.36 (m, 1H), 2.42–2.52 (m, 1H), 2.60–2.71 (m, 1H), 3.12–3.22(m, 2H), 7.29–7.31 (m, 2H)

Reference Example 48 4-cyano-5-methyl-4-(5-cyano-2-thienyl)hexyl Iodide

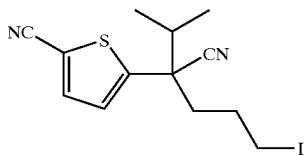

1.05 g (4.23 mmol) of 4-cyano-5-methyl-4-(5-cyano-2-thienyl)hexanol was dissolved in 40 ml of acetonitrile and 0.80 ml (5.71 mmol) of triethylamine. 0.39 ml (5.07 mmol) of mesyl chloride was added thereto. After about 0.10 minutes, 6.34 g (42.3 mmol) of sodium iodide was added. After completion of the reaction, brine and ethyl acetate were added. The ethyl acetate layer was washed with an aqueous sodium thiosulfate and brine, dried over magnesium sulfate and evaporated, to give a crude product. The crude product was subjected to silica gel (eluted with ethyl acetate:hexane=1:2), to give 1.39 g (3.88 mmol, 91.7%) of the title compound as a yellow oil.

$^1$H-NMR (400 MHz, CDCl$_3$) δ 0.93 (d, J=6.8 Hz, 3H), 1.27 (d, J=6.8 Hz, 3H), 1.49–1.62 (m, 1H), 1.98–2.10 (m, 1H), 2.27–2.36 (m, 1H), 2.42–2.52 (m, 1H), 2.60–2.71 (m, 1H), 3.12–3.22 (m, 2H), 7.29–7.31 (m, 2H)

Reference Example 49 Methyl 3-(5-bromo-2-thienyl)propanonate

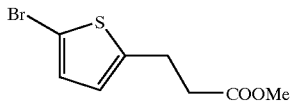

3.50 g (20.6 mmol) of methyl 3-(2-thienyl)propanonate which was synthesized according to the method described in J. Med. Chem., 1992, 35 (21), 3870, was dissolved in 20 ml of DMF, 3.85 g (21.6 mmol) of NBS dissolved in 10 ml of DMF was added thereto, and the mixture was heated at 80° C. After 2 hours, brine was added, and the mixture was extracted with ether. The organic layer was washed with brine, dried over magnesium sulfate and evaporated, to give a crude product. The crude product was subjected to silica gel (ethyl acetate:hexane=9), to give 4.62 g (18.6 mmol, 90.1%) of the title compound as a pale yellow oil.

$^1$H-NMR (400 MHz, CDCl$_3$) δ 2.65 (t, J=7.4 Hz, 2H), 3.08 (t, J=7.4 Hz, 2H), 3.69 (s, 3H), 6.58 (d, J=3.6 Hz, 1H), 6.85 (d, J=3.6 Hz, 1H)

Reference Example 50 Methyl 3-(5-cyano-2-thienyl)propanonate

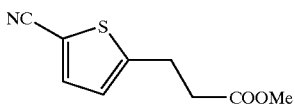

4.62 g (18.6 mmol) of methyl 3-(5-bromo-2-thienyl)propanonate, 1.75 g (14.9 mmol) of Zn(CN)$_2$ and 516 mg (0.93 mmol) of DPPF were suspended in a solution of 100 ml of DMF and 1 ml of water, then 341 mg (0.37 mmol) of Pd$_2$dba$_3$ was added, and the mixture was heated at 120° C. After 2 hours, the mixture was cooled as it was and extracted with ether. The organic layer was washed with brine and and 2N HCl, dried over magnesium sulfate and evaporated, to give a crude product. The crude product was subjected to silica gel (ethyl acetate:hexane=1:9), to give 2.96 g (18.6 mmol, 100%) of the title compound as a green oil.

$^1$H-NMR (400 MHz, CDCl$_3$) δ 2.71 (t, J=7.4 Hz, 2H), 3.19 (t, J=7.4 Hz, 2H). 3.71 (s. 3H), 6.85 (d, J=3.6 Hz, 1H), 7.46 (d, J=3.6 Hz, 1H)

Reference Example 51 3-(2-thienyl)propanol

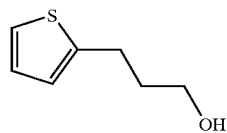

1.32 g (7.75 mmol) of methyl 3-(2-thienyl)propanonate was dissolved in 50 ml of THF. After cooling to −20° C., 6.00 ml of LiAlH$_4$ (1.0 M solution) was added. After completion of the reaction, the mixture was quenched using water and 5N NaOH, and filtered through Celite. The filtrate was concentrated, and the resulting crude product was subjected to silica gel (ethyl acetate:hexane=1:1), to give 1.05 g (7.38 mmol, 95.2%) of the title compound as a colorless oil.

$^1$H-NMR (400 MHz, CDCl$_3$) δ 1.29 (t, J=6.0 Hz, 1H) 1.90–2.00 (m, 2H), 2.95 (t, J=7.6 Hz, 2H), 3.72 (t, J=6.0 Hz, 2H), 6.80–6.83 (m, 1H)1) 6.91–6.94 (m, 1H), 7.11–7.14 (m, 1H)

Reference Example 52 3-(5-cyano-2-thienyl)propanol

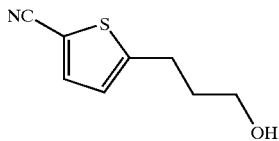

2.96 g (18.6 mmol) of methyl 3-(5-cyano-2-thienyl) propanoate was dissolved in 100 ml of THF, 450 mg (18.6 mmol) of lithium borohydride was added, and the mixture was heated under reflux. After one hour, heating was stopped and 2N HCl was added under ice-cooling. The mixture was extracted with ethyl acetate, and the extract was successively washed with brine and water, and then dried over anhydrous magnesium sulfate. The solvent was evaporated, to give a crude product. The crude product was subjected to silica gel (eluted at ethyl acetate:hexane=25:75 to 50:50), to give 1:37 g (8.19 mmol, 44.0%) of the title compound as a green oil.

$^1$H-NMR (400 MHz, CDCl$_3$) δ 1.32–1.37 (m, 1H), 1.90–2.00 (m, 2H), 2.99 (t, J=7.6 Hz, 2H), 3.68–3.76 (m, 2H), 6.84 (d, J=3.6 Hz, 1H), 7.47 (d, J=3.6 Hz, 1H)

Reference Example 53 tert-butyl 4-[3-(2-thienyl)]propyl]-1-piperazinecarboxylate

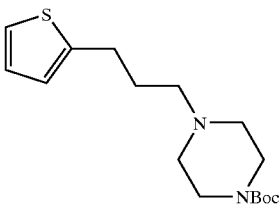

1.05 g (7.38 mmol) of 3-(2-thienyl)propanol was dissolved in 60 ml of acetonitrile, and 2.58 ml (18.5 mmol) of triethylamine and 0.63 ml (8.12 mmol) of mesyl chloride were added to the solution. After 25 minutes, 2.07 g (11.1 mmol) of tert-butyl 1-piperadinecarboxylate, 3.32 g (22.7 mmol) of sodium iodide and 6 ml of water were added, and the mixture was heated to 60° C. After completion of the reaction, brine was added, and the objective product was extracted with ethyl acetate. The organic layer was washed with brine, and then dried on anhydrous magnesium sulfate. The solvent was evaporated, to give a crude product. The crude product was subjected to Cromatorex NH silica gel (eluted at ethyl acetate:hexane=2:8), to give 1.94 g (6.25 mmol, 84.7%) of the title compound as a pale yellow oil.

$^1$H-NMR (400 MHz, CDCl$_3$) δ 1.46 (s, 9H), 1.83–1.91 (m, 2H), 2.35–2.42 (m, 2H), 2.87 (t, J=7.6 Hz, 2H), 3.40–3.46 (m, 4H), 6.77–6.80 (m, 1H), 6.91 (dd, J 3.2 Hz, 5.2 Hz, 1H), 7.11 (dd, J=1.2 Hz, 5.2 Hz, 1H)

Reference Example 54 tert-butyl 4-[3-(5-cyano-2-thienyl]propyl]-1-piperazinecarboxylate

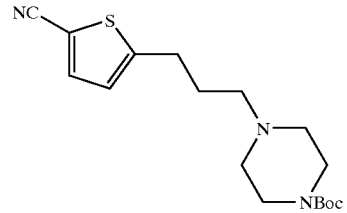

The title compound was synthesized in accordance with the method for producing tert-butyl 4-[3-(2-thienyl)propyl]-1-piperazinecarboxylate in Reference Example 53 (yield: 74.2%).

$^1$H-NMR (400 MHz, CDCl$_3$) δ 1.46 (s, 9H), 1.83–1.91 (t, 2H), 2.34–2.41 (m, 6H), 2.91 (t, J=7.6 Hz, 2H), 3.41–3.46 (m, 4H), 6.81 (d, 1=4.0 Hz, 1H), 7.46 (d, J=4.0 Hz, 1H)

Reference Example 55 1-[3-(2-thienyl)propyl]piperazine

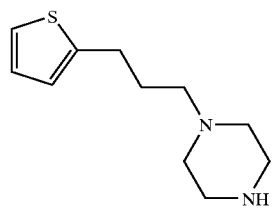

1.94 g (6.25 mmol) of tert-butyl 4-[3-(2-thienyl) propyl]-1-piperazinecarboxylate was dissolved in 20 ml of methanol, and 15 ml of a 4N hydrogen chloride-ethyl acetate solution was added. After completion of the reaction, the mixture was evaporated. The residue was adjusted to pH 11 with a 2N aqueous sodium hydroxide, then the objective product was extracted with chloroform and dried over anhydrous magnesium sulfate. The solvent was evaporated, to give 1.23 g (5.85 mmol, 93.6%) of the title compound as ayellow oil, as acrude product.

$^1$H-NMR (400 MHz, CDCl$_3$) δ 1.84–1.92 (m, 2H), 2.35–2.48 (m, 6H), 2.83–2.93 (m, 6H), 6.77–6.80 (m, 1H), 6.91 (dd, J 3.2 Hz, 5.2 Hz, 1H), 7.11 (dd, J=1.2 Hz, 5.2 Hz, 1H)

Reference Example 56 1-13-(5-cyano-2-thienyl)propyl]piperazine

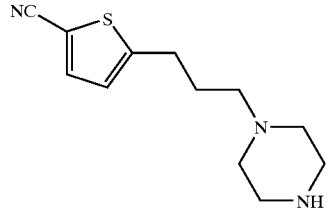

The title compound was synthesized in accordance with the method for producing 1-[3-(2-thienyl)propyl]piperazine in Reference Example 55 (yield: 96.0%).

$^1$H-NMR (400 MHz, CDCl$_3$) δ 1.83–1.91 (m, 2H), 2.33–2.44 (m, 6H), 2.87–2.94 (m, 6H), 6.81 (d, J=4.0 Hz, 1H), 7.46 (d, J=4.0 Hz, 1H)

Reference Example 57 2-(Chloromethyl)benzoxazole

The title compound was produced in accordance with the method described in STNTHETIC COMMUNICATION 19(16) 2921–2924 (1989) (yield: quantitative).

$^1$H-NMR (400 MHz, CDCl$_3$) δ 4.77 (s, 2H), 7.34–7.43 (m, 2H), 7.54–7.58 (m, 1H), 7.73–7.77 (m, 1H)

Reference Example 58 benzyl 4-[[(2-benzoxazoyl)methyl]-1-piperazinecarboxylate

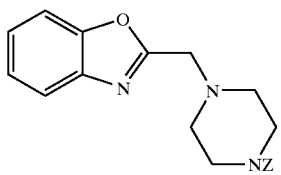

2.00 g (11.9 mmol) of 2-(chloromethyl)benzoxazole was dissolved in 50 ml of acetonitrile, 1.66 ml (11.9 mmol) of triethylamine and 3.15 g (14.3 mmol) of benzyl 1-piprezinecarboxylate were added thereto, and the mixture was stirred at 80° C. After 2 hours, the reaction solution was concentrated, brine was added thereto, and the objective product was extracted with ethyl acetate. The organic layer was washed with brine, and then dried on anhydrous magnesium sulfate. The solvent was evaporated, to give a crude product. The crude product was subjected to Cromatorex NH silica gel (ethyl acetate:hexane=25:75), to give 3.57 g (10.2 mmol, 85.7%) of the title compound as a yellow syrup.

$^1$H-NMR (400 MHz, CDCl$_3$) δ 2.56–2.68 (brd-s, 4H), 3.56–3.62 (m, 4H), 3.89 (s, 2H), 5.12 (s. 2H), 7.28–7.37 (m, 71H), 7.52–7.55 (m, 1H), 7.70–7.74 (m, 1H)

Reference Example 59 1-[(2-benzoxazoyl)methyl]piperazine

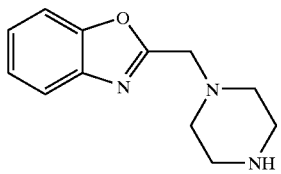

3.57 g (10.2 mmol) of benzyl 4-[(2-benzoxazoyl)methyl]-1-piperazinecarboxylate was dissolved in 50 ml of methanol, and 400 mg of 10% Pd-C was added. After replacing the atmosphere with hydrogen, the mixture was stirred. After completion of the reaction, the reaction solution was filtered and evaporated, to give 2.15 g (9.89 mmol, 97.0%) of the title compound as a yellow oil, as a crude product.

$^1$H-NMR (400 MHz, CDCl$_3$) δ 2.56–2.66 (m, 4H), 2.93–2.98 (m, 4H), 3.87 (s. 2H), 7.31–7.36 (m, 2H), 7.51–7.56 (m, 1H), 7.69–7.74 (m, 1H)

Reference Example 60 2-(Chloromethyl)-5-cyanobenzoxazole

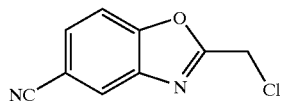

The title compound was synthesized in accordance with the method described in STNTHETIC COMMUNICATION 19(16) 2921–2924 (1989) (yield: 79.8%).

$^1$H-NMR (400 MHz, CDCl$_1$) δ 4.78 (s, 2H), 7.66–7.73 (m, 2H), 8.08–8.10 (m, 1H)

Reference Example 61 Benzyl 4-[[2-(5-cyanobenzoxazoyl)]methyl]-1-piperazinecarboxylate

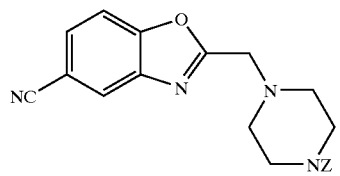

The title compound was synthesized in accordance with the method for the production of benzyl 4-[(2-benzoxazoyl)methyl]-1-piperazinecarboxylate in Reference Example 58 (yield: 85.6%).

$^1$H-NMR (40 MHz, CDCl$_3$) δ 2.57–2.70 (brd-s, 4H), 3.56–3.63 (m, 4H), 3.92 (s, 2H, 5.13 (s, 2H), 7.30–7.38 (m, 5H), 7.62–7.68 (m, 2H), 8.04–8.05 (m, 1H)

Reference Example 62 1-[{2-(5-cyanobenzoxazoyl)}methyl]piperazine

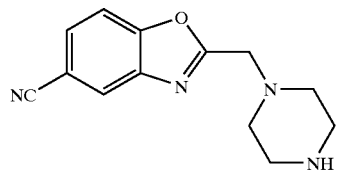

The title compound was synthesized in accordance with the method described in Reference Example 59 (yield: 58.0%).

$^1$H-NMR (400 MHz, CDCl$_3$) δ 2.59–2.66 (m, 4H), 2.93–3.00 (m, 4H), 3.90 (s, 2H), 7.62–7.67 (m, 2H), 8.03–8.05 (m, 1H)

Reference Example 63 Ethyl 4-cyano-5-methyl-4-(3-thienyl)hexanoate

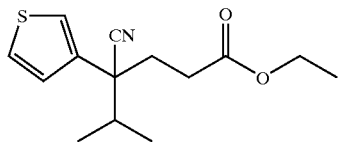

3-Methyl-2-(3-thienyl)butanenitrile (6.23 g) obtained using 3-thienylacetonitrile as a starting material in accordance with the method of Example 114 described in JP-A 11-206862 and ethyl acrylate (4.53 g) were dissolved in dimethylformamide (15 ml), and added at a room temperature to a solution of potassium tert-butoxide (423 mg) in dimethylformamide solution (60 ml). After stirring 5 hours as it was, the organic layer was separated by adding an aqueous saturated ammonium chloride and diethyl ether thereto. The resulting organic layer was washed with water and brine, and dried over anhydrous magnesium sulfate. The drying agent was filtered off, and then the filtrate was evaporated. The residue was purified by silica gel column chromatography (hexane/ethyl acetate system), to give the title compound as a yellow oil (6.66 g, 67%).
$^1$H-NMR (400 MHz, CDCl$_3$) δ 0.85 (d, J=6.8 Hz, 3H), 1.19 (d, J=6.8 Hz, 3H). 1.22 (t, J=7.2 Hz, 3H), 2.00–2.18 (m, 31), 2.38–2.50 (m, 2H), 4.02–4.14 (m, 2H), 6.94 (dd, J=1.4 Hz, 5.0 Hz, 1H), 7.29 (dd, J=1.4 Hz, 2.8 Hz, 1H), 7.37 (dd, J=2.9 Hz, 5.0 Hz, 1H).

Reference Example 64 4-cyano-5-methyl-4-(3-thienyl)hexanol

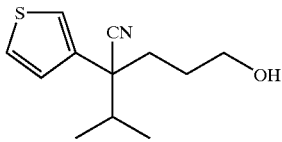

A tetrahydrofuran solution (35 ml) in which ethyl 4-cyano-5-methyl-4-(3-thienyl)hexanoate (6.66 g) was dissolved was added dropwise to a tetrahydrofuran solution (50 ml) of lithium aluminum hydride (686 mg). After stirring for 2 hours, 2N aqueous NaOH and water were added to treat the mixture, and the resulting precipitates were filtered. The resulting filtrate was evaporated, and the residue was purified by silica gel column chromatography (ethyl acetate/hexane system), to give the title compound as a yellow oil (5.30 g, 95%).
$^1$H-NMR (400 MHz, CDCl$_3$) δ 0.85 (d, J=6.8 Hz, 3H), 1.17 (d, J=6.6 Hz, 3H), 1.18–1.22 (m, 1H), 1.22–1.36 (m, 1H), 1.56–1.72 (m, 1H), 1.90 (ddd, J=4.6 Hz, 12.1 Hz, 13.4 Hz, 1H), 2.04–2.12 (m, 1H), 2.14–1.22 (m, 1H), 3.58–3.65 (m, 2H), 6.95 (dd, J=1.5 Hz, 5.1 Hz, 1H), 7.28 (dd, J=1.5 Hz, 3.0 Hz, 1H), 7.35 (dd, J=3.0 Hz, 5.1 Hz, 1H).

Reference Example 65 1-Iodo-4-cyano-5-methyl-4-(3-thienyl)hexane

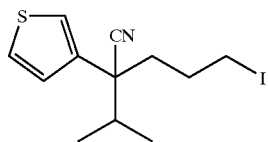

Under nitrogen atmosphere, methanesulfonyl chloride (0.20 ml) was added to an acetonitrile solution (9.0 ml) of 4-cyano-5-methyl-4-(3-thienyl)hexanol (400 mg) and triethylamine (0.75 ml) at a room temperature, and the mixture was stirred. After 2 hours, water and ethyl acetate were added, to separate the organic layer. The resulting organic layer was washed with water and brine, and dried over anhydrous magnesium sulfate. After filtering off the drying agent, the filtrate was evaporated. The resulting residue was dissolved in acetone (18 ml), sodium iodide (2.68 g) was added, and the mixture was stirred at 40° C. for 2 hours. The organic layer was separated by adding water and ethyl acetate thereto. The resulting organic layer was washed with water and brine, and dried over anhydrous magnesium sulfate. After filtering off the drying agent, the filtrate was evaporated, to give the title compound as a yellow oil (670 mg).
$^1$H-NMR (400 MHz, CDCl$_3$) δ 0.85 (d, J=6.8 Hz, 3H), 1.18 (d, J=6.6 Hz, 3H), 1.46–1.60 (m, 1H), 1.86–2.00 (m, 1H), 2.02–2.20 (m 2H), 3.05–3.20 (m, 2H), 6.95 (dd, J=1.2 Hz, 5.2 Hz, 1H), 7.28 (dd, J=1.2 Hz, 2.8 Hz, 1H), 7.37 (dd, J=2.8 Hz, 5.2 Hz, 1H).

Reference Example 66 Ethyl 4-cyano-5-methyl-4-[4-(2-cyano)thienyl]hexanoate

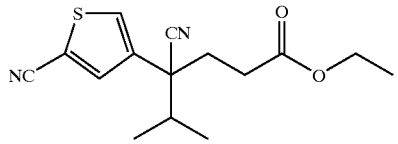

Under a nitrogen atmosphere, ethyl 4-cyano-5-methyl-4-(3-thienyl)hexanoate (1.8 g) was dissolved in dimethylformamide (7 mL), a solution of N-bromosuccinimide (1.33 g)/dimethylformamide (7 mL) was added dropwise thereinto at room temperature over 30 minutes. After stirring at 50° C. for 4.5 hours, the organic layer was separated by adding water and diethyl ether thereto. The resulting organic layer was washed with water and brine, and dried over anhydrous magnesium sulfate. After filtering off the drying agent, the filtrate was evaporated, to give ethyl 4-cyano-5-methyl-4-[4-(2-bromo)thienyl]hexanoate (2.42 g) as a yellow oil. The resulting bromo compound (2.42 g) was dissolved in a solution in which zinc cyanide (637 mg) and 1,1'-bis(diphenylphosphino) ferrocene (188 mg) were dissolved in a mixed solution of dimethylformamide (17 mL)/water (0.17 mL) under a nitrogen atmosphere. Palladium-dibenzilideneacetone complex (124 mg) was added thereto. After replacing the atmosphere with nitrogen three times, the mixture was stirred at 120° C. for S hours. The organic layer was separated by adding water, diethyl ether and an aqueous ammonia water thereto. The resulting organic layer was washed with water and brine, and dried over anhydrous magnesium sulfate. After filtering off the drying agent, the filtrate was evaporated. The residue was purified by silica gel column chromatography (hexane:ethyl acetate system), to give the title compound as a yellow oil (338 mg, 17%, 2 steps). (Reference literature: P. E. Maligres et al, "Tetrahedron 40(1999) 8193–8195")
$^1$H-NMR (400 MHz, CDCl$_3$) δ 0.86 (d, J=6.8 Hz, 3H), 1.20 (d, J=6.4 Hz, 3H), 1.23 (t, J=7.2 Hz, 3H), 1.95–2.15 (m, 3H), 2.40–2.53 (m, 2H), 4.04–4.14 (m, 2H), 7.48 (d, J=1.6 Hz, 1H), 7.58 (d, J=1.6 Hz, 1H).

Reference Example 67 4-cyano-5-methyl-4-(2-cyano-4-thienyl)hexanol

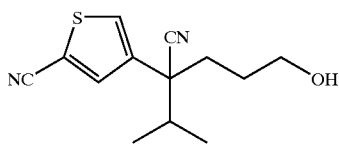

The title compound was obtained as a yellow oil in accordance with the above-mentioned LiBH$_4$ reduction method (30%).
$^1$H-NMR (400 MHz, CDCl$_3$) δ 0.86 (d, J=6.8 Hz, 3H), 1.18 (d, J=6.8 Hz, 31). 1.20–1.33 (m, 1H), 1.60–1.72 (m, 1H), 1.86–1.96 (m, 1H), 2.00–2.12 (m, 1H), 2.16–2.26 (m, 1H), 3.60–3.68 (m, 2H), 7.48 (d, J=1.6 Hz, 1H), 7.57 (d, J=1.6 Hz, 1H).

Reference Example 68 1-Iodo-4-cyano-5-methyl-4-[4-(2-cyano)Thienyl]hexane

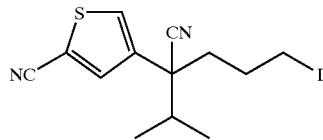

The title compound was synthesized as a yellow oil in accordance with the methods described in Reference Examples 63, 64 and 65 (91%).

$^1$H-NMR (400 MHz, CDCl$_3$) δ 0.86 (d, J=6.8 Hz, 31), 1.19 (d, J=6.8 Hz, 3H), 1.20–1.30 (m, 1H), 1.40–1.55 (m, 1H), 1.90–2.00 (m, 1H), 2.00–2.12 (m, 1H). 2.16–2.26 (m, 1H), 3.06–3.17 (m, 1H), 3.17–3.23 (m, 1H), 7.48 (d, J=1.6 Hz, 1H), 7.57 (d, J=1.6 Hz, 1H).

Reference Example 69 2-(2-cyano-4-fluorophenoxy)ethylpiperazine

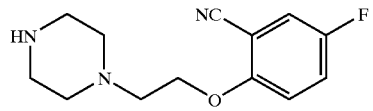

Under nitrogen atmosphere, potassium tert-butoxide (869 mg) was added to a tetrahydrofuran solution (10 ml) of benzyl 4-(2-hydroxyethyl)-1-piperazinecarboxylate (1.86 g) in an ice bath. After stirring for one hour, the reaction system was transferred to a dry ice-methanol bath, and after 10 minutes, a 2,5-difluorobenzonitrile (1.09 g)/tetrahydrofuran solution (5 ml) was added thereto. After stirring for 2 hours while the temperature of the reaction system was naturally returned to a room temperature, an aqueous saturated ammonium chloride and diethyl ether were added thereto, to separate the organic layer. The resulting organic layer was washed with water and brine, and dried over anhydrous magnesium sulfate. After filtering off the drying agent, the filtrate was evaporated. The residue was purified by silica gel column chromatography (hexane:ethyl acetate system), to give a colorless oil as an intermediate (1.10 g, 46%). The intermediate (1.10 g) was dissolved in methanol (10 mL), 10% palladium carbon (100 mg) was added, and the mixture was stirred at room temperature under hydrogen atmosphere. After 1.5 hours, the reaction catalyst was filtered through Celite, and the filtrate was evaporated. The resulting title compound (647 mg, 80%) obtained was used for the next reaction as it was.

Free Body;

$^1$H-NMR (400 MHz, CDCl$_3$) 620.55–2.63 (m, 4H), 2.87 (t, J=5.7 Hz, 2H), 2.89–2.92 (m, 4H), 4.19 (t, J=5.7 Hz, 2H), 6.93 (dd, J=4 Hz, 8.8 Hz, 1H), 7.21–7.29 (m, 2H).

Reference Example 70 4-cyano-5-methyl-4-[4-(2.5-dibromo) Thienyl]hexanol

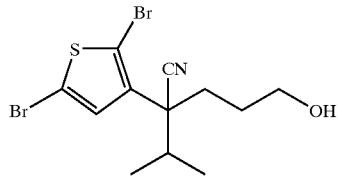

Under nitrogen atmosphere, 4-cyano-5-methyl-4-(3-thienyl)hexanol (500 mg) was dissolved in dimethylformamide (5 mL), and N-bromosuccinimide (1.0 g) was added thereto at room temperature. After stirring at 100° C. for one hour, water and diethyl ether were added thereto, to separate the organic layer. The resulting organic layer was washed with water and brine, and dried over anhydrous magnesium sulfate. After filtering off the drying agent, the filtrate was evaporated. The resulting residue was purified by silica gel column chromatography (hexane:ethyl acetate system), to give the title compound as a yellow oil (670 mg, 78%).

$^1$H-NMR (400 MHz, CDCl$_3$) δ 0.92 (d, J=6.8 Hz, 3H), 1.18 (d, J=6.8 Hz, 3H). 1.31–1.44 (m, 1H), 1.60–1.74 (m, 1H), 2.08 (ddd, J=4.3 Hz, 12.1 Hz, 13.6 Hz, 1H), 2.43 (ddd, J=4.6 Hz, 12.3 Hz, 13.6 Hz, 1H), 2.59 (sept, J=6.8 Hz, 1H)), 7.05 (s, 1H).

Reference Example 71 2-(4-methylsulfonylphenoxy)ethylpierazine

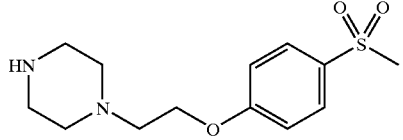

Under a nitrogen atmosphere, 4-(methylthio) phenol (4.2 g) and bromoethanol (5.6 g) were dissolved in dimethylformamide solution (60 ml), potassium carbonate (12.4 g) was added, and the mixture was heating under stirring at 100° C. After 3 hours, the mixture was cooled to room temperature, then the organic layer was separated by adding diethyl ether and water thereto. The resulting organic layer was washed with water and brine, and dried over anhydrous magnesium sulfate. After filtering off the drying agent, the mixture was evaporated. The residue was purified by silica gel column chromatography (hexane/ethyl acetate system), to give (4-methylthiophenoxy) ethanol (3.55 g, 64%) as white crystals. The product (1.0 g) was dissolved in dichloromethane (50 ml), the mixture was cooled on a methanol-dry ice bath, methachloroperbenzoic acid (3.6 g) was added, and the mixture was stirred. After cooling naturally to room temperature over 2 hours, a 1N aqueous sodium bicarbonate and 1N Na$_2$S$_2$O$_3$ were added. After stirring, the mixture was extracted with dichloromethane, and dried over anhydrous magnesium sulfate. After filtering off the drying agent, the mixture was evaporated. The residue was dissolved in acetonitrile (18 ml), triethylamine (2.3 ml) and methanesulfonyl chloride (0.5 ml) were added, and the mixture was stirred at room temperature. After 1.5 hours, sodium iodide (4.9 g) and tert-butyl-1-piperazinecarboxylate (1.2 g) were added, and the mixture was heated under stirring at 60° C. After stirring for 4.5 hours, the organic layer was separated by adding ethyl acetate and water. The resulting organic layer was washed with water and brine, and dried over anhydrous magnesium sulfate. After filtering the drying agent, the mixture was evaporated. The residue was purified by silica gel column chromatography (hexane/ethyl acetate system), to give tert-butyl-2-(4-methylthiophenoxy)ethyl-1-piperazinecarboxylate (1.15 g) as white crystals. The product (1.15 g) was dissolved in methanol (10 ml), and the solution was added to a 4N hydrochloric acid-ethyl acetate solution (30 ml) in an ice bath. After stirring at room temperature overnight, the resulting white crystals were collected by filtration and washed with diethyl ether. A 1N aqueous sodium hydroxide and dichloromethane were added to the crystals, to separate the organic layer. The resulting organic layer was evaporated, to give the title compound as a yellow oil (820 mg, 53%; 3 steps).

$^1$H-NMR (400 MHz, CDCl$_3$) δ 2.52–2.60 (m, 4H), 2.83 (t, J=5.8 Hz, 2H), 2.93 (brt, J=4.8 Hz, 4H), 3.03 (s. 3H), 4.18 (t, J=5.8 Hz, 2H), 7.03 (brd, J=9.0 Hz, 2H), 7.86 (brd, J=9.0 Hz, 2H).

Reference Example 72 2-(3-acetylphenoxy) ethylpiperazine

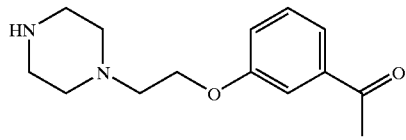

Under a nitrogen atmosphere, 3-hydroxyacetophenone (4.1 g) and brominated ethanol (5.6 g) were dissolved in dimethylformamide solution (60 ml), and potassium carbonate (12.4 g) was added, and the mixture was heated under stirring at 100° C. After 3 hours, the mixture was cooled to room temperature, and the organic layer was separated by adding water and diethyl ether thereto. The resulting organic layer was washed with water and brine, and dried over anhydrous magnesium sulfate. After filtering off the drying agent, the mixture was evaporated. The residue was purified by silica gel column chromatography (hexane/ethyl acetate system), to give (3-acetylphenoxy) ethanol (3.28 g, 61%) as white crystals. The product (977 mg) was dissolved in acetonitrile (18 ml), triethylamine (2.3 ml) and methanesulfonyl chloride (0.5 ml) were added, and the mixture was stirred at room temperature. After 1.5 hours, sodium iodide (4.9 g) and tert-butyl-1-piperazinecarboxylate (1.2 g) were added, and the mixture was heated under stirring at 60° C. After stirring for 4.5 hours, the organic layer was separated by adding water and ethyl acetate thereto. The resulting organic layer was washed with water and brine, and dried over anhydrous magnesium sulfate. After filtering off the drying agent, the mixture was evaporated. The residue was purified by silica gel column chromatography (hexane/ethyl acetate system), to give tert-butyl-2-(3-acetylphenoxy)ethyl-1-piperazinecarboxylate (1.33 g) as a yellow oil. The product (1.33 g) was dissolved in methanol (10 ml), and the solution was added to a 4N hydrochloric acid-ethyl acetate solution (30 ml). The mixture was stirred at a room temperature overnight, the resulting white crystals were collected by filtration and washed with diethyl ether. The organic layer was separated by adding a 1N aqueous sodium hydroxide and dichloromethane to the crystals. The resulting organic layer was evaporated, to give the title compound (830 mg, 62%; 2 steps) as a yellow oil.

$^1$H-NMR (400 MHz, CDCl$_3$) δ 2.52–2.60 (m, 4H), 2.60 (s, 3H), 2.82 (t, J=5.8 Hz, 2H), 2.93 (brt, J=4.9 Hz, 4H), 4.16 (t, J=5.8 Hz, 2H), 7.12 (ddd, J=1.1 Hz, 2.6 Hz, 8.2 Hz, 1H) 7.34–7.40 (m, 1H), 7.50 (dd, J=1.5 Hz, 2.6 Hz, 1H), 7.54 (ddd, J=1.1 Hz, 1.5 Hz, 7.5 Hz, 1H).

Reference Example 73 1-[4-cyano-5-methyl-4-(2-thienyl)hexyl]piperazine

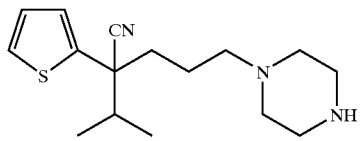

tert-Butyl-1-piperazinecarboxylate (540 mg) was added to an acetonitrile solution (11 ml) of 1-iodo-4-cyano-5-methyl-4-(2-thienyl)hexane (744 mg) and triethylamine (0.93 ml) synthesized according to Example 84, and the mixture was stirred at 50° C. for 5 hours under nitrogen atmosphere. The reaction solution was evaporated, and then the resulting crude product was purified by silica gel column chromatography (hexane/ethyl acetate system), to give a colorless oil (705 mg, 81%). The resulting product (705 mg) was dissolved in methanol (5 ml), a 4N hydrochloric acid-ethyl acetate solution (15 ml) was added, and the mixture was stirred for 10 hours. Diethyl ether and ethyl acetate were added, and the mixture was stirred in an ice bath. The resulting hydrochloride of the title compound was collected by filtration (white crystals, 490 mg, 75%). The hydrochloride of the title compound obtained was extracted with dichloromethane and an aqueous saturated sodium bicarbonate, to be converted into a free body, and it was used for the next reaction. Hydrochloride:

$^1$H NMR (400 MHz, DMSO-d$_6$) δ 0.82 (d, J=6.8 Hz, 3H), 1.10 (d, J=6.6 Hz, 3H), 1.30–1.55 (m, 1H), 1.60–1.83 (m, 1H), 1.83–2.00 (m, 1H), 2.22–2.30 (m, 2H), 3.00–3.80 (m, 10H), 7.07 (dd, J=5.1 Hz, 3.5 Hz, 1H), 7.11 (dd, J=3.5 Hz, 1.3 Hz, 1H), 7.59 (dd, J=5.1 Hz, 1.3 Hz, 1H), 9.30–9.70 (m, 2H).

ESI-MS (m/e): 292 (M+H).

Reference Example 74 1-[3-cyano-4-methyl-3-(2-thienyl)pentyl]piperazine

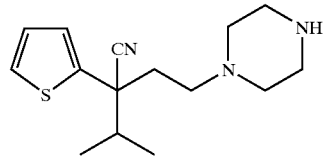

The title compound was synthesized in accordance with the production method of Reference Example 73.

Free Body:

$^1$H NMR (400 MHz, CDCl$_3$) δ 0.91 (d, J=6.6 Hz, 3H), 1.19 (d, J=6.8 Hz, 3H), 1.50–1.60 (m, 1H), 11.88–1.98 (m, 1H), 2.20–2.18 (m, 2H), 2.28–2.52 (m, 6H), 2.83–2.90 (m, 4H), 6.94–6.98 (m, 1H), 7.10–7.13 (m, 1H), 7.25–7.30 (m, 1H).

Reference Example 75 4-(1,4-piazepan-1-yl)-1-isopropyl-1-phenylbutyl Cyanide

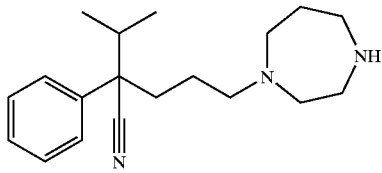

The title compound was synthesized from tert-butyl-1-homopiperazinecarboxylate in accordance with Reference Example 73.
Free Body:
¹H NMR (400 MHz, CDCl₃) δ 0.78 (d, 1=6.8 Hz, 3H), 1.02–1.20 (m, 1H), 1.20 (d, J=6.66 Hz, 3H), 1.44–1.62 (m, 1H), 1.64–1.74 (m, 2H), 1.85–1.95 (m, 1H), 2.06–2.20 (m, 2H), 2.36–2.48 (m, 2H), 2.50–2.59 (m, 4H), 2.80–2.86 (m, 2H), 2.89 (t, J=6.1 Hz, 2H), 7.25–7.34 (m, 1H), 7.36–7.40 (m, 4H).

Reference Example 76 1-(Vinylsulfonyl)piperidine

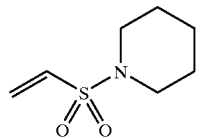

¹H NMR (400 MHz, CDCl₃) δ 1.47–1.60 (m, 2H), 1.60–1.70 (m, 4H), 3.07–3.18 (m, 4H), 5.99 (d, J=9.9 Hz, 1H), 6.20 (d, J=16.7 Hz, 1H), 6.41 (dd, J=16.7 Hz, 9.9 Hz, 1H).

Reference Example 77 1.2.3.4-tetrahydro-1-quinolinylvinylsulfone

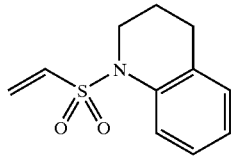

¹H NMR (400 MHz, CDCl₃) δ 1.95–2.05 (m, 2H), 2.81 (t, J=6.8 Hz, 2H), 3.75–3.85 (m, 2H), 5.91 (d, J=10.4 Hz, 1H), 6.23 (d, J=16.44 Hz, 1H), 6.46 (dd, J=16.4 Hz, 10.4 Hz, 1H), 7.00–7.20 (m 3H), 7.65 (d, J=8.4 Hz, 1H).

Reference Example 78 5-(2.5-dihydro-1H-1-pyrrolyl)-2-isopropyl-5-oxo-2-(2-thienyl)pentanenitrile

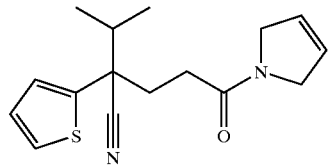

Under nitrogen atmosphere, diethyl cyanophosphonate (618 mg) was added to a tetrahydrofuran solution (15 ml) of 3-pyrroline (262 mg) and 4-cyano-4-(2-thienyl)-5-methylhexanoic acid (692 mg) at room temperature, and the mixture was stirred overnight. After the reaction solution was evaporated, the crude product was purified by silica gel column chromatography (hexane/ethyl acetate system), to give the title compound as a yellow oil (440 mg).

¹H NMR (400 MHz, CDCl₃) δ 0.92 (d, J=6.8 Hz, 3H), 1.22 (d, J=6.6 Hz, 3H), 2.00–2.30 (m, 3H), 2.40–60 (m, 2H), 4.00–4.30 (m, 4H), 5.70–5.80 (m, 1H), 5.80–5.90 (m, 1H)1, 6.87–7.00 (m 1H), 7.15 (m, 1H), 7.23–7.26 (m, 1H).

In the physico-chemical data of the following compounds, the values obtained when NMR was measured for a free body and ESI-MS was measured for a hydrochloride. Further, the hydrochloride was produced in accordance with the method described in JP-A 11-206862.

Reference Example 79 1-[4-cyano-4-(5-cyano-2-thienyl)-5-methylhexyl]-(3R)-3-tert-butoxycarbonylaminopyrrolidine

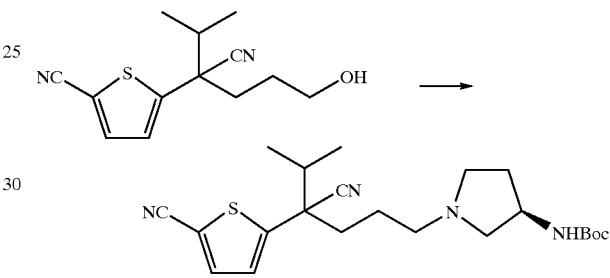

867 mg (3.49 mmol) of 4-cyano-4-(5-cyano-2-thienyl)-5-methylhexanol was dissolved in 20 ml of acetonitrile. 0.58 ml (1.20 eq).of triethylamine and 0.30 ml (1.10 eq) of mesyl chloride were added thereto. After 10 minutes, brine was added, and the objective product was extracted with ethylacetate. The organic layer was washed with brine, and then dried over anhydrous magnesium sulfate. The solvent was evaporated, to give a crude product. The product was dissolved in 30 ml of acetonitrile, 1.57 g (3.00 eq) of sodium iodine, 0.54 ml (1.10 eq) of triethylamine and 845 mg (4.54 mmol) of (3R)-3-tert-butoxycarbonylaminopyrrolidine were added, and the mixture was heated at 60° C. After completion of the reaction, brine was added, and the objective product was extracted with ethyl acetate. The organic layer was washed with brine, and then dried over anhydrous magnesium sulfate. The solvent was evaporated, to give a crude product. The crude product was subjected to 100 g of Cromatorex NH silica gel (ethyl acetate:hexane=25 to 35% of ethyl acetate), to give 1.34 g (3.21 mmol, 92.0%) of the title compound as a yellow oil. The physico-chemical data of the compound was as below.

¹H-NMR (400 MHz, CDCl₃) δ 0.92 (d, J=6.4 Hz, 3H), 1.21 (d, J=6.8 Hz, 3H), 1.17–1.30 (m, 1H), 1.44 (s, 9H), 1.50–1.70 (m, 1H), 1.72–1.84 (m, 1H), 2.00–2.12 (m, 1H), 2.15–2.30 (m, 3H), 2.31–2.49 (m, 4H), 2.49–2.55 (m, 1H), 2.62–2.75 (m, 1H), 4.07–4.20 (m, 1H), 4.70–4.82 (brd-s, 1H), 7.15 (d, J=3.6 Hz, 1H), 7.52 (d, J=3.6 Hz, 1H)

Reference Example 80 1-[4-cyano-4-(5-cyano-2-thienyl)-5-methylhexyl]-(3R)-3-aminopipyrrolidine

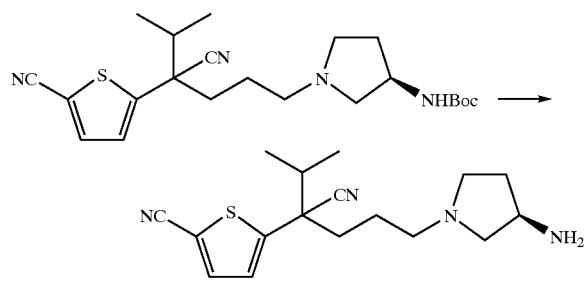

1-[4-Cyano-4-(5-cyano-2-thienyl)-5-methylhexyl)-(3R)-3-tert-butoxycarbonylaminopyrrolidine (1.34 g=3.21 mmol) obtained in Reference Example 79 was dissolved in 10 ml of methanol, and 10 ml of a 4N hydrochloric acid-ethyl acetate solution was added. After completion of the reaction, the mixture was adjusted to basic with a 5N sodium hydroxide, and extracted with chloroform. The organic layer was dried over magnesium sulfate, and then evaporated, to give 998 mg (3.15 mmol, 99.5%, a red oil) of a crude product. The physico-chemical data of the compound was as below.

$^1$H-NMR (400 MHz, CDCl$_3$) δ 0.92 (d, J=6.8 Hz, 3H), 1.21 (d, J=6.4 Hz, 3H), 1.18–1.32 (a 1H), 1.39–1.71 (m, 2H), 1.75–1.85 (m, 1H), 2.01–2.19 (m, 2H), 2.19–2.29 (m, 2H), 2.32–2.41 (m, 2H), 2.42–2.51 (m, 1H), 2.57–2.66 (m, 2H), 3.45–3.52 (m, 1H), 7.15 (d, J=3.6 Hz, 1H), 7.52(d, J=3.6 Hz, 1H)

Reference Example 81 Production of 1-[4-cyano-4-[5-cyano-2-thienyl)-5-methylhexyl]-(3R)-3-[N-(2-cyanoethyl)amino]pyrrolidine

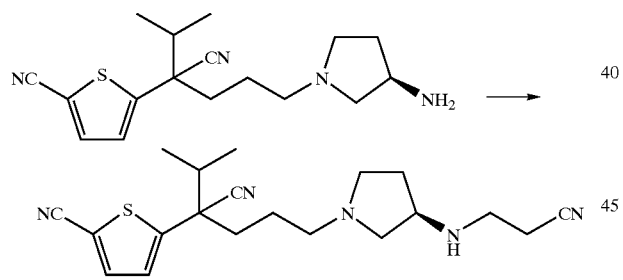

998 mg (3.15 mmol) of 1-[4-Cyano-4-(5-cyano-2-thienyl)-5-methylhexyl]-(3R)-3-aminopipyrrolidine obtained in Reference Example 80 was dissolved in 25 ml of methanol, 0.26 ml (3.94 mmol) of acrylonitrile was added, and the reaction solution was heated under reflux. After completion of the reaction, the mixture was evaporated, to give a crude product. The crude product was subjected to 50 g of Cromatorex NH silica gel (100% of ethyl acetate), to give 1.01 g (2.73 mmol, 86.7%) of the title compound as an orange oil. The physico-chemical data of the compound was as below.

$^1$H-NMR (400 MHz, CDCl$_3$) δ 0.92 (d, J=6.4 Hz, 3H), 1.21 (d, J=6.4 Hz, 3H), 1.20–1.31 (m, 1H), 1.48–1.71 (m, 2H), 1.76–1.86 (m, 1H), 2.02–2.15 (m, 2H), 2.18–2.29 (m, 1H); 2.30–2.39 (m, 3H), 2.43–2.56 (m, 4H), 2.56–2.64 (m, 1H), 2.86 (t, 1=6.4 Hz, 2H), 3.25–3.33 (m, 1H), 7.16 (d, J=40.0 Hz, 1H), 7.52 (d, J=4.0 Hz, 1H)

Reference Example 82 1]-[4-cyano-4-(5-cyano-2-thienyl)-5-methylhexyl]piperazine

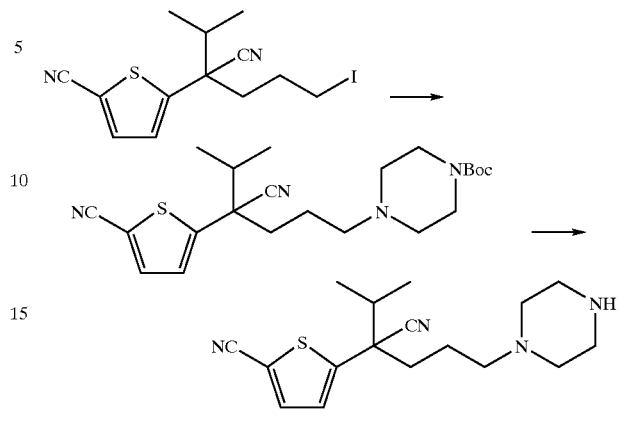

1-[4-cyano-4-(5-cyano-2-thienyl)-5-methylhexyl]-4-(tert-butoxycarbonyl)piperazine was synthesized from 4-cyano-4-(5-cyano-2-thienyl)-5-methylhexyl iodide and tert-butyl 1-piperazinecarboxylate in accordance with the production method of Example 77. The title compound was obtained by carrying out the deprotection of a Boc group in accordance with the production method of Reference Example 79. The physico-chemical data of the compound was as below.

$^1$H-NMR (400 MHz, CDCl$_3$) δ 0.92 (d, J=6.4 Hz, 3H), 1.21 (d, J=6.8 Hz, 3H), 1.20–1.32 (m, 1H), 1.59–1.83 (m, 2H), 2.01–2.11–1.80 (m, 1H), 2.17–2.40 (m, 7H), 2.80–2.92 (m, 4H), 7.15 (d, 1=4.0 Hz, 1H), 7.51 (d, J=4.0 Hz, 1H)

Reference Example 83 1-[4-cyano-5-methyl-4-(4-fluorophenyl)hexyl]piperazine

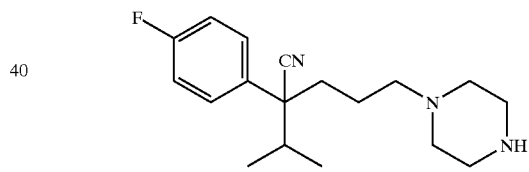

The title compound was synthesized in accordance with Reference Example 73.

Free Body:
$^1$H NMR (400 MHz, CDCl$_3$) δ 0.77 (d, J=6.8 Hz, 3H), 1.08–1.17 (m, 1H), 1.19 (d, J=6.6 Hz, 3H), 1.52–1.62 (m, 1H), 1.81–1.89 (m, 1H), 2.04–2.18 (m, 2H), 2.22–2.29 (m, 6H), 2.83–2.87 (m, 4H), 7.04–7.08 (m, 2H), 7.32–7.36 (m, 2H).

Reference Example 84 1-[4-Cyano-5-methyl-4-(3-fluorophenyl)hexyl]piperazine

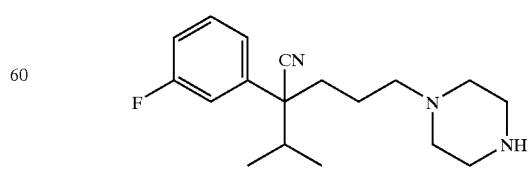

The title compound was synthesized in accordance with Reference Example 73.

Free Body:
¹H NMR (400 MHz, CDCCl₃) δ 0.79 (d, J=6.6 Hz, 3H), 0.81–1.19 (m, 1H), 1.21 (d, J=6.6 Hz, 3H), 1.54–1.59 (m, 1), 1.81–1.89 (m, 1H), 2.05–2.29 (m, 8H), 2.83–2.87 (m 4H), 6.97–7.03 (m, 1H), 7.06–7.10 (m, 1H), 7.17–7.20 (m, 1H), 7.32–7.37 (m, 1H).

Reference Example 85 1-[4-cyano-5-methyl-4-(2-fluorophenyl)hexyl]piperazine

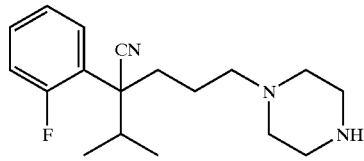

The title compound was synthesized in accordance with Reference Example 73.
Free Body:
¹H NMR (400 MHz, CDCl₃) δ 0.80 (d, J=6.8 Hz, 3H), 1.10–1.16 (m, 1H), 1.22 (d, J=6.6 Hz, 3H), 1.55–1.64 (m, 1H), 2.03–2.11 (m, 1H), 2.17–2.34 (m, 7H), 2.43–2.50 (m, 1H), 2.80–2.87 (m, 4H), 7.01–7.06 (m, 1H), 7.13–7.17 (m, 1H), 7.26–7.34 (m, 1H), 7.56–7.61 (m, 1H).

Reference Example 86 1-[4-cyano-5-methyl-4-(2-tolyl)hexyl]piperazine

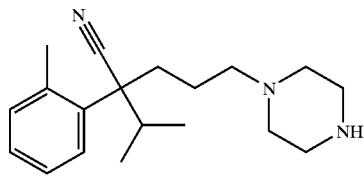

The title compound was obtained as a colorless oil in accordance with Reference Example 73.
¹H NMR (400 MHz, CDCl₃) δ 0.86 (d, J=6.8 Hz, 3H), 1.10–1.24 (m, 1H), 1.18 (d, J=6.8 Hz, 3H), 1.55–1.64 (m, 1H), 2.02–2.14 (m, 1H)2.14–2.30 (m, 1H), 2.20–2.40 (m, 6H), 2.36–2.54 (m, 1H), 2.50 (s, 3H), 2.78–2.90 (m, 4H), 7.10–7.24 (m, 3H), 7.46–7.56 (m, 1H).

Reference Example 87 1-[4-cyano-5-methyl-4-(2-methoxyphenyl)hexyl]piperazine

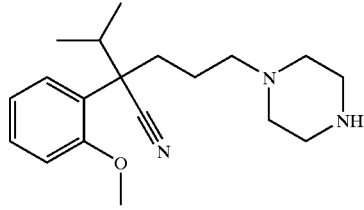

The title compound was obtained as a colorless oil in accordance with Reference Example 73.
¹H NMR (400 MHz, CDCl₃) δ 0.75 (d, J=6.4 Hz, 3H), 1.00–1.20 (m, 1H), 1.18 (d, J=6.8 Hz, 3H), 1.45–1.60 (m, 1H), 1.90–2.00 (m, 1H), 2.20–2.40 (m, 6H), 2.35–2.50 (m, 1H), 2.65–2.75 (m, 1H), 2.75–2.90 (m, 4H), 3.80 (s, 3H), 6.87 (d, J=8.4 Hz, 1H), 6.95 (t, J=7.6 Hz, 1H), 7.24–7.32 (m, 1H), 7.55 (d, J=7.66 Hz, 1H).

Reference Example 88 1-[4-cyano-5-methyl-4-(2-chlorophenyl) Hexyl]piperazine

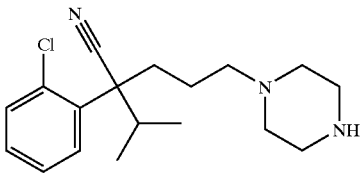

The title compound was obtained as a colorless oil in accordance with Reference Example 73.
¹H NMR (400 MHz, CDCl₃) δ 0.77 (d, J=6.8 Hz, 1H), 1.02–1.18 (m 1H), 1.23 (d, J=6.8 Hz, 3H), 1.45–1.60 (m, 1H), 1.95–2.10 (m, 1H), 2.20–2.40 (m, 6H), 2.64–2.76 (m, 1H), 2.80–2.90 (m, 4H), 2.88–3.02 (m, 1H), 7.22–7.32 (m, 2H), 7.34–7.40 (m, 1H), 7.71–7.77 (m, 1H)).

Reference Example 89 1-benzyl-4-[3-[1-(4-fluorophenyl]Cyclohexyl]-1-oxopropyl]piperazine

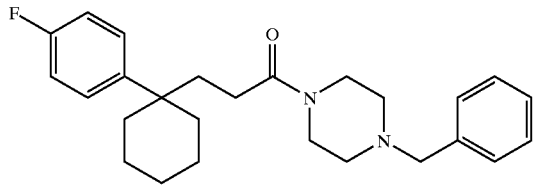

Methyl 4-fluorophenylacetate (10.0 g) was dissolved in tetrahydrofuran (150 ml), and 60% sodium hydride (5.95 g) was added under ice-cooling. After stirring for 10 minutes under ice cooling, 1,5-dibromopentane (11.3 ml) was added dropwise thereinto over one hour. After stirring at room temperature overnight, ice-water was added thereto, and the mixture was extracted with ethyl acetate. The extract was washed with brine, dried over anhydrous magnesium sulfate and evaporated. The resulting residue was purified by silica gel column chromatography (n-hexane/ethyl acetate system), to give 7.37 g (53%) of an oil.

The above-mentioned oil (7.37 g) was dissolved in tetrahydrofuran (100 ml), and a diethyl ether solution (18.7 ml) of 1.0 M lithium aluminum hydride was added dropwise thereinto at −50 to −40° C. After stirring at this temperature for 20 minutes, water, a 5N aqueous sodium hydroxide and further water were added under ice-cooling. The insoluble matters were filtered off through Celite, and the filtrate was evaporated. The resulting residue was purified by silica gel column chromatography (n-hexane/ethyl acetate system), to give 3.43 g (53%) of an oil.

Oxalyl chloride (1.05 ml) was dissolved in methylene chloride (25 ml), and a methylene chloride solution (5 ml) of dimethyl sulfoxide (0.85 ml) was added dropwise at −60 to −50° C. After stirring for 2 minutes, a methylene chloride solution (10 ml) of the above-mentioned oil (2.08 g) was added dropwise therinto within 5 minutes. After stirring for 15 minutes at this temperature, triethylamine (6.96 ml) was added. After stirring for 5 minutes, the temperature was raised to room temperature. The mixture was washed with water and brine, dried over anhydrous magnesium sulfate and evaporated, to give 1.91 g (93%) of an oil.

60% Sodium hydride (0.55 g) was suspended in tetrahydrofuran (10 ml), and triethylphosphonoacetate (2.73 ml) in tetrahydrofuran (5 ml) was added dropwise thereinto under ice-cooling. After stirring for 15 minutes under ice-cooling, a tetrahydrofuran solution (15 ml) of the above-mentioned oil (1.89 g) was added dropwise thereinto. After stirring for 15 minutes at this temperature, the mixture was further stirred at room temperature for one hour. An aqueous saturated ammonium chloride was added thereto and the mixture was extracted with ethyl acetate. The extract was washed with brine, dried over anhydrous magnesium sulfate and evaporated. The resulting residue was purified by silica gel column chromatography (n-hexane/ethyl acetate system), to give 2.07 g (82%) of an oil.

The above-mentioned oil (1.02 g) was dissolved in ethanol (20 ml), 10% palladium-carbon (0.2 g) was added, and hydrogenation was carried out at room temperature under a normal pressure for 30 minutes. After filtering off the catalyst, the filtration was evaporated. The resulting residue was purified by silica gel column chromatography (n-hexane/ethyl acetate system), to give 0.97 g (94%) of an oil.

The above-mentioned oil (9.03 g) was dissolved in ethanol (50 ml), and a 2N aqueous sodium hydroxide (50 ml) was added. After heating under reflux for 2 hours, the mixture was cooled to room temperature, and evaporated. The resulting residue was suspended in ethyl acetate, and the mixture was adjusted to pH 2 with 5N hydrochloric acid. After drying over anhydrous magnesium sulfate, the mixture was evaporated. The resulting residue was recrystallized from ethyl acetate/n-hexane, to give 6.45 g (79%) of white crystals.

1-Benzylpiperazine (2.82 g) was dissolved in N,N-dimethylformamide (40 ml), and the above-mentioned crystals (4.00 g) and 1-hydroxybenzotriazole (2.16 g) were added. Under ice-cooling, a N,N-dimethylformamide solution (30 ml) of 1,3-dicyclohexylcarbodiimide (3.63 g) was added dropwise thereinto. After stirring at room temperature overnight, the insoluble matters were filtered off, and the filtrate was extracted with ethyl acetate and 1N hydrochloric acid. The extract was washed with a 2N aqueous sodium hydroxide and brine, dried over anhydrous magnesium sulfate an d evaporated. The resulting residue was purified by silica gel column chromatography (n-hexane/ethyl acetate system), to give 6.23 g (95%) of the title compound as an oil.

$^1$NMR (400 MHz, CDCl$_3$) δ 1.29–1.50 (m, 4H), 1.50–1.63 (m, 4H), 1.80–1.94 (m, 4H), 1.99–2.07 (m, 2H), 2.27 (t, J=4.8 Hz, 2H), 2.34 (t, J=4.8 Hz, 2H), 3.10 (t, J=4.8 Hz, 2H), 3.47 (s 2H), 3.54 (t, 1=4.8 Hz, 2H), 6.96–7.02 (m, 2H), 7.22–7.34 (m, 7H).

ESI-Mass; 409 (1H$^+$).

Reference Example 90 1-benzyl-4-[3-[1-(4-fluorophenyl)cyclohexyl]propyl]piperazine

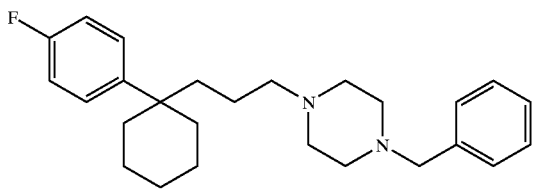

1-Benzyl-4-[3-[1-(4-fluorophenyl)cyclohexyl]-1-oxopropyl]piperazine (5.90 g) was dissolved in tetrahydrofuran (100 ml), and 80% lithium aluminum hydride, (1.03 g) was added thereto under ice-cooling. After heating under reflux for 1.5 hours, the mixture was cooled as it was to room temperature. Under ice-cooling, water, a 1N aqueous sodium hydroxide and further water were added thereto, and the insoluble matters were filtered off. The filtrate was evaporated, and the resulting residue was recrystallized from ethanol, to give 4.48 g (79%) of the title compound as white crystals.

$^1$H-NMR (400 MHz, CDCl$_3$) δ 1.06–1.15 (m, 2H), 1.28–1.58 (m, 12H), 1.98–2.06 (m, 2H), 2.14 (t, J=8 Hz, 2H), 2.20–2.54 (m, 8H1), 3.47 (s 2H), 6.93–7.00 (m, 2H), 7.20–7.32 (m, 7H).

ESI-Mass; 395 (MH$^+$).

Reference Example 91 4-[3-[1-(4-Fluoronhenyl)cyclohexyl]propyl]piperazine

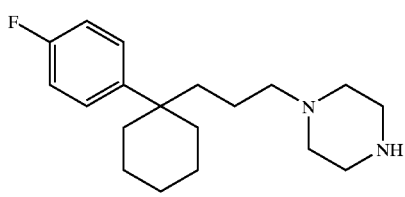

1-Benzyl-4-[3-[1-(4-fluorophenyl)cyclohexyl]propyl]piperazine (4.00 g) was dissolved in methanol (100 ml), and 20% palladium hydroxide-carbon (0.4 g) was added, and hydrogenation was carried out at room temperature under a normal pressure for 6 hours. After filtering off the catalyst, the filtrate was evaporated, to give 3.09 g of the title compound as an oil (quantitative).

$^1$H-NMR (400 MHz, CDCl$_3$) δ 1.07–1.17 (m, 2H), 1.28–1.60 (m, 10H), 1.75 (bs, 1H) 1.99–2.07 (m, 2H), 2.12 (t, J=8 Hz, 2H), 2.25 (bs, 4H), 2.82 (t, J=4.8 Hz, 2H), 6.94–7.01 (m, 2H), 7.21–7.27 (m, 2H).

ESI-Mass: 305 (MH$^+$).

Reference Example 92 Ethyl 4-(4-cyano-5-methyl-4-phenylhexyl)-2-piperazinecarboxylate

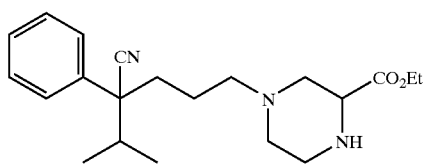

Ethyl 1-benzyl-4-(4-cyano-5-methyl-4-phenylhexyl)-2-piperazinecarboxylate (857 mg) was dissolved in ethanol (15 ml), and 770 mg of 10% Pd-C was added. After replacing the atmosphere with hydrogen, the mixture was stirred. After completion of the reaction, the solution was evaporated, to give 639 mg (93%) of the title compound as a crude product.

Free Body:

$^1$H NMR (400 MHz, CDCl$_3$) δ 0.77 (d, J=6.6 Hz, 3H), 1.08–1.16 (m, 1fl), 1.20 (d, J=6.6 Hz, 3H), 1.22–1.29 (m, 3H), 1.53–1.64 (m, 1H), 1.86–1.95 (m, 1H), 2.05–2.33 (m, 6H), 2.41–2.49 (m, 1H), 2.74–2.83 (m, 2H), 2.97–3.04 (m, 1H), 3.47–3.52 (m, 1H), 4.14–4.21 (m, 2H), 7.26–7.31 (m, 1H), 7.34–7.39 (m, 4H).

Reference Example 93 Ethyl 4-[2-(4-fluorophenoxy)ethyl]-2-piperazinecarboxylate

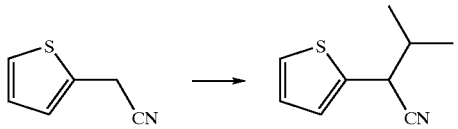

Ethyl 1-benzyl-4-[2-(4-fluorophenoxy)ethyl]-2-piperazinecarboxylate (977 mg) synthesized in accordance with Example 241 described later was dissolved in ethanol (15 ml), and 210 mg of 10% Pd-C was added. After replacing the atmosphere with hydrogen, the mixture was stirred. After completion of the reaction, the solution was evaporated, to give 752 mg (100%) of the title compound as a crude product.

Free Body:

$^1$H NMR (400 MHz, CDC$_3$) δ 1.24–1.28 (m, 31), 2.33–2.34 (m, 1H), 2.48–2.50 (m, 1H), 2.72–2.91 (t, 4H), 3.04–3.10 (m, 2H), 3.56–3.59 (m, 1H), 4.04–4.08 (m, 2H), 4.16–4.22 (m 2H), 6.82–6.86 (m, 2H), 6.94–6.99 (m, 2H)

Among the production intermediates for producing the compound according to the present invention, optically active intermediates can be produced in accordance with known production methods or methods according to them, and additionally, for example, can be produced according to the following methods.

Reference Example 94 3-methyl-2-(2-thienyl)butanenitrile

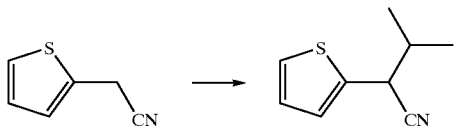

47.6 g (0.39 mol) of 2-thiopheneacetonitrile and 57.0 g (0.46 mol) of 2-bromopropane were dissolved in 100 ml of DMSO, and a 50% KOH aqueous solution was added dropwise to the solution. After completion of the reaction, water was added, and the mixture was extracted with toluene. After washing with brine and an aqueous saturated ammonium chloride, the mixture was dried over magnesium sulfate and evaporated, to give a crude product. The crude product was subjected to distillation under a reduced pressure (2 to 3 mmHg: 132 to 137 deg), to give 46.4 g (0.28 mol, 72.7%) of the title compound as a colorless oil. The physico-chemical data of the compound was as below.

$^1$H-NMR (400 MHz, CDCl$_3$) δ 1.08 (d, J=6.8 Hz, 3H), 1.12 (d, J=6.8 Hz, 3H), 2.14–2.24 (m, 1H), 3.95 (d, J=6.0 Hz, 1H), 6.99 (dd, J=4.0 Hz, 5.20 Hz, 1H), 7.05–7.08 (m, 1H), 7.27 (dd, J=. 2 Hz, 5.2 Hz, 1H)

Reference Example 95 Ethyl 4-cyano-5-methyl-4-(2-thienyl)hexanolate

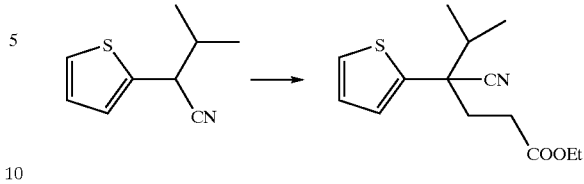

1.49 g (13.3 mmol, cat.) of potassium tert-butoxide was dissolved in 120 ml of DMF, and a mixed solution of 43.9 g (0.27 mol) of 3-methyl-2-(2-thienyl)butanenitrile and 30.2 ml (0.28 mol) of ethyl acrylate was added littleby little to the solution at room temperature. (when a raw material remains, ethyl acrylate and potassium tert-butoxide were additionally added.) It was exothermically continued during the addition. After completion of the reaction, 100 ml of brine and 200 ml of an aqueous saturated ammonium chloride were successively added, and the objective product was extracted with 500 ml of hexane. The organic layer was washed with 400 ml of brine, and dried over anhydrous magnesium sulfate. The solvent was evaporated, to give 67.0 g of a crude product of an ester (ethyl 4-cyano-5-methyl-4-(2-thienyl)hexanolate) as a yellow oil. The physico-chemical data of the compound was as below.

$^1$H-NMR (400 MHz, CDCl$_3$) δ 0.92 (d, J=6.8 Hz, 3H), 1.22 (d, J=7.1 Hz, 3H), 1.23 (t, J=7.1 Hz, 3H), 2.01–2.19 (m, 3H), 2.41–2.58 (m, 2H), 4.01–4.15 (m, 2H), 6.96 (dd, J=3.6 Hz, 5.1 Hz 1H), 7.12 (dd, J=1.2 Hz, 3.6 Hz, 1H), 7.29 (dd, J=1.2 Hz, 5.1 Hz, 1H)

Reference Example 96 Cyclohexylamine Salt of dl-4-cyano-4-(2-thienyl)-5-methylhexanoic Acid

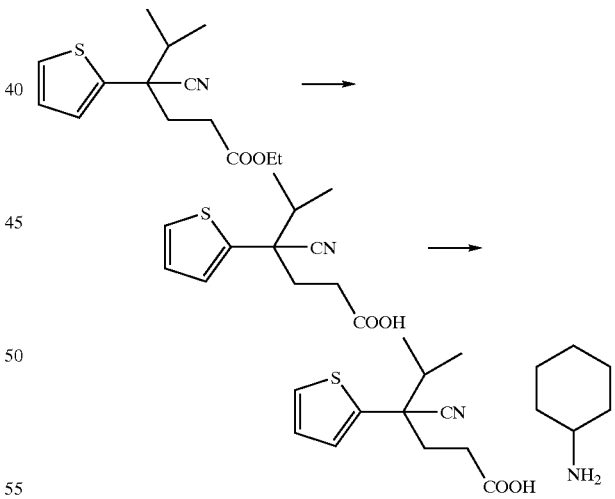

67.0 g of the above-mentioned ester obtained in Example was dissolved in 500 ml of tetrahydrofuran, 200 ml of 5N NaOH and 50 ml of ethanol were added to the solution, and the mixture was stirred. After completion of the reaction, the solution was evaporated. The aqueous layer containing the objective product was washed 4 times with 200 ml of toluene. Then, 320 ml of 5N HCl was added thereto, to adjust pH to 1–2, and the objective product was extracted with 750 ml of toluene. The organic layer was washed with brine, and then dried over anhydrous magnesium sulfate.

The solvent was evaporated, to give 55.6 g (yellow oil) as a crude carboxylic acid. The carboxylic acid was dissolved in 150 ml of toluene, and 22.5 g (0.23 mol) of cyclohexylamine was added. The resulting white crystals were collected by filtration, to give 55.6 g (0.17 mol) of the title compound. The physico-chemical data of the compound was as below.
$^1$H-NMR (400 MHz, CDCl$_3$) δ 0.92 (d, J=6.8 Hz, 3H), 1.20 (d, J=6.4 Hz, 3H), 1.20–1.40 (m, 6H), 1.57–1.67 (m, 1H), 1.72–1.81 (m, 2H), 1.92–2.11 (m, 3H), 2.30–2.42 (m, 1H), 2.44–2.54 (m, 1H), 2.85–2.96 (m, 1H), 6.95 (dd, J=3.2 Hz, 5.2 Hz1H), 7.11 (dd, J=1.2 Hz, 3.2 Hz, 1H), 7.25–7.28 (m, 1H)

Reference Example 97 Ethylamine Salt of 4-cyano-4-(2-thienyl)-5-methylhexanoic Acid.(S)-1-(4-methylphenyl)

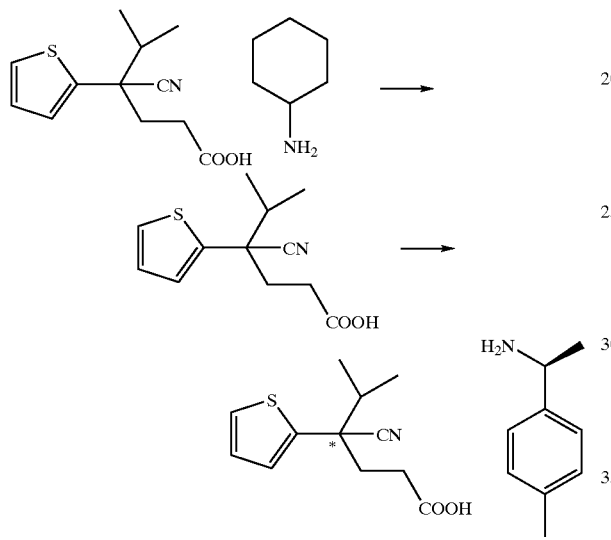

55 g (0.16 mol) of cyclohexylamine salt of dl-4-cyano-4-(2-thienyl)-5-methylhexanoic acid was suspended in 100 ml of 5N HCl and 50 ml of water, and the mixture was extracted with 300 ml of toluene. The extract was washed with 2N HCl and brine, and dried over anhydrous magnesium sulfate. The solvent was evaporated, to give 38.7 g crude carboxylic acid. 38.7 g of the crude dl-4-cyano-4-(2-thienyl)-5-methylhexanoic acid was dissolved in 120 ml of toluene. 18.8 g (0.14 mol, 0.85 eq) of (S)-1-(4-methylphenyl) ethylamine/40 ml of toluene was added to the solution containing this carboxylic acid. To the mixture was added the crystals (6 mg) of the title compound previously prepared, and the mixture was cooled as it was. The resulting diastereomer salt (Salt 1) was collected by filtration. The Salt 1 was dissolved by heating in 250 ml of toluene, and the mixture was cooled as it was to room temperature under stirring. The resulting diastereomer salt (Salt 2: optical purityof 90.5% ee) was collected by filtration, to give 21.3 g (57.2 mmol, 35.1%) (optical purity of 90.5% ee) of the title compound.

Example 2 dl-4-Cyano-4-(2-thienyl)-5-methylhexanoic acid (96.6 mmol) was converted into a salt in accordance with the above-mentioned dividing method and crystallized, and then recrystallization was repeated twice, to give 14.5 g (38.9 mmol, 40.3%) (optical purity of 95% ee<) of the title compound. The physico-chemical data of the compound was as below. Further, the condition for HPLC analysis was shown below, and the analysis data (HPLC chart) were shown in FIG. 1.
$^1$H-NMR (400 MHz, CDCl$_3$) δ 0.91 (d, 1=6.8 Hz, 3H), 1.19 (d, J=6.4 Hz, 3H), 1.42 (d, J=6.8 Hz, 3H), 1.95–2.11 (m, 3H), 2.33 (s, 3H), 2.30–2.50 (m, 2H), 3.74 (brd-s, 3H), 6.95 (dd, 1=3.6 Hz, 5.2 Hz, 1H), 7.10 (dd, J=1.2 Hz, 3.6 Hz, 1H), 7.14 (d, J=8.4 Hz, 21), 7.21 (d, J=8.4 Hz, 2H), 7.25–7.29 (m, 1H)

Condition for HPLC analysis:
  Column: Daicel Chemical Industries, Ltd., CHIRALCEL OJ, 4.6×250 mm
  Mobile phase: 20%(B),
  (A) Mixed solution of n-hexane/trifluoroacetic acid (1000:1)
  (B) Mixed solution of n-hexane/isopropanol/trifluoroacetic acid (500:500:1)
  Flow rate: 0.5 ml/min.
  Detector: UV 231 nm
  Retention time: 15.5 min.

Reference Example 98 4-cyano-4-(2-thienyl)-5-methylhexanoic Acid.(S)-1-phenylethylamine Salt

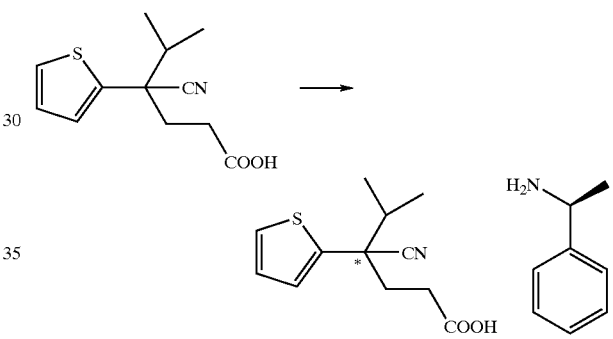

Optically active 4-cyano-4-(2-thienyl)-5-methylhexanoic acid (S)-1-phenylethylamine salt (107.7 g, 39%) (white crystals, optical purity of 96.9% ee) could be obtained also by using (S)-1-phenylethylamine (67.4 g) and toluene (990 ml) to dl-4-cyano-4-(2-thienyl)-5-methylhexanoic acid (168.8 g) in accordance with the method of Reference Example 97. The physico-chemical data of the compound was as below.
$^1$H-NMR (400 MHz, CD$_3$OD) δ 0.94 (d, J=7 Hz, 3H), 1.23 (d, J=7 Hz, 3H), 1.65 (d, J=7 Hz, 3H), 2.02 (ddd, J=15 Hz, 12 Hz, 4 Hz, 1H), 2.14 (ddd, J=14 Hz, 12 Hz, 4 Hz, 1H), 2.18 (qq, J=7 Hz, 7 Hz, 1H), 2.33 (ddd, J=15 Hz, 12 Hz, 4 Hz, 1H), 2.52. (ddd, J=14 Hz, 12 Hz, 4 Hz, 1H), 4.44 (q, J=7 Hz, 1H), 7.04 (dd, J=5 Hz, 3 Hz, 1H), 7.14 (dd, J=3 Hz, 1 Hz, 1H), 7.44 (dd, J=5 Hz, 1 Hz, 1H), 7.40–7.50 (m, 5H).
EI-Mass (m/z): 135, 177, 195, 273 (M$^+$)
Melting point: 136–144° C.
Condition for HPLC analysis:
  Column: Daicel Chemical Industries Ltd, (Tokyo) CHIRALCEL OJ,
  Mobile phase: 10% (B),
  (A) n-hexane/trifluoroacetic acid (1000:1)
  (B) n-hexane/2-propanol/trifluoroacetic acid (500:500:1)
  Flow rate: 0.5 ml/min.
  Detector: UV 231 nm
  Retention time: 26.2 min.

Reference Example 99 4-cyano-4-(2-thienyl)-5-methylhexanoic Acid.(R)-1-phenylethylamine Salt

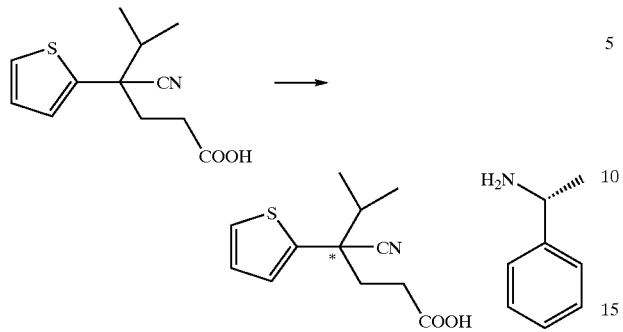

The title compound was obtained as white crystals using (R)-1-phenylethylamine and d1-4-cyano-4-(2-thienyl)-5-methylhexanoic acid in accordance with the method of Reference Example 98.

Melting point: 136–144° C.
Condition of HPLC analysis:
  Column: Daicel Chemical Industries Ltd., (Tokyo) CHIRALCEL OJ,
  Mobile phase: 10%(B),
  (A) n-hexane/trifluoroacetic acid (1000:1)
  (B) n-hexane/2-propanol/trifluoroacetic acid (500:500:1)
  Flow rate: 0.5 ml/min.
  Detector: UV 231 nm
  Retention time: 19.9 min.

Reference Example 100 4-cyano-4-(3-thienyl)-5-methylhexanoic Acid.(S)-1-(4-methylphenyl)ethylamine Salt

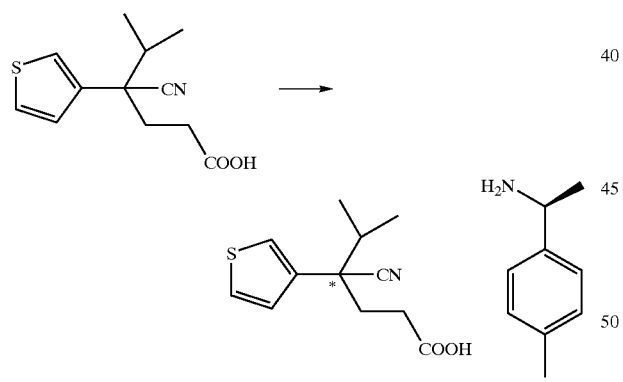

5.6 g (optical purity of 86.7% ee) of the title compound was obtained as white crystals from d1-4-cyano-4-(3-thienyl)-5-methylhexanoic acid (11.4 g) and (S)-1-(4-methylphenyl)ethylamine (5.45 g) synthesized in accordance with Reference Examples 96 and 97. The physico-chemical data of the compound was as below. Further, the condition for HPLC analysis was shown below, and the analysis data (HPLC chart) were shown in FIG. 2.

Free Body: 4-cyano-4-(3-thienyl)-5-methylhexanoic Acid;
$^1$H-NMR (400 MHz, CDCl$_3$) δ 0.85 (d, J=6.8 Hz, 3H); 1.19 (d, J=6.6 Hz, 3H), 2.02–2.18 (m, 3H), 2.38–2.58 (m, 2H), 6.94 (dd, 1=3.1 Hz, 1.5 Hz, 1H), 7.30 (dd, 1=3.1 Hz, 1.5 Hz, 1H), 7.38 (dd, 1=5.1 Hz, 3.11 Hz, 1H).

Salt: 4-cyano-4-(3-thienyl)-5-methylhexanoic acid (S)-1-(4-methylphenyl)ethylamine Salt
$^1$H-NMR (400 MHz, CDCl$_3$) δ 0.83 (d, J=6.8 Hz, 3H), 1.15 (d, J=6.6 Hz, 3H), 1.42 (d, J=6.6 Hz, 3H), 1.80–2.10 (m, 3H), 2.27–2.42 (m, 2H), 2.33 (s, 3H), 4.14 (q, J=6.8 Hz, 1H), 6.91 (dd, 1=5.1 Hz, 1.5 Hz, 1H), 7.13 (brd, J=8.0 Hz, 2H). 7.20 (brd, 1=8.0 Hz, 2H), 7.24 (dd, J=3.1 Hz, 1.5 Hz, 1H), 7.33 (dd, J=5.1 Hz, 3.1 Hz, 1H).

Melting point: 140–143° C.
Condition of HPLC analysis:
  Column: Daicel Chemical Industries Ltd., (Tokyo) CHIRALCEL OJ,
  Mobile phase: Hexane:IPA:TFA (900:100:1)
  Flow rate: 0.5 ml/min.
  Detector: UV 235 nm
  Retention time: 15.7 min.

Reference Example 101 Optically Active 4-cyano-4-(3-thienyl)-5-methylhexanoic Acid

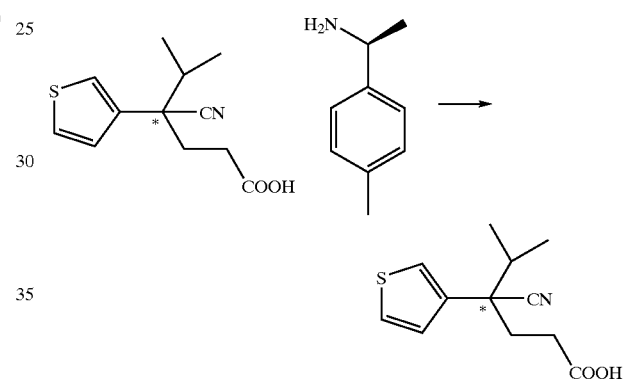

Figure 2:
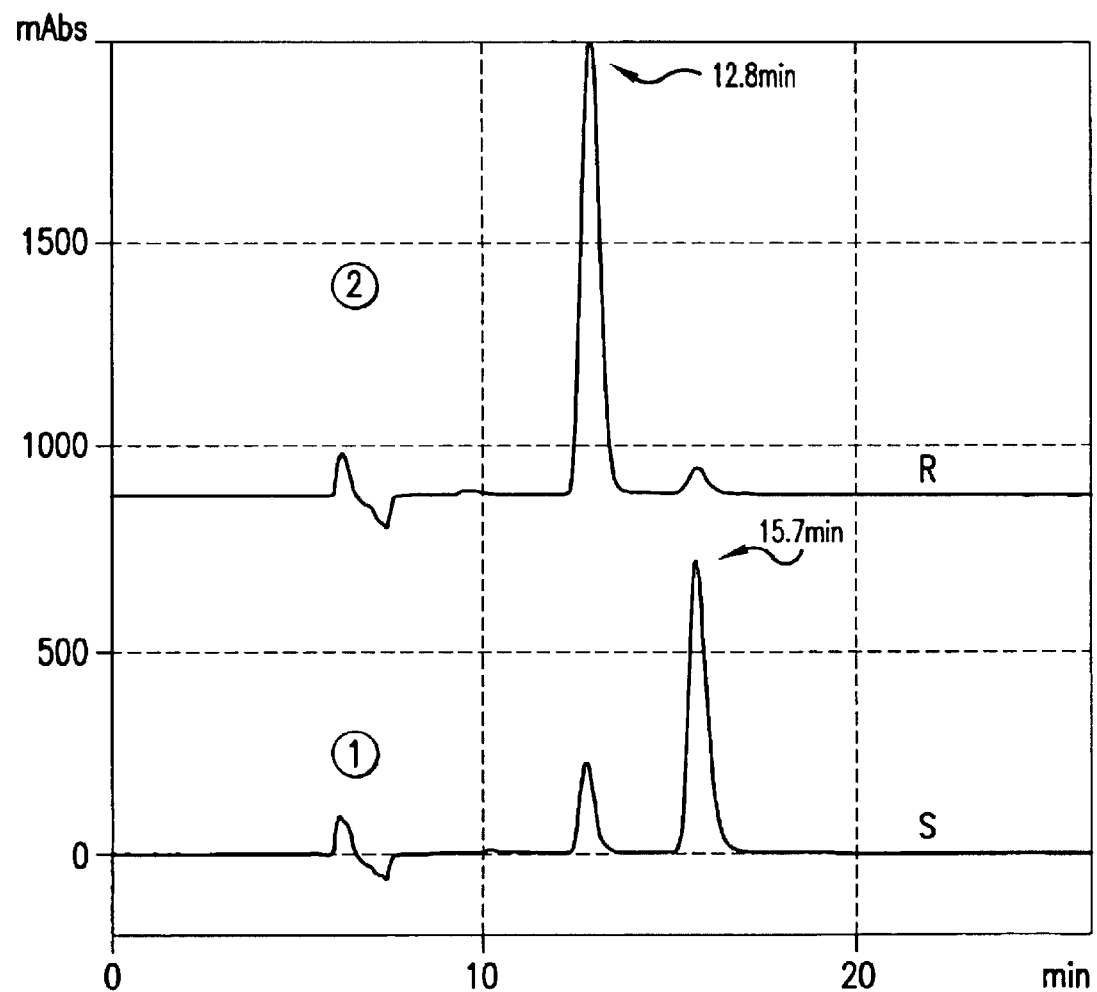
FIG. 2 shows a HPLC chart in Reference Examples 100 and 101, the spectrum of No. 1 in the drawing shows a spectrum in Reference Example 100 and the spectrum of No. 2 shows a spectrum in Reference Example 101, respectively.

The free body of the title compound (3.94 g) was obtained by treating 4-cyano-4-(3-thienyl)-5-methylhexanoic acid, (S)-1-(4-methylphenyl)ethylamine salt (5.6 g) with an aqueous hydrochloric acid, in accordance with the method of Reference Example 97, to produce the title free compound (3.94 g). The physico-chemical data of the compound was as below. Further, the condition of HPLC analysis are shown below, and the analysis data (HPLC chart) are shown in FIG. 2.

$^1$H-NMR (400 MHz, CDCl3) δ 0.85 (d, J=6.8 Hz, 3H), 1.19 (d, J=6.6 Hz, 3H), 2.02–2.18 (m, 3H), 2.38–2.58 (m, 2H), 6.94 (dd, J=3.1 Hz, 1.5 Hz, 1H), 7.30 (dd, J=3.1 Hz, 1.5 Hz, 1H), 7.38 (dd, J=5.1 Hz, 3.1 Hz, 1H).

Reference Example 102 4-cyano-4-(3-thienyl]-5-methylhexanoic Acid.(R)-1-(4-methylphenyl)ethylamine Salt

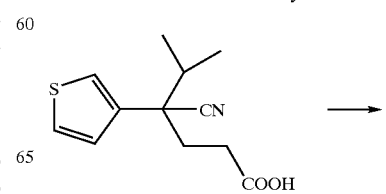

-continued

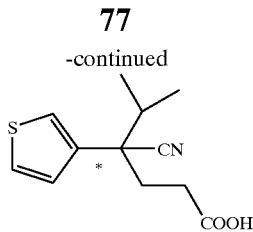 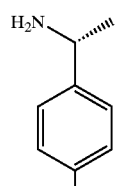

The title compound (35%, optical purity of 88.5% ee) was obtained as white crystals using (R)-1-(4-methylphenyl)ethylamine and dl-4-cyano-4-(3-thienyl)-5-methylhexanoic acid, in accordance with the production method of Example.

Melting point: 140–143° C.

Condition of HPLC analysis:

Column: Daicel Chemical Industries Ltd., (Tokyo) CHIRALCEL OJ,

Mobile phase: Hexane:IPA:TFA (900:100:1)

Flow rate: 0.5 ml/min.

Detector: UV 235 nm

Retention time: 12.8 min.

Reference Example 103 4-cyano-4-(2-thienyl)-5-methylhexanoic Acid.(R)-1-(4-methylphenyl)ethylamine Salt

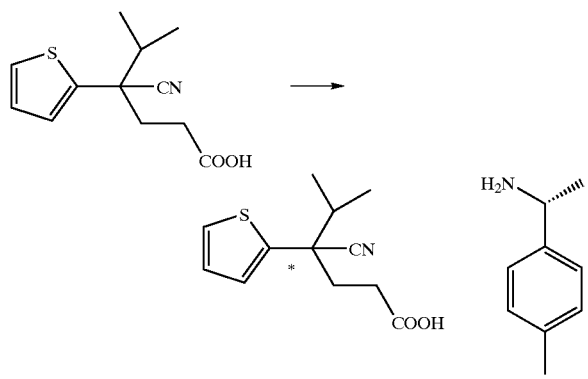

Figure 3:
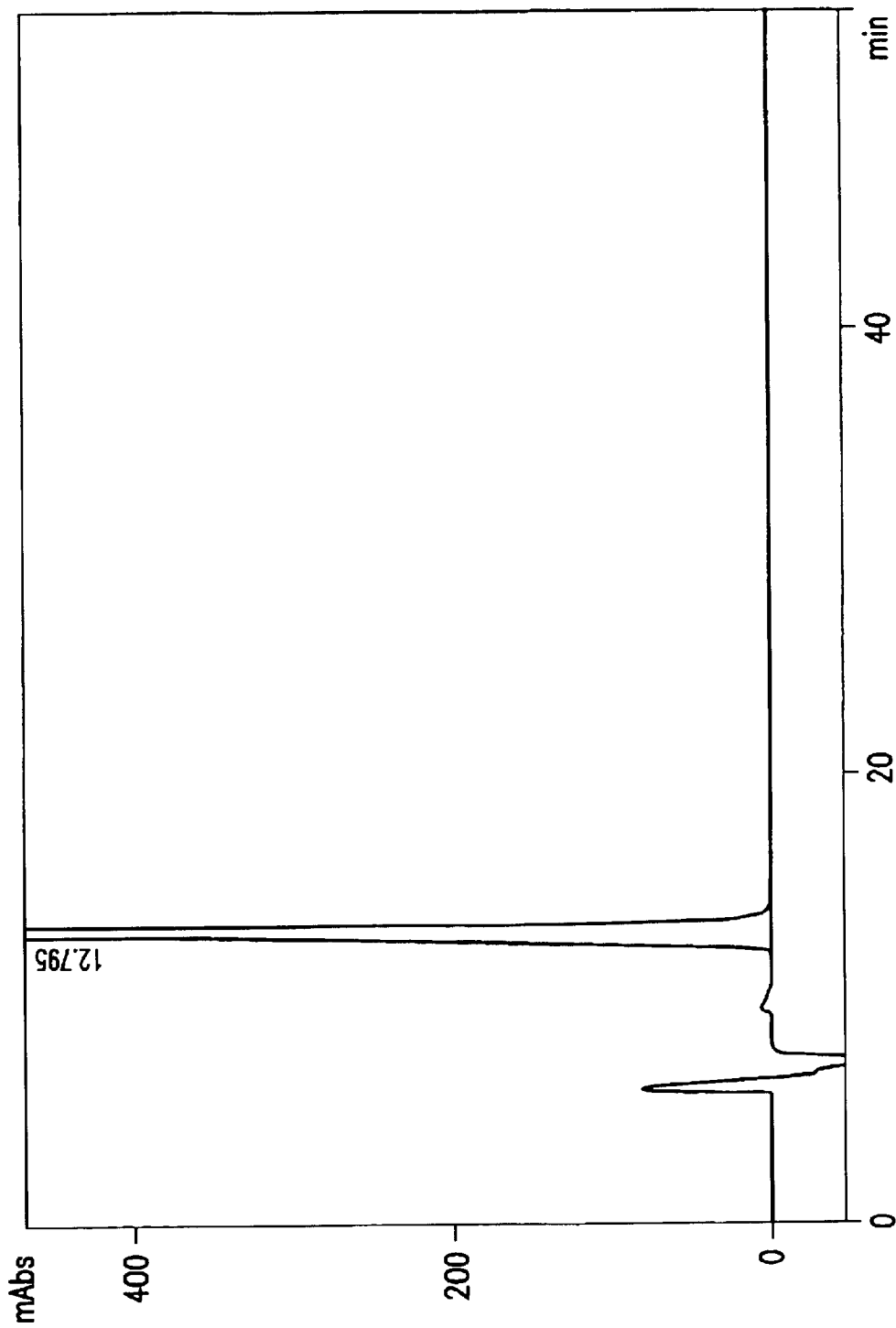
FIG. 3 shows a HPLC chart in Reference Example 103.

The title compound was produced using (R)-1-(4-methylphenyl)ethylamine and dl-4-cyano-4(2-thienyl)-5-methylhexanoic acid, in accordance with the production method of Reference Example 97. The condition of HPLC analysis are shown below, and the analysis data (HPLC chart) are shown in FIG. 3.

Condition of HPLC analysis:

Column: Daicel Chemical Industries, Ltd., CHIRALCEL OJ, 4.6×250 mm

Mobile phase: 20%(B), (A) Mixed solution of n-hexane/trifluoroacetic acid (1000:1)

(B) Mixed solution of n-hexane/isopropanol/trifluoroacetic acid (500:500:1)

Flow rate: 0.5 ml/min.

Detector: UV 231 nm

Retention time: 12.8 min.

Reference Example 104 4-cyano-4-(2-thienyl)-5-methylhexanol (Optically Active Compound)

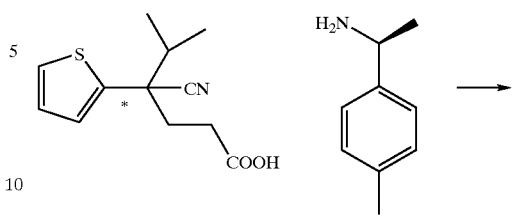

carboxylic acid A alcohol A

4-Cyano-4-(2-thienyl)-5-methylhexanoic acid (S)-1-(4-methylphenyl)ethylamine salt obtained from Reference Example 97 was returned to its carboxylic acid free form in accordance with Reference Example 97.8.31 g (35.0 mmol) of this form was dissolved in 140 ml of tetrahydrofuran, 3 drops of N,N-dimethylformamide were added by Pasteur pipette, and the mixture was ice-cooled. To the reaction solution was added dropwise 3.5 ml (40.3 mmol) of oxalyl chloride, followed by warming to room temperature and stirring for 1.5 hours. After evaporating the reaction solvent, 80 ml of tetrahydrofuran was added and the solution was ice-cooled again. 75 ml of methanol and. 6.10 ml (43.8 mmol) of triethylamine were added thereto, and the solution was stirred while warming to room temperature. After completion of the reaction, the solution was extracted with ethyl acetate. The extract was washed with an aqueous saturated sodium bicarbonate and brine, and dried over magnesium sulfate. The solvent was evaporated, and the resulting crude product obtained was crudely purified by silica gel column chromatography (hexane/ethyl acetate system), to give 8.00 g (31.8 mmol, 90.9%) of a methyl ester. 8.00 g (31.8 mmol, 90.9%) of the ester was dissolved in 50 ml of tetrahydrofuran. The solution was added dropwise into a THF suspension of 845 mg (22.3 mmol) of lithium aluminum hydride cooled to the outer temperature of −50 to −40° C., followed by heating to the outer temperature of −20° C. over 0.5 hour. After completion of the reaction, the solution was cooled again, 0–0.9 ml of water, 0.9 ml of 5N NaOH and 2.70 ml of water were successively added, and then filtered through Celite. Then, the filtrate was evaporated, and the resulting crude product was purified by silica gel column chromatography (n-hexane/ethyl acetate system), to give 6.60 g (29.6 mmol, 93.1%) of the title compound as a colorless oil. The physico-chemical data of the compound was as below. Carboxylic acid A:

¹H-NMR (400 MHz, CDCl₃) δ 0.93 (d, J=6.8 Hz, 3H), 1.21 (d, J=6.4 Hz, 3H), 2.01–2.23 (m, 3H), 2.47–2.58 (m, 2H), 6.97 (dd, J=3.6 Hz, 5.2 Hz, 1H), 7.12 (dd, J=1.2 Hz, 3.6 Hz, 1H), 7.29 (dd, J=1.2 Hz, 5.2 Hz, 1H)

Methyl ester obtained from carboxylic acid A:

¹H-NMR (400 MHz, CDCl₃) δ 0.92 (d, 1=6.8 Hz, 3H), 1.22 (d, 1=6.4 Hz, 3H), 2.03–2.20 (m, 3H), 2.43–2.58 (m, 2H), 3.64 (s, 3H), 6.96 (dd, J=3.6 Hz, 5.2 Hz, 1H), 7.12 (dd, J=1.2 Hz, 3.6 Hz, 1H), 7.29 (dd, J=1.2 Hz, 5.2 Hz, 1H)

Alcohol A:

¹H-NMR (400 MHz, CDCl₃) δ 0.92 (d, J=6.8 Hz, 3H), 1.19 (d, J=6.8 Hz, 31), 1.33–1.46 (m, 1H), 1.65–1.77 (m, 11), 1.80–1.90 (m, 1H), 2.08 (sept, J=6.8 Hz, 1H), 2.27 (ddd, J=4.4 Hz, 12.0 Hz, 13.2 Hz, 1H), 3.63 (brd-s, 2H), 6.96 (dd, J=3.6 Hz, 5.2 Hz, 11), 7.11–7.14 (1H), 7.27 (dd, J=1.2 Hz, 5.2 Hz, 1H)

Reference Example 105 4-cyano-4-(5-cyano-2-thienyl)-5-methylhexanol (Optically Active Compound)

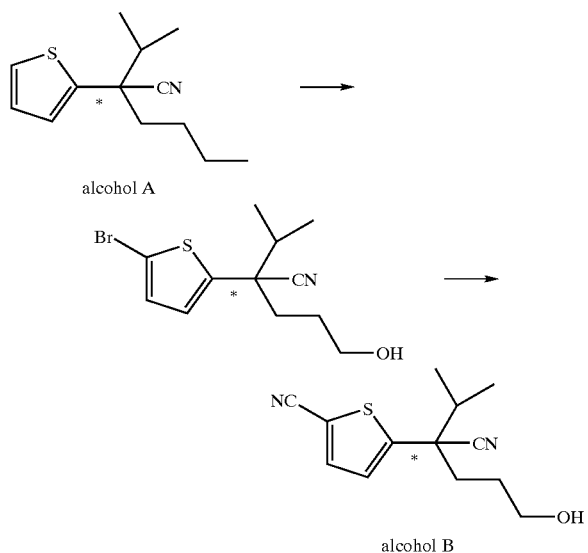

alcohol A alcohol B

Bromination reaction and successively cyanation reaction were carried out using the alcohol A obtained in Reference Example 104, as a starting material in accordance with Example 80. Namely, optically active 4-cyano-4-(5-bromo-2-thienyl)-5-methylhexanol was synthesized by the bromination reaction, and the cyanation reaction was carried out without purifying it, to give the title compound at a yield of 77:9%. The physico-chemical data of the compound was as below.

¹H-NMR (400 MHz, CDCl₃) δ 0.94 (d, J=6.59 Hz, 3H), 1.22 (d, J=6.78 Hz, 3H), 1.28–1.42 (m, 1H), 1.66–1.78 (m, 1H), 1.83–1.93 (m, 1H), 2.03–2.16 (m, 1H), 2.32 (ddd, J=4.40 Hz, 12.4 Hz, 13.2 Hz, 1H), 3.58–3.74 (m, 2H), 7.16 (d, J=3.60 Hz, 1H), 7.52 (d, J=3.60 Hz, 1H)

Example 1 1-[4-cyano-5-methyl-4-phenyl]hexyl]-4-[2-(3-acetylphenoxy)ethyl]piperpzine

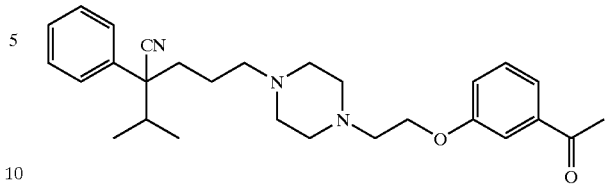

The title compound was synthesized in accordance with the method of Example 86-5) described in JP-A 11-206862.

¹H-NMR (400 MHz, CDCl₃) δ 0.77 (d, J=6.8 Hz, 3H), 1.05–1.20 (m, 1H), 1.20 (d, J=6.6 Hz, 3H), 1.50–1.60 (m, 1H), 1.80–1.95 (m, 1H), 2.05–2.20 (m, 2H), 2.25–2.35 (m, 2H), 2.35–2.48 (m, 4H), 2.48–2.65 (m, 4H), 2.59 (s, 3H), 2.81 (t, J=5.8 Hz, 2H), 4.13 (t, J=5.8 Hz, 2H), 7.08–7.13 (m, 1H), 7.26–7.32 (m, 1H), 7.34–7.40 (m, 5H), 7.46–7.50 (m, 1H), 7.52–7.56 (m, 1H).

Further, the free body is treated in accordance with the method of Example 20 described in JP-A 11-206862, to give the hydrochloride of the title compound.

ESI-Mass; 448(MH⁺)

Example 2 1-[4-cyano-5-methyl-4-phenyl)hexyl]-4-[(1-benzyl-2-pyrrolidine)methyl]piperazine

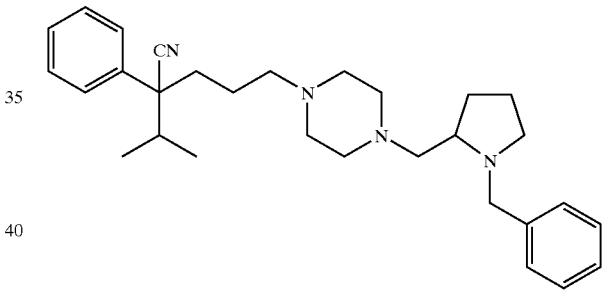

In acetonitrile (3 ml) was dissolved 1-benzyl-2-pyrrolidinemethanol (83 mg), followed by adding triethylamine (0.18 ml) and mesyl chloride (0.037 ml). After stirring at room temperature for one hour, an acetonitrile solution (3 ml) of 1-[(4-cyano-5-methyl-4-phenyl)hexyl]piperazine (124 mg) was added. After heating under reflux for 3 hours, the mixture was left to be cooled to room temperature. Ethyl acetate was added thereto, and the mixture was washed with water and brine. After drying over anhydrous magnesium sulfate, it was evaporated. The resulting residue was purified by (NH) silica gel column chromatography (hexane/ethyl acetate system), to give the title compound as a pale yellow oil (58 mg, 29%). Further, the free body was converted into a hydrochloride in a conventional method, to give the hydrochloride of the title compound.

Free Body:

¹H-NMR (400 MHz, CDCl₃) δ 0.77 (d, J=6.8 Hz, 3H), 1.05–1.18 (m, 110) 1.20 (d, J=6.8 Hz, 31), 1.49–1.73 (m, 4H), 1.83–2.00 (m, 3H), 2.07–2.18 (m, 2H), 2.20–2.64 (m, 13H), 2.87–2.93 (m 1H), 3.23 (d, J=12.8 Hz, 1H), 4.19 (d, J=12.8 Hz, 1H), 7.19–7.39 (m, 10H).

Hydrochloride:

ESI-Mass; 459(MH⁺)

Example 3 1-[4-cyano-5-methyl-4-phenyl)hexyl]-4-[(2-benzofuranyl) Methyl]piperazine

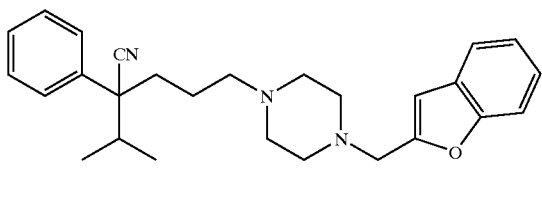

In 1,2-dichloroethane (6 ml) was dissolved 1-[4-cyano-5-methyl-4-phenyl)hexyl]piperazine (0.19 g), followed by adding benzofuran-2-carboaldehyde (0.11 g), acetic acid (0.095 ml) and sodium triacetoxyborohydride. After stirring for 3 hours at a room temperature, ethyl acetate was added thereto and the mixture was washed with water and further brine. After drying over anhydrous magnesium sulfate, it was evaporated. The resulting residue was purified by (NH) silica gel column chromatography (hexane/ethyl acetate system), to give the title compound as a pale yellow oil (0.28 g, quantitatively). Further, the free body was converted into a hydrochloride in a conventional method, to give a hydrochloride of the title compound.

Free Body:

¹H-NMR (400 MHz, CDCl₃) δ 0.76 (d, J=6.8 Hz, 31), 1.05–1.18 (m, 11), 1.19 (d, J=6.8 Hz, 3H), 1.48–1.60 (m, 1H), 1.87 (dt, J=4.4 Hz, J=12 Hz, 1H, 2.07–2.17 (m, 2H), 2.27 (t, J=7.22 Hz, 2H), 2.38 (bs, 4H, 2.52 (bs, 4H), 3.66 (s, 2H), 6.57 (s, 1H), 7.17–70.30 (m, 31), 7.32–7.37 (m, 41), 7.44–7.53 (m, 2H).

Hydrochloride:

ESI-Mass; 416(MH⁺)

Example 4 1-[(4-cyano-5-methyl-4-phenyl)hexyl]-4-[(1-methyl-2-benzimidazolyl)methyl]piperazine

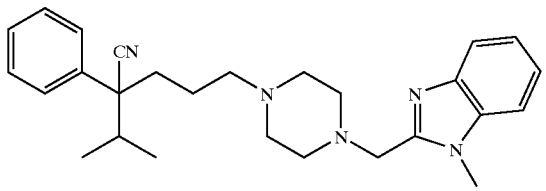

The title compound was obtained as a pale yellow oil in accordance with the method of Example 3 (86%). Further, the free body was converted into a hydrochloride in a conventional method.

Free Body:

¹H-NMR (400 MHz, CDCl₃) δ 0.77 (d, J=6.8 Hz, 3H), 1.05–1.18 (m, 11), 1.19 (d, J=6.8 Hz, 3H), 1.47–1.60 (m, 1H), 1.90 (dt, J=4.4 Hz, J=12.4 Hz, 1H), 2.05–2.38 (a, 8H), 2.50 (bs, 4H), 3.79 (s, 2H), 3.84 (s, 3H), 7.21–7.40 (m, 8H), 7.71–7.75 (m, 1H).

Hydrochloride:

ESI-Mass; 430(MH⁺)

Example 5 1-[(4-cyano-5-methyl-4-phenyl)hexyl]-4-[(3-indolyl)methyl]piperazine

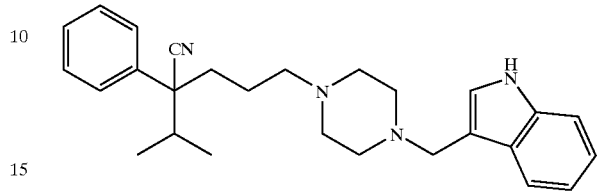

The title compound was obtained as a pale yellow oil in accordance with the method of Example 3 (76%). Further, the hydrochloride of the title compound was obtained in a conventional method.

Free Body:

¹H-NMR (400 MHz, CDcl₃) δ 0.76 (d, J=6.8 Hz, 3H), 1.04–1.18 (m, 1H), 1.18 (d, J=6.8 Hz, 3H), 1.47–1.60 (m, 1H), 1.86 (dt, J=4.4 Hz, J=12.4 Hz, 1H), 2.03–2.16 (m, 2H), 2.22–2.32 (m, 2H), 2.33 (bs, 4H), 2.49 (bs, 4H), 3.70 (s, 2H), 7.05–7.20 (m, 4H), 7.23–7.48 (m, 1H), 7.70 (d, J=6.8 Hz, 1H), 8.25–8.40 (m, 1H).

Hydrochloride:

ESI-Mass; 415(MH⁺)

Example 6 1-[(4-cyano-5-methyl-4-phenyl)hexyl]-4-[2-quinolinyl)methyl]piperazine

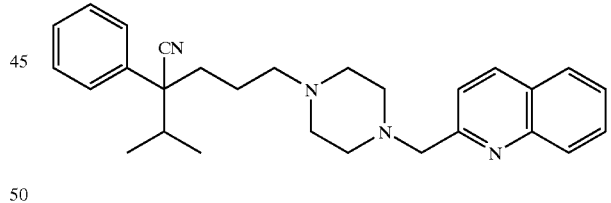

The title compound was obtained as a pale yellow oil in accordance with the method of Example 3 (62%). Further, the hydrochloride of the title compound was obtained in a conventional method.

Free Body:

¹H-NMR (400 MHz, CDCl₃) δ 0.77 (d, J=6.8 Hz, 3H), 1.06–1.18 (m, 1H), 1.20 (d, J=6.8 Hz, 3H), 1.50–1.62 (m, 1H), 1.90 (dt, J=4.4 Hz, J=12 Hz, 1H), 2.07–2.18 (m, 2H), 2.24–2.35 (m, 2H), 2.38 (bs, 4H), 2.54 (bs, 41), 3.82 (s, 2H), 7.24–7.30 (m, 1H), 7.32–7.38 (m, 4H), 7.51 (d, J=8 Hz, 1H), 7.60 (d, J=8.4 Hz, 1H), 7.66–7.72 (m, 1H), 7.79 (d, J=8 Hz, 1H), 8.06 (d, J=8.4 Hz, 1H), 8.10 (d, J=8.4 Hz, 1H).

Hydrochloride:
ESI-Mass; 427(MH⁺)

Example 7 1-[(4-cyano-5-methyl-4-phenyl)hexyl]-4-[(4-phenyl-3-pyridyl) Methyl]piperazine

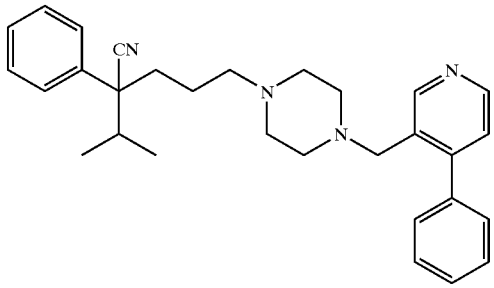

The title compound was obtained as a pale yellow oil in accordance with the method of Example 3 (47%). Further, the hydrochloride of the target compound was obtained in a conventional method.
Free Body:
$^1$H-NMR (400 MHz, CDCl$_3$) δ 0.76 (d, J=6.8 Hz, 3H), 1.04–1.18 (m, 1H), 1.19 (d, J=6.8 Hz, 3H), 1.47–1.59 (m, 1H), 1.87 (dt, J=4 Hz, J=12 Hz, 1H), 2.06–2.34 (m, 8H), 2.34 (bs. 4H), 3.39 (s, 2H), 1.18 (d, J=4.8 Hz, 1H), 7.25–7.46 (m, 10H) 8.52 (d, J=4.8 Hz, 1H), 8.63 (s, 1H).
Hydrochloride:
ESI-Mass; 427(M*')

Example 8 1-[(4-cyano-5-methyl-4-phenyl)hexyl]-4-(1.2.3.4-tetrahydro-2-naphthoyl)piperazine

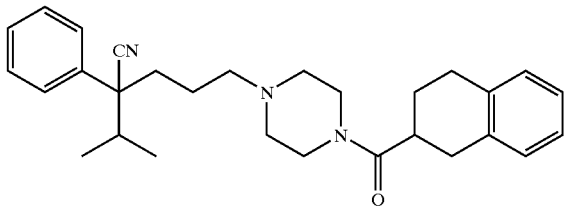

1-[(4-Cyano-5-methyl-4-phenyl)hexyl]piperazine (150 mg) was dissolved in N,N-dimethylformamide (5 ml). To the mixture were added 1-hydroxybenzotriazole (71 mg) and 1,2,3,4-tetrahydro-2-naphthenoic acid (93 mg), followed by further adding a N,N-dimethylformamide solution (2 ml) of dicyclohexylcarbodiimide (120 mg). After stirring overnight at room temperature, the insoluble matters were filtered off and ethyl acetate was added to the filtrate. A small amount of 1N hydrochloric acid was added and the mixture was stirred. Then, the mixture was washed with an aqueous saturated sodium carbonate and further with brine, dried over anhydrous magnesium sulfate, and then evaporated. The resulting residue was purified by (NH) silica gel column chromatography (n-hexane/ethyl acetate system), to give the title compound as a pale yellow oil (220 mg, 94%). Further, the hydrochloride of the free body (the title compound) was obtained in a conventional method.
Free Body:
$^1$H-NMR (400 MHz, CDCl$_3$) δ 0.78 (d, J=6.8 Hz, 3H), 1.04–1.20 (m, 1H), 1.21 (d, J=6.8 Hz, 31), 1.50–1.63 (m, 1H), 1.86–2.04 (m, 3H), 2.09–2.23 (m, 2H), 2.24–2.36 (m, 6H), 2.75–2.94 (m, 4H), 3.03–3.12 (m, 1H), 3.49 (t, J=4.8 Hz, 2H), 3.56–3.68 (m, 2H), 7.06–7.13 (m, 4H), 7.27–7.40 (m, 5H).

Hydrochloride:
ESI-Mass; 444(MH⁺)

Example 9
1-[(4-cyano-5-methyl-4-phenyl)hexyl]-4-[(1.2.3.4-tetrahydro-2-naphthyl)methyl]piperazine

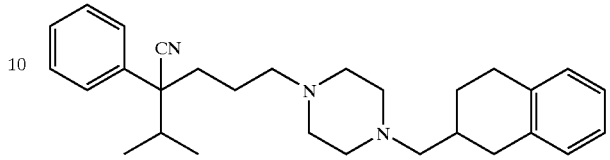

In tetrahydrofuran (5 ml) was dissolved 1-[4-cyano-5-methyl-4-phenyl]hexyl]-4-(1,2,3,4-tetrahydro-2-naphthoyl)piperazine (150 mg), followed by adding 1.0 M borane/tetrahydrofuran complex (1.35 ml) under ice-cooling. After stirring at room temperature for 5 hours, the mixture was evaporated. Methanol (5 ml) and 2N hydrochloric acid (5 ml) were added to the residue, followed by stirring at 80° C. for one hour. After cooling as it was to room temperature, the mixture was evaporated. Ethyl acetate was added thereto, and the mixture was washed with an aqueous saturated sodium carbonate and further brine, dried over anhydrous magnesium sulfate, and then evaporated. The resulting residue was purified by preparative thin layer silica gel column chromatography (methylene chloride/methanol), to give the title compound as a pale yellow oil (72 mg, 50%). Further, the hydrochloride of the free body (the title compound) was obtained in a conventional method.
Free Body:
$^1$H-NMR (400 MHz, CDCl$_3$) 6(0.78 (d, J=6.8 Hz, 3H), 1.04–1.20 (m, 21), 1.20 (d, J=6.8 Hz, 3H), 1.29–1.43 (m, 2H), 1.51–1.63 (m, 2H), 1.65–1.73 (m, 1H), 1.90 (dt, J=4.4 Hz, J=12 Hz, 1H), 1.90–2.00 (x. 4H), 2.08–2.19 (m, 2H), 2.25–2.48 (m, 7H), 2.77–2.92 (m, 3H), 7.04–7.10 (m, 4H), 7.26–7.48 (m, 5H).
Hydrochloride:
ESI-Mass; 430(MH⁺)

Example 10 1-[(4-cyano-5-methyl-4-phenyl)hexyl]-4-[2-(1,4-benzodioxanoyl]piperazine

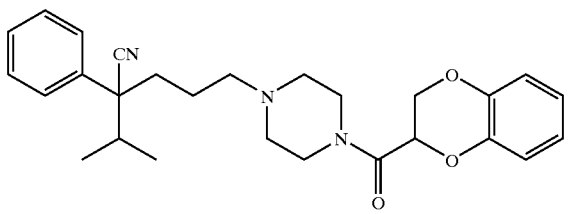

The title compound was obtained as a pale yellow oil in accordance with the method of Example 8 (86%). Further, the hydrochloride of the free body (the title compound) was obtained in a conventional method.
Free Body:
$^1$H-NMR (400 MHz, CDCl$_3$) δ 0.78 (d, J=6.8 Hz, 3H), 1.08–1.20 (m, 1H), 1.21 (d, 1=6.8 Hz, 3H), 1.51–1.63 (m, 1H. 1.92 (dt, J=4.4 Hz, J=12 Hz, 11). 2.09–2.23 (m, 2H), 2.25–2.40 (m, 6H), 3.49–3.57 (m, 2H), 3.63–3.76 (m, 2H), 4.30 (dd, J=8 Hz, J=12 Hz, 1H), 4.46 (dd, J=2.8 Hz, J=12 Hz, 1H), 4.79 (dd, J=2.8 Hz, J=8 Hz, 1H), 6.83–6.91 (m, 4), 7.27–7.40 (m, 5H).

Hydrochloride:
ESI-Mass; 448(MH+)

Example 11  1-[(4-cyano-5-methyl-4-phenyl)hexyl]-4-[2-(1,4-benzodioxanyl) Methyl]piperazine

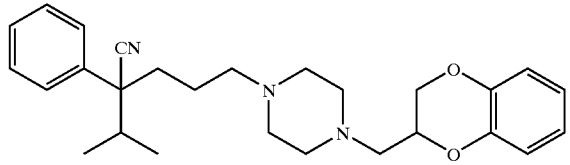

The title compound was obtained as a pale yellow oil in accordance with the method of Example 9 (56%). Further, the hydrochloride of the free body (the title compound) was obtained in a conventional method.
Free Body:
$^1$H-MMR (400 MHz, CDCl$_3$) δ 0.78 (d, J=6.8 Hz, 31), 1.16–1.20 (m, 1H), 1.20 (d, J=6.8 Hz, 3H), 1.50–1.63 (m, 1H), 1.92 (dt, J=4.44 Hz, J=12.8 Hz, 1H), 2.08–2.19 (m, 21H, 2.24–2.34 (m, 2H), 2.36 (bs, 4H), 2.52 (bs, 4H), 2.61 (ddd, J=5.6 Hz, J=13.2 Hz, J=40.4 Hz, 2H), 3.96 (dd, J=7.6 Hz, J=11.6 Hz, 1H), 4.24–4.31 (m, 2H), 6.79–6.89 (m 4H), 7.26–7.39 (m, 5H).
Hydrochloride:
ESI-Mass; 434(MH+)

Example 12  1-[(4-cyano-5-methyl-4-phenyl)hexyl]-4-(1-methyl-2-indoloyl)piperazine

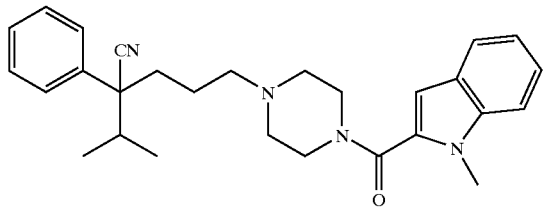

The title compound was obtained as a pale yellow oil in accordance with the method of Example 8 (82%). Further, the hydrochloride of the free body (the title compound) was obtained in a conventional method.
Free Body:
$^1$H-NMR (400 MHz, CDCl$_3$) δ 0.78 (d, J=6.8 Hz, 3H), 1.08–1.20 (nm 1H), 1.21 (d, J=6.8 Hz, 3H), 1.50–1.62 (m, 1H), 1.87–1.97: (m 1H), 2.08–2.22 (m, 2H), 2.28–2.38 (m, 6H), 3.72 (bs, 4H), 3.81 (s, 3H), 6.56 (s, 1H), 7.10–7.16 (m, 1H), 7.25–7.39 (m, 7H), 7.61 (d, 1=8 Hz, 1H).
Hydrochloride:
ESI-Mass; 443(MH+)

Example 13  1-[(4-cyano-5-methyl-4-phenyl)hexyl]-4-[(1-methyl-2-indolyl)methyl]piperazine

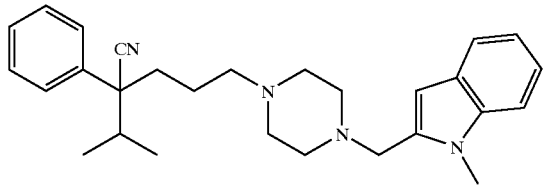

The title compound was obtained as a pale yellow oil in accordance with the method of Example 9 (40%). Further, the hydrochloride of the free body (the title compound) was obtained in a conventional method.

Free Body:
$^1$H-NMR (400 MHz, CDCl$_3$) δ 0.77 (d, J=6.8 Hz, 3H), 1.06–1.20 (m, 1H), 1.19 (d, J=6.8 Hz, 3H), 1.49–1.62 (m, 1H), 1.89 (dt, J=4.4 Hz, J=12 Hz, 1H), 2.07–2.17 (m, 2H), 2.21–2.37 (m, 6H), 2.44 (bs, 4H), 3.60 (s, 2H), 3.76 (s, 3H), 6.34 (s, 1H), 7.07 (t, J=8 Hz, 1H), 7.18 (t, J=8 Hz, 1H), 7.25–7.38 (m, 6H), 7.54 (d, J=8 Hz, 1H).

Hydrochloride:

ESI-Mass; 429(MH+)

Example 14  2-[(4-cyano-5-methyl-4-phenyl)hexyl]-5-[2-(4-fluorophenoxy)ethyl]-2.5-diazabicycl[2,2,1] heptane

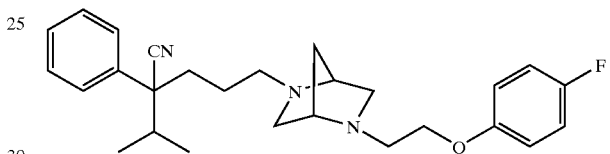

In methanol (5 ml) was dissolved 2-[(4-cyano-5-methyl-4-phenyl)hexyl]-5-benzyl-2,5-diazabicyclo[2,2,1]heptane (37 mg). To the mixture was added 20% palladium hydroxide-carbon (10 mg), followed by subjecting to hydrogenation at room temperature under normal pressure for 8 hours. After the catalyst was filtered off, the filtrate was evaporated, to give the residue as a pale yellow oil (29 mg). In N,N-dimethylformamide (3 ml) was dissolved the residue, followed by adding a N,N-dimethylformamide solution (2 ml) of triethylamine (0.027 ml) and 2-(4-fluorophenoxy) ethyl bromide (25 mg). After stirring at 50° C. overnight, the solution was left to be cooled to room temperature. Ethyl acetate was added thereto, and the mixture was washed with water and further brine. After drying over anhydrous magnesium sulfate, it was evaporated. The resulting residue was purified by preparative thin layer silica gel column chromatography (methylene chloride/methanol) to give the title compound as a pale yellow oil (20 mg, 48%). Further, the hydrochloride of the free body (the title compound) was obtained in a conventional method.

Free Body:

$^1$H-NMR (400 MHz, CDCl$_3$) δ 0.78 (d, J=6.8 Hz, 3H), 1.06–1.20 (m, 1H), 1.20 (d, J=6.8 Hz, 3H), 1.45–1.57 (m, 1H), 1.66–1.73 (m, 21), 1.95 (dt, 1=4.4 Hz, J=12 Hz, 1H), 2.11(qui, J=6.8 Hz, 1H), 2.14–2.23 (m, 1H), 2.32–2.40 (m, 1H), 2.51–2.61 (m, 2H), 2.63–2.81 (m, 3H), 2.91 (dQui, J=6 Hz, J=40.4 Hz, 2H), 3.21 (s, 1H), 3.36 (s, 1H), 3.94–4.03 (m, 2H), 6.79–6.85 (m, 2H), 6.92–7.00 (m, 2H), 7.26–7.40 (m, 5H).

Example 15 8-[(4-cyano-5-methyl-4-phenyl)hexyl]-1-phenyl-1.3.8-triazaspiro[4.5]Decan-4-One

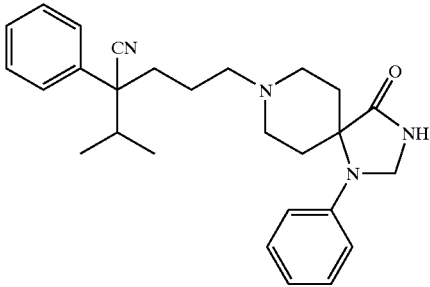

In acetonitrile (6 ml) was dissolved 4-cyano-5-methyl-4-phenylhexanol (120 mg), followed by adding triethylamine (0.23 ml) and mesyl chloride (0.051 ml) at room temperature. After stirring at room temperature for one hour, an acetonitrile solution (3 ml) of 1-phenyl-1,3,8-triazaspiro-[4,5]decan-4-one (140 mg) was added thereto. After heating under reflux for 2.5 hours, the solution was left to be cooled to room temperature. Ethyl acetate was added thereto, and the mixture was washed with water and further brine. After drying over anhydrous magnesium sulfate, it was evaporated. The resulting residue was purified by preparative thin layer silica gel column chromatography (hexane/ethyl acetate system), to give the title compound as a pale yellow oil (61 mg, 26%). Further, the hydrochloride of the free body (the title compound) was obtained in a conventional method.

Free Body:
$^1$H-NMR (400 MHz, CDCl$_3$) δ 0.79 (d, J=6.4 Hz, 3H), 1.22 (d, J=6.4 Hz, 31), 1.26 (t, J=7.2 Hz, 2H), 1.551.73 (m, 3H), 1.94–2.05(m, 1H), 2.08–2.25 (m, 2H), 2.38–2.52 (m, 2H), 2.60–2.90 (m, 6H), 4.72 (s, 2H), 6.85 (t, J=7.2 Hz, 1H), 6.90 (d, J=8 Hz, 2H), 7.24–7.31 (m, 2H), 7.33–7.41 (m, 4H)), 7.62 (bs, 1H).
Hydrochloride:
ESI-Mass; 431(MH$^+$)

Example 16 1-[(4-cyano-5-methyl-4-phenyl)hexyl-4-(2-keto-1-benzimidazolinyl)piperidine

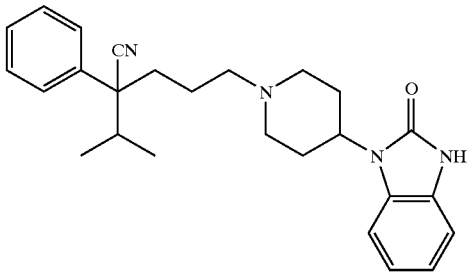

The title compound was obtained as a pale yellow oil in accordance with the method of Example 15 (23%). Further, the hydrochloride of the free body (the title compound) was obtained in a conventional method.
Free Body:
$^1$H-NMR (400 MHz, CDCl$_3$) δ 0.79 (d, J=6.8 Hz, 3H), 1.11–1.34 (m, 2H), 1.23 (d, J=6.8 Hz, 3H), 1.55–1.67 (m, 1H), 1.73–1.82 (m, 2H), 1.90–2.05 (m, 2H), 2.08–2.23 (m, 3H), 2.30–2.52 (m, 41), 2.88–3.02 (m, 2H), 4.28–4.38 (m, 1H) 7.00–7.07 (m, 2H), 7.09–7.13 (m, 1H), 7.22–7.32 (m, 2H) 7.33–7.43 (m, 4H), 10.12–10.30 (m, 1H).

Hydrochloride:
ESI-Mass; 417(MH$^+$)

Example 17 1-[4-cyano-5-methyl-4-phenyl)hexyl]-4-[(2-benzoxazolyl)amino]piperidine

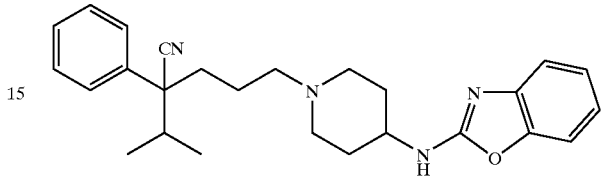

The title compound was obtained as a pale yellow oil in accordance with the method of Example 15 (30%). Further, the hydrochloride of the free body (the title compound) was obtained in a conventional method.

Free Body:

$^1$H-NMR (400 MHz, CDCl$_3$) δ 0.78 (d, J=6.8 Hz, 3H), 1.08–1.19 (m, 1H), 1.20 (d, J=6.8 Hz, 3H), 1.47–1.62 (m, 3H), 1.75–1.83 (m, 1H), 1.89 (dt, J=4.4 Hz, J=13.6 Hz, 1H), 2.00 (bt, J=12.4 Hz, 1H), 2.04–2.20 (m, 4H), 2.25–2.31 (m, 2H), 2.72 (bt, J=11.6 Hz, 2H), 3.69–3.80 (m, 1H), 4.92–5.02 (m, 1H), 6.99–7.05 (m, 1H), 7.13–7.17 (m, 1H), 7.20–7.25 (m, 1H), 7.25–7.32 (m 1H), 7.33–7.40 (m, 5H).

Hydrochloride:

ESI-Mass; 417(MH$^+$)

Example 18 1-[(4-cyano-5-methyl-4-phenyl)hexyl-4-(2-benzothiazolyl)aminopiperidine

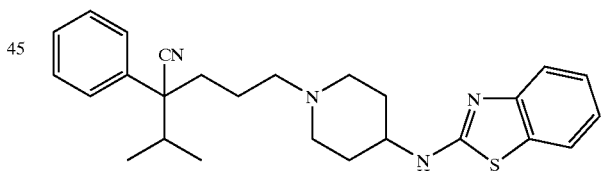

The title compound was obtained as a pale yellow oil in accordance with the method of Example 15 (52%). Further, the hydrochloride of the free body (the title compound) was obtained in a conventional method.

Free Body:

$^1$H-NMR (400 MHz, CDCl$_3$) δ 0.78 (d, J=6.8 Hz, 3H), 1.06–1.20 (m, 1H), 1.20 (d, J=6.8 Hz, 3H), 1.46–1.62 (m, 3H), 1.77 (bs, 11), 1.85–1.94 (m, 1H). 1.96–2.05 (m, 1H), 2.05–2.18 (m, 4H) 2.25–2.32 (m, 2H), 2.70 (bt, J=12.4 Hz, 2H), 3.56–3.66 (m, 1H), 5.24 (bd, J=6.8 Hz, 1H), 7.04–7.09 (m, 1H), 7.25–7.32 (m, 2H), 7.33–7.39 (m, 4H), 7.50–7.58 (m, 2H).

Hydrochloride:
ESI-Mass; 433(MH⁺)

Example 19 1-[(4-cyano-5-methyl-4-phenyl)hexyl]-4-[(2-benzothiazolyl)(methyl)amino]piperidin

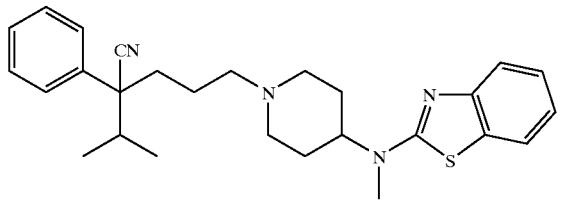

The title compound was obtained as a pale yellow oil in accordance with the method of Example 15 (30%). Further, the hydrochloride of the free body (the title compound) was obtained in a conventional method.

Free Body:
$^1$H-NMR (400 MHz, CDCl$_3$) δ 0.78 (d, J=6.8 Hz, 3H), 1.08–1.20 (m, 1H), 1.21 (d, J=6.8 Hz, 3H), 1.51–1.64 (m, 1H)1.74–2.20 (m, 9H), 2.30 (t, J=7.2 Hz, 2H), 2.82–2.93 (m, 2H), 3.05 (s. 3H), 3.94–4.05 (m, 1H), 7.01–7.06 (m, 1H), 7.24–7.33 (m, 2H), 7.34–7.40 (m, 4H), 7.51–7.59 (m, 2H).

Hydrochloride:
ESI-Mass; 447(MH⁺)

Example 20 1-[(4-Cyano-5-methyl-4-phenyl)hexyl]-4-[(2-benzothiazolyl)(2-propyl)aminopiperidine

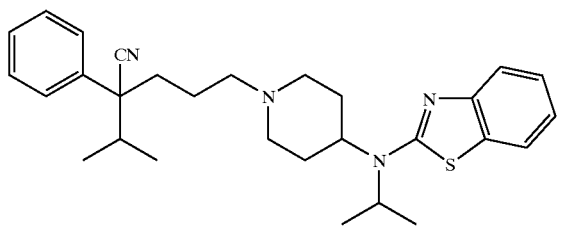

In N,N-dimethylformamide (3 ml) was dissolved 1-((4-cyano-5-methyl-4-phenyl)hexyl]-4-[(2-benzothiazolyl)amino]piperidine (50 mg) synthesized in Example 18, followed by adding 60% sodium hydride (7 mg). After stirring at 50° C. for one hour, 2-bromopropane (0.012 ml) was added. After further stirring at 50° C. overnight, 2-bromopropane (0.012 ml) was additionally added. After further stirring at 50° C. for 6 hours, 60% sodium hydride (7 mg) was additionally added. After further stirring at 50° C. overnight, the solution was left to be cooled to room temperature. Ethyl acetate was added, and the mixture was washed with water and further brine. After drying over anhydrous magnesium sulfate, it was evaporated. The resulting residue was purified by (NH) silica gel column chromatography (hexane/ethyl acetate system), to give the title compound as a pale yellow oil (31 mg, 57%). Further, the hydrochloride of the free body (the title compound) was obtained in a conventional method.

Free Body:
$^1$H-NMR (400 MHz, CDCl$_3$) δ 0.78 (d, J=6.4 Hz, 3H) 1.08–1.20 (m, 1H), 1.20 (d, J=6.4 Hz, 3H), 1.50 (d, J=6.8 Hz, 6H), 1.69–2.34 (×13H), 2.63–2.74 (m, 2H), 2.81–2.90 (m, 1H), 6.86–6.91 (m, 1H), 6.96–7.02 (m, 1H), 7.11–7.16 (m, 1H), 7.25–7.32 (m, 2H), 7.33–7.41 (m, 4H).

Hydrochloride:
ESI-Mass; 475(MH⁺)

Example 21 1-[(4-cyano-5-methyl-4-phenyl)hexyl]-4-[(1-methyl-2-benzimidazolyl)amino]piperidine

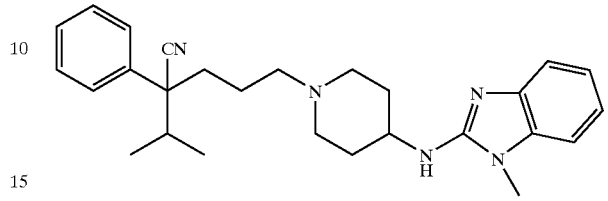

The title compound was obtained as a pale yellow oil in accordance with the method of Example 15 (12%). Further, the hydrochloride of the free body (the title compound) was obtained in a conventional method.

Free Body:

$^1$H-NMR (400 MHz, CDCl$_3$) δ 0.78 (d, J=6.8 Hz, 3H), 1.06–1.20 (m, 1H), 1.20 (d, J=6.8 Hz, 3H), 1.42–1.61 (m, 3H), 1.84–1.93 (m, 1H), 1.98–2.20 (m, 6H), 2.27 (t, J=7.2 Hz, 2H), 2.69–2.76 (m, 2H), 3.45 (s, 3H), 3.86–4.01 (m, 2H), 7.01–7.12 (m, 3H), 7.26–7.31 (m, 1H), 7.33–7.39 (m, 4H), 7.45 (d, J=7.6 Hz, 1H).

Hydrochloride:

ESI-Mass; 430(MH⁺)

Example 22 1-[(4-cyano-5-methyl-4-phenyl]hexyl]-4-[[1-(2-propyl)-2-benzimidazolyl]Aminopiperidine

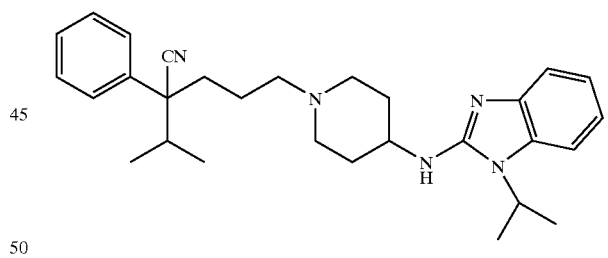

The title compound was obtained as a pale yellow oil in accordance with the method of Example 15 (54%). Further, the hydrochloride of the free body (the title compound) was obtained in a conventional method.

Free Body:

$^1$H-NMR (400 MHz, CDCl$_3$) δ 0.78 (d, J=6.8 Hz, 3H), 1.08–1.20 (m, 1H), 1.20 (d, J=6.8 Hz, 3H), 1.40–1.55 (m, 3H), 1.57 (d, J=6.8 Hz, 61), 1.85–1.93 (m, 2H), 2.02–2.20 (m, 5H), 2.28 (t, J=7.2 Hz, 2H), 2.67–2.75 (m, 2H), 3.85–4.00 (m, 2H), 4.33 (qui, J=6.8 Hz, 1H), 6.97–7.10 (m, 2H), 7.20–7.32 (m, 2H), 7.34–7.39 (m, 4H), 7.46–7.48 (m, 1H).

Hydrochloride:
ESI-Mass; 458(MH+)

Example 23 1-[(4-cyano-5-methyl-4-phenyl)hexyl]-4-[(5,6-dimethoxy-1-indanon)-2-yl]methylpiperidine

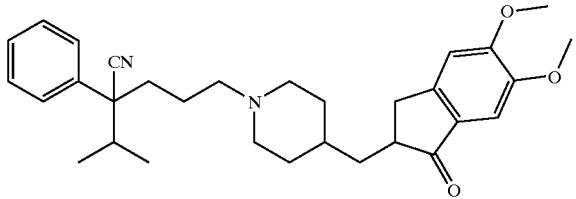

The title compound was obtained as a pale yellow oil in accordance with the method of Example 15 (30%). Further, the hydrochloride of the free body (the title compound) was obtained in a conventional method.
Free Body:
$^1$H-NMR (400 MHz, CDCl$_3$) δ 0.78 (d, J=6.8 Hz, 3H), 1.08–1.36 (m, 4H), 1.20 (d, J=6.8 Hz, 3H), 1.38–1.95 (m, 8H), 2.08–2.18 (m, 2H), 2.18–2.32 ([, 2H), 2.65–2.83 (m, 4H), 3.22 (dd, J=8 Hz, J=17.6 Hz, 1H), 3.90 (s, 3H), 3.96 (s, 3I), 6.86 (s, 1H), 7.16 (s, 1H), 7.26–7.41 ([. 5H).
Hydrochloride:
ESI-Mass; 489(MH+)

Example 24 1-[(4-cyano-5-methyl-4-phenyl)hexyl]-4-[2-(4-fluorophenoxy)ethyl](2-cyanoethyl)aminopiperidine

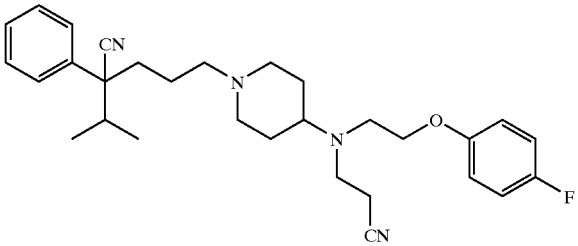

The title compound was obtained as a pale yellow oil (21%) in accordance with the method of Example 35 described later. Further, the hydrochloride of the free body (the title compound) was obtained in a conventional method.
$^1$H-NMR (400 MHz, CDCl$_3$) δ 0.77 (d, J=6.8 Hz, 3H), 1.06–1.18 (m, 1H), 1.20 (d, 1=6.8 Hz, 3H), 1.42–1.61 (m, 3H), 1.66–1.80 (m, 3H), 1.83–1.92 (m, 2H), 2.08–2.17 (m, 2H), 2.19–2.32 (m, 2H), 2.43–2.53 (m, 1H), 2.44 (t, J=6.8 Hz, 2I), 2.78–2.94 (m, 6H), 3.92 (t, J=6 Hz, 2H), 6.79–6.85 (m, 2H), 6.94–7.00 (m, 2H), 7.27–7.39 (m, 5I).
Hydrochloride:
ESI-Mass; 491(MH+)

Example 25 1-[4-cyano-5-methyl-4-(2-naphthyl)hexyl]-4-[2-(4-fluorophenoxy)ethyl]piperazine

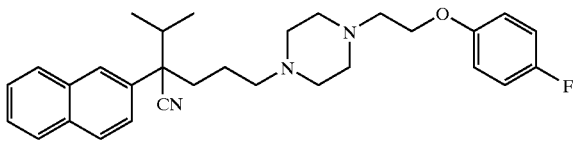

In acetonitrile (5 ml) was dissolved 310 mg (1.16 mmol) of 4-cyano-5-methyl-4-(2-naphthyl)hexanol, followed by adding 190 μL (1.36 mmol) of triethylamine and 105 μl (1.36 mmol) of mesyl chloride. After completion of mesylation, 1.11 g (7.38 mmol) of sodium iodide, 255 mg (1.85 mmol) of potassium carbonate, 414 mg (1.85 mmol) of 1-[2-(4-fluorophenoxy) ethyl]piperazine, 5 ml of dimethylformamide and 1 ml of water were added thereto, followed by heating to 60° C. After completion of the reaction, brine was added thereto and the objective product was extracted with ethyl acetate. The organic layer was washed with brine, and then dried over anhydrous magnesium sulfate. The solvent was evaporated, to give a crude product. The crude product was subjected to (NH) silica gel (eluted with ethyl acetate/hexane=2/3), to give 384 mg (0.81 mmol, 69.9%) of the title compound as a yellow syrup.
$^1$H-NMR (400 MHz, CDCl$_3$) δ 0.79 (d, J=6.8 Hz, 3H), 1.05–1.15 (m, 1H), 1.26 (d, J=6.8 Hz, 3H), 1.50–1.65 (m, 1H), 1.93–2.05 (m, 1H), 2.18–2.60 (m, 12H), 2.75 (t, J=5.8 Hz, 1R), 4.02 (t, J=5.8 Hz, 2I), 6.78–6.83 (m, 2I). 6.91–6.97 (m, 2H), 7.36 (dd, J=2.0 Hz, 8.8 Hz, 1H), 7.48–7.54 (m, 2H), 7.81–7.88 (m, 3H), 7.94 (brd-s, 1H)
ESI-Mass; 474(M+H+)

Example 26 1-[4-cyano-5-methyl-4-(1-naphthyl)hexyl]-4-[2-(4-fluorophenoxy)ethyl]piperazine

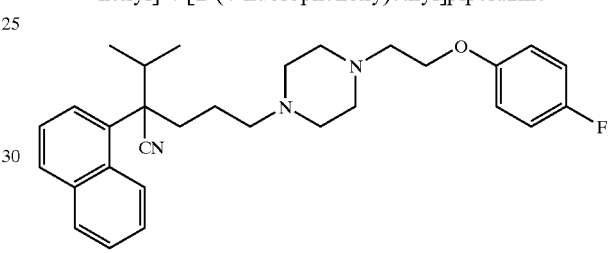

The title compound was obtained as a colorless oil in accordance with the method of Example 25 (yield: 57.8%).
$^1$H-NMR (400 MHz, CDCl$_3$) δ 0.70–0.90 (m, 3H), 0.95–1.10 (m, 1H), 1.20–1.40 (m, 4H), 1.50–1.65 (m, 1H), 1.93–2.05 (m, 1H), 2.10–2.56 (m, 10H), 2.56–2.70 (m, 1H), 2.73 (t, J=5.8 Hz, 1H), 2.90–3.00 (m, 1H), 4.01 (t, J=5.8 Hz, 2H) 6.78–6.83 (m, 2H), 6.91–6.97 (m, 2H), 7.40–7.50 (m, 3I), 7.78–7.92 (m, 3H), 8.22–8.31 (brd-s, 1H)
ESI-Mass; 474(M+H+)

Example 27 1-[4-cyano-5-methyl-4-(2-pyridyl)hexyl]-4-[2-(4-fluorophenoxy)ethyl]piperazine

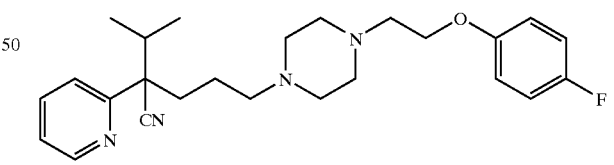

4-Cyano-5-methyl-4-(2-pyridyl)hexanol synthesized in accordance with the method of Example 25 was oxidized by SO$_3$-pyridine, which is a conventional method. The resulting crude aldehyde compound was subjected to reductive amination reaction in accordance with the method of Example 42 which is described later, to synthesize the title compound as a colorless oil (yield: 69.1%).
$^1$H-NMR (400 MHz, CDCl$_3$) δ 0.74 (d, J=6.8 Hz, 3H), 0.90–1.10 (m, 1H), 1.20 (d, J=6.4 Hz, 3H), 1.24–1.30 (in 1H), 1.53–1.66 (m, 1H), 2.03–2.23 (m, 2H), 2.24–2.74 (m, 10H), 2.81 (t, J=5.4 Hz, 2H), 4.06 t, J=5.4 Hz, 2H), 6.79–6.85 (m, 2H), 6.92–6.98 (m, 2H), 7.21 (ddd, J=1.2 Hz, 4.8 Hz, 8.0 Hz, 1H), 7.57 (dt, J=1.2 Hz, 8.0 Hz, 1H), 7.69 (dt, J=2.0 Hz, 8.0 Hz, 1H), 8.58–8.62 (m, 1H)

ESI-Mass; 425(M+H$^+$)

Example 28 1-[4-cyano-5-methyl-4-(4-pyridyl) Hexyl]-4-[2-(4-fluoronhenoxy)ethyl]piperazine

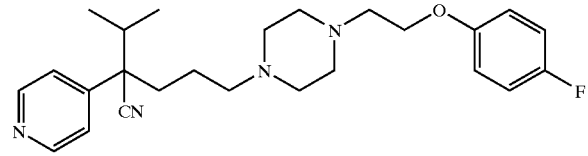

The title compound was obtained as a yellow oil in accordance with the method of Example 25 (yield: 70%).

$^1$H-NMR (400 MHz, CDCl$_3$) δ 0.79 (d, J=6.8 Hz, 3H), 1.00–1.20 (m, 1H), 1.22 (d, J=6.4 Hz, 3H1), 1.50–1.64 (m, 1H), 1.85–2.00 (m, 1H), 2.08–2.25 (m, 2H), 2.26–2.75 (m, 10H), 2.82 (t, J=5.4 Hz, 2H), 4.07 (t, J=5.4 Hz, 2H)), 6.79–6.85 (m, 2H), 6.92–6.98 (m, 2H), 7.31 (dd, J=1.6 Hz, 4.4 Hz, 2H), 8.63 (dd, J=1.6 Hz, 4.4 Hz, 2H)

ESI-Mass; 425(M+H$^+$)

Example 29 1-[(4-cyano-5-methyl-4-phenyl)hexyl]-4-phenylpiperazine

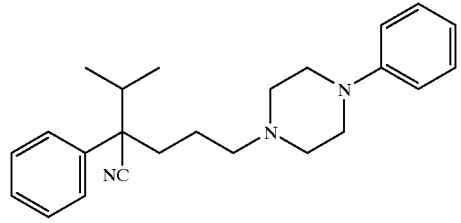

In acetonitrile (2 ml) was dissolved 100 mg (0.30 mmol) of 4-cyano-5-methyl-5-phenylhexyl iodide. To the mixture were added 55 mg (0.36 mmol) of potassium carbonate and 60 mg (0.36 mmol) of phenylpiperazine, followed by heating to 60° C. After completion of the reaction, the solution was partitioned with ethyl acetate and brine. The organic layer was dried over magnesium sulfate, and then evaporated, to give a crude product. The crude product was subjected to 20 g of Chromatorex NH silica gel (ethyl acetate/hexane-1/5), to give 137 mg (quantitative) of the title compound as a colorless syrup. The physico-chemical data of the title compound was as below.

$^1$H-NMR (400 MHz, CDCl$_3$) δ 0.78 (d, J=6.4 Hz, 3H), 1.08–1.26 (m 1H)1, 1.21 (d, J=6.8 Hz, 3H), 1.52–1.66 (m, 1H), 1.88–1.98 (m 1H), 2.08–2.23 (m, 2H), 2.28–2.37 (m, 2H), 2.42–2.52 (m, 4H), 3.10–3.20 (m, 4H), 6.82–6.86 (m, 1H), 6.88–6.92 (m, 2H), 7.22–7.32 (m, 4H), 7.34–7.40 (m, 3H)

ESI-Mass; 362(M+H$^+$)

Example 30 1-[(4-cyano-5-methyl-4-phenyl)hexyl]-4-(2-phenylethyl)piperazine

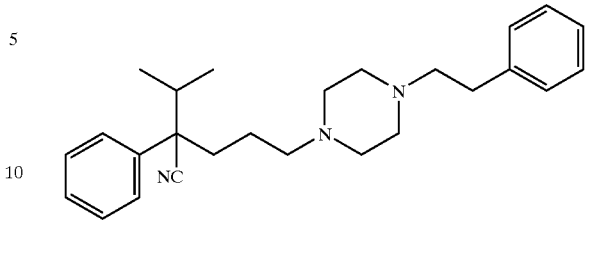

The title compound was synthesized by using 1-(2-phenylethyl)piperazine in accordance with the method of Example 29 (yield: 100%: a colorless oil).

$^1$H-NMR (400 MHz, CDCl$_3$) δ 0.78 (d, J=6.4 Hz, 31), 1.08–1.20 (m, 1H), 1.20 (d, J=6.8 Hz, 31), 1.50–1.63 (m, 1H), 1.84–1.93 (m, 1H), 2.07–2.19 (m, 2H), 2.24–2.60 (m, 2H), 2.74–2.82 (m, 2H), 7.16–7.21 (m, 3H), 7.24–7.31 (m, 3H), 7.35–7.38 (m, 4H)

ESI-Mass; 390(M+H$^+$)

Example 31 1-[(4-cyano-5-methyl-4-phenyl)hexyl]-4-(3-phenylpropyl)]piperazine

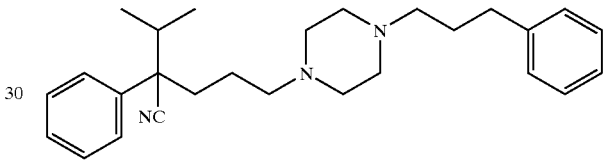

The title compound was synthesized by using 1-(3-phenylpropyl)piperazine in accordance with the method of Example 29 (yield; 100%: a colorless oil).

$^1$H-NMR (400 MHz, CDCl$_3$) δ 0.77 (d, J=6.8 Hz, 3H), 1.04–1.20 (m, 1H), 1.20 (d, J=6.4 Hz, 3H), 1.50–1.62 (m, 1H), 1.74–1.92 (m, 3H), 2.06–2.18 (m, 2H), 2.20–2.50 (m, 12H), 2.61 (t, J=7.6 Hz, 2H), 7.14–7.19 (m, 31), 7.23–7.31 (m, 3H), 7.34–7.37 (m, 4H)

ESI-Mass; 404(M+H$^+$)

Example 32 1-[(4-cyano-5-methyl-4-phenyl)hexyl]-3-[N-(2-cyanoethyl)-N-[2-(3-fluorophenoxy)ethyl] Amino]pyrrolidine

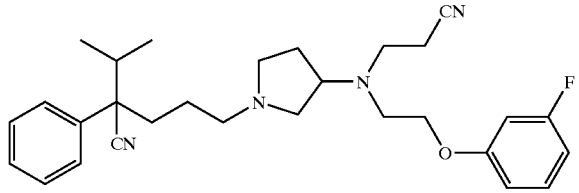

In dichloromethane (7 ml) was dissolved 250 mg (0.74 mmol) of 1-[(4-cyano-5-methyl-4-phenyl)hexyl]-3-[N-(2-cyanoethyl)amino]pyrrolidine, followed by successively adding 171 mg (1.11 mmol) of 3-fluorophenoxyacetaldehyde separately synthesized, 0.08 ml (1.48 mmol) of acetic acid and 235 mg (1.11 mmol) of sodium triacetoxyborohydride. After completion of the reaction, the solution was adjusted to basic with a 2N sodium hydroxide, and extracted with ethyl acetate. The organic layer was washed with brine, dried over magnesium sulfate, and evaporated, to give a crude product. The crude product was subjected to 25 g of Chromatorex NH silica gel (ethyl acetate/hexane=1/3), to give 290 mg (0.61 mmol, 82.2%) of the title compound as a colorless syrup.
¹H-NMR (400 MHz, CDCl₃) δ 0.77 (d, J=6.8 Hz, 3H), 1.05–1.25 (m, H), 1.20 (d, J=6.8 Hz, 3H), 1.47–1.80 (m, 2H), 1.85–2.28 (m, 41), 2.29–2.70 (m, 6H), 2.48 (t, J=6.8 Hz, 2H), 2.90–3.25 (m, 4H), 3.40–3.55 (m, 1H), 3.98 (t, J=5.6 Hz, 2H), 6.56–6.62 (k 1H), 6.63–6.90 (mL 3H), 7.18–7.25 (m, 11), 7.26–7.40 (m, 5H)
ESI-Mass; 477(M+H⁺)

Example 33 1-[(4-cyano-5-methyl-4-phenyl)hexyl]-3-[N-(2-cyanoethyl)-N-(2-(3-cyanothenoxy)ethyl] Amino]pyrrolidine

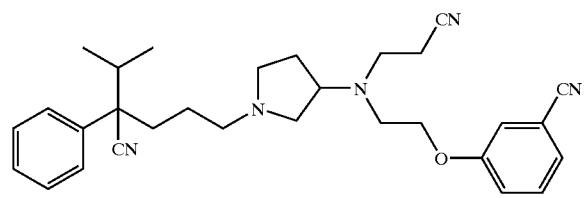

In dichloromethane (7 ml) was dissolved 250 mg (0.74 mmol) of 1-[(4-cyano-5-methyl-4-phenyl)hexyl]-3-[N-(2-cyanoethyl)amino]pyrrolidine, followed by successively adding 179 mg (1.11 mmol) of 3-cyanophenoxyacetaldehyde separately synthesized in the same manner as in the production of 3-fluorophenoxyacetaldehyde, 0.08 ml (1.48 mmol) of acetic acid and 235 mg (1.11 mmol) of sodium triacetoxyborohydride. After completion of the reaction, the solution was adjusted to basic with a 2N sodium hydroxide and extracted with ethyl acetate. The organic layer was washed with brine, dried over magnesium sulfate and evaporated, to give a crude product. The crude product was subjected to 25 g of Cromatorex NH silica gel (ethyl acetate/hexane-1/3), to give 318 mg (0.66 mmol, 88.9%) of the title compound as a colorless syrup.
¹H-NMR (400 MHz, CDCl₃) δ 0.77 (d, J=6.8 Hz, 31), 1.05–1.25 (m, 1H), 1.20 (d, J=6.8 Hz, 3H), 1.47–1.80 (m, 2H), 1.85–2.28 (m, 4H), 2.29–2.72 (m, 6H), 2.48 (t, J=6.8 Hz, 2H), 2.90–3.05 (m, 4H), 3.42–3.55 (m 1H), 4.01 (t, J=5.6 Hz, 2H), 7.11–7.15 (m, 2H), 7.23–7.40 (m, 7H)
ESI-Mass; 484(M+H⁺)

Example 34 1-[(4-cyano-5-methyl-4-phenyl)hexyl]-3-[N-(2-cyanoethyl)-N-[2-(2-cyanophenoxy)ethyl] Amino]pyrrolidine

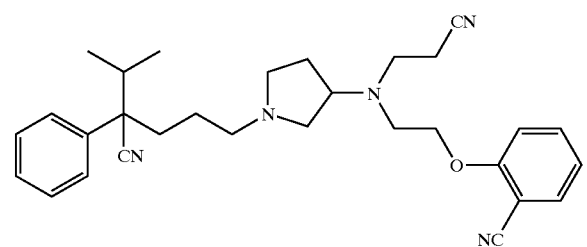

In dichloromethane (7 ml) was dissolved 263 mg (0.78 mmol) of 1-[(4-cyano-5-methyl-4-phenyl)hexyl]-3-EN-(2-cyanoethyl)amino]pyrrolidine, followed by successively adding 251 mg (1.56 mmol) of 3-cyanophenoxyacetaldehyde separately synthesized, 0.09 ml (1.56 mmol) of acetic acid and 247 mg (1.17 mmol) of sodium triacetoxyborohydride. After completion of the reaction, the solution was adjusted to basic with a 2N sodium hydroxide, and extracted with ethyl acetate. The organic layer was washed with brine, dried over magnesium sulfate and evaporated, to give a crude product. The crude product was subjected to 25 g of Cromatorex NH silica gel (ethyl acetate/hexane-1/3), to give 311 mg (0.64 mmol, 82.4%) of the title compound as a yellow syrup.

¹H-NMR (400 MHz, CDCl₃) δ 0.77 (d, J=6.8 Hz, 3H), 1.05–1.25 (m, 1H)1, 1.19 (d, J=6.4 Hz, 3H), 1.45–1.80 (a. 2H), 1.85–2.16 (x. 3H), 2.16–2.70 (m, 7H), 2.54 (t, J=6.8 Hz, 2H), 2.90–3.12 (m, 4H), 3.45–3.60 (m, 1H), 4.11 (t, J=6.8 Hz, 2H), 6.40–7.04 (m, 2H), 7.26–7.40 (m, 5H), 7.50–7.58 (x, 2H)

ESI-Mass; 484(M+H⁺)

Example 35 1-[(4-cyano-5-methyl-4-phenyl)hexyl]-3-[N-(2-cyanoethyl)-N-(2-(4-cyanophenoxy)ethyl) amino]pyrrolidine

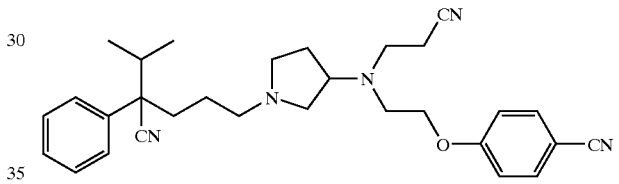

In acetonitrile (5.00 ml) was dissolved 217 mg (1.00 mmol) of 4-cyano-5-methyl-5-phenylhexylhexanol, followed by cooling to 0° C. To the mixture were added 320 μl (2.30 eq) of triethylamine and 85 μl (1.10 eq) of mesyl chloride, followed by heating to room temperature. After 15 minutes, 450 mg (3.00 eq) of sodium iodide and 370 mg (1.30 mmol) of 3-[N-(2-cyanoethyl)-N-(2-(4-cyanophenoxy)ethyl)amino]pyrrolidine were added, and the mixture was heated to 60° C. After completion of the reaction, brine was added and the objective product was extracted with ethyl acetate. The organic layer was washed with brine, and then dried over anhydrous magnesium sulfate. The solvent was evaporated, to give a crude product. The crude product was subjected to 37 g of Cromatorex NH silica gel (ethyl acetate/hexane=1/1), to give 316 mg (0.65 mmol, 65%) of the title compound as a yellow syrup.

¹H-NMR (400 MHz, CDCl₃) δ 0.77 (d, J=6.8 Hz, 3H), 1.10–1.25 (m, 1H), 1.19 (d, J=6.4 Hz, 3H), 1.48–1.63 (m, 1H), 1.65–1.77 (m, 1H), 1.78–1.97 (m, 1H), 1.98–2.17 (m, 2H), 2.19–2.30 (m, 1H), 2.30–2.73 (m, 6H), 2.48 (t, J 6.8 Hz, 2H), 2.90–3.07 (m, 4H), 3.43–3.56 (u 1H)., 4.04 (t, J=5.8 Hz, 2H), 6.94 (d, J=9.2 Hz, 2H), 7.27–7.34 (m, 1H), 7.34–7.40 (m, 4H), 7.59 (d, J=9.2 Hz, 2H)

ESI-Mass; 484(M+H⁺)

Example 36 1-[((4-cyano-5-methyl-4-(2-thienyl))hexyl]-3-[N-(2-cyanoethyl)-N-[2-(4-cyanophenoxy)ethyl]Amino]pyrrolidine

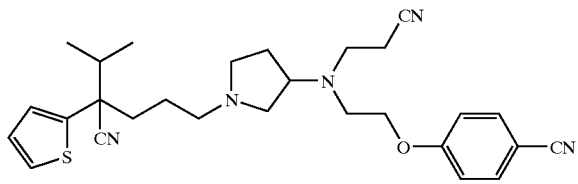

The title compound was synthesized by using 4-cyano-5-methyl-5-(2-thienyl)hexanol in accordance with the method of Example 35 (yield: 38%; a pale yellow syrup).
$^1$H-NMR (400 MHz, CDCl$_3$) δ 0.90 (d, J=6.8 Hz, 3H), 1.18 (d, J=6.4 Hz, 3H). 1.25–1.40 (m, 1H), 1.55–1.85 (m, 2H), 1.98–2.12 (m, 3N), 2.18–2.78 (m, 7H), 2.48 (t, J=6.8 Hz, 2H), 2.90–3.10 (m, 41), 3.44–3.58 (m, 1H), 4.05 (t, J=5.6 Hz, 2H), 6.92–6.98 (m, 3H), 7.10–7.13 (m, 1H), 7.25–7.29 (m, 1H), 7.59 (d, J=8.8 Hz, 2H)
ESI-Mass; 490(M+H$^+$)

Example 37 1-[(4-cyano-5-methyl-4-(2-thienyl))hexyl]-3-[N-(2-cyanoethyl)-N-{2-(3-cyanophenoxy)ethyl}amino]pyrrolidine

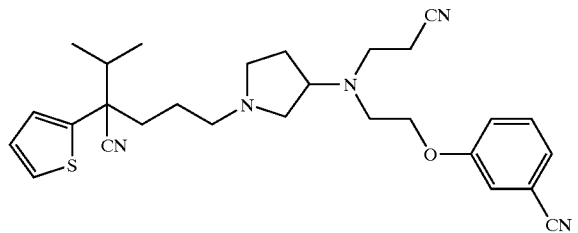

The title compound was synthesized by using 4-cyano-5-methyl-5-(2-thienyl)hexanol and 3-cyanophenoxyacetaldehyde in accordance with the method of Example 35 (yield: 98%; a pale yellow syrup).
$^1$H-NMR (400 MHz, CDCl$_3$) δ 0.90 (d, J=6.4 Hz, 3H), 1.18 (d, J=6.4 Hz, 3H), 1.28–1.45 (m, 1H), 1.58–1.90 (m, 2H), 2.00–2.15 (m, 3H), 2.20–2.31 (m 1H). 2.32–2.80 (m, 6H), 2.49 (t, J=6.8 Hz, 2H), 2.90–3.08 (m, 4H), 3.47–3.62 (m, 1H), 4.02 (t, J=5.6 Hz, 2H), 6.96 (dd, J=5.2 Hz, 3.6 Hz, 1H), 7.11–7.16 (m, 3H), 7.24–7.29 (m, 2H), 7.38 (dd, J=7.8 Hz, 9.0 Hz, 1H)
ESI-Mass; 490(M+H$^+$)

Example 38 1-[(4-cyano-5-methyl-4-phenyl)hexyl]-4-[(6-phenylpyridine-3-yl)methyl]piperazine

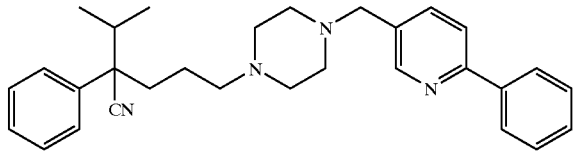

(6-Phenylpyridin-3-yl)methanol (185 mg, 1.00 mmol) and triethylamine 0.29 ml were dissolved in 5 ml of acetonitrile, and 85.1 μl (1.10 mmol) of methanesulfonyl chloride was added dropwise thereinto. After confirming the extinction of a raw material by thin layer chromatography, 340 mg (1.19 mmol) of 1-[(4-cyano-5-methyl-4-phenyl)hexyl]piperazine was added to the reaction solution at room temperature, and successively 899 mg of sodium iodide, 5 ml of dimethylformamide and 1 ml of water were added. Then, the mixture was heated to 80° C. After completion of the reaction, brine was added and the mixture was extracted with ethyl acetate. The organic layer was washed with brine, dried over magnesium sulfate and evaporated, to give a crude product. The crude product was subjected to 50 g of Cromatorex NH silica gel (ethyl acetate/hexane=1/2), to give 300 mg (0.66 mmol, 66.3%) of the title compound as a yellow oil.
$^1$H-NMR (400 MHz, CDCl$_3$) δ 0.77 (d, J=6.8 Hz, 3H), 1.06–1.26 (m, 1H), 1.20 (d, J=6.4 Hz, 3H), 1.48–1.64 (m, 1H), 1.84–1.97 (m, 1H), 2.06–2.22 (m, 2H), 2.23–2.60 (m, 10H), 3.54 (s, 2H), 7.24–7.32 (m, 1H), 7.32–7.43 (m, 5H), 7.43–7.50 (m, 2H), 7.66–7.74 (m, 2H), 7.95–7.99 (m, 2H), 8.58 (brd-s, 1H)
ESI-Mass; 453(M+H$^+$)

Example 39 1-[(4-cyano-5-methyl-4-phenyl)hexyl]-4-[(5-phenylisoxazo-3-yl)methyl]piperazine

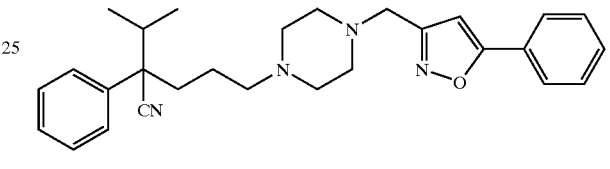

(5-Phenylisoxazol-3-yl)methanol (61.3 mg, 0.35 mmol) and triethylamine 0.10 ml were dissolved in 3 ml of acetonitrile, followed by adding dropwise 27.1 μl (0.35 mmol) of methanesulfonyl chloride thereinto. After confirming the extinction of a raw material by thin layer chromatography, 100 mg (0.35 mmol) of 1-[(4-cyano-5-methyl-4-phenyl)hexyl]piperazine was added to the reaction solution at room temperature, and successively 262 mg of sodium iodide and 2 ml of dimethylformamide were added. Then, the mixture was heated to 70° C. After completion of the reaction, brine was added and the mixture was extracted with ethyl acetate. The organic layer was washed with brine, dried over magnesium sulfate and evaporated, to give a crude product. The crude product was subjected to 15 g of Cromatorex NH silica gel (ethyl acetate/hexane=2/3), to give 45 mg (0.10 mmol, 29.0%) of the title compound as a yellow syrup.
$^1$H-NMR (400 MHz, CDCl$_3$) δ 0.77 (d, J=6.8 Hz, 3H), 1.06–1.26 (m, 1H), 1.20 (d, J=6.4 Hz, 3H), 1.48–1.64 (m, 1H), 1.86–1.98 (m, 1H), 2.06–2.20 (m, 2H), 2.25–2.70 (m, 10H), 3.63 (s, 2H), 6.54 (s, 1H), 7.24–7.32 (m, 1H), 7.32–7.39 (m, 4H), 7.39–7.49 (m, 3H), 7.74–7.79 (m, 2H)
ESI-Mass; 443(M+H$^+$)

Example 40 1-[(4-cyano-5-methyl-4-phenyl)hexyl]-4-[(2-phenylthiazo-4-yl)methyl]piperazine

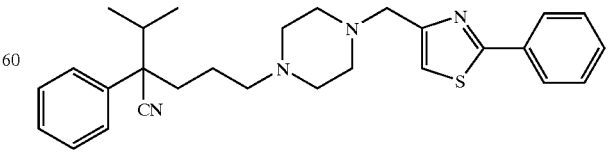

(2-Phenylthiazol-4-yl)methanol (66.9 mg, 0.35 mmol) and 0.10 ml of triethylamine were dissolved in acetonitrile, and 27.1 µl (0.35 mmol) of methanesulfonyl chloride was added dropwise thereinto. After confirming the extinction of a raw material by thin layer chromatography, 100 mg (0.35 mmol) of 1-[(4-cyano-5-methyl-4-phenyl)hexyl]piperazine was added to the reaction solution at room temperature. Further, 262 mg of sodium iodide, 2 ml of dimethylformamide and 2 ml of acetonitrile were added thereto, followed by heating to 70° C. After completion of the reaction, brine was added thereto and the mixture was extracted with ethylacetate. The organic layer was washed with brine, dried over magnesium sulfate and evaporated, to give a crude product. The crude product was subjected to 15 g of Cromatorex NH silica gel (ethyl acetate/hexane-1/2), to give 63 mg (0.14 mmol, 40.0%) of the title compound as a colorless syrup.

$^1$H-NMR (400 MHz, CDCl$_3$) δ 0.77 (d, J=6.8 Hz, 3H), 1.05–1.25 (m, 1H), 1.20 (d, J=6.4 Hz, 3H), 1.48–1.64 (m, 1H), 1.82–1.98. (m, 1H), 2.05–2.22 (x. 2H), 2.23–2.80 (m, 10H), 3.74 (s, 2H), 7.13 (s, 1H), 7.25–7.32 (m, 1H), 7.32–7.39 (m, 4H), 7.39–7.45 (m, 3H), 7.91–7.95 (m, 2H)
ESI-Mass; 459(M+H$^+$)

Example 41 1-[(4-Cyano-5-methyl-4-phenyl)hexyl]-4-[(2-phenyloxazo-4-yl)methyl]piperazine

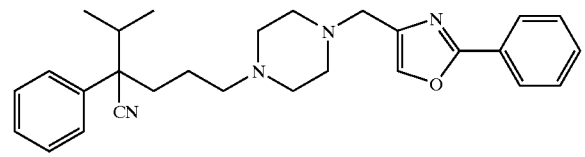

(2-Phenyloxazol-4-yl) methanol (61.3 mg, 0.35 mmol) and 0.10 ml of triethylamine were dissolved in 3 ml of acetonitrile, and 27.1 µl (0.35 mmol) of methanesulfonyl chloride was added dropwise thereinto. After confirming the extinction of a raw material by thin layer chromatography, 100 mg (0.35 mmol) of 1-[(4-cyano-5-methyl-4-phenyl)hexyl]piperazine was added to the reaction solution at room temperature. Further, 262 mg of sodium iodide and 2 ml of dimethylformamide were added thereto, followed by heating to 70° C. After completion of the reaction, brine was added thereto and the mixture was extracted with ethyl acetate. The organic layer was washed with brine, dried over magnesium sulfate and evaporated, to give a crude product. The crude product was subjected to 15 g of Cromatorex NH silica gel (ethyl acetate/hexane=2/3), to give 41 mg (0.09 mmol, 26.5%) of the title compound as a colorless syrup.

$^1$H-NMR (400 MHz, CDCl$_3$) δ 0.77 (d, J=6.8 Hz, 3H), 1.07–1.24 (m, 1H), 1.19 (d, J=6.8 Hz, 3H), 1.49–1.64 (m, 1H), 1.84–1.96 (m, 1H), 2.06–2.20 (m, 2H), 2.26–2.74 (m, 10H), 3.54 (s. 2H), 7.24–7.32 (m, 1H), 7.32–7.39 (m, 4H), 7.41–7.46 (m, 3H), 7.58 (s, 110, 8.01–8.06 (m, 2H)
ESI-Mass; 443(M+H$^+$)

Further, in the above-mentioned Examples, (6-phenylpyridin-3-yl)methanol and (5-phenylisoxazol-3-yl)methanol are synthesized in accordance with the method described in Med.Chem. 1998, 41, 2390–2410, (2-phenyloxazol-4-yl)methanol was synthesized in accordance with the method described in Org.Chem. 1996, 61, 6496–6497, and (2-phenylthiazol-4-yl)methanol was synthesized in accordance with the method described in Bull. Chem. Soc. Jpn. 71, 1391-1396 (1998).

Example 42 1-[14-cyano-5-methyl-4-phenyl)hexyl]-4-[2-(4-phenyl-2-oxo-3-oxazolidinyl)ethyl] piperazine

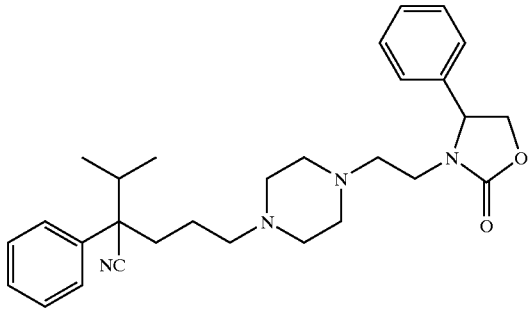

5 ml of 2-(4-phenyl-2-oxo-3-oxazolidinyl)acetaldehyde dimethylacetal was dissolved in 5 ml of acetone and 6 mL of 2.5 N hydrochloric acid, and the mixture was heated. After completion of the reaction, the mixture was extracted with ethyl acetate. The organic layer was washed with brine, dried over magnesium sulfate and evaporated, to give 300 mg of a crude product of 2-(4-phenyl-2-oxo-3-oxazolidinyl) acetaldehyde. The crude product was used for the following reaction without purification. Namely, 2-(4-phenyl-2-oxo-3-oxazolidinyl)acetaldehyde was dissolved in 5 ml of dichloroethane, and 300 mg (1.46 mmol) of the above-mentioned 2-(4-phenyl-2-oxo-3-oxazolidinyl)acetaldehyde, 0.11 ml (2.00 mmol) of acetic acid and 318 mg (1.50 mmol) of sodium triacetoxyborohydride were successively added. After completion of the reaction, the solution was adjusted to basic with a 2N sodium hydroxide, and extracted with ethyl acetate. The organic layer was washed with brine, dried over magnesium sulfate and evaporated, to give a crude product. The crude product was subjected to 50 g of Cromatorex NH silica gel (ethyl acetate/hexane=1/1), to give 477 mg (0.94 mmol, 94.2%) of the title compound as a colorless syrup.

$^1$H-NMR (400 MHz, CDCl$_3$) δ 0.77 (d, J=6.8 Hz, 3H), 1.08–1.22 (m, 1H), 1.20 (d, J=6.4 Hz, 3H), 1.48–1.63 (m, 1H), 1.85–1.96 (m, 1H), 2.06–2.18 (m, 2H), 2.20–2.52 (m, 12H), 2.84 (dt, J=6.4 Hz, 14.4 Hz, 1H), 3.57 (dt, J=6.4 Hz, 14.4 Hz, 1H, 4.05 (dd, J=7.6 Hz, 8.8 Hz, 1H), 4.61 (t, J=8.8 Hz, 1H), 4.90–4.98 (m, 1H), 7.25–7.32 (m, 2H), 7.34–7.43 (m, 8H)
ESI-Mass; 475(M+H$^+$)

Example 43 1-[(4-cyano-5-methyl-4-phenyl)hexyl]-4-[(3-phenyl-2-oxo-5-oxazolidinyl)methyl] piperazine

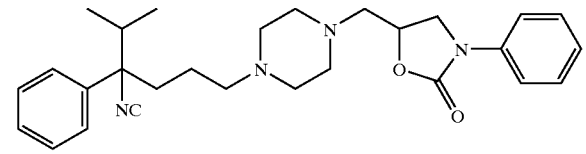

5-(Hydroxymethyl)-3-phenyl-2-oxooxazolidine was synthesized in accordance with the method described in J. Med. Chem. 989 673–1681. The 5-(hydroxymethyl)-3-phenyl-2-oxooxazolidine (193 mg, 1.00 mmol) and 0.29 ml of triethylamine were dissolved in 5 ml of acetonitrile, followed by adding dropwise 85.1 µl (1.10 mmol) of methanesulfonyl chloride thereinto. After confirming the extinction of a raw material by thin layer chromatography, 340 mg (1.19 mmol) of 1-[(4-cyano-5-methyl-4-phenyl) hexyl]piperazine was added to the reaction solution at a room temperature, and successively 899 mg of sodium iodide, 5 ml of dimethylformamide and 1 ml of water were added. Then, the mixture was heated to 60° C. After completion of the reaction, brine was added and the mixture was extracted with ethyl acetate. The organic layer was washed with brine, dried over magnesium sulfate and evaporated, to give a crude product. The crude product was subjected to 50 g of Cromatorex NH silica gel (ethyl acetate/hexane=1/1), to give 110 mg (0.24 mmol, 23.9%) of the title compound as a yellow oil.
$^1$H-NMR (400 MHz, CDCl$_3$) δ 0.77 (d, J=6.8 Hz, 3H), 1.10–1.25 (m, 11), 1.20 (d, J=6.8 Hz, 3H), 1.50–1.65 (m, 11, 1.86–2.03 (m, 1H), 2.05–2.22 (m, 2H), 2.22–2.80 (m, 12H), 3.75–3.82 ([. 1H, 4.06 (t, J=8.8 Hz, 1H), 4.70–4.80 (m, 1H), 7.11–7.16 (m, 1H), 7.27–7.33 (m, 1H), 7.33–7.40 (m, 6H). 7.51–7.56 (m, 2H)
ESI-Mass; 461(M+H$^+$)

Example 44 1-[(4-cyano-5-methyl-4-phenyl)hexyl]-4-[(5-phenyl-12.4-oxadiazol-3-yl)methyl]piperazine

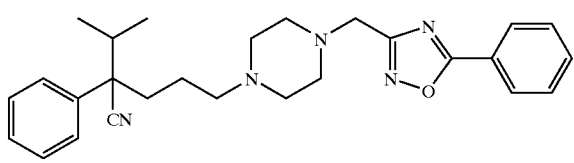

In tetrahydrofuran (3 ml) were dissolved 95.3 Mg (0.70 mmol) of benzamidoxime and molecular sieve 4A (400 mg). To the mixture were added 32 mg (0.8 mmol) of sodium hydride and further 20 mg were added, followed by heating to 60° C. After 10 minutes, 3 ml of tetrahydrofuran solution of 500 mg (1.40 mmol) of 1-[(4-cyano-5-methyl-4-phenyl) hexyl]-4-[(methoxycarbonyl)methyl]piperazine was added thereto, followed by heating under reflux. After completion of the reaction, brine was added and the mixture was extracted with ethyl acetate. The organic layer was washed with brine, dried over magnesium sulfate and evaporated, to give a crude product. The crude product was subjected to preparative chromatography (ethyl acetate: 10%) and further subjected to 25 g of Cromatorex NH silica gel (ethyl acetate/hexane=3:5), to give 127 mg (0.29 mmol, 40.9%) of the title compound as a colorless oil.
$^1$H-NMR (400 MHz, CDCl$_3$) δ 0.77 (d, J=6.4 Hz, 31), 1.04–1.20 (m, 1H), 1.19 (d, J=6.4 Hz, 3H), 1.45–1.60 (m, 1H), 1.80–1.92 (m, 1H), 2.05–2.18 (m, 2H), 2.22–2.31 (×2H), 2.31–2.50 (m, 4H), 2.55–2.70 (m, 4H), 3.90 (s, 2H), 4.06 (t, J=8.8 Hz, 1H), 4.70–4.80 (m, 1H), 7.25–7.32 (m, 1H), 7.33–7.37 (m, 4H), 7.45–7.51 (m, 3H), 8.06–8.10 (m, 2H)
ESI-MS; 444(M+H$^+$)

Example 45 1-[(4-cyano-5-methyl-4-phenyl)hexyl]-4-[5-(3-Fluorophenyl)-1.2.4-oxadiazol-3-yl)methyl]piperazine

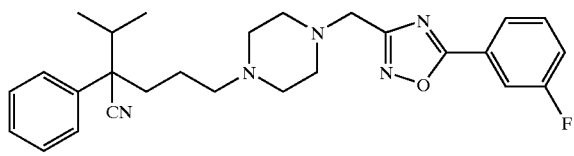

The title compound was synthesized by using 3-fluorobenzamidoxime in accordance with the method for producing 1-[(4-cyano-5-methyl-4-phenyl)hexyl]-4-[(5-phenyl-1,2,4-oxadiazol-3-yl)methyl]piperazine in Example 44 (yield; 26%: a pale yellow syrup).
$^1$H-NMR (400 MHz, CDCL$_3$) δ 0.77 (d, J=6.8 Hz, 3H), 1.06–1.22 (m, 1H), 1.20 (d, J=6.8 Hz, 3H), 1.50–1.62 (m, 1H), 1.83–1.96 (m, 1H), 2.05–2.20 (m, 2H), 2.20–2.54 (m, 6H), 2.55–2.76 (m, 4H), 3.90 (s, 2H), 4.06 (t, J=8.8 Hz, 1H), 4.70–4.80 (m, 1H), 7.17–7.25 (m, 1H), 7.25–7.32 (m, I), 7.32–7.38 (m, 4H), 7.42–7.48 (m, 1H), 7.77–7.82 (m, 1H), 7.86–7.90 (m, 1H)
ESI-MS; 462(M+H$^+$)

Example 46 1-1-[(4-cyano-5-methyl-4-phenyl) hexyl]-4-[(2-(4-fluorophenoxy)ethyl]piperidine

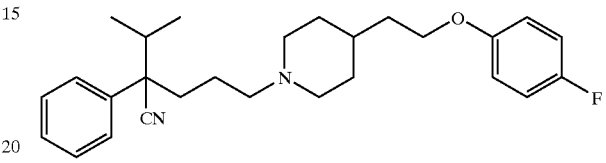

In acetonitrile (2 ml) was dissolved 100 mg (0.30 mmol) of 4-cyano-5-methyl-4-phenylhexyl iodide. To the mixture were added 55 mg (0.36 mmol) of sodium carbonate and 80 mg (0.36 mmol) of 4-[(2-(4-fluorophenoxy)ethyl)piperidine, followed by heating to 60° C. After completion of the reaction, the mixture was partitioned between ethyl acetate and brine. The organic layer was dried over magnesium sulfate and then evaporated, to give a crude product. The crude product was subjected to 40 g of Cromatorex NH silica gel (ethyl acetate/hexanel=1:5), to give 120 mg (0.28 mmol, 94.7%) of the title compound as a colorless syrup. The physico-chemical data of the title compound was as below.
$^1$H-NMR (400 MHz, CDCl$_3$) δ 0.77 (d, J=6.8 Hz, 3H), 1.05–1.24 (m, 1H), 1.20 (d, J=6.8 Hz, 3H), 1.22–1.32 (m, 2H), 1.42–1.80 (m, 7H), 1.81–1.92 (m, 2H), 2.07–2.18 (m, 2H), 2.20–2.28 (m, 2H), 2.70–2.80 (m, 2H), 3.93 (t, J=6.8 Hz, 2H), 6.78–6.83 (m, 2H), 6.92–6.98 (m, 2H), 7.25–7.38 (m, 5H)
ESI-MS; 423(M+H$^+$)

Example 47 1-Benzyl-4-[(4-cyano-5-methyl-4-phenyl)hexyl]]piperidine

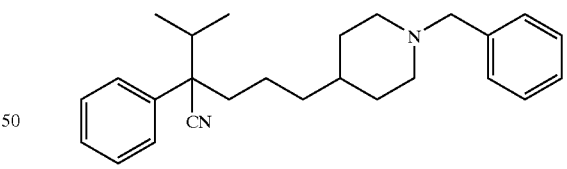

In DMF (70 ml) was dissolved 2.39 g (15.0 mmol) of 3-methyl-2-phenylpentanenitrile. To the mixture was added 600 mg (60% by weight, 15.0 mmol) of sodium hydride, followed by heating to 60° C. After 30 minutes, the reaction solution was returned to room temperature, 2.90 g (9.31 mmol) of 1-benzyl-4-methanesulfonyloxypropylpiperidine dissolved in 10 ml of DMF was added, and the mixture was heated again. After completion of the reaction, the mixture was partitioned between ethyl acetate and brine. The organic layer was dried over magnesium sulfate, and then evaporated, to give a crude product. The crude product was subjected to 100 g of silica gel (ethyl acetate/hexane=1/00 to 1/0), to give 2.57 g (6.86 mmol, 73.7%) of the title compound as a yellow oil.

¹H-NMR (400 MHz, CDCl₃) δ 0.77 (d, J=6.8 Hz, 3H) 0.85–0.98 (m, 1H)1, 1.06–1.26 (m, 6H), 1.18 (d, J=6.4 Hz, 3H), 1.30–1.44 (m, 1H), 1.44–1.56 (m, 2H), 1.74–1.90 (m, 3H), 2.03–2.15 (m, 2H), 2.76–2.86 (m, 2H), 3.44 (s, 2H), 7.20–7.38 (m, 10H)

Example 48 1-[(2-(4-Fluorophenoxy)ethyl]-4-[(4-cyano-5-methyl-4-phenyl)hexyl]piperidine

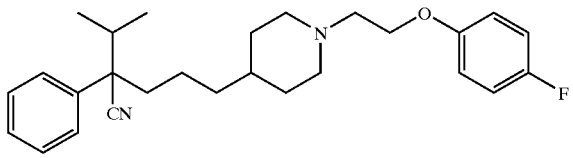

In acetonitrile (5 ml) was dissolved 200 mg (0.70 mmol) of 4-((4-cyano-5-methyl-4-phenyl)hexyl]piperidine. To the mixture were added 69 mg (0.50 mmol) of potassium carbonate and 110 mg (0.50 mmol) of 4-fluorophenoxyethyl bromide, followed by heating to 60° C. After completion of the reaction, the mixture was partitioned between ethyl acetate and brine. The organic layer was dried over magnesium sulfate, and then evaporated, to give a crude product. The crude product was subjected to 40 g of Cromatorex NH silica gel (ethyl acetate/hexane=1/7), to give 160 mg (0.38 mmol, 76.0%) of the title compound as a colorless syrup. The physico-chemical data of the compound was as below.
¹H-NMR (400 MHz, CDCl₃) δ 0.77 (d, J=6.8 Hz, 3H), 0.85–0.98 (m, 1H), 1.10–1.30 (m, 5H), 1.19 (d, J=6.8 Hz, 3H), 1.30–1.43 (m, 1H), 1.50–1.66 (m, 2H), 1.74–1.85 (m, 11), 1.92–2.03 (m, 2H), 2.05–2.14 (m, 2H), 2.72 (t, J=6.0 Hz, 2H), 2.88–2.95 (m, 2H), 4.03 (t, J=6.0 Hz, (m, 2H), 6.79–6.84 (m, 2H), 6.92–6.98 (m, 2H), 7.26–7.38 (m, 5H)
ESI-MS; 423(M+H⁺)

Example 49 1-[(4-cyano-5-methyl-4-phenyl)hexly]-4-[3-cyano-3-(2-thienyl)propyl]piperazine

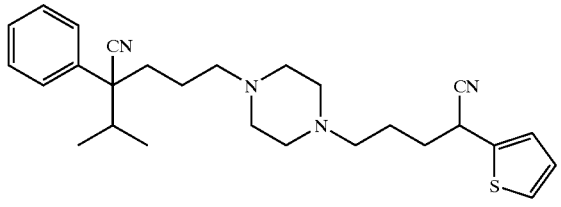

The free body of the title compound was obtained as a yellow oil from 3-cyano-3-(2-thienyl)propanol (114 mg) and 1-[(4-cyano-5-methyl-4-phenyl)hexyl]piperazine (90 mg) (refer to Formula 86 shown in JP-A 10-280103) (63 mg, 22%).
Free Body:
¹H-NMR (400 MHz, CDCl₃) δ 0.77 (d, J=6.8 Hz, 3H), 1.05–1.20 (m, 1H), 1.20 (d, J=6.8 Hz, 3H), 1.50–1.73 (m, 2H), 1.82–1.95 (m, 2H), 1.95–2.08 (m, 2H), 2.08–2.18 (m, 2H), 2.20–2.45 (m, 10H), 4.10–4.15 (m, 1H), 6.90–6.99 (m, 1H), 7.04–7.06 (m, 1H), 7.26–7.30 (m, 1H), 7.35–7.40 (m, 5H).
Further, 63 mg of the above-mentioned free body (the title compound) was treated in a conventional method, to give 60 mg of the hydrochloride.

Hydrochloride:
ESI-Mass; 449(MH⁺)

Example 50 1-[(4-Cyano-5-methyl-4-phenyl)hexyl]-4-[(4-cyano-4-(4'-fluorohenyl)butyl)piperazine

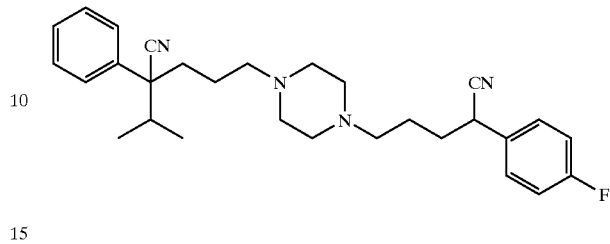

2-[(3-Cyano-3-phenyl)propyl]-1,3-dioxolane (1.77 g) was dissolved in a solution of 2N HCl (15 mL) and tetrahydrofuran (15 mL). After stirring at room temperature for 13 hours, 2N NaOH (15 mL) and ethyl acetate were added thereto, to separate the organic layer. The resulting organic layer was washed with water and brine, and dried over anhydrous magnesium sulfate. After filtering off the drying agent, the mixture was evaporated. 99 mg among the residue obtained (5-oxo-2-phenylpropanenitrile), 1-[(4-cyano-5-methyl-4-phenyl)hexyl]piperazine (99 mg) and acetic acid (0.1 mL) were dissolved in dichloromethane (3.5 mL), and sodium triacetoxyborohydride (147 mg) was added. After stirring at room temperature for 18 hours 30 minutes, the mixture was neutralized by adding an aqueous saturated sodium bicarbonate thereto, and then extracted with dichloromethane. The resulting organic layer was dried over anhydrous magnesium sulfate. After filtering off the drying agent, the mixture was evaporated. The resulting residue was purified by NH silica gel column chromatography (hexane/ethyl acetate system), to give the title compound (136 mg, 88%: yield was calculated based on 1-[(4-cyano-5-methyl-4-phenyl)hexyl]piperazine).
¹H-NMR (400 MHz, CDCl₃) δ 0.77 (d, J=6.8 Hz, 3H), 1.04–1.19 (m, 1H), 1.19 (d, J=6.8 Hz, 3H), 1.50–1.70 (m, 3H), 1.80–2.00 (m, 3H), 2.08–2.20 (m, 2H), 2.20–2.45 (m, 12H), 3.80–3.88 (m, 1H), 7.25–7.40 (m, 9H).
Further, 136 mg of the above-mentioned free body (the title compound) was treated according to a conventional method, to give 141 mg of the hydrochloride.
Hydrochloride:
ESI-Mass; 461(MH⁺)

Example 51 1-[(4-Cyano-5-methyl-4-phenyl)hexyl]-4-[4-hydroxime-4-(4'-fluorophenyl)butyl]piperazine

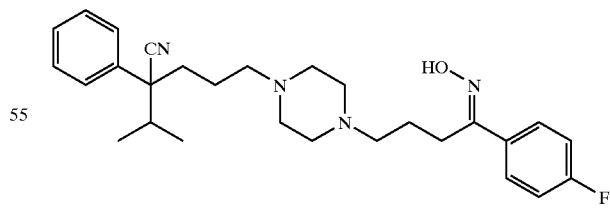

An acetonitrile solution (10 mL) in which 1-[(4-cyano-5-methyl-4-phenyl)hexyl]piperazine (100 mg), 4-chloro-4'-fluorobutyrophenone (91 mg) and triethylamine (0.1 mL) were dissolved was stirred under a reflux condition. After 6 hours, the reaction solution was cooled to a room temperature, the organic layer was seprated by adding water and ethyl acetate. The resulting organic layer was washed with water and brine, and dried over anhydrous magnesium sulfate. After filtering off the drying agent, the filtrate was evaporated. The resulting residue was purified with silica gel column chromatography (methanol/ethyl acetate system), to give 1-[(4-cyano-5-methyl-4-phenyl)hexyl]-4-[4-(4-fluorophenyl)butane-1-on]piperazine as a precursor (56 mg). 27 mg among the product was dissolved in ethanol (2 mL), and hydroxyammonium chloride (8.3 mg) and sodium acetate (9.8 mg) were added, and the mixture was stirred under a reflux condition. After 2 hours, the solution was cooled to a room temperature, and the organic layer was separated by adding water and ethyl acetate. The resulting organic layer was washed with water and brine, and dried over anhydrous magnesium sulfate. After filtering off the drying agent, the filtrate was evaporated. The resulting residue was purified by silica gel column chromatography (methanol/ethyl acetate system), to give the title compound as a colorless oil (17 mg).

$^1$H-NMR (400 MHz, CDCl$_3$) δ 0.76 (d, J=6.1 Hz, 3H), 1.06–1.20 (m, 1H) 1.18 (d, J=6.8 Hz, 3H), 1.50–1.62 (m, 1H), 1.75–1.82 (m, 2H), 1.82–1.92 (m, 1H), 2.05–2.20 (m, 21), 2.22–2.55 (m, 12H), 2.72–2.78 (m, 2H), 6.99–7.05 (m, 2H), 7.25–7.30 (m, 1H), 7.31–7.36 (m, 4H), 7.58–7.62 (m, 2H).

Further, 17 mg of the above-mentioned free body (the title compound) was treated in a conventional method, to give 14 mg the hydrochloride.

Hydrochloride:

ESI-Mass; 465(MH$^+$)

Example 52 1-[(4-Cyano-5-methyl-4-phenyl)hexyl]-4-(4-methyl-3-phenylpentane)piperazine

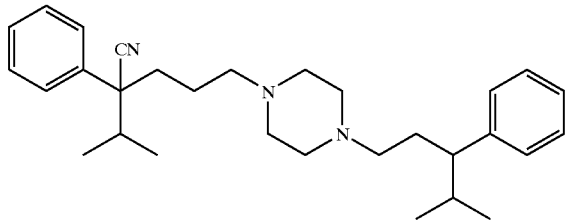

The title compound was obtained as a pale yellow oil in accordance with the method of Example 49 (85 mg, 60%).

Free Body:

$^1$H-NMR (400 MHz, CDCl$_3$) δ 0.71 (d, J=6.6 Hz, 3H), 0.76 (d, J=6.8 Hz, 3H), 0.92 (d, J=6.8 Hz, 3H), 1.03–1.16 (m, 2H), 1.18 (d, J=6.8 Hz, 3H), 1.46–1.60 (m, 3H), 1.70–2.16 (m, 6H), 2.18–2.42 (m, 10H), 7.07–7.13 (m, 2H), 7.14–7.18 (m, 1H), 7.20–7.32 (m, 4H), 7.33–7.36 (m, 4H).

Further, the hydrochloride (80 mg) of the title compound was obtained by treating the free body in a similar method as in Example 1.

Hydrochloride:

ESI-Mass; 446(MH$^+$)

Example 53 1-[(4-Cyano-5-methyl-4-phenyl)hexyl]-4-(4-methyl-3-phenyl-hexane)piperazine

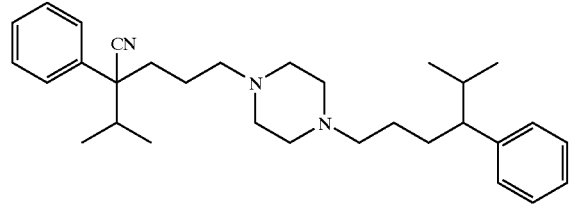

The title compound was obtained in accordance with the method of Example 1 described in JP-A 11-206862 (150 mg, yield: 94%).

Free Body:

$^1$H-NMR (400 MHz, CDCl$_3$) δ 0.69 (d, J=6.86 Hz, 3H), 0.76 (d, J=6.8 Hz, 3H), 0.92 (d, J=6.6 Hz, 31), 1.03–1.16 (i. 2H), 1.19 (d, J=6.6 Hz, 3H), 1.18–1.28 (m, 2H), 1.65–1.90 (m, 4H), 2.05–2.14 (m, 3H), 2.14–2.44 (m, 10H), 7.07–7.13 (m, 2H), 7.14–7.18 (m, 1H), 7.20–7.32 (m, 3H), 7.33–7.36 (m, 4H).

Further, the hydrochloride was obtained by treating the free body (the title compound) in a similar method as in Example 1.

Hydrochloride:

ESI-Mass; 460(MH$^+$)

Example 54 1-[(4-Cyano-5-methyl-4-phenyl)hexyl]-4-[2-(4-fluorophenoxy)buty-3-yl]piperazine

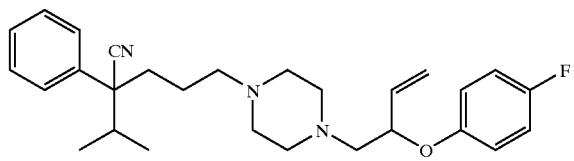

The title compound was obtained as a pale yellow oil (183 mg, 38%) in accordance with the method of Example 104 described in JP-A 11-206862.

Free Body:

$^1$H-NMR (400 MHz, CDCl$_3$) δ 0.77 (d, J=6.8 Hz, 3H), 1.04–1.19 (m, 1H), 1.19 (d, J=6.6 Hz, 3H), 1.50–1.64 (m, 1H), 1.82–1.92 (m, 1H), 2.06–2.18 (m, 2H), 2.22–2.28 (m, 2H), 2.28–2.40 (m, 4H), 2.48–2.64 (m, 5H), 2.75 (dd, J=7.7 Hz, 13.4 Hz, 1H), 4.65–4.73 (m, 1H), 5.20 (d, J=10.6 Hz, 1H), 5.25 (d, J=17.4 Hz, 1H), 5.85 (ddd, J=5.8 Hz, 10.6 Hz, 17.4 Hz, 1H), 6.81–6.88 (m, 2H), 6.88–6.97 (m, 2H), 7.25–7.31 (m, 1H), 7.32–7.40 (m, 4H Further, the hydrochloride was obtained by treating the free body (the title compound) in a similar method as in Example 1.

Hydrochloride:

ESI-Mass; 450(MH$^+$)

Example 55 1-[(4-Cyano-5-methyl-4-phenyl)hexyl]-4-[3-allyloxy-2-(4-fluorophenoxy)propyl]piperazine

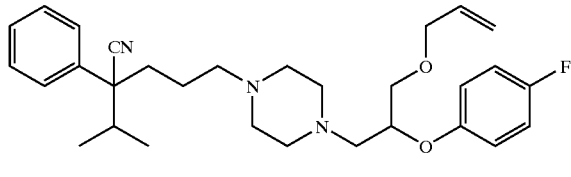

The title compound was obtained as a colorless oil (67 mg, 62%) in accordance with the method of Example 104 described in JP-A 11-206862.

Free Body:
$^1$H-NMR (400 MHz, CDCl$_3$) δ 0.77 (d, J=6.8 Hz, 3H), 1.05–1.18 (m 1H), 1.19 (d, J=6.4 Hz, 3H), 1.48–1.66 (m, 1H), 1.87 (dt, J=4.4 Hz, 12.4 Hz, 1H), 2.06–2.18 (m, 2H), 2.22–2.40 (m, 6H), 2.44–2.54 (m, 1H), 2.68–2.74 (m, 211. 2.93–3.00 (m, 1H), 3.95–3.98 (m, 2H), 4.06 (d, J=5.2 Hz, 2H), 5.16 (brd, J=10.4 Hz, 1H), 5.24 (dd, J=1.6 Hz, 17.2 Hz, 1H), 5.81–5.92 (m, 1H), 6.80–6.97 (m, 4H), 7.24–7.33 (m, 1H), 7.34–7.39 ((m, 4H).

Further, the hydrochloride was obtained by treating the free body (the title compound) in a similar method as in Example 1.

Hydrochloride:
ESI-Mass; 494(MH$^+$)

Example 56 1-[(4-Cyano-5-methyl-4-phenyl)hexyl]-4-[3-(n-propanoxy)-2-(4-fluorophenoxy)propyl]piperazine

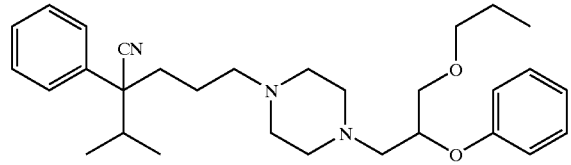

In hydrogen atmosphere, 1-[(4-cyano-5-methyl-4-phenyl)hexyl]-4-[3-arloxy-2-(4-fluorophenoxy)propyl]piperazine (85 mg) was dissolved in ethanol (3.5 mL) at room temperature. To the mixture was added 10% palladium-carbon (10 mg), followed by stirring. After 3 hours 20 minutes, palladium-carbon was separated by filtration, and then the filtrate was evaporated. The resulting residue was purified by NH silica gel column chromatography (hexane/ethyl acetate system), to give the title compound (34 mg, 40%).

Free Body:
$^1$H-NMR (400 MHz, CDCl$_3$) δ 0.77 (d, J=6.6 Hz, 3H), 0.88 (dt, I=2.7 Hz, 7.2 Hz, 3H), 1.05–1.20 (m, 1H), 1.19 (d, J=6.6 Hz, 3H), 1.50–1.60 (m, 4H), 1.82–1.92 (m, 2H), 2.05–2.20 (m, 3H), 2.20–2.60 (m, 9), 2.66–2.78 (m, 2H), 3.31–3.41 (m, 2H), 3.61 (d, J=5.5 Hz, 1H), 4.06 (d, J=5.1 Hz, 1H), 6.81–6.98 (m, 4H), 7.25–7.32 (m, 1H), 7.32–7.40 (m, 4H).

Further, the hydrochloride was obtained by treating the free body (the title compound) in a similar method as in Example 1.

Hydrochloride:
ESI-Mass; 496(MH$^+$)

Example 57 1-[(4-cyano-5-methyl-4-phenyl)hexyl]-4-[3-hydoxy-2-(4-fluorophenoxy)propyl]piperazine

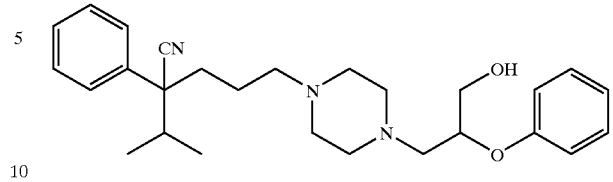

In tetrahydrofuran (5 ml) was dissolved 1-[(4-cyano-5-methyl-4-phenyl)hexyl]-4-[3-allyloxy-2-(4-fluorophenoxy)propyl]piperazine (125 mg), followed by adding sodium borohydride (14.4 mg) and then iodine (64 mg)/tetrahydrofuran (2 mL). After stirring for one hour, the organic layer was separated by adding ethyl acetate and water. The resulting organic layer was washed with water and brine, and dried over anhydrous magnesium sulfate. After filtering off the drying agent, the filtrate was evaporated. The residue was purified by NH silica gel column chromatography (hexane/ethyl acetate system), to give the title compound as a pale yellow oil (70 mg, 61%). The hydrochloride was obtained by treating the free body (the title compound) in a similar method as in Example 1.

Hydrochloride:
ESI-Mass; 436(MH$^+$)

Example 58 1-[(4-cyano-5-methyl-4-phenyl)hexyl]-4-[2-(1,2,3,4)-tetrahydroquinolyl)ethyl]piperazine

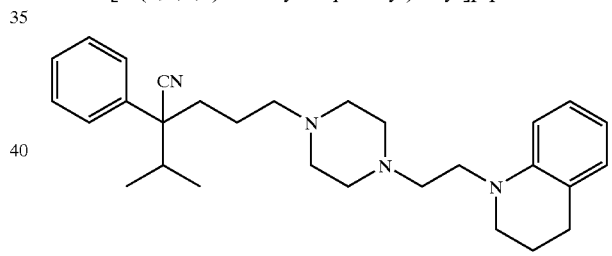

The title compound was obtained from 1,2,3,4-tetrahydroquinoline in accordance with the method of Example 89 described in JP-A 11-206862 (34%).

Free Body:
$^1$H-NMR (400 MHz, CDCl$_3$) δ 0.77 (d, J=6.8 Hz, 3H), 1.05–1.20 (m, 1H) (d, J=6.8 Hz, 3H), 1.50–1.66 (m, 1H), 1.85–1.98 (m, 2H), 2.05–2.20 (m, 2H), 2.24–2.56 (m, 1H), 2.73 (brt, J=6.4 Hz, 2H), 3.29 (brt, J=5.6 Hz, 3H), 3.36–3.41 (m, 2H), 3.39 (brt, J=7.8 Hz 2H) 3.45–3.52 (m, 2H), 6.52–6.59 (in 2H), 6.90–6.194 (m, 1H)7.00–7.15 (m, 1H), 7.26–7.132 (m, 1H) 7.34–7.38 (m, 4H).

Further, the hydrochloride was obtained by treating the free body (the title compound) in a similar method as in Example 1.

Hydrochloride:
ESI-Mass; 445(MH$^+$)

Example 59 4-[(4-Cyano-5-methyl-4-phenyl)hexyl]-N-(4-fluorophenyl)-N²-(2-methylpropyl)-1(2H)-pyrazinecarboxyimidamide

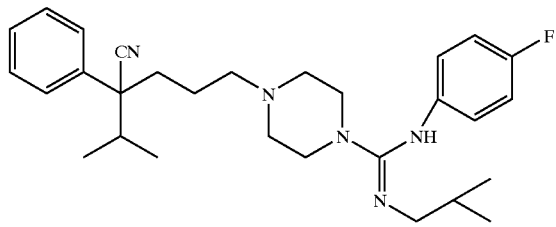

Under a nitrogen atmosphere, to a solution of 1-(fluorophenyl)-3-isobutylurea (300 mg), triphenylphosphine (561 mg) and triethylamine (0.3 mL) added in dichloromethane (10 ml) were added a solution of carbon tetrabromide (948 mg) dissolved in dichloromethane (4 ml). After 45 minutes, the reaction solution was cooled to room temperature, and the organic layer was separated by adding water and dichloromethane thereto. The resulting organic layer was washed with water and brine, and dried over anhydrous magnesium sulfate. After filtering off the drying agent, the filtrate was evaporated. The resulting residue was immediately purified by NH silica gel column chromatography (hexane/ethyl acetate system), to give a colorless oily carbodiimide as an intermediate. The carbodiimide and 1-[(4-cyano-5-methyl-4-phenyl)hexyl]piperazine (100 mg) were dissolved in 2-propanol (10 mL), followed by stirring under a reflux condition. After 2 hours, the solvent was evaporated, and the resulting residue was purified by NH silica gel column chromatography (hexane/ethyl acetate system), to give the title compound as a colorless solid (174 mg, 25%, 2 steps).
Free Body:
$^1$H-NMR (400 MHz, CDCl$_3$) δ 0.77 (d, J=6.8 Hz, 3H), 0.88–0.91 (m, 6H), 1.05–1.18 (m, 1H), 11.20 (d, J=6.8 Hz, 3H), 1.50–1.65 (m, 2H), 1.67–1.80 (m, 2H), 1.88–1.98 (m, 1H), 2.06–2.20 (m, 2H), 2.22–2.36 (m, 4H), 2.79 (brd, J=6.8 Hz, 1H), 3.05 (dd, J=6.0 Hz, 6.8 Hz, 1H), 3.14–3.20 (m, 1H), 4.82–4.91 (m, 1H), 6.52–6.58 (m, 1H), 6.72–6.78-(m, 1H), 6.91–7.04 (m, 3H), 7.22–7.31 (m, 4H), 7.35–7.38 (m, 3H).
Further, the hydrochloride was obtained by treating the free body (the title compound) in a similar method as in Example 1.
Hydrochloride:
ESI-Mass; 478(MH⁺)

Example 60 4-[(4-cyano-5-methyl-4-phenyl)hexyl]-N-(4-fluorobenzyl)-N'-(2-methylpropyl)-1 (2H)-pyrazinecarboxyimidamide

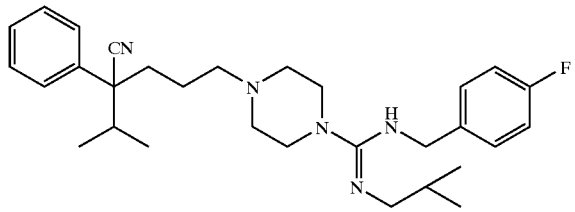

The title compound was obtained as a colorless oil in accordance with the method of Example 59 (62%).
Free Body:
$^1$H-NMR (400 MHz, CDCL$_3$) δ 0.77 (d, J=6.8 Hz, 3H), 0.80–0.88 (m, 6H), 1.05–1.18 (m, 1H), 1.20 (d, J=6.4 Hz, 3H), 1.43–1.60 (m, 1H), 1.84–1.95 (m, 1H), 2.05–2.20 (m, 2H), 2.25–2.40 (m, 6H), 2.87–2.95 (m, 2H), 3.22–3.38 (m 41), 3.49 (s, 2H), 4.35–4.45 (m, 2H), 7.02–7.09 (m, 2H), 7.27–7.34 (m, 31), 7.34–7.41 (m, 4H).
Further, the hydrochloride was obtained by treating the free body (the title compound) in a similar method as in Example 1.
Hydrochloride:
ESI-Mass; 492(MH⁺)

Example 61 4-[(4-Cyano-5-methyl-4-phenyl)hexyl[-N,N'-dicylohexylpyrazinecarboxyimidamide

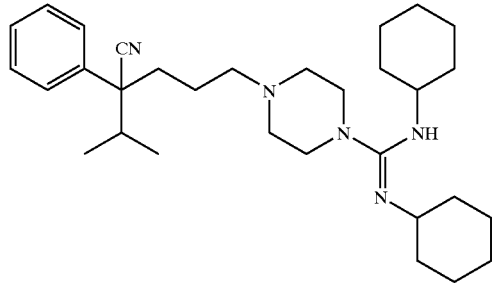

The title compound was obtained as a colorless oil in accordance with the method of Example 59 (62%).
Free Body:
$^1$H-NMR (400 MHz, CDCl$_3$) δ 0.78 (d, J=6.8 Hz, 3H), 1.04–1.46 (m, 91), 1.21 (d, J=6.8 Hz, 3H), 1.46–1.74 (m, 6H), 1.74–1.86 (m, 6H), 1.86–1.18 (m, 2H), 2.07–2.22 (m, 21), 2.24–2.40 (m, 6H), 3.05–3.16 (m, 2H), 3.23–3.32 (m, 4H), 3.41–3.52 (m, 1H), 7.28–7.34 (m, 1H), 7.35–7.42 (m, 4H).
Further, the hydrochloride was obtained by treating the free body (the title compound) in a similar method as in Example 1.
Hydrochloride:
ESI-Mass; 492(MH⁺)

Example 62 N-Cyano-4-[1(4-cyano-5-methyl-4-phenyl)hexyl]-N'-[(4-fluorophenoxy)ethyl] pyrazinecarboxyimidamide

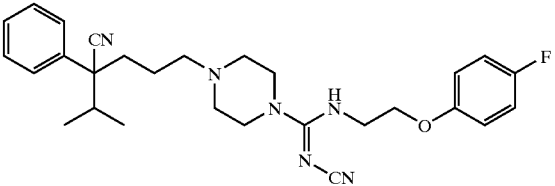

In nitrogen atmosphere, N-cyano-N'-ethyl(4-fluorophenoxy)-O-phenylisourea (168 mg) and 1-[(4-cyano-5-methyl-4-phenyl)hexyl]piperazine (100 mg) were dissolved in 2-propanol (5 mL), followed by stirring under reflux. After 24 hours, the solvent was evaporated, and the resulting residue was purified by NH silica gel column chromatography (hexane/ethyl acetate system), to give the title compound as a colorless solid (98 mg, 71%).
Free Body:
$^1$H-NMR (400 MHz, CDCl$_3$) δ 0.77 (d, J=6.6 Hz, 3H), 1.08 (d, J=6.6 Hz, 3H), 1.20–1.34 (m, 1H), 1.50–1.70 (m, 1H), 1.92 (ddd; J=4.9 Hz, 11.6 Hz, 13.6 Hz, 1H), 2.05–2.23 (m, 2H), 2.24–2.38 (m, 60), 3.43–3.50 (m, 21), 3.78–3.82 (m, 21), 4.04–4.09 (m, 2H), 5.00–5.05 (m, 1H), 6.80–6.85 (m, 2H), 6.92–7.01 (m, 2H), 7.27–7.32 (m, 1H), 7.34–7.39 (m, 4H).

Further, the hydrochloride was obtained by treating the free body (the title compound) in a similar method as in Example 1.
Hydrochloride:
ESI-Mass; 491(MH⁺)

Example 63 (2-Thienyl)-[(4-cyano-5-methyl-4-phenyl)hexylpiperazino]methaneimine

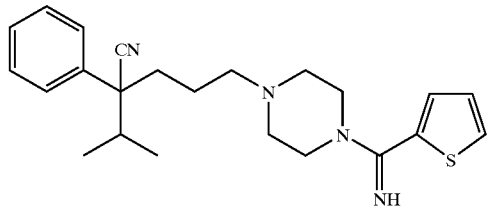

The title compound was obtained as a colorless oil in accordance with the method of Example 62 (62%).
Free Body:
$^{1}$H-NMR (400 MHz, CDCl$_{3}$) δ 0.77 (d, J=6.8 Hz, 3H), 1.05–1.20 (m, 1H), 1.20 (d, J=6.6 Hz, 3H), 1.50–1.64 (m, 1H), 1.88–2.08 (m, 1H), 2.08–2.22 (m, 2H), 2.28–2.38 (m, 6H), 3.32–3.44 (m, 4H), 7.00 (dd, J=3.6 Hz, 5.2 Hz, 1H), 7.14 (dd, J=1.2 Hz, 3.6 Hz, 1H), 7.26–7.32 (m 1H), 7.34 (dd, J=1.2 Hz, 5.2 Hz, 1H), 7.35–7.39 (m, 4H).

The hydrochloride of the title compound was obtained by treating the free body in a similar method as in Example 1.
Hydrochloride:
ESI-Mass; 345(MH⁺)

Example 64 1]-isopropyl-4-[4-isobutyl-1H-benzof[d]imidazol-2-yl)piperazinol-1-phenylbutyl Cyanide

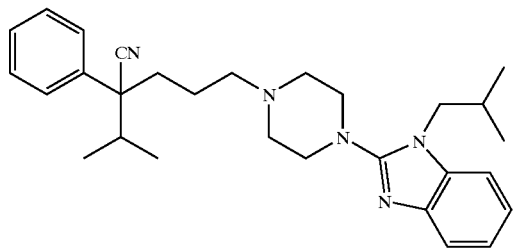

2-Chloro-1-isobutyl-1H-benzo[d]imidazole (4 g) and 1-[(4-cyano-5-methyl-4-hexyl]piperazine (5 g) were dissolved in tetrahydrofuran (10 mL), followed by stirring on an oil bath at 150° C. for 6 hours in an open system. The reaction product was purified by NH silica gel (ethyl acetate/hexane system), to give the title compound as a brown oil (6.8 g, 85%).
Free Body:
$^{1}$H-NMR (400 MHz, CDCl$_{3}$) δ 0.78 (d, J=6.8 Hz, 3H), 0.83 (d, J=6.8 Hz, 3H), 0.84 (d, J=6.4 Hz, 3H), 1.20–1.35 (m, 1H), 1.21 (d, J=6.8 Hz, 3H), 1.52–1.67 (m, 1H), 1.95–2.07 (m, 1H), 2.08–2.23 (m, 1H), 2.23–2.43 (m, 4H), 2.43–2.50 (m, 4H), 3.21–3.25 (m, 4H), 3.80 (d, J=7.6 Hz, 2H), 7.08–7.64 (m, 9H)

Further, the hydrochloride was obtained by treating the free body (the title compound) in a similar method as in Example 1.
Hydrochloride:
ESI-Mass; 458(MH⁺)

Example 65 Bis-1,4-[(4-cyano-5-methyl-4-phenyl)hexyl]piperazine

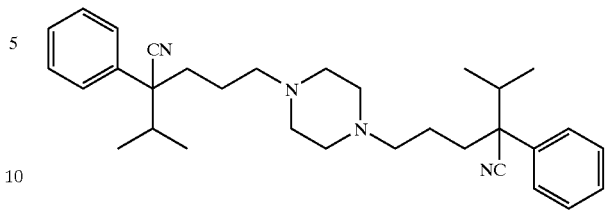

In nitrogen atmosphere, thionyl chloride (4 mL) was added to (4-cyano-5-methyl-4-phenyl)hexanol (2.33 g) under ice cooling, followed by heating under stirring under reflux condition. After 2 hours, the mixture was evaporated. Then, the resulting residue was purified by silica gel column chromatography (hexane/ethyl acetate system), to give (4-cyano-5-methyl-4-phenyl)hexyl chloride (2.35 g, 93%) as a yellow oil. The resulting chloride (454 mg), [(4-cyano-5-methyl-4-phenyl)hexyl]piperazine (166 mg) and sodium iodide (289 mg) were dissolved in acetonitrile (5 mL), followed by stirring under a reflux condition. After 2 hours, the mixture was cooled to a room temperature, and the organic layer was separated by adding ethyl acetate and water thereto. The resulting organic layer was washed with water and brine, and dried over anhydrous magnesium sulfate. After the drying agent was filtered off, the mixture was evaporated. The residue was purified by NH silica gel column chromatography (hexane/ethyl acetate), to give the title compound as a pale yellow oil (213 mg, 23%).
Free Body:
$^{1}$H-NMR (400 MHz, CDCl$_{3}$) δ 0.77 (d, J=6.8 Hz, 6H), 1.02–1.16 (m, 2H), 1.19 (d, J=6.8 Hz, 6H), 1.46–1.60 (m, 2H), 1.80–1.92 (m, 2H), 2.40–2.17 (m, 4H), 2.17–2.36 (m, 12H), 7.23–7.31 (m, 2H), 7.33–7.37 (m, 8H).

Further, the hydrochloride was obtained by treating the free body (the title compound) in the same manner as in Example 1.
Hydrochloride:
ESI-Mass; 485(MH⁺)

Example 66 1-[(4-cyano-5-methyl-4-phenyl)hexyl]-4-[(3-cyano-4-methyl-3-phenyl)pentyl]piperazine

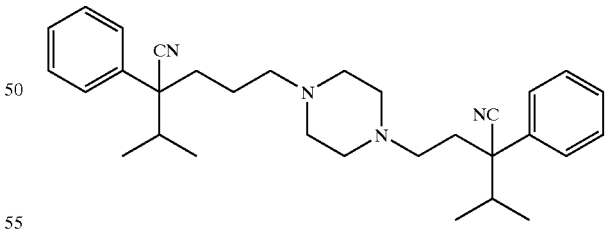

The title compound was obtained as a pale yellow oil in accordance with the method of Example 65 (yield: 52%).
$^{1}$H-NMR (400 MHz, CDCL$_{3}$) δ 0.76 (d, J=6.8 Hz, 3H), 0.765 (d, J=6.4 Hz, 3H), 1.00–1.18 (m 1H), 11.18 (d, J=6.4 Hz, 3H), 1.19 (d, J=6.8 Hz, 3H), 1.44–1.60 (m, 1H), 1.80–2.00 (m, 4H), 2.00–2.18 (m, 4H), 2.18–2.44 (m, 10H), 7.26–7.32 (m, 21), 7.33–7.40 (m, 8H).

Further, the hydrochloride of the title compound was obtained by treating the free body (the title compound) in the same manner as in Example 1.

Hydrochloride:
ESI-Mass; 471(MH+)

Example 67 1-[(4-Cyano-5-methyl-4-phenyl)hexyl]-4-12-(1',2'-methylenedioxyphenyl)ethyl]piperidine

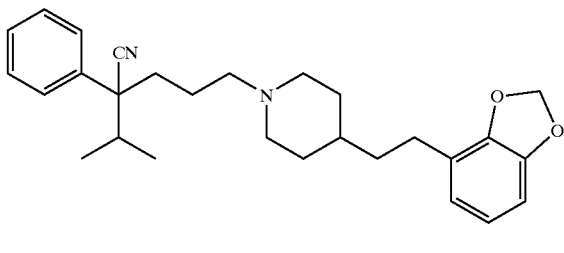

The title compound was obtained in accordance with the method of Example 49 (yield: 51%).
Free Body:
$^1$H-NMR (400 MHz, CDCl$_3$) δ 0.77 (d, 1=6.8 Hz, 3H), 1.10–1.30 (m, 31), 1.20 (d, J=6.4 Hz, 3H), 1.48–1.76 (m, 71), 1.80–1.94 (m, 2H), 2.06–2.18 (m, 2H), 2.18–2.28 (m, 2H), 2.53–2.60 (m, 2H), 2.70–2.80 (m, 2H), 5.92 (s, 21). 6.82–6.70 (m, 2H), 6.70–6.78 (m, 1H), 7.26–7.40 (m, 5H).

Further, the hydrochloride was obtained by treating the free body (the title compound) in the same method as in Example 1.
Hydrochloride:
ESI-Mass; 433(MH+)

Example 68 1-[(4-Cyano-4-(3-cyano-5-thienyl)-5-methylhexyl]-4-[2-(4-cyanophenoxy)ethyl] piperazine

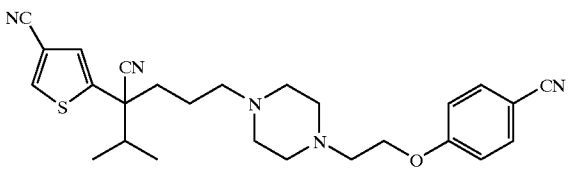

In acetonitrile (5 ml) was dissolved 4-cyano-4-(3-cyano-5-thienyl)-5-methylhexanol (0.13 g). To the mixture were added triethylamine (0.21 ml) and mesyl chloride (0.048 ml), followed by stirring at room temperature for one hour. Water was added thereto, and the mixture was extracted with ethyl acetate and further washed with brine. After drying over anhydrous magnesium sulfate, the mixture was evaporated, to give a pale yellow oil. The resulting oil was dissolved in DMF (2 ml), followed by adding a DMF solution (4 ml) of 1-[2-(4-cyanophenoxy)ethyl]piperazine (0.14 g), triethylamine (0.21 ml) and sodium iodide (0.15 g). After stirring at 60° C. overnight, ethyl acetate was added thereto, and the mixture was washed with water and further brine. After drying over anhydrous magnesium sulfate, the solvent was evaporated, and the resulting residue was purified by NH silica gel column chromatography (hexane/ethyl acetate system), to give the title compound as a pale yellow oil (0.09 g, 33%).
Free Body:
$^1$H-NMR (400 MHz, CDCl$_3$) δ 0.92 d, J=6.8 Hz, 3H), 1.20 (d, J=6.8 Hz, 3H), 1.21–1.31 (m, 1H), 1.60–1.73 (x. 1H), 1.77 (dt, J=4 Hz, J=13.2 Hz, 1H), 2.06 (qui, J=6.8 Hz, 1H), 2.20 (dt, J=4 Hz, J=13.2 Hz, 11), 2.33 (t, J=7.6 Hz, 2H), 2.42 (bs, 4H), 2.58 (bs, 4H), 2.82 (t, J=5.6 Hz, 2H), 4.13 (t, J=5.6 Hz, 2H), 6.95 (d, J=8.8 Hz, 2H1), 7.28 (d, J=1.2 Hz, 1H), 7.58 (d, J=8.8 Hz, 2H), 7.90 (d, J=1.2 Hz, 1H).

Further, the hydrochloride was obtained by treating the above free body (the title compound) in a conventional method.
Hydrochloride:
ESI-Mass; 462(MH+)

Example 69 1-[(4-Cyano-4-(3-cyano-5-thienyl)-5-methylhexyl]-4-[2-(3-cyanophenoxy)ethyl] piperazine

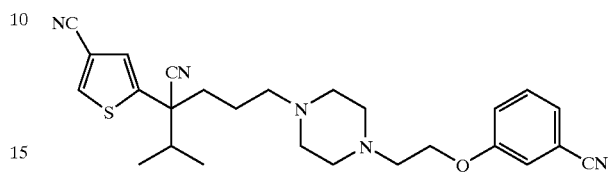

The title compound was obtained as a pale yellow oil (0.15 g, 58%) from 4-cyano-4-(3-cyano-5-thienyl)-5-methylhexanol and 1-[2-(3-cyanophenoxy)ethyl]piperazine in the same manner as in Example 68.
Free Body:
$^1$H-NMR (400 MHz, CDCl$_3$) δ 0.93 (d, J=6.8 Hz, 3H), 1.21 (d, J=6.8 Hz, 3H), 1.22–1.32 (m 1H), 1.60–1.73 (m, 1H), 1.79 (dt, J=4 Hz, J=12.4 Hz, 1H 2.07 (qui, J=6.8 Hz, 1H), 2.21 (dt, J=4 Hz, J=12.4 Hz, 1H), 2.34 (t, J=7.2 Hz, 2H), 2.43 (bs, 4H), 2.59 (bs, 4H), 2.82 (t, J=5.6 Hz, 2H), 4.11 (t, J=5.6 Hz, 2H), 7.12–7.40 (m, 5H), 7.91 (s, 1H).

Further, the hydrochloride was obtained by treating the free body (the title compound) in a conventional method.
Hydrochloride:
ESI-Mass; 462(MH+)

Example 70 1-[(4-Cyano-5-methyl-4-(5-cyano-2-thienyl)hexyl]-4-[2-(3-cyanophenoxy)ethyl] piperazine

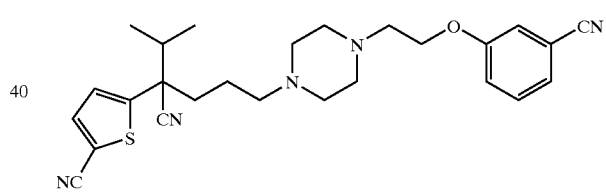

In acetonitrile (10.0 ml) was dissolved 400 mg (1.61 mmol) of 4-cyano-5-methyl-4-(5-cyano-2-thienyl)hexanol, followed by cooling to 0° C. To the mixture were added 0.26 ml (1.85 mmol) of triethylamine and 0.14 ml (1.77 mmol) of mesyl chloride, followed by heating to room temperature. After 20 minutes, ether and brine were added thereto. The ether layer was washed with an aqueous saturated sodium bicarbonate and dried over anhydrous magnesium sulfate. The solvent was evaporated, to give a crude product. The half amount (ca. 0.1 mmol) of the crude mesyl compound was dissolved in 8.00 ml of dimethylformamide. To the mixture were added 724 mg (4.83 mmol) of sodium iodide, ill mg (0.81 mmol) of potassium carbonate and 243 mg (1.05 mmol) of 1-[2-(3-cyanophenoxy)ethyl]piperazine, followed by heating to 60° C. After completion of the reaction, brine was added thereto, and the objective product was extracted with ethyl acetate. The organic layer was washed with brine, and then dried over anhydrous magnesium sulfate. The solvent was evaporated, to give a crude product. The crude product was subjected to Cromatorex NH silica gel (eluted with ethyl acetate/hexane=1/1), to give 289 mg (0.63 mmol, 77.3%) of the title compound as a yellow syrup.

¹H-NMR (400 MHz, CDCl₃) δ 0.92 (d, J=6.80 Hz, 3H), 1.21 (d, J=6.40 Hz, 3H), 1.20–1.38 (m, 1H), 1.60–1.86 (m, 21), 2.01–2.12 (m, 0.11), 2.18–2.30 (m, 1H), 2.30–2.75 (m, 10H), 2.80–2.90 (m, 2H), 4.08–4.18 (m, 2H), 7.11–7.18 (m, 3H), 7.23–7.28 (m, 1H), 7.34–7.40 (m, 1H), 7.52 (d, J=3.60 Hz, 1H)
ESI-Mass; 462(MH⁺)

Example 71 1-[(4-Cyano-5-methyl-4-(5-cyano-2-thienyl)hexyl]-4-[2-{N-(2-cyanoethyl)anilino}ethyl]piperazine

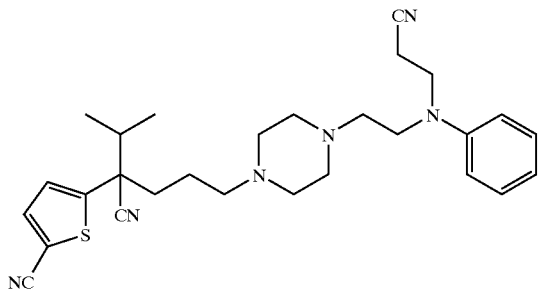

The title compound was synthesized using [2-{N-(2-cyanoethyl)anilino]ethyl]piperazine in accordance with the method for producing 1-[(4-cyano-5-methyl-4-(5-cyano-2-thienyl)hexyl]-4-[2-(3-cyanophenoxy)ethyl]piperazine in Example 70 (yield; 90.1%: a pale yellow oil).
¹H-NMR (400 MHz, CDCl₃) δ 0.92 (d, J=6.4 Hz, 3H), 1.20–1.33 (m, 1H), 1.21 (d, J=6.4 Hz, 3H), 1.58–1.73 (m, 1H), 1.73–1.84 (m, 1H), 2.02–2.11 (m, 1H), 2.23 (dt, J=4.0 Hz, 12.8 Hz, 1H), 2.31–2.64 (m, 12H), 2.68 t, J=7.2 Hz, 2H), 3.51 (m, J=6.8 Hz, 211, 3.69 (m, J=7.2 Hz, 2H), 6.67 (m, J=8.0 Hz, 3H), 6.76 (m, J=7.4 Hz, 1H), 7.15 (m, J=4.00 Hz, 1H), 7.23–7.30 (m, 2H) 7.52 (d, J=4.0 Hz, 1H)
ESI-MS; 489(M+H⁺)

Example 72 1-[(4-Cyano-5-methyl-4-(3-cyano-2-thienyl)hexyl]-4-[2-(3-cyanophenoxy)ethyl]piperazine

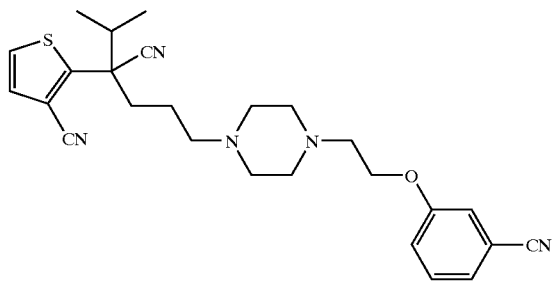

In 1.5 ml of acetonitrile was dissolved 111 mg (0.31 mmol) of 4-cyano-5-methyl-4-(3-cyano-2-thienyl)hexyl iodide. To the mixture were added 56.2 μl (0.40 mmol) of triethylamine and 109 mg (0.47 mmol) of 1-(3-cyanophenoxyethyl)piperazine, followed by stirring for 3 days. The organic layer separated by adding ethyl acetate and brine to the reaction solution was dried over magnesium sulfate, and then evaporated, to give a crude product. The crude product was subjected to 12.5 g of Cromatorex NH silica gel (ethyl acetate/hexane-1/2), to give 144 mg (quantitative) of the title compound as a yellow syrup.
¹H-NMR (400 MHz, CDCL₃) δ 0.92 (d, J=6.4 Hz, 3H), 1.15–1.28 (m, 1H), 1.26 (d, J=6.4 Hz, 3H), 1.60–1.75 (m, 1H), 2.17–2.27 (m, 1H), 2.27–2.70 (m, 12H), 2.81 (t, I=6.0 Hz, 2H), 4.10 (t, J=6. Hz, 2H), 7.11–7.16 (m, 2H). 7.22–7.26 (m, 1H), 7.26–7.28 (m, 2H), 7.33–39 (m, 1H)

ESI-Mass; 462(MH⁺)

Example 73 1-[(4-Cyano-5-methyl-4-(3-cyano-2-thienyl)hexyl]-4-[2-(3-fluorophenoxy)ethyyl]piperazine

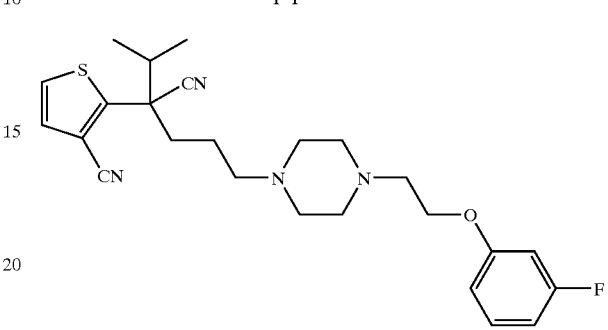

The title compound was synthesized in accordance with the method of Example 72 (yield: 82.3%).

¹H-NMR (400 MHz, CDCl₃) δ 0.92 d, J=6.4 Hz, 3H) 1.15–1.29 (m, 1H), 1.26 (d, J=6.8 Hz, 3H), 1.60–1.74 (m, 1H), 2.17–2.27 (m, 1H), 2.27–2.70 (m, 12H), 2.80 (t, J=6.0 Hz, 2H), 4.08 (t, J=6.0 Hz, 2H), 6.59–6.70 (m, 3H), 7.16–7.24 (m, 1H), 7.26–7.28 (m, 2H)

ESI-MS; 455(M+H⁺)

Example 74 1-[(4-Cyano-5-methyl-4-(3-cyano-2-thienyl)hexyl]-4-[2-(4-fluorophenoxy)ethyl]piperazine

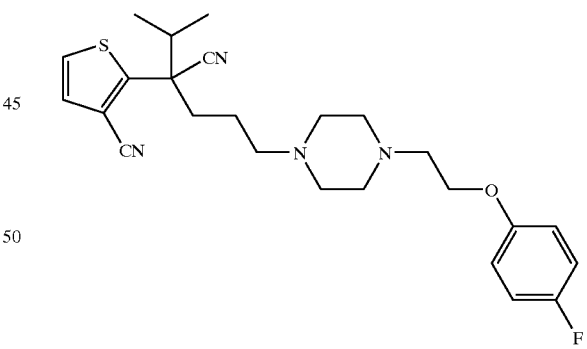

The title compound was synthesized in accordance with the method of Example 72 (yield: 70.2%).

¹H-NMR (400 MHz, CDCl₃) δ 0.92 (d, J=6.8 Hz, 3H), 1.14–1.29 (m, 1H), 1.26 (d, J=6.8 Hz, 3H), 160–1.74 (m, 1H), 2.17–2.27 (m, 1H), 2.27–2.70 (m, 12H, 2.78 (t, J=6.0 Hz, 2H), 4.05 (t, J=6.0 Hz, 2H), 6.81–6.85 (m, 2H). 6.93–6.98 (m, 1"), 7.26–7.28 (m, 2H)

ESI-MS; 455(M+H⁺)

Example 75 1-[(4-cyano-5-methyl-4-(2-thienyl)hexyl]-4-[2-(3-cyanophenoxy)ethyl]piperazine

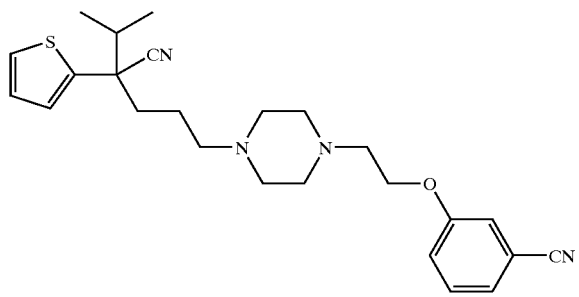

The title compound was synthesized using 4-cyano-5-methyl-4-(2-thienyl)hexyl iodide in accordance with the method of Example 72 (yield: 94.7%).
$^1$H-NMR (400 MHz, CDCl$_3$) δ 0.90 (d, J=6.6 Hz, 3H), 1.18 (d, J=6.8 Hz, 3H), 1.20–1.38 (m, 1H), 1.55–1.72 (m, 1H), 1.73–1.83 (m, 1H), 2.02–2.12 (m, 1H), 2.12–2.22 (m, 1H), 2.28–2.35 (m, 20, 2.35–2.65 (m, 8H), 2.81 (t, J=5.9 Hz, 2H), 4.10 (t, J=5.9 Hz, 2H), 6.93–6.97 (m, 1H), 7.10–7.17 (m, 3H), 7.22–7.30 (m, 2H), 7.33–7.39 (m, 1H).
ESI-MS; 437(M+H$^+$)

Example 76 1-[(4-Cyano-5-methyl-4-(2-thienyl]hexyl]-4-[2-(4-cyanophenoxy)ethyl]piperazine

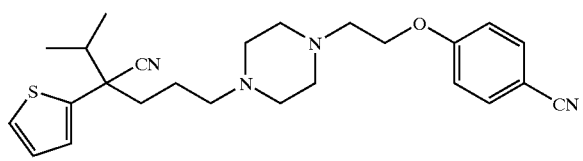

The title compound was synthesized using 4-cyano-5-methyl-4-(2-thienyl)hexyl iodide in accordance with the method of Example 72 (yield: 40.9%).
$^1$H-NMR (400 MHz, CDCl$_3$) δ 0.90 (d, 1=6.8 Hz, 3H. 1.18 (d, J=6.8 Hz, 3H), 1.22–1.38 (m, 1H), 1.56–1.70 (m, 1H), 1.72–1.81 (m, 1H), 2.01–2.10 (m, 1H), 2.10–2.21 (m, 1H), 2.27–2.34 (m, 2H), 2.34–2.62 (m, 8H), 2.81 (t, J=6.0 Hz, 2H), 4.12 (t, J=6.0 Hz, 2H), 6.92–6.96 (m, 3H), 7.11 (dd, J=1.2 Hz, 3.6 Hz, 1H), 7.24–7.27 (m, 2H), 7.57 (d, J=8.8 Hz, 2H).
ESI-MS; 437(M+H$^+$)

Example 77 1-[(4-cyano-5-methyl-4-(5-cyano-2-thienyl)hexyl]-4-[3-(5-cyano-2-thienyl)propyl]piperazine

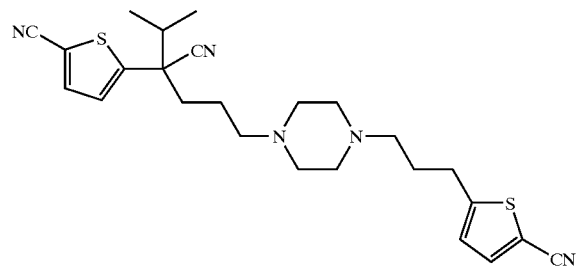

In acetonitrile (3 ml) was dissolved 200 mg (0.56 mmol) of 4-cyano-5-methyl-4-(5-cyano-2-thienyl)hexyl iodide. To the mixture were added 78.0 μl (0.56 mmol) of triethylamine and 178 mg (0.76 mmol) of 1-[3-(5-cyano-2-thieny)propyl]piperazine, followed by stirring at 55° C. After 5 hours, the reaction solution was concentrated, and the residue was subjected to Cromatorex NH silica gel (ethyl acetate/hexane=1/2), to give 243 mg (0.52 mmol, 92.8%) of the title compound as a yellow syrup.
$^1$H-NMR (400 MHz, CDCl$_3$) δ 0.92 (d, J=6.8 Hz, 3H), 1.18–1.31 (m, 1H), 1.21 (d, J=6.8 Hz, 3H), 1.60–1.72 (m, 1H), 1.73–1.91 (m, 31), 2.00–2.10 (in 1H), 2.17–2.27 (m, 1H), 2.28–2.50 (m, 12H), 2.88 (t, J=7.6 Hz, 2H), 6.80 (d, J=4.0 Hz, 1H), 7.15 (d, J=4.0 Hz, 1H), 7.45 (d, J=4.0 Hz, 1H), 7.51 (d, J=4.0 Hz, 1H)
ESI-Mass; 466(M+H$^+$)

Example 78 1-[(4-Cyano-5-methyl-4-(5-cyano-2-thienyl)hexyl]-4-[3-(2-thieny)propyl]piperazine

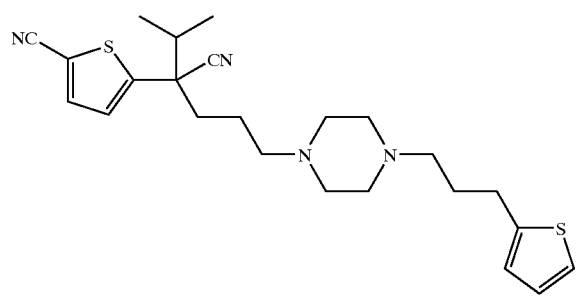

The title compound was synthesized in accordance with the production method described in Example 77 (yield: 96.4%).
$^1$H-NMR (400 MHz, CDCl$_3$) δ 0.92 (d, J=6.8 Hz, 3H), 1.19–1.31 (m, 1H), 1.20 (d, J=6.8 Hz, 3H), 1.60–1.72 (m, 1H), 1.72–1.81 (m, 110.1.82–1.91 (m, 2H), 2.00–2.10 (UL 1H), 2.17–2.24 (m, 1H), 2.27–2.54 (m, 12H), 2.85 (t, J=7.6 Hz, 2H), 6.78 (dd, J=0.8 Hz, 3.6 Hz, 1H), 6.91 (dd, J=3.6 Hz, 5.2 Hz, 1H), 7.10 (dd, J=0.8 Hz, 5.2 Hz, 1H), 7.14 (d, J=4.0 Hz, 1H), 7.51 (d, 1=4.0 Hz, 1H)
ESI-MS; 441(M+H$^+$)

Example 79 1-[(4-Cyano-5-methyl-4-(2-thienyl)hexyl]-4-[3-(5-cyano-2-thienyl)propyl]piperazine

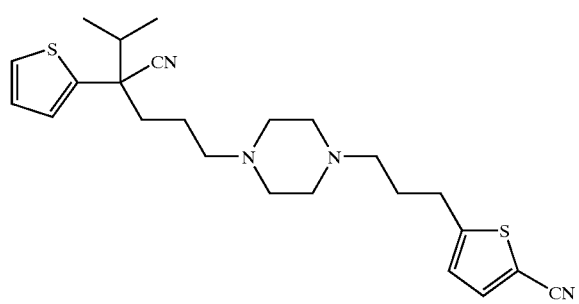

The title compound was synthesized using 4-cyano-5-methyl-4-(2-thienyl)hexyl iodide in accordance with the production method described in Example 77 (yield: 96.4%).
$^1$H-NMR (400 MHz, CDCl$_3$) δ 0.90 (d, J=6.8 Hz, 3H), 1.18 (d, J=6.4 Hz, 3H), 1.23–1.37 (m, 1H), 1.60–1.70 (m, 1H, 1.72–1.90 (m, 3H), 2.02–2.09 (m, 1H), 2.11–2.20 (m, 1H), 2.26–2.52 (m, 12H), 2.88 (t, J=7.6 Hz, 2H), 6.80 (d, J=3.6 Hz, 1H), 6.94 (dd, J=3.6 Hz, 5.2 Hz, 1H), 7.11 (dd, J=1.2 Hz, 3.6 Hz, 1H), 7.26 (dd, J=1.2 Hz, 5.2 Hz, 1H), 7.45 (d, J=3.6 Hz, 1H)

ESI-MS; 441(M+H⁺)

Example 80 1-[(4-cyano-5-methyl-4-(4-cyano-2-thienyl)hexyl]-4-[3-(2-thieny)propyl]piperazine

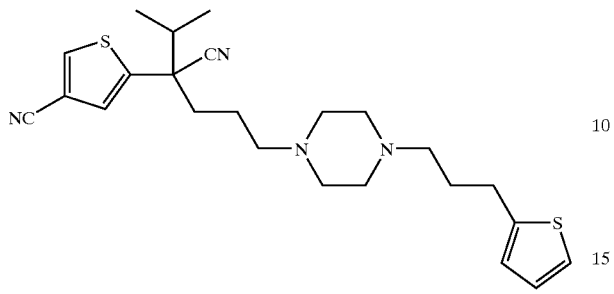

The title compound was produced in the synthesis condition of tert-butyl 4-(3-(2-thienyl)propyl)-1-piperazinecrboxylate which is described below (yield: 23.6%), by using 4-cyano-5-methyl-4-(4-cyano-2-thienyl) hexanol and 1-[3-(2-thienyl)propyl]piperazine synthesized according to the method of Example 69.
¹NMR (400 MHz, CDCl₃) δ 0.92 (d, J=6.8 Hz, 3l), 1.20 (d, J=6.8 Hz, 3l), 1.22–1.32 (m, 1H), 1.59–1.72 (m, 1H), 1.72–1.91 (m, 3H), 2.02–2.12 (m, 1H) 2.15–2.24 (m, 1H), 2.28–2.56 (m, 12H), 2.85 (t, J=7.6 Hz, 2H), 6.77–6.80 (m, 1H), 6.91 (dd, J=3.6 Hz, 5.2 Hz, 1H)7.11 (dd, J=1.2 Hz, 5.2 Hz, 1H). 7.28 (d, J=1.2 Hz, 1H), 7.89 (d, J=1.2 Hz, 1H)
ESI-MS; 441(M+H⁺)

Example 81 1-[4-Cyano-5-methyl-4-(2-thienyl) hexyl]-4-[(2-benzoxazoyl)methyl]piperazine

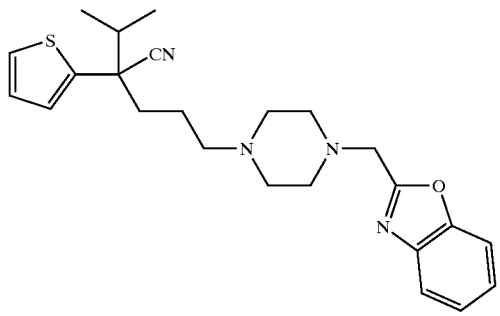

In acetonitrile (5 ml) was dissolved 230 mg (0.82 mmol) of 1-[4-cyano-5-methyl-4-(2-thienyl)hexyl]piperazine synthesized in a similar manner as the above-mentioned 1-[3-(5-cyano-2-thienyl)propyl]piperazine. To the mixture were added 120 mg (0.72 mmol) of 2-(chloromethyl)benzoxazole and 0.10 ml (0.72 mmol) of triethylamine, followed by heating to 50° C. After 5 hours, the reaction solution was concentrated, and the residue was subjected to Cromatorex NH silica gel (ethyl acetate/hexane=1/2), to give 244 mg (0.58 mmol, 80.5%) of the title compound as a yellow syrup.
¹H-NMR (400 MHz, CDCl₃) δ 0.89 (d, J=6.8 Hz, 3H), 1.18 (d, J=6.4 Hz, 3H), 1.20–1.38 (m, 1H), 1.55–1.69 (m, 1H), 1.71–1.81 (m, 1H), 2.00–2.09 (M 1H), 2.10–2.19 (m, 1H), 2.28–2.53 (m, 6H), 2.55–2.73 (mL 4H), 3.86 (s, 2H), 6.93 (dd, J=3.6 Hz, 5.2 Hz, 1), 7.10 (dd, J=1.2 Hz, 3.6 Hz, 1H), 7.24 (dd, J=1.2 Hz, 5.2 Hz, 1H), 7.30–7.36 (m, 2H), 7.50–7.55 (m, 1H), 7.68–7.73 (m, 1H)
ESI-Mass; 423(M+H⁺)

Example 82 1-[4-Cyano-5-methyl-4-(5-cyano-2-thienyl)hexyl]-4-[(2-benzoxazyl)methyl]piperazine

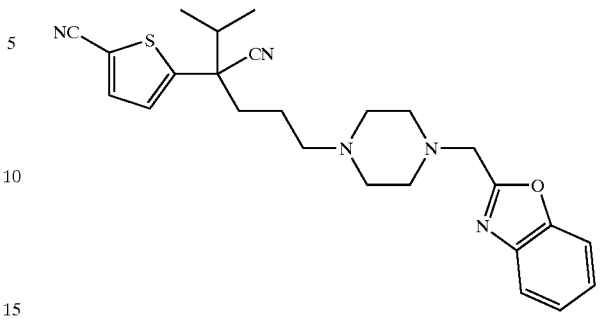

In acetonitrile (3 ml) was dissolved 200 mg (0.56 mmol) of 4-cyano-5-methyl-4-(5-cyano-2-thienyl)hexyl iodide. To the mixture were added 78.0 μl (0.56 mmol) of triethylamine and 146 mg (0.67 mmol) of 1-[(2-benzoxazoyl)methyl] piperazine, followed by stirring at 55° C. After 14 hours, the reaction solution was concentrated, and the residue was subjected to Cromatorex NH silica gel (ethyl acetate/hexane=1/2), to give 237 mg (0.53 mmol, 94.6%) of the titlecompoundasayellow syrup.
¹H-NMR (400 MHz, CDCl₃) δ 0.91 (d, J=6.8 Hz, 3H), 1.20 (d, J=6.8 Hz, 3l0, 1.20–1.30 (m, 1H), 1.59–1.70 (m, 1H), 1.70–1.80 (m, 1H), 2.00–2.09 (m, 1H), 2.15–2.25 (m, 11), 2.33 (t, J=7.2 Hz, 2H), 2.37–2.52 (m, 4H), 2.57–2.72 (m, 4H), 3.87 (s, 2H), 7.14 (d, J=4.0 Hz, 1H), 7.30–7.36 (m, 2H), 7.50 (d, J=4.0 Hz, 1H), 7.51–7.55 (m, 1H), 7.68–7.73 (m, 1H)
ESI-Mass; 448(M+H⁺)

Example 83 1-[4-Cyano-5-methyl-4-(2-thienyl) hexyl]-4-[{2-(5-cyanobenzoxazoyl)}methyl] piperazine

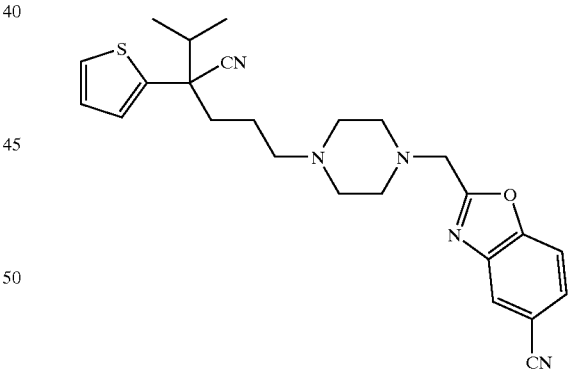

The title compound was synthesized in accordance with the production method described in Example 82 (yield: 89.3%).
¹H-NMR (400 MHz, CDCl₃) δ 0.90 (d, J=6.4 Hz, 3H), 1.18 (d, J=6.8 Hz, 3H), 1.22–1.36 (m, 1H), 1.56–1.70 (m, 1H), 1.71–1.80 (m, 1H), 2.00–2.09 (m, 1H), 2.10–2.19 (m, 1H), 2.29–2.36 (m, 2H), 2.36–2.52 (m, 4H), 2.56–2.71 (m, 4H), 3.89 (s, 2H), 6.93 (dd, J=3.6 Hz, 5.2 Hz, 1H), 7.10 (dd, J=1.2 Hz, 3.6 Hz, 1H), 7.25 (dd, J=1.2 Hz, 5.2 Hz, 1H), 7.60–7.66 (m, 2H), 8.02–8.04 (m, 1H)
ESI-MS; 448(M+H⁺)

Example 84 1-[4-cyano-5-methyl-4-(3-thienyl)hexyl]-4-[2-(3-fluorophenoxy)ethyl]piperazine

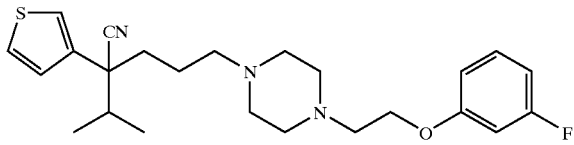

In nitrogen atmosphere, 1-[2-(4-fluorophenoxy)ethyl]piperazine (50 mg) synthesized in accordance with the method described in Production Example 1 in JP-A 11-206862 was added to an acetonitrile solution (3 ml) of 1-iodo-4-cyano-5-methyl-4-(3-thienyl)hexane (50 mg) and triethylamine (0.06 ml) at room temperature. After stirring at 50° C. for 4 hours, the solvent was evaporated, and the resulting residue was purified by Cromatorex NH silica gel column chromatography (hexane/ethyl acetate system), to give the title compound as a yellow oil (62 mg, 96%).
Free Body:
$^1$H-NMR (400 MHz, CDCl$_3$) δ 0.83 (d, J=6.8 Hz, 3), 1.16 (d, J 6.6 Hz, 3H), 1.55–1.65 (m, 1H), 1.74–1.84 (m, 1H), 2.02–2.12 (m, 2H), 2.29 (t, J=7.2 Hz, 2H), 2.30–2.47 (m, 4H), 2.47–2.65 (m, 4H), 2.79 (t, J=6.0 Hz, 2H), 4.07 (t, J=6.0 Hz, 2H), 6.58–6.70 (m, 3H), 6.92 (dd, 11.5 Hz, 5.0 Hz, 1H). 7.17–7.24 (m, 1H), 7.26–7.28 (m, 1H), 7.33 (dd, I=3.0 Hz, 5.0 Hz, 1H).

Further, 62 mg of the above-mentioned free body (the title compound) was dissolved in methanol, followed by adding an excessive 4N hydrochloric acid/ethyl acetate solution thereto. After stirring, the mixture was evaporated. After water was added to the resulting residue, the aqueous solution was frozen by being immersed in a dry ice-methanol bath. The solvent was removed by freeze-dry process over day and night, to give the hydrochloride of the title compound (white amorphous, 62 mg).
Hydrochloride:
ESI-Mass; 430(MH$^+$)

Example 85 1-[4-cyano-5-methyl-4-(3-thienyl)hexyl]-4-[2-(3-cyanaphenoxy)ethyl]piperazine

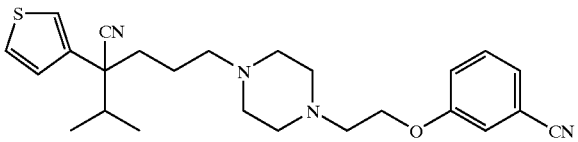

The title compound was obtained as a colorless oil in accordance with the production method described in Example 84 (85%).
Free Body:
$^1$H-NMR (400 MHz, CDCl$_3$) δ 0.83 (d, J16.8 Hz, 3H), 1.16 (d, J=6.6 Hz, 3H). 1.15–1.30 (m, 1H), 1.54–1.66 (m 1H), 1.75–1.85 (m, 1H), 2.02–2.15 (m, 2H), 2.25–2.33 (m, 2H), 2.33–2.48 (m 4H), 2.48–2.65 (m, 4H), 2.80 (t, J=5.7 Hz, 2H), 4.10 (t, J=5.7 Hz, 2H), 6.93 (dd, J=1.3 Hz, 5.1 Hz, 1H), 7.10–7.30 (m, 2H), 7.20–7.26 (m, 110, 7.26–7.28 (m, 1H)1.7.32–7.39 (m, 2H).

Further, the hydrochloride of the free body (the title compound) was obtained in accordance with the method described in Example 84.
Hydrochloride:
ESI-Mass; 437(MH$^+$)

Example 86 1-[4-cyano-5-methyl-4-[4-(2-cyano)Thienyl]hexyl]-4-[2-(3-fluorophenoxy)ethyl]piperazine

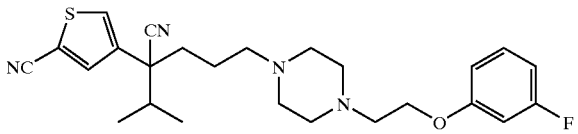

The title compound was obtained as a colorless oil in accordance with the production method described in Example 84 (76%).
Free Body:
$^1$H-NMR (400 MHz, CDCl$_3$) δ 0.84 (d, J=6.8 Hz, 3H), 1.01–1.02 (m, 1.17(d, J=6.6 Hz, 3H), 1.50–1.70 (x. 1H), 1.75–1.85 (m, 1H), 2.00–2.08 (m 1H), 2.08–2.18 (m, 1H), 2.27–2.33 (m, 2H), 2.33–2.48 (m, 4H), 2.48–2.66 (m, 4H), 2.80 (t, J=5.8 Hz, 2H), 4.07 (t, J=5.8 Hz, 2H), 6.59–6.70 (Ex 3H), 7.17–7.25 (m, 1H), 7.46 (d, J=1.6 Hz, 110), 7.56 (d, J=1.6 Hz, 1H).

Further, the hydrochloride of the free body (the title compound) was obtained in accordance with the method described in Example 84.
ESI-Mass; 455(MH$^+$)

Example 87 1-[4-cyano-5-methyl-4-[4-(2-cyano)-thienyl]hexyl]-4-[2-(3-cyanophenoxy)ethyl]piperazine

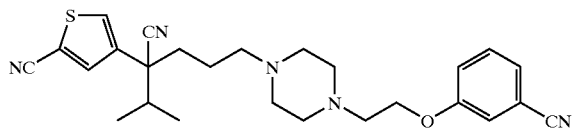

The title compound was obtained as a colorless oil in accordance with the production method described in Example 84 (78%).
Free Body:
$^1$H-NMR (400 MHz, CDCl$_3$) δ 0.84 (d, J=6.8 Hz, 3H), 1.01–1.02 (m, 1H), 1.17 (d, J=6.6 Hz, 3H), 1.50–1.65 (m, 1H), 1.75–1.85 (m, 1H), 2.00–2.09 (m, 1H), 2.09–2.18 (m, 1H), 2.27–2.33 (m, 2H), 2.33–2.48 (m, 4H), 2.48–2.66 (m, 4H), 2.81 (t, J=5.8 Hz, 2H), 4.10 (t, J=5.8 Hz, 21), 7.12–7.16 (m, 2H), 7.23–7.28 (m, 1H), 7.36 (t, J=0.8 Hz, 7.8 Hz, 1H), 7.46 (d, J=1.6 Hz, 1H), 7.56 (d, J=1.6 Hz, 1H).

Further, the hydrochloride of the free body (the title compound) was obtained in accordance with the method described in Example 84.
ESI-Mass; 462(MH$^+$)

Example 88 1-[4-cyano-5-methyl-4-(2-thienyl)hexyl]-4-[2-(2-cyano-4-fluorophenoxy)ethyl]piperazine

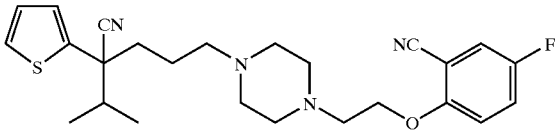

The title compound was obtained as a colorless oil in accordance with the production method described in Example 84 (72%).

Free Body:
¹H-NMR (400 MHz, CDCl₃) δ 0.90 (d, J=6.8 Hz, 3H), 1.18 (d, J=6.6 Hz, 3H), 1.22–1.38 (m 11H), 1.52–1.70 (m, 1H), 1.73–1.83 (m, 1H), 2.00–2.11 (m, 1H). 2.11–2.20 (m, 1H), 2.27–2.33 (m, 2H), 2.33–2.51 (m, 4H); 2.51–2.70 (m, 4H). 2.86 (t, J=5.8 Hz, 2H), 4.17 (t, J=5.8 Hz, 2H), 6.89–6.97 (m, 2H), 7.09–7.12 (m, 1H), 7.20–7.30 (m, 2H).

Further, the hydrochloride of the free body (the title compound) was obtained in accordance with the method described in Example 84.
ESI-Mass; 455(MH⁺)

Example 89 1-[4-cyano-5-methyl-4-(3-thienyl) hexyl]-4-[2-(2-cyano-4-fluorophenoxy)ethyl] piperazine

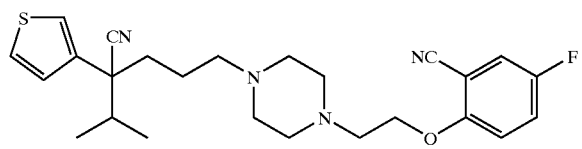

The title compound was obtained as a colorless oil in accordance with the production method described in Example 84 (72%).
Free Body:
¹H-NMR (400 MHz, CDCl₃) δ 0.83 (d, J=6.8 Hz, 3H), 1.16 (d, J=6.6 Hz, 3H). 1.16–1.20 (m, 1H), 1.50–1.66 (m, 1H) 1.76–1.86 (m, 1H), 2.01–2.13 (m, 2H), 2.24–2.33 (m, H), 2.33–2.51 (m, 4H), 2.51–2.70 (m, 4H), 2.87 (t, J=5.8 Hz, 2H), 4.17 (t, J=5.8 Hz, 2H), 6.89–6.97 (m, 2H), 7.20–7.30 (m, 3H), 7.33–7.38 (m, 1H).

Further, the hydrochloride of the free body (the title compound) was obtained in accordance with the method described in Example 84.
ESI-Mass; 455(MH⁺)

Example 90 1-[4-cyano-5-methyl-4-(2-thienyl) hexyl]-4-[2-(4-cyano-2-fluorophenoxy)ethyl] piperazine

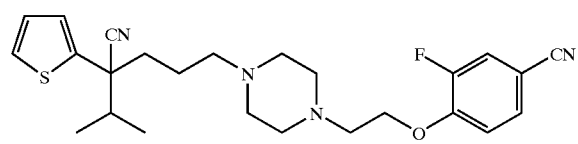

The title compound was obtained as a colorless oil in a similar method as in Example 84 (64%), by using 2-(4-cyano-2-fluorophenoxy)ethyl]piperazine synthesized in the same manner as in Reference Example 69 as a raw material.
Free Body:
¹H-NMR (400 MHz, CDCl₃) 0.90 (d, J=6.6 Hz, 3H), 1.18 (d, J=6.8 Hz, 3H), 1.22–1.38 (m, 1H), 1.52–1.70 (m, 1H), 1.72–1.82 (m, 1H), 2.00–2.10 (m, 1H), 2.11–2.20 (m, 1H), 2.27–2.33 (m, 2H), 2.33–2.51 (m, 4H), 2.51–2.70 (m, 4H). 2.85 (t, J=5.8 Hz, 2H), 4.20 (t, J=5.8 Hz, 2H), 6.94 (dd, J=3.7 Hz, 5.2 Hz, 1H), 7.00 (t, J=8.2 Hz, 1H), 7.10 (dd, 11.3 Hz, 3.7 Hz, 1H), 7.24–7.27 (m, 1H), 7.35 (dd, J=1.9 Hz, 10.4 Hz, 1H), 7.38–7.42 (m, 1H.

The hydrochloride of the target compound was obtained by treating the free body in the similar manner as in Example 84.
ESI-Mass; 455(MH⁺)

Example 91 1-[4-cyano-5-methyl-4-(3-thienyl) hexyl]-4-[2-(4-cyano-?2-fluorophenoxy)ethyl] piperazine

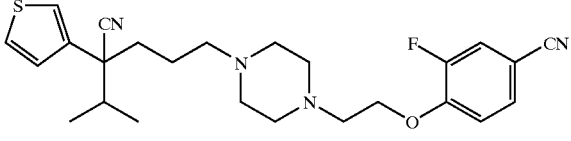

The title compound was obtained as a colorless oil according to a similar method as in Example 84 (64%), by using 2-(4-cyano-2-fluorophenoxy)ethylpiperazine synthesized in accordance with Reference Example 69 as a raw material, Free Body:

¹H-NMR (400 MHz, CDCl₃) δ 0.83 (d, J=6.8 Hz, 3H), 1.16 (d, J=6.8 Hz, 3H), 1.22–1.38 (m, 1H), 1.52–1.70 (m, 1H), 1.74–1.84 (m, 1H), 2.00–2.13 (m, 2H), 2.25–2.33 (m, 2H), 2.33–2.49 (m, 4H), 2.49–2.68 (m, 4H), 2.85 (t, I=5.8 Hz, 2H), 4.20 (t, J=5.8 Hz, 2H), 6.92 (dd, J=1.5 Hz, 5.1 Hz, 1H), 7.00 (t, J=8.4 Hz, 1H), 7.25–7.28 (m, 11H), 7.32–7.37 (m, 2H), 7.40 (ddd, J=1.3 Hz, 1.8 Hz, 8.4 Hz, 1H).

Further, the hydrochloride of the free body (the title compound) was obtained in accordance with the method described in Example 84.

ESI-Mass; 455(MH⁺)

Example 92 1-[4-cyano-5-methyl-4-[(2.5-dibromo)-3-thienyl]hexyl]-4-[2-(3-cyanophenoxy)ethyl] piperazine

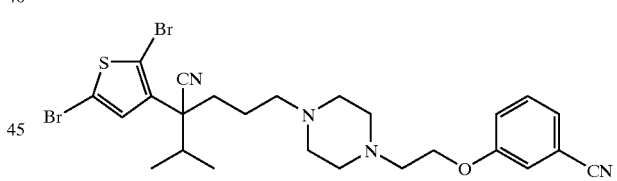

The title compound was obtained as a colorless oil in accordance with the production method described in Example 84 (78%).

Free Body:

¹H-NMR (400 MHz, CDCl₃) δ 0.90 (d, J=6.6 Hz, 3H), 1.17 (d, J=6.8 Hz, 3H), 1.22–1.38 (m, 1H), 1.52–1.70 (m, 1H), 1.82–2.02 (m, 1H), 2.30–2.53 (a, 8H), 2.53–2.68 (m, 4H), 2.81 t, J=5.8 Hz, 2H), 4.10 (t, J=5.8 Hz, 2H), 7.04 (s, 1H), 7.11–7.20 (m, 2H), 7.22–7.29 (m 1H), 7.34–7.39 (m, 1H).

Further, the hydrochloride of the free body (the title compound) was obtained in accordance with the method described in Example 84.

ESI-Mass; 593, 595, 597(MH⁺)

Example 93 1-(4-cyano-5-methyl-4-[2-bromo-5-cyano-3-thienyl)hexyl]-4-[2-(3-cyanophenoxy)ethyl]piperazine

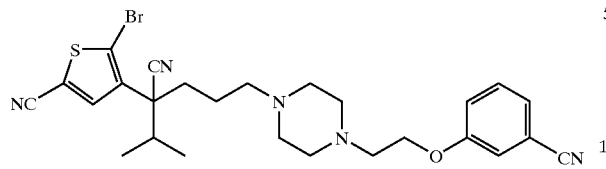

In a nitrogen atmosphere, 1-(4-cyano-5-methyl-4-[(2,5-dibromo)-3-thienyl]hexyl)-4-[2-(3-cyanophenoxy) ethyl] piperazine (145 mg) was dissolved in a mixed solvent of dimethylformamide (10 mL)/water (0.1 mL) of zinc cyanide (57.3 mg) and 1,1'-bis(diphenylphosphino)ferrocene (13.5 mg). Palladium-dibenzylidene acetone complex (8.9 mg) was added thereto, the atmosphere of the mixture was replaced 3 times with nitrogen, and then the solution was stirred at 120° C. for 4 hours. Water, diethyl ether and an aqueous ammonia were added thereto, to separate the organic layer. The resulting organic layer was washed with water and brine, dried over anhydrous magnesium sulfate. After filtering off the drying agent, the filtrate was evaporated, and the residue was purified by LC-MS (ODS column; acetonitrile/water system), to give the title compound as a yellow oil (8 mg, 6.7%).

Free Body:
$^1$H-NMR (400 MHz, CDCl$_3$) δ 0.89 (d, J=6.6 Hz, 3H), 1.19 (d, J=6.6 Hz, 3H), 1.19–1.25 (m, 1H), 1.53–1.68 (m, 1H), 2.00–2.10 (m, 1H), 2.30–2.70 (m, 12H), 2.83 (t, J=5.7 Hz, 2H), 4.11 (t, J=5.7 Hz, 2H), 7.11–7.17 (m, 2H), 7.22–7.27 (m, 1H), 7.34–7.39 (m 1H), 7.55 (s, 1H).

Further, the hydrochloride of the free body (the title compound) was obtained in accordance with the method described in Example 84.
ESI-Mass; 540, 542(MH$^+$)

Example 94 1-[4-cyano-5-methyl-4-(2-thienyl)hexyl]-4-[2-(4-methyltiophenoxy)ethyl]piperazine

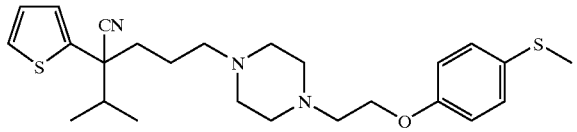

The title compound was obtained as a colorless oil in accordance with Example 45 described in JP-A 11-206862 (64%).

Free Body:
$^1$H-NMR (400 MHz, CDCl$_3$) δ 0.90 (d, J=6.8 Hz, 3H), 1.18 (d, 1=6.8 Hz, 3H), 1.22–1.38 (m, 1H), 1.55–1.70 (m, 1H), 1.71–1.82 (m, 1H), 2.02–2.10 (m, 1H), 2.11–2.21 (m, 1H), 2.27–2.35 (m, 2H), 2.35–2.50 (m, 4H), 2.44 (s, 3H), 2.50–2.65 (in 4H), 2.78 (t, J=5.9 Hz, 2H), 4.07 (t, J=5.9 Hz, 2H), 6.84 (brd, 1=8.8 Hz, 2H), 6.94 (dd, J=3.7 Hz, 4.9 Hz, 1H), 7.11 (brd, J=3.7 Hz, 1H), 7.22–7.29 (m, 3H).

Further, the hydrochloride of the free body (the title compound) was obtained in accordance with the method described in Example 84.
ESI-Mass; 456(MH$^+$)

Example 95 1-[4-cyano-5-methyl-4-(2-thienyl)hexyl]-4-[2-(4-methylsulfonylphenoxy)ethyl]piperazine

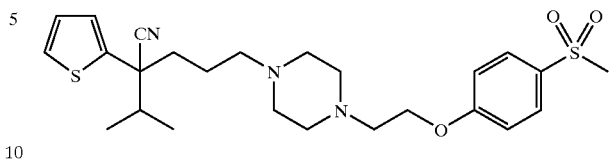

The title compound was obatined as a colorless oil in accordance with the production method described in Example 84 (85%).

Free Body:
$^1$H-NMR (400 MHz, CDCl$_3$) δ 0.90 (d, J=6.8 Hz, 3H), 1.18 (d, J=6.6 Hz, 3H), 1.22–1.38 (m, 1H), 1.55–1.71 (m, 1), (d, J=6.6 Hz, 3H), 1.22–1.38 (m, 1H), 1.55–1.71 (m, 1), 1.71–1.82 (m, 1H), 2.02–2.10 (m 1H) 2.11–2.21 (m, 1H), 2.27–2.35 (m, 2H), 2.35–2.50 (m, 4H), 2.50–2.65 (m, 4H). 2.83 (t, J=5.8 Hz, 2H), 3.03 (s, 3H), 4.16 (t, J=5.8 Hz, 2H), 6.84 (brd, J=8.8 Hz, 2H), 6.94 (dd, J=3.7 Hz, 4.9 Hz, 11), 7.11 (brd, J=3.7 Hz, 1H), 7.22–7.29 (m, 3H).

Further, the hydrochloride of the free body (the title compound) was obtained in accordance with the method described in Example 84.
ESI-Mass; 490(MH$^+$)

Example 96 1-[4-cyano-5-methyl-4-(2-thienyl)hexyl]-4-[2-(3-acetylphenoxy)ethyl]piperazine

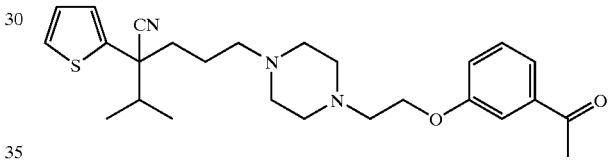

The title compound was obtained as a colorless oil in accordance with the production method described in Example 84 (72%).

Free Body:
$^1$H-NMR (400 MHz, CDCl$_3$) δ 0.90 (d, J=6.8 Hz, 3H), 1.18 (d, J=6.6 Hz, 3H), 1.22–1.38 (m, 1H), 1.55–1.71 (m, 1H), 1.71–1.82 (m, 1H), 2.02–2.10 (m, 1H), 2.11–2.21 (m, 1H), 2.28–2.35 (m, 2H), 2.35–2.50 (m, 4H), 2.50–2.65 (m, 41), 2.59 (s, 3H), 2.82 (t, J=5.8 Hz, 2H), 4.14 (t, J=5.8 Hz, 2H), 6.94 (dd, J=3.5 Hz, 4.9 Hz, 1H), 7.09–7.13 (oL 2H), 7.24–7.28 (m, 11), 7.36 (t, J=7.9 Hz, 1H), 7.47–7.50 (m, 1H), 7.54 (brd, J=7.9 Hz, 1H).

Further, the hydrochloride of the free body (the title compound) was obtained in accordance with the method described in Example 84.
ESI-Mass; 454(MH$^+$)

Example 97 1-[4-cyano-5-methyl-4-(3-thienyl)hexyl]-4-[2-(3-acetylphenoxy)ethyl]piperazine

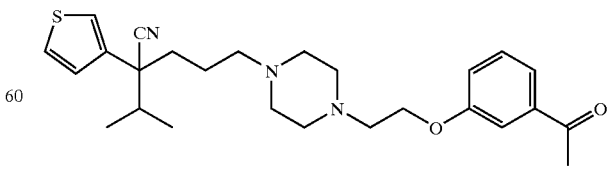

The title compound was obtained as a colorless oil in accordance with the production method described in Example 84 (60%).

Free Body:
¹H-NMR (400 MHz, CDCl₃) δ 0.83 (d, J=6.6 Hz, 310, 1.16 (d, J=6.8 Hz, 3H), 1.16–1.30 (m, 1H), 1.50–1.68 (m, 1H), 1.75–1.84 (m, 1H), 2.02–2.13 (m, 2H), 2.25–2.35 (m, 2H), 2.35–2.47 (m, 4H), 2.47–2.68 (m, 4H), 2.59 (s, 3H), 2.81 (t, J=5.9 Hz, 2H), 4.14 (t, J=5.9 Hz, 2H), 6.92 (dd, J=1.4 Hz, 4.9 Hz, 1H), 7.09–7.13 (m, 11H), 7.25–7.28 (m, 1H), 7.32–7.38 (mL 2H), 7.47–7.50 (m, 1H), 7.51–7.56 (m, 1H).

Further, the hydrochloride of the free body (the title compound) was obtained in accordance with the method described in Example 84.
ESI-Mass; 454(MH⁺)

Example 98 1-[4-cyano-5-methyl-4-(3-thienyl) hexyl]-4-[2-(4-cyanophenoxy)ethyl]piperazine

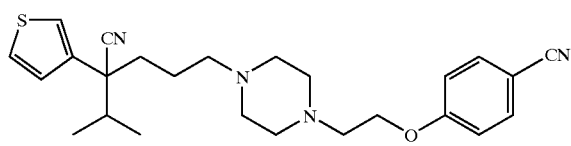

The title compound was obtained as a colorless oil in accordance with the production method described in Example 84 (55%).
Free Body:
¹H-NMR (400 MHz, CDCl₃) δ 0.83 (d, J=6.8 Hz, 3H), 1.16 (d, J=6.8 Hz, 3H), 1.16–1.30 (m 1H), 1.50–1.68 (m, 1H), 1.72–1.84 (m, 1H), 2.02–2.12 (m, 2H), 2.25–2.35 (m, 2H), 2.35–2.45 (m, 4H), 2.45–2.65 (m, 4H), 2.81 (t, J=5.8 Hz, 2H), 4.12 (t, J=5.8 Hz, 2H), 6.90–6.97 (m, 3H), 7.23–7.32 (m, 1H), 7.32–7.36 (m, 1H), 7.57 (d, J=8.6 Hz, 2H).

Further, the hydrochloride of the free body (the title compound) was obtained in accordance with the method described in Example 84.
ESI-Mass; 437(MH⁺)

Example 99 1-[4-cyano-5-methyl-4-(3-thienyl) hexyl]-4-[2-(4-methylthiophenoxy)eTHYL] pIPERAZINE

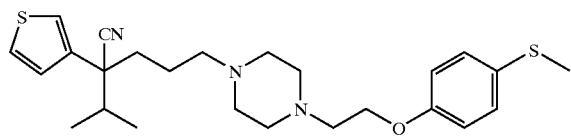

The title compound was obtained as a colorless oil in accordance with Example 45 described in JP-A 11-206862 (59%).
¹H-NMR (400 MHz, CDCl₃) δ 0.83 (d, J=6.6 Hz, 3H), 1.16 (d, J=6.8 Hz, 3H), 1.16–1.30 (m, 1H), 1.50–1.68 (m, 1H), 1.72–1.84 (m, 1H), 2.02–2.12 (m, 2H), 2.25–2.35 (m, 2H), 2.35–2.48 (m, 4H), 2.44 (s, 3H), 2.48–2.65 (m, 4H), 2.78 (t, J=5.9 Hz, 2H), 4.06 (t, J=5.9 Hz, 2H), 6.84 (brd, J=6.6 Hz, 2H), 6.92 (dd, J=1.5 Hz, 5.1 Hz, 1H), 7.22–7.28 (m, 3H), 7.33 (dd, J=3.0 Hz, 5.1 Hz, 1H).

Further, the hydrochloride of the free body (the title compound) was obtained in accordance with the method described in Example 84.
ESI-Mass; 456(MH⁺)

Example 100 1-[4-cyano-5-methyl-4-(3-thienyl] hexyl]-4-[2-(4-methylsulfonylphenoxy)ethyl] piperazine

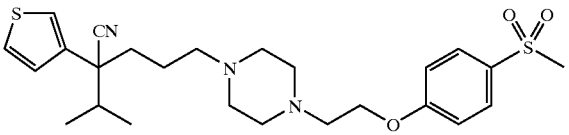

The title compound was obtatined as a colorless oil in accordance with the production method described in Example 84 (56%).
Free Body:
¹H-NMR (400 MHz, CDCl₃) δ 0.83 (d, J=6.6 Hz, 3H), 1.16 (d, J=6.8 Hz, 3H), 1.16–1.30 (m, 1H), 1.50–1.68 (d, 1H), 1.74–1.84 (m, 1H), 2.02–2.12 (m, 2H), 2.25–2.35 (m, 2H), 2.35–2.48 (m, 4H), 2.48–2.65 (t, 4H), 2.82 (t, J=5.9 Hz, 2H), 3.03 (s, 3H), 4.16 (t, J=5.9 Hz, 2H), 6.92 (dd, J=1.5 Hz, 5.1 Hz, 1H), 7.02 (brd, J=8.8 Hz, 2H), 7.24–7.29 (m, 1H); 7.33 (dd, J=3.0 Hz, 5.1 Hz, 1H), 7.86 (brd, J=8.8 Hz, 2H).

Further, the hydrochloride of the free body (the title compound) was obtained in accordance with the method described in Example 84.
ESI-Mass; 490(MH⁺)

Example 101 1-[4-cyano-5-methyl-4-(2-thienyl) hexyl]-4-[2-(3-bromophenoxy)ethyl]piperazine

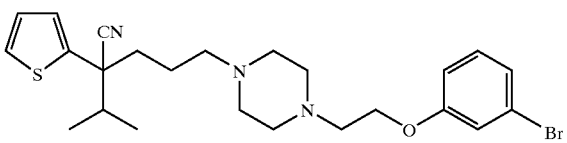

The title compound was obtained as a colorless oil in accordance with the production method described in Example 84 (87%).
Free Body:
¹H-NMR (400 MHz, CDCl₃) δ 0.90 (d, J=6.6 Hz, 3H), 1.18 (d, 1=6.6 Hz, 3H), 1.20–1.40 (m, 1H), 1.55–1.70 (m, 1H), 1.72–1.82 (m, 1H), 2.00–2.10 (m, 2H), 2.10–2.22 (m, 2H), 2.25–2.35 (m, 210, 2.35–2.50 (m, 4H), 2.50–2.65 (m, 4H). 2.78 (t, J=5.8 Hz, 2H), 4.06 (t, J=5.8 Hz, 210, 6.80–6.85 (m, 1H), 6.94 (brdd, J=3.5 Hz, 5.0 Hz, 1H), 7.04–7.15 (m, 4H), 7.24–7.28 (m, 1H).

Further, the hydrochloride of the free body (the title compound) was obtained in accordance with the method described in Example 84.
ESI-Mass; 490, 492(MH⁺)

Example 102 1-[4-cyano-5-methyl-4-(2-thienyl) hexyl]-4-(2-phenoxyethyl)piperazine

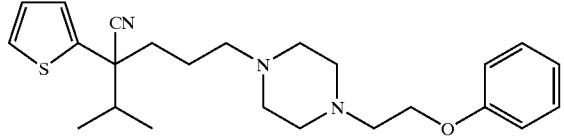

The title compound was obtained as a colorless oil in accordance with the production method described in Example 84 (97%).
Free Body:

¹H-NMR (400 MHz, CDCl₃) δ 0.90 (d, J=6.6 Hz, 3H), 1.18 (d, J=6.6 Hz, 3H). 1.20–1.40 (m, 1H), 1.55–1.70 (m, 1H), 1.72–1.82 (m, 1), 2.00–2.10 (m, 2H), 2.10–2.22 (m, 2H), 2.25–2.35 (m, 2H), 2.35–2.50 (m, 4H), 2.50–2.65 (m, 4H), 2.80 (t, J=5.8 Hz, 2), 4.09 (t, J=5.8 Hz, 2H), 6.87–6.97 (m, 41), 7.08–7.12 (m, 1H), 7.23–7.30 (m, 2H).

Further, the hydrochloride of the free body (the title compound) was obtained in accordance with the method described in Example 84.

ESI-Mass; 412(MH⁺)

Example 103 1-[4-cyano-5-methyl-4-(2-bromo-5-thienyl)hexyl]-4-[2-(3-cyanophenoxy)ethyl] piperazine

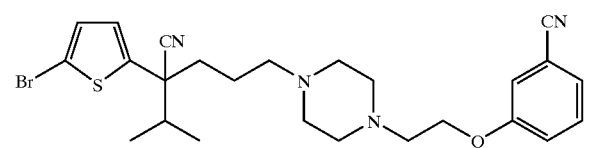

By using [4-cyano-5-methyl-4-(2-bromo-5-thienyl)hexyloxy]-tert-butyldimethylsilane (700 mg) which was obtained in Example 114-5) described in JP-A 11-206862, 4-cyano-5-methyl-4-(2-bromo-5-thienyl)hexanol (371 mg, 80%) was synthesized as a yellow oil in accordance with Example 114-8) described in JP-A 11-206862. From 105 mg of the resulting compound and 96 mg of 2-(3-cyanophenoxy)ethylpiperazine, the title compound was synthesized as a colorless oil in accordance with the production method described in Example 84 (138 mg, 62%).

Free Body:
¹H-NMR (400 MHz, CDCl₃) δ 0.93 (d, J=6.8 Hz, 3H), 1.18 (d, J=6.8 Hz, 3H), 1.20–1.40 (m, 1H), 1.55–1.70 (m, 1H), 1.90–2.05 (m, 1H), 2.05–2.20 (m, 2H), 2.30–2.38 (m, 2H), 2.38–2.50 (m, 4H), 2.50–2.65 (m, 4H), 2.81 (t, J=5.8 Hz, 2H), 4.10 (t, J=5.8 Hz, 2H), 6.90 (dd, J=30.8 Hz, 8.6 Hz, 2H), 7.10–7.17 (m, 2H), 7.22–7.30 (m, 1H), 7.33–7.40 (m, 1H).

Further, the hydrochloride of the free body (the title compound) was obtained in accordance with the method described in Example 84.

ESI-Mass; 515, 517(MH⁺)

Example 104 1-[4-cyano-4-(3-cyano-5-thienyl]-5-methylhexyl]-4-[2-(4-methylaulfonylphenoxy)ethyl] piperazine

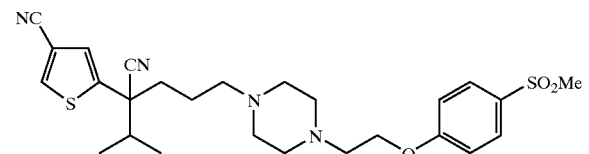

From 4-cyano-4-(3-cyano-5-thienyl)-5-methylhexanol and 1-[2-(4-methylsulfonylphenoxy)ethyl]piperazine, the title compound was synthesized as a pale yellow oil in accordance with the method of Example 68 (39%). Further, the hydrochloride was obtained by treating the free body (the title compound) in a conventional method.

Free Body:
¹H-NMR (400 MHz, CDCl₃) δ 0.92 (d, J=6.8 Hz, 3H), 1.20 (d, J=6.8 Hz, 3H), 1.21–1.31 (m, 1H), 1.60–1.72 (m, 1H), 1.78 (dt, J=4 Hz, J=13.2 Hz, 1H), 2.07 (qui, J=6.8 Hz, 1H), 2.20 (dt, J=4 Hz, J=13.2 Hz, 1H), 2.33 (t, J=7.2 Hz, 2H), 2.42 (bs, 4H), 2.59 (bs, 4H), 2.83 (t, J=5.6 Hz, 2H), 3.03 (s, 3H), 4.16 (t, J=5.6 Hz, 2H), 7.02 (d, J=8.8 Hz, 1H), 7.29 (d, 1=1.2 Hz, 1H), 7.86 (d, J=8.8 Hz, 2H), 7.90 (d, J=1.2 Hz, 1H).

Hydrochloride:
ESI-Mass; 515(MH⁺)

Example 105 1-[4-cyano-4-(3-cyano-5-thienyl)-5-methylhexyl]-4-[2-(3-acetylphenoxy)ethyl] piperazine

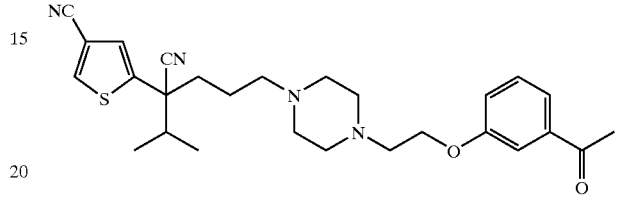

From 4-cyano-4-(3-cyano-5-thienyl)-5-methylhexanol and 1-[2-(3-acetylphenoxy)ethyl]piperazine, the title compound was obtained as a pale yellow oil in accordance with the method of Example 68 (yield: 38%). Further, the hydrochloride was obtained by treating the free body (the title compound) in a conventional method.

Free Body:
¹H-NMR (400 MHz, CDCL₃) δ 0.92 (d, J=6.8 Hz, 3H), 1.20 (d, 1=6.8 Hz, 3H), 1.21–1.32 (m, 1H), 1.60–1.74 (m, 1H)1, 1.78 (dt, J=4 Hz, J=13.2 Hz, 1H). 2.07 (qui, J=6.8 Hz, 1H), 2.20 (dt, J=4 Hz, J=13.2 Hz, 1H), 2.29–2.37 (m, 2H), 2.43 (bs, 4H), 2.59 (bs, 4H), 2.60 (s, 3H), 2.83 (t, J=5.6 Hz, 2H), 4.15 (t, J=5.6 Hz, 2H), 7.10–7.13 (m, 1H), 7.29 (d, J=1.2 Hz, 1H), 7.37 (t, J=8 Hz, 1H), 7.49 (dd, 11.6 Hz, J=2.8 Hz, 1H), 7.52–7.55 (m, 1H), 7.90 (d, J=1.2 Hz, 1H).

Hydrochloride:
ESI-Mass; 479(MH⁺)

Example 106 1-[4-Cyano-5-methyl-4-(2-thienyl) hexyl]-4-{[2-(5-cyanobenzofuranyl)]methyl} piperazine

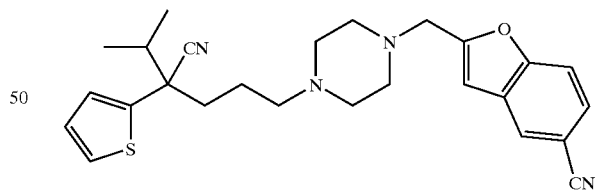

By using 1-[(2-(5-cyanobenzofuranyl)]methyl piperazine, the title compound was synthesized in accordance with the method of Example 75 (yield: 100%).

¹H-NMR (400 MHz, CDCl₃) δ 0.90 (d, J=6.4 Hz, 3H), 1.18 (d, J=6.8 Hz, 3H), 1.22–1.37 (m, 1H), 1.56–1.70 (m, 1H)1, 1.70–1 80 (m, 1H), 2.00–2.09 (m, 11), 2.10–2.19 (m, 1H), 2.32 (t, J=7.2 Hz, 2H), 2.35–2.65 (m, 8H), 3.70 (s, 2H), 6.65 (brd-s, 1H), 6.93 (dd, J=3.2 Hz, 5.2 Hz, 1H), 7.10 (dd, J=1.2 Hz, 3.2 Hz, 1H), 7.24 (dd, J=1.2 Hz, 5.2 Hz, 1H)1, 7.52–7.54 (m, 2H), 7.85–7.87 (m, 1H)

ESI-MS; 447(M+H)⁺

Example 107 1-[4-cyano-5-methyl-4-(5-cyano-2-thienyl)hexyl]-4-(2-phenoxyethyl)piperazine

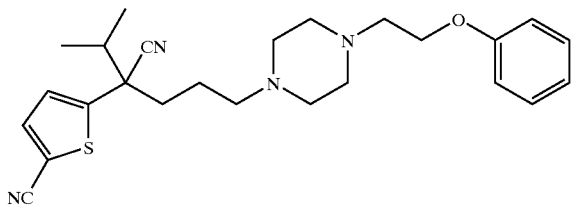

By using 1-[2-phenoxyethyl]piperazine, the target compound was synthesized in accordance with the method of Example 77 (yield: 96.5%). The physico-chemical data of the title compound was as indicated below.

$^1$H-NMR (400 MHz, CDCl$_3$) δ 0.92 (d, J=6.8 Hz, 3H), 1.21 (d, J=6.4 Hz, 3H). 1.20–1.32 (m, 1H), 1.60–1.72 (m, 1H), 1.72–1.82 (m, 1H), 2.00–2.12 (m, 1H), 2.17–2.27 (m, 1H), 2.33 (t, J=7.2 Hz, 2H), 2.32–2.48 (m, 4H), 2.50–2.70 (m, 4H), 2.81 (t, J=6.0 Hz, 2H), 4.10 (t, J=6.0 Hz, 210, 6.88–6.97 (m, 3H), 7.15 (d, J=4.0 Hz, 1H), 7.25–7.30 (m, 2H), 7.51 (d, J 4.0 Hz, 1H)

ESI-MS; 437(M+H)$^+$

Example 108 1-[4-cyano-5-methyl-4-(5-cyano-2-thienyl)hexyl]-4-[2-(3-bromophenoxy)ethyl]piperazine

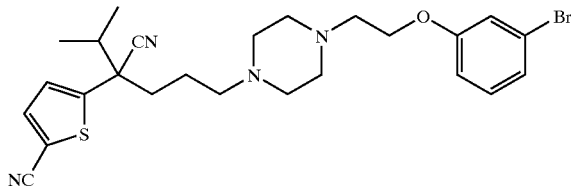

By using 1-[2-(3-bromophenoxy)ethyl]piperazine, the title compound was synthesized in accordance with the method of Example 77 (yield: 83.5%). The physico-chemical data of the title compound was as indicated below.

$^1$H-NMR (400 MHz, CDCL$_3$) δ 0.93 (d, J=6.4 Hz, 3H), 1.22 (d, J=6.8 Hz, 3H), 1.20–1.32 (m, 1H), 1.60–1.72 (m, 1H), 1.72–1.83 (m, 1H), 2.02–2.12 (m, 1H), 2.17–2.28 (m, 1), 2.28–2.50 (m, 6H), 2.50–2.67 (m, 4H), 2.80 (t, J=6.0 Hz, 2H), 4.10 (t, J=6.0 Hz, 2H), 6.81–6.86 (m, 1H), 7.05–7.10 (m, 2H), 7.10–7.14 (m, 1H), 7.16 (d, J=3.6 Hz, 1H), 7.52 (d, J=3.6 Hz, 1H)

MS(ESI)m/z; 515, 517(M+H)$^+$

The compounds of Examples 110, 111, 112, 113, 114, 115, 116, 117, 118, 119 and 120 were synthesized in accordance with the method of Example 1, 89 or 99 described in JP-A 11-206862, or according to the methods.

Example 109 1-[4-Cyano-5-methyl-4-(2-bromo-5-thienyl)hexyl]-4-[2-(3-cyanophenoxy)ethyl]piperazine

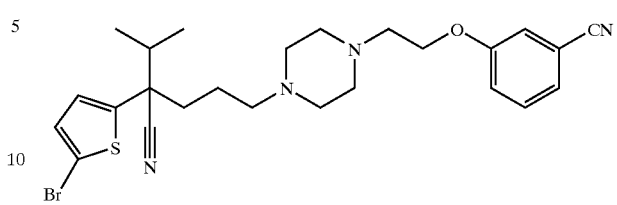

The title compoud was obtained as a pale brown oil in accordance with Example 1 described in JP-A 11-206862.

Hydrochloride:

ESI-MS (m/e); 515, 517(M+H)

Example 110 1-[4-cyano-5-methyl-4-(2-cyano-5-thienyl)hexyl]-4-[2-(3-chlorophenoxy)ethyl]piperazine

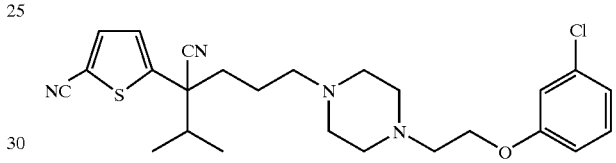

Free Body:

$^1$H NMR (400 MHz; CDCl$_3$) δ 0.92 (d, J=6.6 Hz, 3H), 1.21 (d, J=6.6 Hz, 3H), 1.21–1.32 (m, 1H), 1.55–1.73 (m, 2H), 2.00–2.12 (m, 1H), 2.15–2.30 (m, 1H). 2.30–2.38 (m, 2H), 2.38–2.45 (m, 4H), 2.50–2.65 (m, 4H), 2.80 (t, J=5.8 Hz, 2H), 4.07 (t, J=5.8 Hz, 2H), 6.76–6.82 (m, 1H), 6.88–6.95 (m, 1H), 7.13–7.21 (m, 3H), 7.51 (d, J=3.8 Hz, 1H).

Hydrochloride:

ESI-MS (m/e); 471(M+H)

Example 111 1-[4-cyano-5-methyl-4-(2-cyano-5-thienyl)hexyl]-4-[2-(3-iodophenoxy)ethyl]piperazine

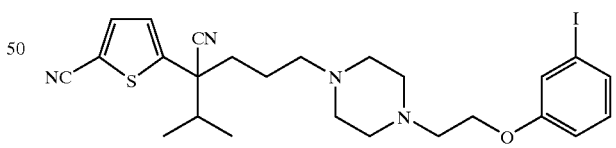

Free Body:

$^1$H NMR (400 MHz, CDCl$_3$) δ 0.92 (d, J=6.6 Hz, 3H), 1.21 (d, J=6.6 Hz, 3H), 1.21–1.32 (m, 1H), 1.55–1.73 (m, 2H), 2.00–2.12 (m, 1H), 2.15–2.30 (m, 1H), 2.30–2.38 (m, 2H), 2.38–2.45 (m, 4H), 2.50–2.65 (m, 4H), 2.79 (t, J=5.8 Hz, 2H), 4.06 (t, J=5.8 Hz, 2H), 6.86–6.99 (m, 1H), 6.96–7.01 (m, 1H), 7.15 (d, J=3.8 Hz, 1H), 7.25–7.30 (m, 2H), 7.51 (d, J=3.8 Hz, 1H).

Hydrochloride:

ESI-MS (m/e); 563(M+H)

Example 112 1-[4-Cyano-5-methyl-4-(2-thienyl)hexyl]-4-{N-[(3-cyanophenyl)-N-isopropylamino]ethyl}piperazine

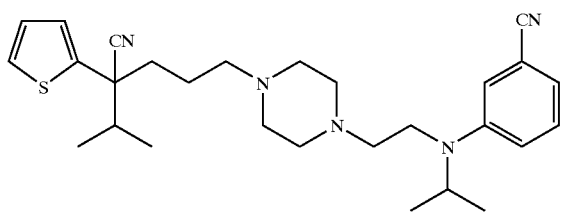

Hydrochloride:

ESI-MS (m/e); 478(M+H)

Example 113 1-[4-cyano-5-methyl-4-(2-thienyl)hexyl]-4-{N-[(3-cyanophenyl)-N-methylamino]ethyl}piperazine

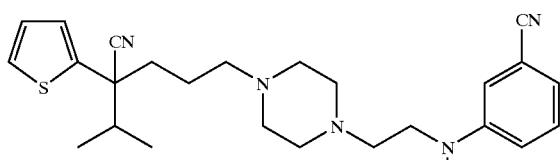

Free Body:

$^1$H NMR (400 MHz, CDCl$_3$) δ 0.90 (d, J=6.6 Hz, 3H), 1.18 (d, J=6.6 Hz, 3H), 1.20–1.40 (m, 1H), 1.45–1.70 (m, 1H), 1.70–1.82 ([, 1H), 2.00–2.10 (m, 1H), 2.10–2.20 (m, 1H), 2.24–2.60 (m, 12H), 3.00 (s, 3H), 3.46 (t, J=7.4 Hz, 2H), 6.84–6.98 (m, 4H), 7.11 (dd, J=3.5 Hz, 1.1 Hz, 1H), 7.23–7.33 (m, 2H).

Hydrochloride:

ESI-MS (m/e); 450(M+H)

Example 114 Synthesis of 1-[3-cyano-4-methyl-5-(2-thienyl)mentyl]-4-[2-(3-cyanophenoxy)ethyl]piperazine

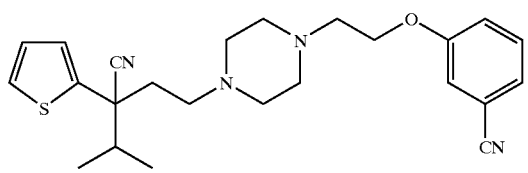

Free Body:

$^1$H NMR (400 MHz, CDCl$_3$) δ 0.91 (d, J=6.8 Hz, 3H), 1.19 (d, J=6.6 Hz, 3H), 1.85–1.98 (m 1H), 2.00–2.20 (m, 2H), 2.30–2.70 (m, 10H), 2.80 (t, J=5.9 Hz, 2H), 4.09 (t, J=5.9 Hz, 2H), 6.95 (dd, J=5.1 Hz, 3.7 Hz, 1H), 7.10–7.15 (m, 3H), 7.22–7.29 (m, 2H), 7.33–7.39 (m, 1H).

Hydrochloride:

ESI-MS (m/e); 423(M+H)

Example 115 1-[3-cyano-4-methyl-5-(2-thienyl)pentyl]-4-[2-(4-fluorophenoxy)ethyl]piperazine

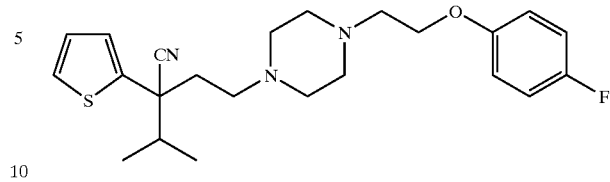

Free Body:

$^1$H NMR (400 MHz, CDCl$_3$) δ 0.91 (d, J=6.8 Hz, 31), 1.19 (d, J=6.8 Hz, 3H), 1.85–1.98 (m, 1H), 2.00–2.20 (m, 2H), 2.30–2.70 (m, 10H), 2.78 (t, J=5.9 Hz, 2H), 4.04 (t, 1=5.9 Hz, 2H), 6.80–6.85 (m, 2H), 6.92–6.99 (m, 3H), 7.10–7.13 (m, 1H), 7.26–7.30 (m, 1H).

Hydrochloride:

ESI-MS (m/e); 416(M+H)

Example 116 1-[4-Cyano-5-methyl-4-(2-thienyl)hexyl]-4-(cyclohexylmethyl)piperazine

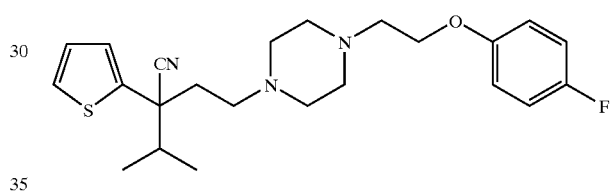

Trifluoroacetate:

ESI-MS (m/e); 388(M+H)

Example 117 4-[4-(4-phenylpiperidinyl)-piperidinyl]-1-isopropyl-1-phenylbutyl Cyanide

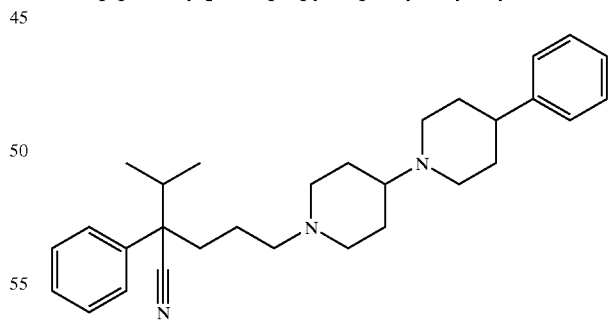

Free Body:

Rf-0.5 (developing solvent; ethyl acetate:hexane=2:1, Fuji Silysia Chemical Ltd., NH TLC)

Hydrochloride:

ESI-MS (m/e); 444(M+H)

Example 118 4-[4-(4-Cyano-4-phenylpiperidinyl)-piperidinyl]-1-isopropyl-1-phenylbutyl Cyanide

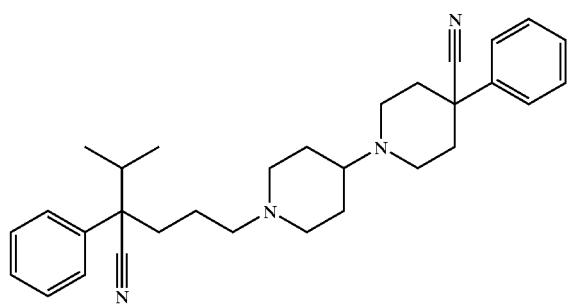

Free Body:

Rf=0.4 (developing solvent; ethyl acetate:hexane=2:1, Fuji Silysia Chemical Ltd., NH TLC)

Hydrochloride:

ESI-MS (m/e); 469(M+H)

Example 119 4-[4-(4-benzylpiperidinyl)-piperidinyl]-1-isoproryl-1-phenylbutyl Cyanide

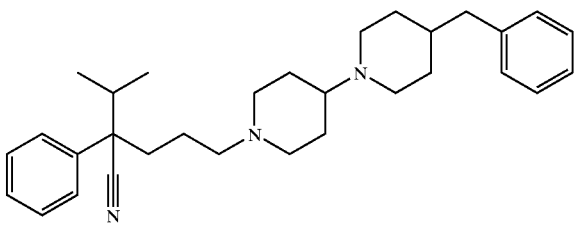

Free Body:

R=0.5 (developing solvent; ethyl acetate:hexane=2:1, Fuji Silysia Chemical Ltd., NH TLC)

Hydrochloride:

ESI-MS (m/e); 458(M+H)

Example 120 1-[4-Cyano-5-methyl-4-(2-thienyl)hexyl]-4-[2-[N-(1.2.3.4-tetrahydro-1-quinolinyl)Sulfamoyl]ethyl]piperazine

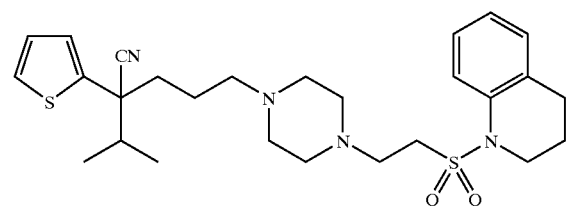

The title compound was synthesized in accordance with the method of Example 63 or 67 described in JP-A 11-206862, or according to those methods.

Trifluoroacetate:

ESI-MS (m/e); 515(M+H)

Example 121 1-[3-Cyano-4-methyl-5-(2-thienyl)pentyl]-4-[2-[N-(1 2.3.4-tetrahydro-1-quinolinyl)Sulfamoyl]ethyl]piperazine

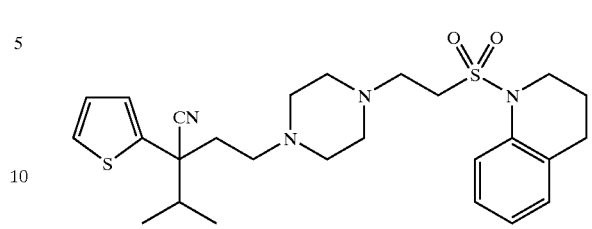

The title compound was synthesized in accordance with the method of Example 63 or 67 described in JP-A 11-206862, or according to the methods.

Trifluoroacetate:

ESI-MS (m/e); 501(M+H)

Example 122 1-[4-Cyano-5-methyl-4-(2-thienyl)hexyl]-4-[2-[N-(piperidinyl)Sulfamoyl]ethyl]piperazine

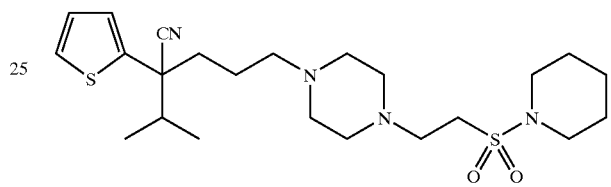

The title compound was synthesized in accordance with the method of Example 63 or 67 described in JP-A 11-206862, or according to the methods.

Hydrochloride:

ESI-MS (m/e); 467(M+H)

Example 123 Bis-1,4-[(3-cyano-4-methyl-3-phenyl)pentyl]piperazine

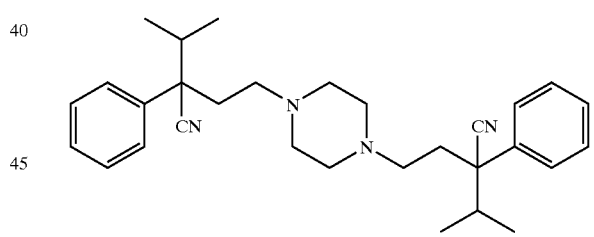

3-Methyl-2-(2-oxoethyl)-2-phenylbutanenitrile (100 mg) and anhydrous piperazine (22 mg) were dissolved in methylene chloride (5 ml). To the mixture were added acetic acid (0.085 ml) and sodium triacetoxyborohydride (158 mg), followed by stirring overnight at room temperature. The organic layer was separated by adding an aqueous saturated sodium bicarbonate and methylene chloride, and it was washed with water, dried over anhydrous magnesium sulfate and evaporated. The resulting residue was purified by Chromatorex NH silica gel column chromatography (hexane/ethyl acetate system), to give the title compound as a colorless oil (81 mg, 71%). The hydrochloride (89 mg) of the title compound was obtained by treating the free body in a conventional method.

Free Body:

$^1$H NMR (400 MHz, CDCl$_3$) δ 0.76 (d, J=6.8 Hz, 61), 1.10–1.20 (m, 2H), 1.19 (d, J=6.8 Hz, 6H), 1.50–1.60 (m, 2H), 1.90–2.15 (m, 6H), 2.00–2.45 (m, 8H). 7.25–7.42 (m, 10H).

Hydrochloride:
ESI-MS (m/e); 457(M+H)

The title compounds of Examples 124 to 126 were synthesized in accordance with the method of Example 123.

Example 124 Bis-1,4-[(3-cyano-4-methyl-3-phenyl)pentyl]homopiperazine

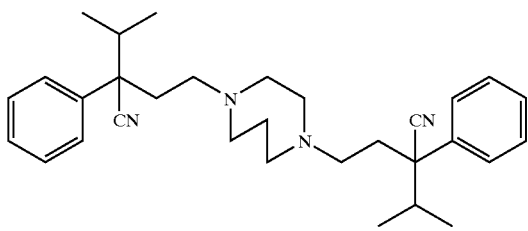

Hydrochloride;
ESI-MS (m/e); 471(M+H)

Example 125 Bis-1,4-[(3-cyano-4-methyl-3-phenyl)hexyl]homopiperazine

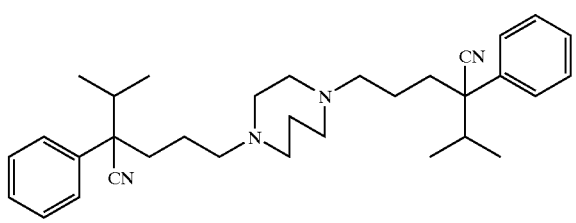

Hydrochloride:
ESI-MS (m/e); 499(M+H)

Example 126 Bis-1,4-[(3-cyano-4-methyl-3-(2-thienyl)pentyl]piperazine

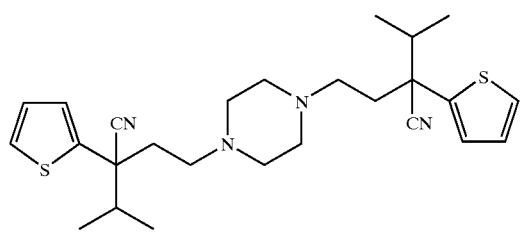

Hydrochloride:
ESI-MS (m/e); 469(M+H)

Example 127 (S)-3-phenyl-2-aminopropanic Acid {1-[(4-cyano-5-methyl-4-phenyl)hexyl]piperazinyl]Amide

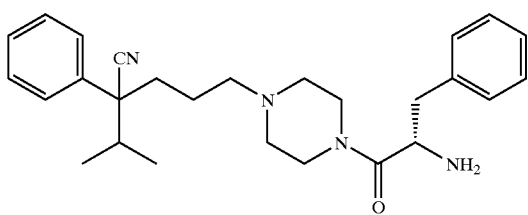

After dissolving 1-t(4-cyano-5-methyl-4-phenyl)hexyl] piperazine (14 mg) and N-(tert-butoxycarbonyl)-L-phenylalanine (10 mg) in methylene chloride (0.5 ml), 1-(3-dimethylaminopropyl)-3-ethylcarbodiimide (10 mg) and triethylamine (0.015 ml) were added thereto, and the mixture was stirred overnight at room temperature. After the solution was purified by silica gel column chromatography (diethyl ether), the solvent was removed by blowing of nitrogen. After dissolving the resulting residue in methylene chloride (0.4 ml), trifluoroacetic acid (0.2 ml) was added thereto and the mixture was stirred at room temperature for 9 hours. The reaction solvent was removed by standing the mixture as it was at 35° C. by blowing of nitrogen overnight, to give the hydrochloride (21 mg, 91%) of the title compound.

Hydrochloride:
ESI-MS (m/e); 433(M+H)

The title compounds of Examples 128 and 129 were synthesized in accordance with the method of Example 127.

Example 128 (S)-3-phenyl-2-aminonpropanic acid {1-[(4-cyano-5-methyl-5-(2-thionyl)hexyl]piperazinyl]Amide

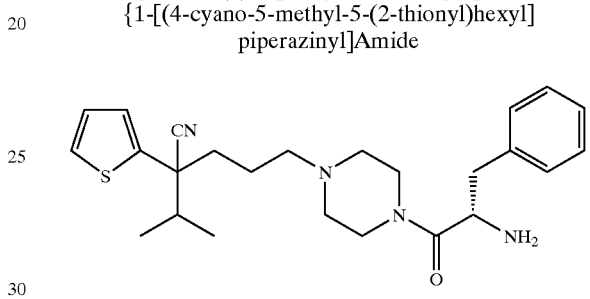

Hydrochloride:
ESI-MS (m/e); 439(M+H)

Example 129 (S)-3-phenyl-2-amino-propanic Acid {1-[(3-cyano-4-methyl-4-(2-thionyl)hexyl]piperazinyl}amide

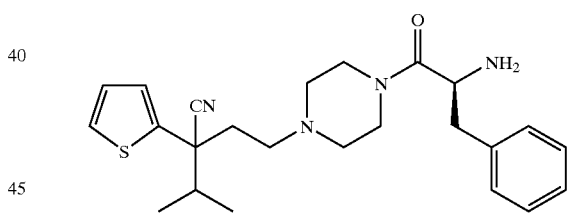

Hydrochloride:
ESI-MS (m/e); 425(M+H)

Example 130 5-[3-(Benzylamino)-4-hydroxytetrahydro-1H-1-pyrrolyl]-2-isopropyl-5-oxo-2-(2-thienyl)pentane Nitrile

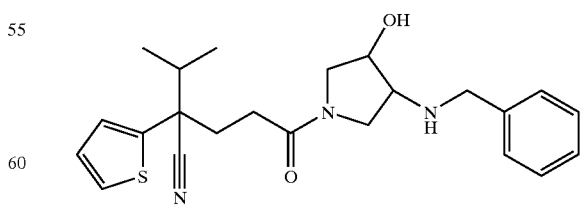

Under a nitrogen atmosphere, 5-(2,5-dihydro-1H-1-pyrrolyl)-2-isopropyl-5-oxo-2-(2-thienyl)pentanenitrile (260 mg) was dissolved in a mixed solvent of dimethyl sulfoxide (2 ml) and water (0.1 ml) at room temperature. To the mixture was added N-bromosuccinimide (177 mg), followed by stirring overnight. The reaction solution was partitioned between ethyl acetate and water, and the resulting organic layer was dried over anhydrous magnesium sulfate and then evaporated. The residue was purified by silica gel column chromatography (ethyl acetate/hexane system), to give a colorless oily intermediate (140 mg). The intermediate (20 mg) was dissolved in tetrahydrofuran (0.05 ml), a 1N aqueous sodium hydroxide (0.06 ml) was added, and the mixture was stirred at room temperature. After stirring for 45 minutes, a benzylamine (11 mg)/tetrahydrofuran solution (0.05 ml) was added thereto, and the mixture was stirred at 70° C. overnight. The reaction solution was cooled to room temperature and partitioned between ethyl acetate and water. The resulting organic layer was dried over anhydrous magnesium sulfate and then evaporated. The residue was purified by Cromatorex NH silica gel column chromatography (ethyl acetate/hexane system), to give the title compound as a colorless oil (20 mg).

Hydrochloride:

ESI-MS (m/e); 412(M+H)

The title compounds of Examples 131 to 136 were synthesized in accordance with the method of Example 130.

Example 131 5-[3-(N-methylbenzylamino)-4-hydroxytetrahydro-1H-1-pyrrolyl]-2-isopropyl-5-oxo-2-(2-thienyl)pentane Nitrile

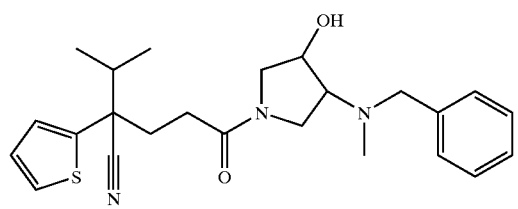

Hydrochloride:

ESI-MS (m/e); 426(M+H)

Example 132 5-[3-(2-thienylethylamino)-4-hydroxytetrahydro-1H-1-pyrrolyl]-2-isopropyl-5-oxo-2-(2-Thienyl Pentane nitrile

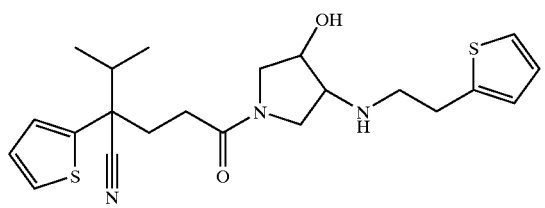

Hydrochloride:

ESI-MS (m/e); 432(M+H)

Example 133 5-[3-(N-phenylpiperazino-4-hydroxytetrahydro-1H-1-pyrrolyl]-2-isopropyl-5-oxo-2-(2-thienyl)pentane Nitrile

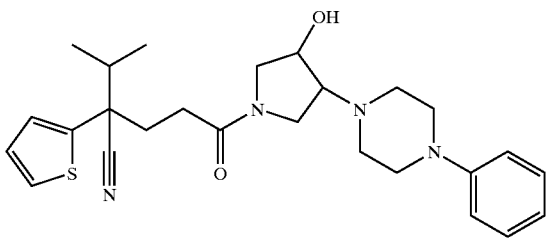

Trifluoroacetate:
ESI-MS (m/e); 467(M+H)

Example 134 5-[3-[4-(2.3-Dihydro-1H-1-indolyl)piperazinol-4-hydroxytetrahydro-1H-pyrrolyl]-2-isopropyl-5-oxo-2-(2-thienyl)pentane Nitrile

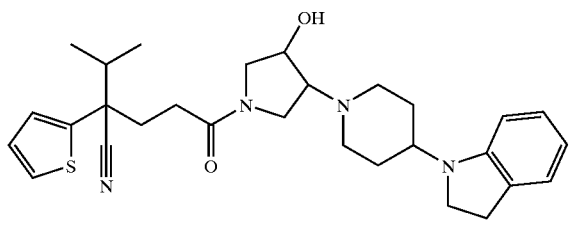

Trifluoroacetate:
ESI-MS (m/e); 507(M+H)

Example 135 5-{3-[(3-pyridylethylamino)-4-hydroxytetrahydro-1H-pyrrolyl]-2-isopropyl-5-oxo-2-(2-thienyl)pentane Nitrile

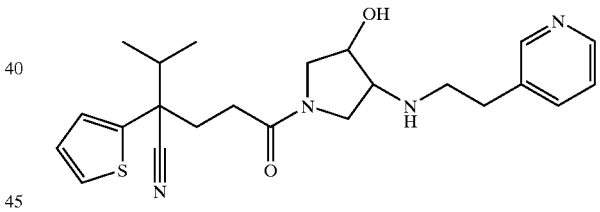

Trifluoroacetate:
ESI-MS (m/e); 427(M+H)

Example 136 5-{3-[4-(1H-1-Indolyl)piperidino)-4-hydroxytetrahydro-1H-pyrrolyl]-2-isopropyl-5-oxo-2-[2-thienyl)pentanenitrile

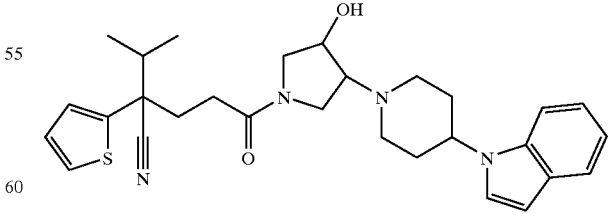

Trifluoroacetate:
ESI-MS (m/e); 505(M+H)

The title compounds of Examples 137 to 172 were synthesized in accordance with the method of the above-mentioned Example 64.

Example 137 1-[(4-cyano-5-methyl-4-phenyl)hexyl]-4-(benzothiazolyl)piperazine

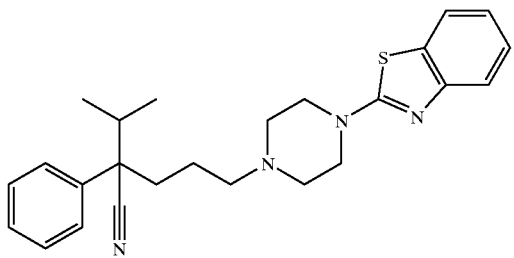

Free Body:
$^1$H NMR (400 MHz, CDCl$_3$) 0.78 (d, J=6.8 Hz, 3H), 1.10–1.30 (m, 1H), 1.21 (d, 1=6.6 Hz, 3H), 1.50–1.70 (m, 1H), 1.87–1.20 (m, 1H), 2.08–2.24 (m, 2H), 2.30–2.38 (m 1H), 2.40–2.48 (m, 4H), 3.52–3.64 (m, 4H), 7.04–7.10 (m, 1H). 7.24–7.34 (m, 2H), 7.35–7.40 (m, 4H), 7.50–7.61 (m, 2H).
Hydrochloride:
ESI-MS (m/e); 449(M+H)

Example 138 1-[(4-cyano-5-methyl-d-phenyl)hexyl]-4-[2-(6-methoxy)benzothiazolyl]piperazine

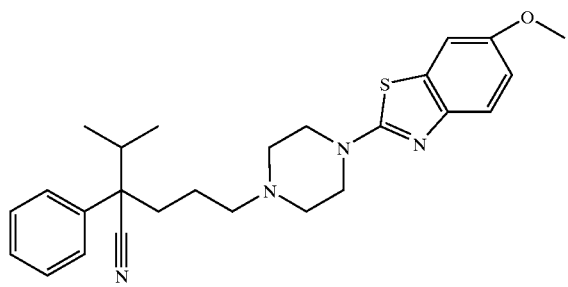

Free Body:
$^1$H NMR (400 MHz, CDCl$_3$) δ 0.78 (d, J=6.8 Hz, 3H), 1.10–1.30 (m, 1H), 1.21 (d, J=6.6 Hz, 3H), 1.50–1.70 (m, 1H), 1.87–1.20 (m 1H), 2.08–2.24 (m, 2H). 2.30–2.38 (m, 1H), 2.38–2.48 (m, 4H), 3.50–3.62 (m, 4H), 3.82 (s. 3H), 6.86–6.92 (m, 1H), 7.12–7.15 (m, 1H), 7.22–7.35 (m, 3H), 7.35–7.40 (m, 3H, 7.43–7.48 (m, 1H).
Hydrochloride:
ESI-MS (m/e); 419(M+H)

Example 139 1-[4-Cyano-methyl-4-phenyl)hexyl]-4-(2-benzoxazolyl)piperazine

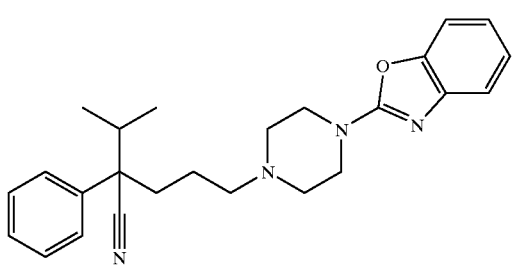

Free Body:
$^1$H NMR (400 MHz, CDCl$_3$) δ 0.78 (d, J=6.8 Hz, 3H), 1.10–1.30 (m, 1H), 1.21 (d, J=6.6 Hz, 3H), 1.50–1.70 (m, 1H), 1.77–1.20 (m, 1H), 2.08–2.25 (m, 2H). 2.28–2.38 (m, 1H), 2.38–2.48 (m, 4H), 3.60–3.72 (m, 4H), 6.98–7.04 (m, 1H), 7.12–7.18 (m, 1H), 7.22–7.28 (m, 1H), 7.28–7.43 (m, 5H).
Hydrochloride:
ESI-MS (m/e); 403(M+H)

Example 140 1-[(4-Cyano-5-methyl-4-phenyl)hexyl]-4-(2-quinolinyl)piperazine

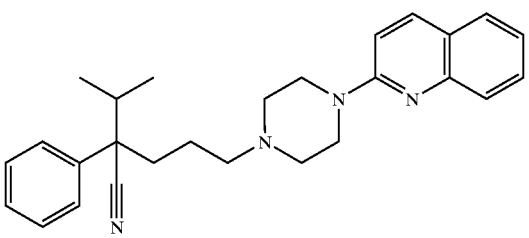

Free Body:
Rf=0.6 (developing solvent; diethyl ether, Merck silica gel 60F254 TLC)
Hydrochloride:
ESI-MS (m/e); 413(M+H)

Example 141 1-[(4-cyano-5-methyl-4-phenyl)hexyl]-4-(1-quinolinyl)piperazine

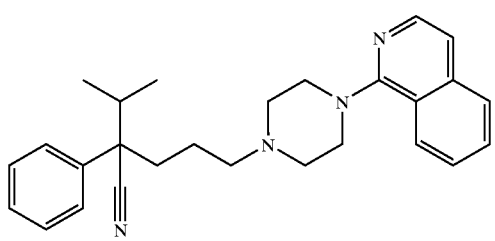

Free Body:
Rf-0.45 (developing solvent; diethyl ether, Merck silica gel 60F254 TLC)
Hydrochloric acid salt:
ESI-MS (m/e); 413(M+H)

Example 142 4-[4-(1-isobutyl-1H-benzo[d]imidazol-2-yl)-1,4-diazepan-1-yl]-1-isopropyl-1-phenylbutyl Cyanide

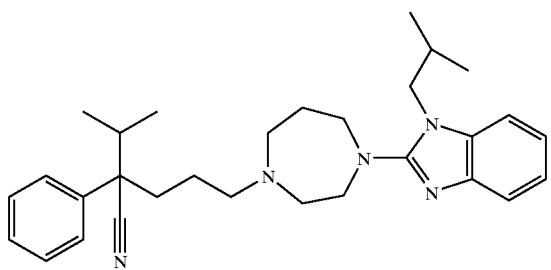

Free Body:
$^1$H NMR (400 MHz, CDCl$_3$) δ 0.78 (d, J=6.8 Hz, 3H), 0.81 (d, J=8.1 Hz, 6H), 1.08–1.30 (m 1H), 1.20 (d, J=7.0 Hz, 3H), 1.50–1.70 (m, 1H), 1.77–1.20 (m, 2H), 2.00–2.32 (m, 4H), 2.40–2.52 (m, 2H), 2.60–2.67 (m, 2H), 2.67–2.73 (m, 2H), 3.48–3.60 (m, 4H), 3.81 (d, J=7.3 Hz, 2H), 7.07–7.18 (m, 3H), 7.25–7.42 (m, 5H), 7.51–7.56 (m 1H).
Hydrochloride:
ESI-MS (m/e); 472(M+H)

Example 143 4-[4-(1-isobutyl-1H-benzo[d]imidazol-2-yl)-1,4-diazepan-1-yl]-1-isopropyl-(2-chlorophenyl)butyl Cyanide

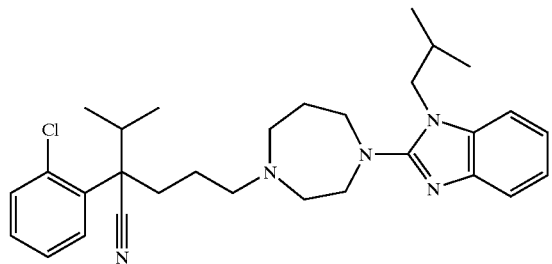

Free Body:
$^1$H NMR (400 MHz, CDCl$_3$) δ 0.78 (d, J=6.8 Hz, 3H), 0.81 (d, J=8.1 Hz, 6H). 1.08–1.30 (m, 1H), 1.20 (d, J=7.0 Hz, 3H), 1.50–1.70 (m, 1H), 1.77–1.20 (m, 2H), 2.00–2.32 (m, 41), 2.40–2.52 (m, 2H), 2.60–2.67 (m, 2H), 2.67–2.73 (m, 2H), 3.48–3.60 (m, 4H), 3.81 (d, J=7.3 Hz, 2H), 7.05–7.35 (m, 5H), 7.3035–7.40 (m, 1H), 7.51–7.56 (m, 1H), 7.72–7.79 (m, 1H).
Hydrochloride:
ESI-MS (m/e); 506 (M[$^{34}$Cl]+H), 508 (M[$^{36}$Cl]+H)

Example 144 1-isopropyl-4-[4-(1H-benzo[d]imidazol-2-yl)piperazinol-1-phenylbutyl Cyanide

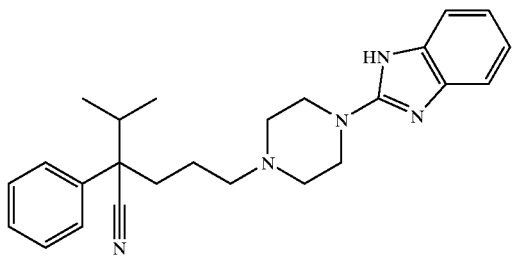

Free Body:
$^1$H NMR (400 MHz, CDCl$_3$) δ 0.78 (d, J=6.8 Hz, 3H), 1.04–1.25 (m, 1H), 1.20 (d, J=6.6 Hz, 31), 1.50–1.70 (m, 1H), 1.87–1.99 (m, 1H), 2.05–2.23 (m, 2H), 2.25–2.40 (m, 2H), 2.40–2.47 (m, 4H), 3.42–3.58 (m, 4H), 7.00–7.40 (m, 9H).
Hydrochloride:
ESI-MS (m/e); 402(M+H)

Example 145 1-isopropyl-4-[4-(1-methyl-1H-benzo[d]imidazol-2-yl)piperazino]-1-phenylbutyl Cyanide

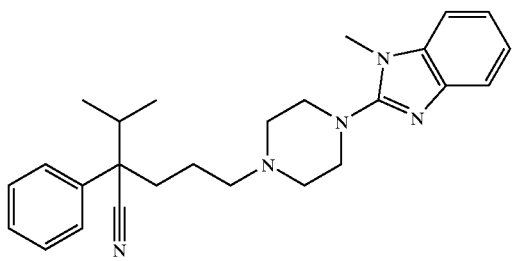

Free Body:
$^1$H NMR (400 MHz, CDCL$_3$) 60.78 (d, J=6.8 Hz, 3H), 1.10–1.30 (m, 1H)1, 1.21 (d, J=6.8 Hz, 3H), 1.50–1.70 (m, 1H), 1.92–2.03 (m, 1H), 2.08–2.25 (m, 2H), 2.28–2.45 (m, 2H), 2.45–2.56 (m, 4H), 3.25–3.35 (m, 4H), 3.59 (s, 3H), 7.02–7.62 (m, 9H).
Hydrochloride:
ESI-MS (m/e); 416(M+H)

Example 146 1-isopropyl-4-[4-(1-ethyl-1H-benzo[d]imidazol-2-yl)piperazino]-1-phenylbutyl Cyanide

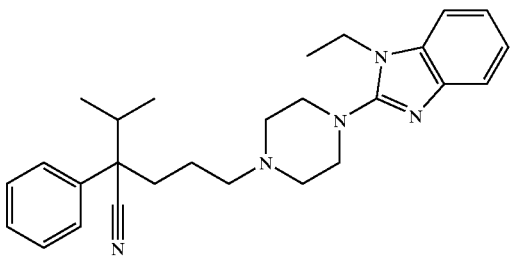

Free Body:
$^1$H NMR (400 MHz, CDCl$_3$) δ 0.78 (d, J=6.8 Hz, 3H), 1.10–1.30 (m, 1H), 1.21 (d, J=6.8 Hz, 3H), 1.44 (t, J=7.3 Hz, 3H), 1.50–1.70 (m 1H), 1.92–2.03 (m, 1H), 2.08–2.25 (m, 2H), 2.28–2.45 (m, 2H), 2.45–2.56 (m, 0.4H), 3.20–3.35 (m, 4H), 4.03 (q, J=7.3 Hz, 2H), 7.14–7.64 (m, 9H).
Hydrochloride:
ESI-MS (m/e); 430(M+H)

Example 147 4-[4-(1-Ethyl-1H-benzo[d]imidazol-2-yl)piperazinol-1-isopropyl-1-(2-thienyl)butyl Cyanide

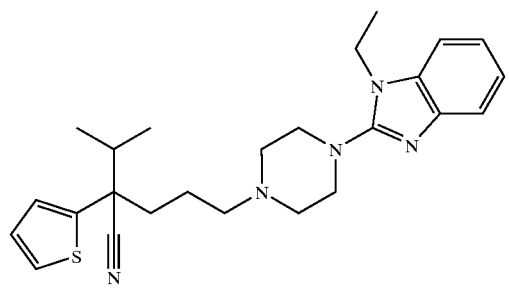

Free Body:
Rf=0.35 (developing solvent; ethyl acetate:hexane=1:1, Fuji Silysia Chemical Ltd., NH TLC)
Hydrochloride:
ESI-MS (m/e); 436(M+H)

Example 148 4-[4-(1-isobutyl-1H-benzo[d]imidazol-2-yl)piperazinol-1-isopropyl-1-(2-thienyl)butyl Cyanide

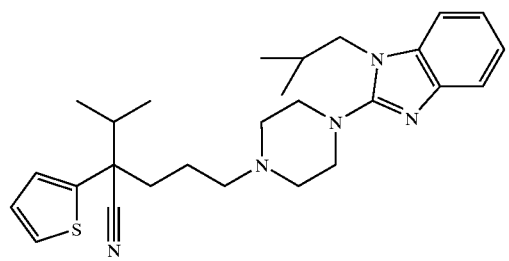

Free Body:
Rf=0.4 (evolution solvent; ethyl acetate:hexane=1:1; Fuji Silysia Chemical Ltd., NH TLC)

Hydrochloride:
ESI-MS (m/e); 464(M+H)

Example 149 1-isopropyl-4-[4-(-isopropyl-1H-benzo[d]imidazol-2-yl)piperazino]-1-phenylbutyl Cyanide

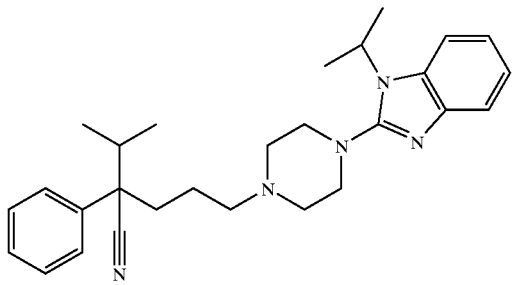

Free Body:
¹H NMR (400 MHz, CDCl₃) δ 0.78 (d, J=6.6 Hz, 3H), 1.10–1.25 (m, 1H), 1.21 (d, J=6.6 Hz, 3H), 1.50–1.68 (m, 7H), 1.90–2.04 (m, 1H), 2.05–2.24 (m, 2H), 2.25–2.45 (m, 2H), 2.45–2.53 (m, 4H), 3.15–3.25 (m, 4H), 4.56–4.68 (m, 1H), 7.09–7.19 (m, 2H), 7.25–7.33 (m, 1H), 7.34–7.42 (m, 5H), 7.60–7.64 (m, 1H).
Hydrochloride:
ESI-MS (m/e); 444(M+H)

Example 150 4-[4-(1H-benzo[d]imidazol-2-yl)-1,4-diazepan-1-yl]-1-isopropyl-1-phenylbuty]Cyanide

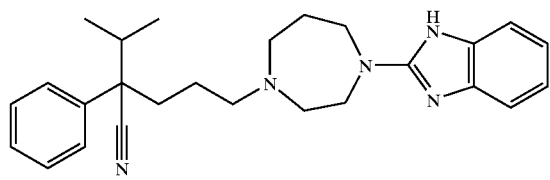

Free Body:
¹H NMR (400 MHz, CDCl₃) δ 0.74 (d, J=6.6 Hz, 3H), 1.00–1.15 (m, 1H), 1.14 (d, J=6.6 Hz, 3H), 1.40–1.50 (m, 1H), 1.78–1.93 (m, 3H), 2.00–2.17 (m, 2H), 2.30–2.40 (m, 2H), 2.45–2.55 (m, 2H), 2.57–2.64 (m, 2H), 3.57–3.63 (m, 4H), 6.96–7.52 (m, 9H).
Hydrochloride:
ESI-MS (m/e); 416(M+H)

Example 151 4-[4-(1-methyl-1H-benzo[d]imidazol-2-yl)-1,4-diazepan-1-yl]-1-isopropyl-1-phenylbutyl Cyanide

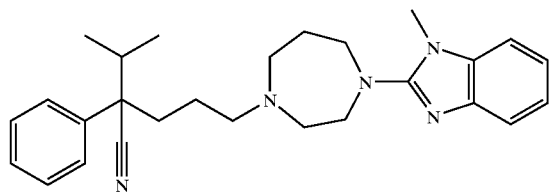

Free Body:
¹H NMR (400 MHz, CDCl₃) δ 0.76 (d, J=6.8 Hz, 3H), 1.07–1.17 (m, 1H), 1.18 (d, J=6.6 Hz, 3H), 1.45–1.60 (m, 1H), 1.76–2.25 (m, 5H), 2.40–2.50 (m, 2H), 2.60–2.67 (n. 2H), 2.68–2.76 (m, 2H), 3.53–3.63 (m, 4H), 3.57 (s, 31), 7.08–7.54 (m, 9H).

Hydrochloride:
ESI-MS (m/e); 430(M+H)

Example 152 4-[4-(1-Ethyl-1H-benzo[d]imidazol-2-yl)-1,4-diazepan-1-yl]-1-isopropyl-1-phenylbutyl Cyanide

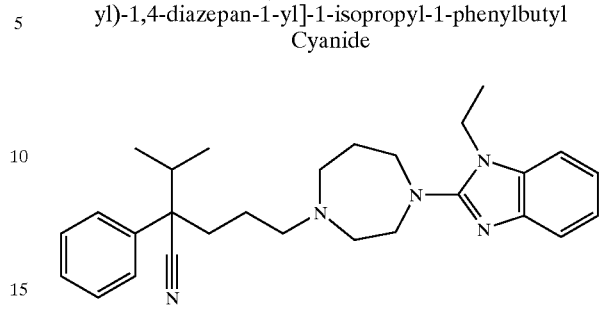

Free Body:
¹H NMR (400 MHz, CDCL₃) δ 0.77 (d, 1=6.8 Hz, 3H), 1.05–1.17 (m, 1H), 1.19 (d, J=6.6 Hz, 3H), 1.40 (t, J=7.2 Hz, 3H), 1.47–1.62 (m, 1H), 1.76–2.23 (m, 5H), 2.40–2.50 (m, 2H), 2.60–2.67 (m, 2H), 2.68–2.76 (m, 2H), 3.51–3.63 (m, 4H), 4.02 (d, J=7.2 Hz, 31D), 7.06–7.54 (in 9H1).
Hydrochloride:
ESI-MS (m/e); 444(M+H)

Example 153 1-isopropyl-4-[4-(1-ethyl-1H-benzo[d]imidazol-2-yl]piperazino]-1-(4-fluorophenyl)butyl Cyanide

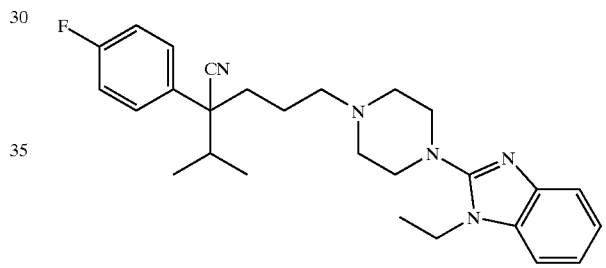

Free Body:
¹H NMR (400 MHz, CDCl₃) δ 0.78 (d, J=6.8 Hz, 3H), 1.13–1.23 (m, 1H), 1.20 (d, J=6.8 Hz, 3H), 1.44 (t, J=7.1 Hz, 3H), 1.56–1.66 (m, 1H), 1.89–1.97 (m, 1H), 2.04–2.22 (m, 2H), 2.34–2.41 (m, 2H), 2.50–2.51 (m, 4H), 3.26–3.29 (m, 4H), 4.01–4.07 (m, 2H), 7.05–7.10 (m, 2H), 7.14–7.25 (m, 3H), 7.34–7.38 (m, 2H). 7.60–7.62 (m, 1H).

Example 154 1-isopropyl-4-[4-(1-benzyl-1H-benzo[d]imidazol-2-yl)(Piperazino]-1-(4Fluorophenyl)butyl Cyanide

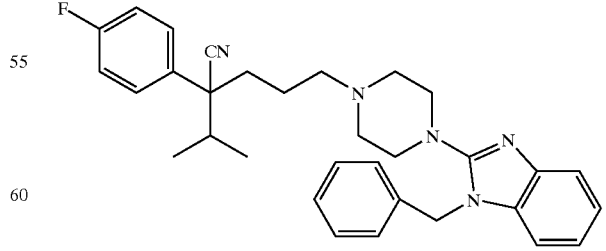

Free Body:
¹H NMR (400 MHz, CDCl₃) δ 0.77 (d, J=6.6 Hz, 3H), 1.08–1.15 (m, 1H), 1.18 (d, J=6.6 Hz, 3H), 1.53–1.57 (m, 1H), 1.85–1.93 (m, 1H), 2.02–2.19 (m, 2H), 2.29–2.38 in, 2H), 2.42 (m, 4H), 3.21–3.24 (m, 4H), 5.20 (s, 2H), 6.99–7.11 ([, 41), 7.15–7.21 (m, 3H), 7.26–7.35 (m, 5H), 7.62–7.65 (m, 1H).

Example 155 1-isopropyl-4-[4-(1-isobutyl-1H-benzo[d]imidazol-2-yl)piperazino]-1-(4-Fluorophenyl)butyl cyanide

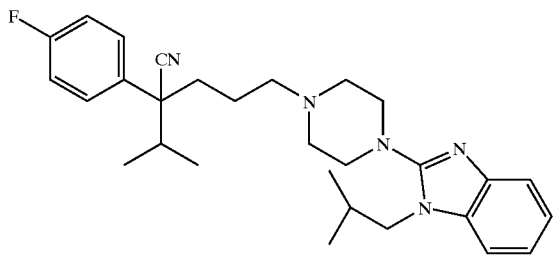

Free Body:
$^1$H NMR (400 MHz, CDCl$_3$) δ 0.78 (d, J=6.8 Hz, 3H), 0.82–0.85 (m, 6H), 1.12–1.25 (m, 1H), 1.20 (d, J=6.6 Hz, 3H), 1.57–1.63 (m, 1H), 1.90–1.98 (m, 1H), 2.04–2.12 (m, 1H), 2.14–2.42 (m, 4H), 2.48 (m, 4H), 3.23–3.25 (m, 41), 3.81 (d, J=7.3 Hz, 2H), 7.05–7.20 (m, 2H), 7.21–7.23 (m, 3H), 7.33–7.38 (m, 2H). 7.60–7.63 (m, 1H).

Example 156 1-isopropyl-4-[4-(1-isobutyl-1H-benzo[d]imidazol-2-yl)piperazino]-1-(3-fluorophenyl)butyl cyanide

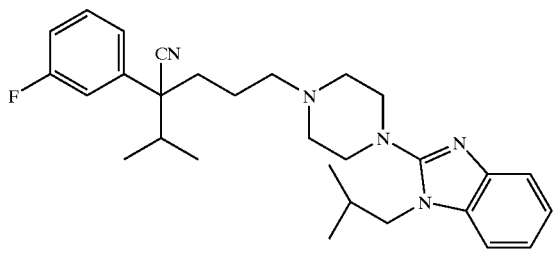

Free Body:
$^1$H NMR (400 MHz, CDCl$_3$) δ 0.77–0.89 (m, 9H), 1.13–1.26 (m, 1H), 1.21 (d, J=6.6 Hz, 3H), 1.58–1.65 (m, 1H), 1.90–1.98 (m 1H), 2.04–2.41 (m, 5H), 2.41–2.50 (m, 4H), 3.23–3.25 (m, 4H), 3.80(d, J=7.5 Hz, 20, 6.98–7.03 (m, 1H), 7.08–7.23 (m, 5H), 7.33–7.39 (m, 1H), 7.60–7.63 (m, 1H).

Example 157 1-isopropyl-4-[4-(1-isobutyl-1H-benzo[d]imidazol-2-yl)piperazino]-1-(2-fluorophenyl)butyl Cyanide

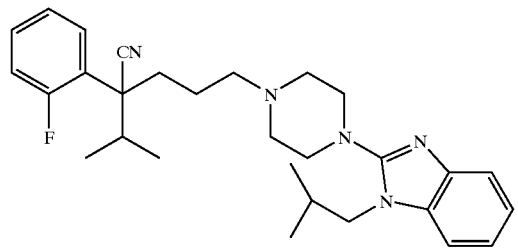

Free Body:
$^1$H NMR (400 MHz, CDCl$_3$) 60.80–0.88 (m, 9H), 1.15–1.25 (m, 1H), 1.23 (d, J=6.6 Hz, 3H), 1.58–1.64 (m, 1H), 2.04–2.16 (m, 1H), 2.25–2.51 (m, 9H), 3.22–3.25 (m, 4H), 3.80(d, J=7.5 Hz, 2H), 7.02–7.08 (m, 1H), 7.13–7.21 (m, 4H), 7.29–7.33 (m, 1H), 7.58–7.62 (m, 21).

Example 158 1-isopropyl-4-[4-(1-methyl-1H-benzo[d]imidazol-2-yl)piperazino]-1-(3-fluorophenyl)butyl Cyanide

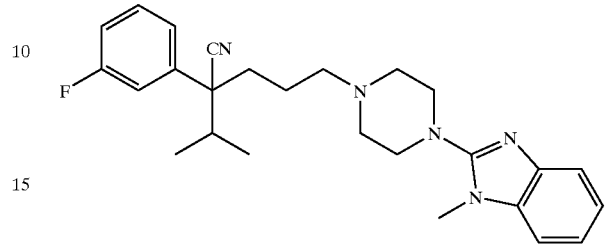

Free Body:
$^1$H NMR (400 MHz, CDCl$_3$) δ 0.80 (d, 1=6.8 Hz, 3H), 1.15–1.27 (m, 1H), 1.22 (d, 1=6.8 Hz, 3H), 1.58–1.66 (m, 1H), 1.89–1.97 (m, 1H), 2.01–2.24 (m, 2H), 2.34–2.41(m, 2H), 2.51–2.53(m, 4H), 3.29–3.32 (m, 4H), 3.59(s, 3H), 6.98–7.04 (m, 1H, 7.08–7.21 (m, 5H), 7.33–7.39 (m, 1H), 7.58–7.61 (m, 1H).

Example 159 1-isopropyl-4-[4-(1-ethyl-1H-benzo[d]imidazol-2-yl)piperazino]-1-(3-fluorophenyl)butyl Cyanide

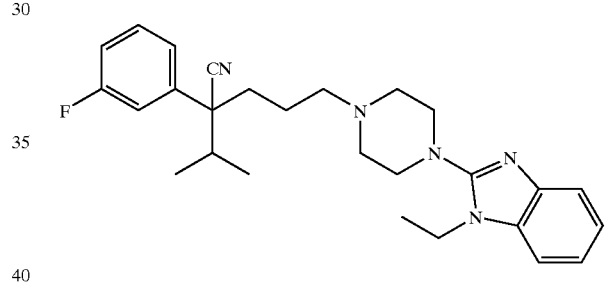

Free Body:
$^1$H NMR (400 MHz, CDCL$_3$) δ 0.80 (d, J=6.8 Hz, 3H), 1.13–1.28 (m, 1H), 1.22 (d, J=6.8 Hz, 310, 1.44(t, 1=7.1 Hz, 3H), 1.58–1.66 (m, 1H), 1.89–1.97 (m, 1H), 2.04–2.24 (m, 2H), 2.33–2.41 (m, 2H), 2.51–2.52(m, 4H), 3.27–3.30 (m, 4H), 4.01–4.07 (m, 1H), 6.98–7.04 (m, 1H), 7.08–7.27 (m, 5H), 7.33–7.39 (m, 1H), 7.59–7.62 (m, 1H).

Example 160 1-isopropyl-4-[4-(1-benzyl-1H-benzo[d]imidazol-2-yl)piperazino]-1-(3-fluorophenyl)butyl Cyanide

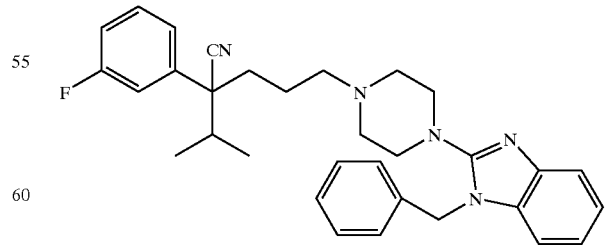

Free Body:
$^1$H NMR (400 MHz, CDCl$_3$) δ 0.78 (d, 1=6.6 Hz, 3H), 1.08–1.18 (m, 1H), 1.20 (d, J=6.8 Hz, 3H), 1.54–1.65 (m, 1H), 1.84–1.92 (m, 1H), 2.04–2.20 (m, 2H), 2.28–2.36 (m, 2H), 2.38–2.43 (m, 4H), 3.22–3.25 (m, 4H), 5.20 (s, 2H), 6.96–7.01 (m, 2H), 7.05–7.10 (m, 2H), 7.14–7.21 (m, 4H), 7.26–7.36(m, 4H), 7.63–7.64 (m, 1H).

Example 161 1-isopropyl-4-[4-(1-ethyl-1H-benzo[d]imidazol-2-yl)piperazino]-1-(2-fluorophenyl)butyl Cyanide

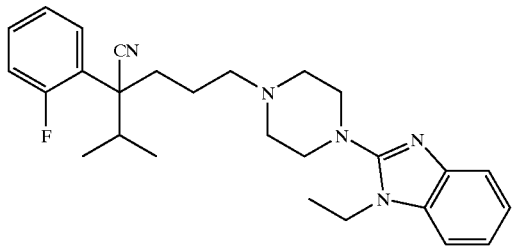

Free Body:
¹H NMR (400 MHz, CDCl₃) δ 0.81 (d, J=6.8 Hz, 3H), 1.15–1.28 (m, 1H), 1.23 (d, J=6.8 Hz, 3H), 1.44 (t, J=7.1 Hz, 3H), 1.59–1.68 (m, 1H), 2.04–2.16 (m, 1H), 2.25–2.54 (m, 8H), 3.27–3.30 (m, 4H), 4.00–4.06 (m, 2H), 7.02–7.08 (m, 1H), 7.13–7.24 (m, 4H), 7.29–7.34 (m, 1H), 7.58–7.63 (m, 2H).

Example 162 Synthesis of 1-isopropyl-4-[4-(1-methyl-1H-benzo[d]imidazol-2-yl)piperazino]-1-(2-tolyl)butyl Cyanide

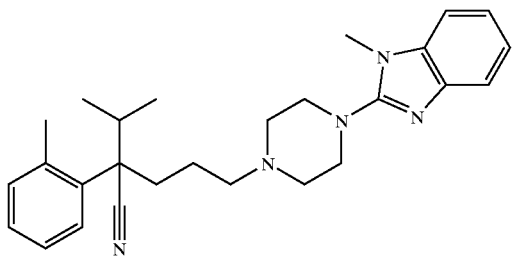

Oxalate:
¹H NMR (400 MHz, DMSO-d₆) δ 0.77 (d, J=6.8 Hz, 3H), 1.07 (d, J=6.8 Hz, 3H), 1.25–1.40 (m, 1H), 1.53–1.70 (m, 1H), 1.97–2.10 (m, 1H), 2.20–2.35 (m, 1H), 2.40–2.50 (m, 1H), 2.47 (s, 3H), 3.05–3.20 (m, 2H), 3.10–3.30 (m, 4H), 3.33–3.50 (m, 4H), 3.59 (s, 3H), 7.07–7.15 (1, 2H), 7.20–7.29 (m, 31), 7.34–7.46 (m, 3H).

Example 163 1-isopropyl-4-[4-(1-methyl-1-benzo[d]imidazol-2-yl)piperazino]-1-(4-fluorophenyl)butyl Cyanide

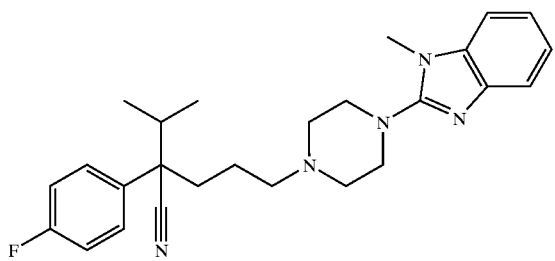

Oxalate:
¹H NMR (400 MHz, DMSO-d₆) δ 0.66(d, J=6.4 Hz, 3H), 1.10 (d, J=6.4 Hz, 3H). 1.10–1.30 (m, 1H), 1.50–1.67 (m, 1H), 1.95–2.30 (m, 2H), 2.15–2.27 (m, 1H), 2.95–3.20 (m, 2H), 3.10–3.30 (m, 4H), 3.35–3.50 (m, 4H), 3.59 (s, 3H), 7.07–7.15 (m, 2H), 7.28 (t,]=8.8 Hz, 2H. 7.34–7.46 (m, 2H), 7.43–7.50 (m, 2H).

Example 164 1-isopropyl-4-[4-(1-ethyl-1H-benzo[d]imidazol-2-yl)piperazino]-1-(2-chlorophenyl)butyl Cyanide

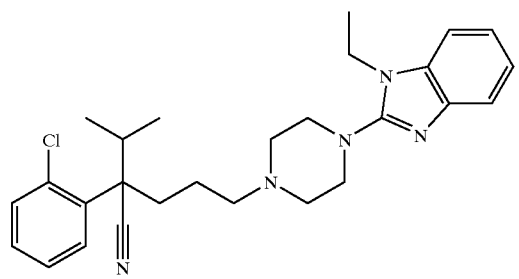

Oxalate:

¹H NMR (400 MHz, DMSO-d₆) δ 0.73 (d, J=6.8 Hz, 3H), 1.12 (d, J=6.8 Hz, 3H), 1.10–1.35 (m, 1H), 1.30 (t, J=7.2 Hz, 3H), 1.50–1.68 (1, 1H), 2.00–2.15 (m, 1H), 2.50–2.70 (m, 1H), 2.78–2.90 (m, 1H), 3.00–3.20 (m, 2H), 3.05–3.30 (m, 4H), 3.25–3.45 (m, 4H), 4.06 (q, J=7.2 Hz, 2H), 7.06–7.15 (m, 2H), 7.38–7.49 (m, 4H)), 7.54 (dd, J=7.6 Hz, 2.0 Hz, 1H), 7.65 (dd, J=7.6 Hz, 2.0 Hz, 1H).

Example 165 1-isopropyl-4-[4-(1-isobutyl-1H-benzo[d]imidazol-2-yl)piperazino]-1-(2-chlorophenyl)butyl Cyanide

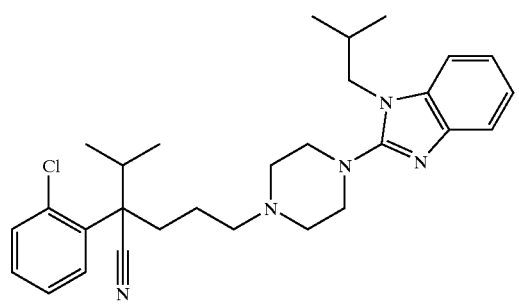

Oxalate:

¹H NMR (400 MHz, DMSO-d₆) δ 0.75 (d, J=6.8 Hz, 9H), 1.12 (d, J=6.4 Hz, 3H), 1.15–1.45 (m, 1H), 1.50–1.70 (m, 1H), 2.00–2.25 (m, 1H), 2.50–2.65 (m, 1H), 2.75–2.90 (m, 1H), 3.00–3.30 (m, 2H), 3.00–3.30 (m, 4H), 3.20–3.45 (m, 4H), 3.87 (d, J=7.2 Hz, 2H), 7.00–7.18 (m, 21), 7.38–7.48 (m, 4H), 7.54 (d, J=7.6 Hz, 1H), 7.64 (d, J=7.6 Hz, 1H).

Example 166 1-isopropyl-4-[4-(1-methyl-1H-benzo[d]imidazol-2-yl)piperazino]-1-(2-methoxyphenyl)butyl Cyanide

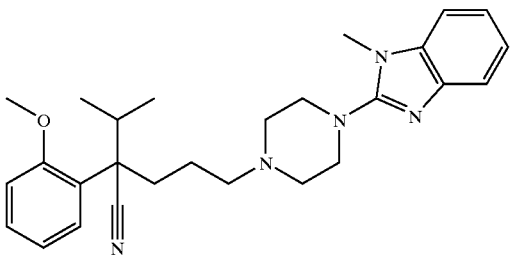

Oxalate:
$^1$H NMR (400 MHz, DMSO-$d_6$) δ 0.68 (d, J=6.8 Hz, 3H), 1.09 (d, J=6.8 Hz, 3H), 1.10–1.30 (m, 1H), 1.50–1.65 (m, 11), 1.90–2.05 (m, 1H), 2.35–2.50 (m, 1H), 2.57–2.70 (m, 1H), 2.95–3.20 (m, 2H), 3.05–3.25 (m, 4H), 3.30–3.50 (m, 4H), 3.59 (s, 3H), 3.81 (s, 3H), 6.98–7.04 (m, 1H), 7.07–7.15 (m, 3H), 7.33–7.43 (m, 4H).

Example 167 1-isopropyl-4-[4-(1-ethyl-1H-benzo[d]imidazol-2-yl)piperazino]-1-(2-methoxyphenyl)butyl Cyanide

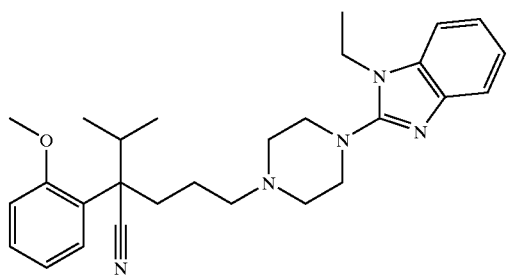

Oxalate:
$^1$H NMR (400 MHz, DMSO-$d_6$) δ 0.67 (d, 1=6.4 Hz, 3H), 1.08 (d, 1=6.8 Hz, 3H), 1.10–1.30 (m, 1H), 1.30 (t, J=7.2 Hz, 3H), 1.45–1.60 (m, 1H), 1.90–2.05 (t, 1H), 2.35–2.50 (m 1H), 2.58–2.70 (m, 1H), 2.90–3.10 (m, 2H), 3.00–3.20 (m, 4H), 3.25–3.45 (m, 4H), 3.81 (s, 3H), 4.06 (q, J=7.2 Hz, 2H), 7.01 (t, J=7.6 Hz, 1H), 7.06–7.14 (m, 3H), 7.36 (t, J=7.6 Hz, 1H), 7.35–7.45 (m, 3H).

Example 168 1-isopropyl-4-[4-(1-isobutyl-1H-benzo[d]imidazol-2-yl)piperazino]-1-(2-methoxyphenyl)butyl Cyanide

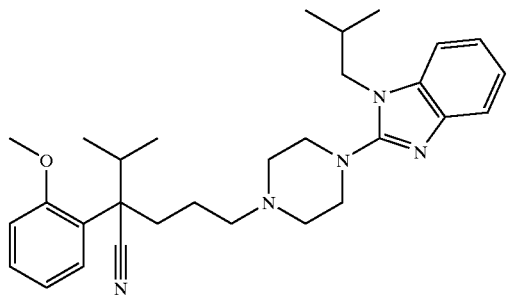

Oxalate:
$^1$H NMR (400 MHz, DMSO-$d_6$) δ 0.67 (d, J=6.8 Hz, 3H), 0.74 (d, 1=6.4 Hz, 6H), 1.09 (d, 3=6.4 Hz, 3H), 1.05–1.30 (m 1H), 1.45–1.65 (m, 1H), 1.90–2.03 ([, 1H), 2.10–2.20 (m, 1H), 2.35–2.50 (m, 1H), 2.57–2.70 (m, 1H), 3.00–3.20 (m, 21), 3.10–3.25 (m, 4H), 3.25–3.45 (m, 4H), 3.81 (s, 3H), 3.86 (d, J=7.6 Hz, 2H), 7.01 (td, J=7.6 Hz, 2.0 Hz, 1H), 7.06–7.14 (m, 3H), 7.33–7.46 (m, 4H).

Example 169 1-isopropyl-4-[4-(1-benzyl-1H-benzo[d]imidazol-2-yl)piperazinol]-1-(2-methoxyphenyl)butyl Cyanide

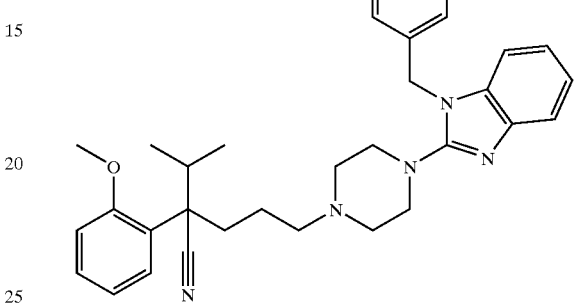

Oxalate:
$^1$H NMR (400 MHz, DMSO-$d_6$) δ 0.67 (d, J=6.8 Hz, 3H), 1.08 (d, J=6.8 Hz, 3H), 1.10–1.25 (m, 1H), 1.45–1.65 (m, 1H), 1.90–2.00 (m, 1H), 2.33–2.45 (m, 1H), 2.55–2.70 (m, 1H), 2.90–3.20 (m, 21), 3.10–3.25 (m, 4H), 3.25–3.45 (m, 4H), 3.79 (s, 3H), 5.30 (s, 2H), 6.97–7.20 (m, 7H), 7.21–7.47 (m, 6H).

Example 170 1-isopropyl-4-[4-(1-ethyl-1H-benzo[d]imidazol-2-yl)piperazino]-1-(2-methylphenyl)butyl Cyanide

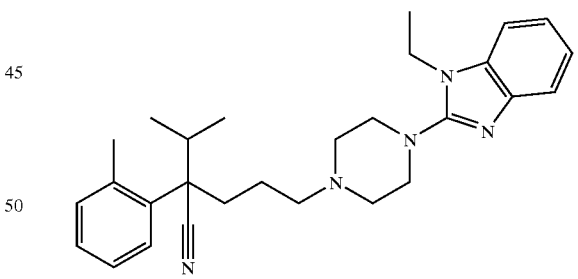

Free Body:
$^1$H NMR (400 MHz, CDCl$_3$) δ 0.87 (d, J=6.8 Hz, 3H), 1.19 (d, J=6.8 Hz, 3H), 1.20–1.28 (m, 1H), 1.44 (t, J=7.3 Hz, 3H), 1.55–1.70 (m, 1H), 2.06–2.20 (m, 1H), 2.25–2.45 (m, 4H), 2.45–2.58. (m, 7H), 3.25–3.35 (m, 4H), 4.04 (q, J=7.3 Hz, 2H), 7.15–7.23 (m, 6H), 7.57–7.68 (m, 1H), 7.59–7.60 (m, 1H).

Hydrochloride:

ESI-MS (m/e); 444(M+H)

Example 171 1-isopropyl-4-[4-(1-benzyl-1H-benzo[d]imidazol-2-yl)piperazino]-1-(2-methylphenyl)butyl Cyanide

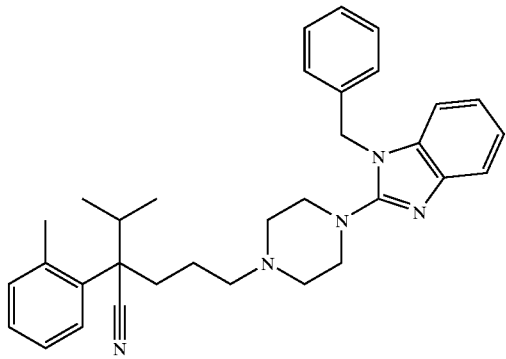

Free Body:
$^1$H NMR (400 MHz, CDCl$_3$) δ 0.86 (d, J=6.8 Hz, 3H), 1.17 (d, J=6.8 Hz, 3H), 1.17–1.25 (m, 1H), 1.50–1.65 (m, 1H_, 2.00–2.10 (1, 1H), 2.20–2.48 (m, 8H), 2.49 (s, 3H), 3.19–3.24 (m, 4H), 5.19 (s, 2H), 6.99–7.01 (m, 1H), 7.08–7.21 (m, 81), 7.27–7.38 (m, 2H), 7.43–7.55 (m, 1H), 7.63–7.65 (m, 1H).

Hydrochloride:
ESI-MS (m/e); 506(M+H)

Example 172 1-isopropyl-4-[4-(1-isobutyl-1H-benzo[d]imidazol-2-yl)piperazino]-1-(2-methylphenyl)butyl Cyanide

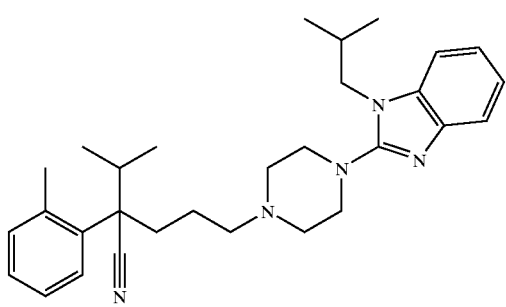

Free Body:
$^1$H NMR (400 MHz, CDCl$_3$) δ 0.83 (d, J=4.0 Hz, 3H), 0.85 (d, J=4.0 Hz, 3H), 0.87 (d, 1=6.6 Hz, 3H), 1.19 (d, J=6.6 Hz, 3H), 1.20–1.29 (m, 1H), 1.54–1.65 (m, 1H), 2.05–2.16 (m, 1H), 2.24–2.51 (m, 9H), 2.52 (s, 3H), 3.20–3.25 (m, 4H), 3.80 (d, J=7.5 Hz, 2H), 7.12–7.22 (m, 6H), 7.48–7.56 (m, 1H), 7.59–7.60 (m, 1H).

Hydrochloride:
ESI-MS (m/e); 472(M+H)

Example 173 1-[4-Cyano-4-(5-cyano-2-thienyl)-5-methylhexyl]-(3R)-3-[N-(2-cyanoethyl)-N-benzylamino]Pyrrolidine

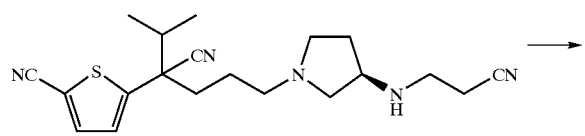

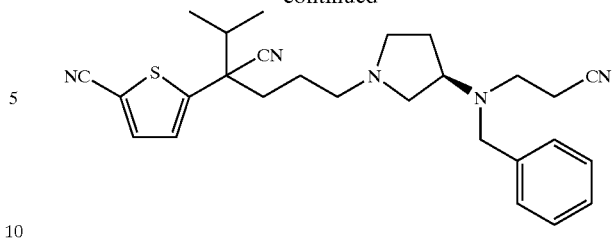

In dichloromethane (8 ml) was dissolved 300 mg (0.81 mmol) of 41-[4-cyano-4-(5-cyano-2-thienyl)-5-methylhexyl]-(3R)-3-(N-(2-cyanoethyl)amino]pyrrolidine obtained in Reference Example 81, followed by successively adding 98.9 mg (0.93 mmol) of benzaldehyde, 0.09 ml (1.62 mmol) of acetic acid and 258 mg (1.22 mmol) of sodium triacetoxyborohydride. After completion of the reaction, the reaction solution was adjusted to basic with a 5N sodium hydroxide and extracted with ethylacetate. The organic layer was washed with brine, dried over magnesium sulfate and evaporated, to give a crude product. The crude product was subjected to 25 g of Cromatorex NH silica gel (ethyl acetate:hexane=25% of ethyl acetate), to give 220 mg (0.48 mmol, 59.1%) of the title compound as a colorless syrup. The physico-chemical data of the compound was as below.

$^1$HNR (400 MHz, CDCl$_3$) δ 0.90 (d, J=6.4 Hz, 3H), 1.19 (d, J=6.4 Hz, 3H), 1.16–1.29 (m, 1H), 1.54–1.66 (m, 1H), 1.70–1.84 (m, 2H), 1.91–2.08 (m; 2H). 2.17–2.37 (m, 5H), 2.38–2.51 (m, 2H), 2.51–2.58 (m, 1H), 2.61–2.68 (m, 1H), 2.78–2.94 (m, 21), 3.40–3.50 (m, 1H), 3.60 (d, J=14 Hz, 1H), 3.71 (d, J=14 Hz, 1H), 7.13 (d, J=3.6 Hz, 1H), 7.32–7.39 (m, 5H), 7.50 (d, J=3.6 Hz, 1H)

Further, the diastereomer of the title compound of Example 173 is synthesized in accordance with the production method of the above-mentioned Example 173 from 4-cyano-4-(5-cyano-2-thienyl)-5-methylhexanol (hereinafter, referred to as "alcohol b") synthesized in accordance with Reference Examples 104 and 105 from 4-cyano-4-(2-thienyl)-5-methylhexanoic acid obtained from Reference Example 103, and (3R)-3-tert-butoxycarbonylaminopyrrolidine. Similarly, the mirror isomer of the title compound of Example 173 is synthesized in accordance with the production method of the above-mentioned Example 173 from the alcohol b and (3S)-3-tert-butoxycarbonylaminopyrrolidine.

Example 174 1-[4-Cyano-4-(5-cyano-2-thienyl)-5-methylhexyl]-(3R)-3-[N-(2-cyanoethyl)-N-(2-thienylmethyl)amino]pyrrolidine

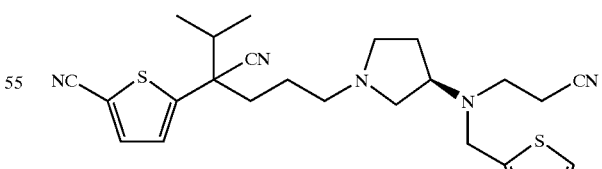

The title compound was synthesized in accordance with the production method of Example 173 from 1-[4-cyano-4-(5-cyano-2-thienyl)-5-methylhexyl]-(3R)-3-[N-(2-cyanoethyl)amino]pyrrolidine obtained from Reference Example 81 and 2-thiophenecarboxyaldehyde. The physico-chemical data of the compound was as below.

Yield: 46.7%

¹H-NMR (400 MHz, CDCl₃) δ 0.90 (d, J=6.8 Hz, 3H), 1.19 (d, J=6.4 Hz, 3H), 1.16–1.29 (m, 1H), 1.54–1.67(m, 1H), 1.67–1.84 (m, 2H), 11.95–2.09 (m, 2H), 2.17–2.35 (m, 3H), 2.35–2.56 (m, 5H), 2.61–2.70 (m, 1H), 2.80–2.96 (m, 2H), 3.44–3.54 (m, 1H), 3.84 (d, J=15.0 Hz, 1H), 3.92 (d, J=15.0 Hz, 1H), 6.92–7.04 (m, 2H), 7.13 (d, J=4.0 Hz, 1H), 7.23–7.31 (m, 1H), 7.51 (d, J-4.0 Hz, 1H)

Example 175 1-[4-cyano-4-(5-cyano-2-thienyl)-5-methylhexyl]-(3S)-3-[N-(2-cyanoethyl)-N-benzylamino]Pyrrolidine

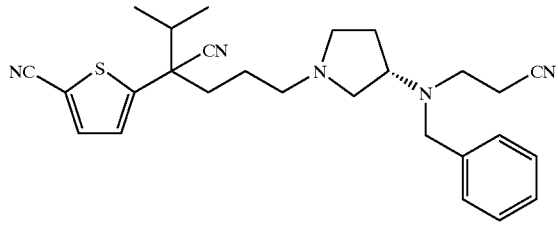

The title compound could be synthesized in accordance with the following two methods (synthetic methods A and B).

Synthetic Method A (1) (3S)-3-[N-(2-Cyanoethyl)-N-benzylamino]pyrrolidine

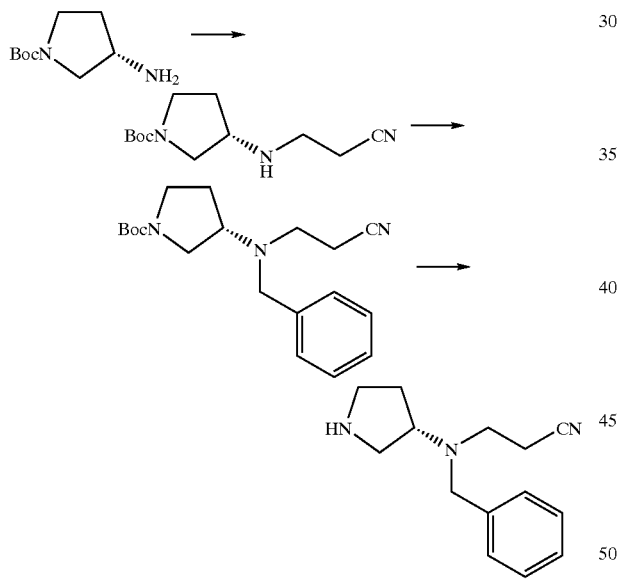

(3S)-3-[N-(2-Cyanoethyl)-N-benzylamino]-1-(tert-butoxycarbonyl)pyrrolidine was synthesized in accordance with the production methods of Reference Example 81 and Example 173 from (3S)-3-amino-1-(tert-butoxycarbonyl) pyrrolidine. The title compound was obtained by de-protecting the Boc group in accordance with Reference Example 80 (yield; 78.2%, (3 steps)). The physico-chemical data of the compound was as below. The physico-chemical data of (3S)-3-[N-(2-cyanoethyl)-N-benzylamino]-1-(tert-butoxycarbonyl)pyrrolidine ¹H-NMR (400 MHz, CDCl₃) δ 1.46 (s, 9H), 1.77–1.95 (m, 1H), 1.98–2.12 (m, 1H), 2.32 (t, 1=6.8 Hz, 2H), 2.87 (t, J=6.8 Hz, 2H), 3.10–3.78 (×7H), 7.27–7.39 (m, 5H)

The physico-chemical data of (3S)-3-[N-(2-cyanoethyl)-N-benzylamino]pyrrolidine

¹H-NMR (400 MHz, CDCl₃) δ 1.66–1.78 (m, 1H), 1.88–2.02 (m, 1H)2.31 (t, J=6.8 Hz, 2H), 2.78–2.95 (m, 4H), 3.02–3.12 (m, 2H), 3.32–3.41 (m, 1H), 2.87 (t, J=6.8 Hz, 2H), 3.64 (d, J=14 Hz, 1H), 3.71 (d, J=14 Hz, 1H), 7.27–7.38 (m, 5H)

(2) 1-[4-Cyano-4-(5-cyano-2-thienyl)-5-methylhexyl]-(3s)-3-[N-(2-cyanoethyl)-N-benzylamino]pyrrolidine Optically active body, 4-cyano-4-(5-cyano-2-thienyl)-5-methylhexyl iodide (iodide C (optically active body)) was synthesized from the alcohol B in accordance with Example 77 (1). The title compound was synthesized in accordance with Example 77(2) from the iodide C and (3S)-3-[N-(2-cyanoethyl)-N-benzylamino]pyrrolidine which was obtained in (1). The physico-chemical data of the compound was as below.

Yield; 90.6%.

ESI-MS; 460(M+H)⁺

¹H-NMR (400 MHz, CDCl₃) δ 0.91 (d, J=6.8 Hz, 3H), 1.19 (d, J=6.8 Hz, 3H). 1.16–1.30 (m, 1H), 1.56–1.68 (m, 1H), 1.70–1.81 (m, 2H), 1.93–2.10 (m, 2H), 2.21–2.44 (m, 7H), 2.57–2.67 (m, 2H), 2.80–2.95 (m, 21H), 3.39–3.48 (m, 1H), 3.62 (d, J=14 Hz, 1H), 3.69 (d, J=14 Hz, 1H), 7.15 (d, J=4.0 Hz, 1H), 7.23–7.37 (m, 5H), 7.52 (d, J=4.0 Hz, 1H)

Synthetic Method B

The title compound was synthesized in accordance with the production of Example 173 from the above-mentioned iodide C (or the alcohol B) and (3S)-3-tert-butoxycarbonylaminopyrrolidine.

Example 176 1-[4-cyano-4-(2-thienyl)-5-methylhexyl]-(3s)-3-[N-(2-cyanoethyl)-N-Benzylamino]pyrrolidine

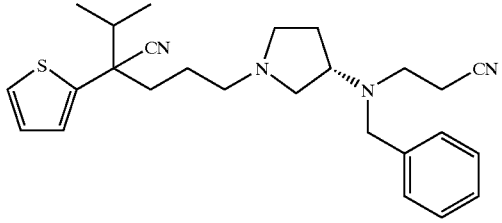

Optically active body, 4-cyano-4-(2-thienyl)-5-methylhexyl iodide (iodide D (optically active body)) was synthesized from the alcohol A in accordance with Example 77 (1). The title compound was synthesized in accordance with Example 75 from the iodide D and (3S)-3-[N-(2-cyanoethyl)-N-benzylamino]pyrrolidine of "Synthetic method A" (1) (1) of Example 175. The physico-chemical data of the title compound was as below.

Yield; 97%.

¹H-NMR (400 MHz, CDCl₃) δ 0.90 (d, J=6.8 Hz, 31), 1.17 (d, J=6.4 Hz, 3H). 1.20–1.35 (m, 1H), 1.55–1.68 (m, 1H), 1.69–1.82 (m, 2H), 1.92–2.10 (m, 2H), 2.17–2.43 (m, 7H), 2.54–2.66 (m, 2H), 2.87 (t, J=6.8 Hz, 2H), 3.37–3.46 (m, 1H), 3.62 (d, J=14 Hz, 1H), 3.68 (d, J=14 Hz, 11), 6.95 (dd, J=3.6 Hz, 5.2 Hz, 1H), 7.15 (dd, J=1.2 Hz, 3.6 Hz, 1H), 7.23–7.39 (m, 6H),

Example 177 1-[4-cyano-4-(2-thienyl)-5-methylhexyl]-(3S)-3-[N-(2-cyanoethyl)-N-(3-cyanobenzyl)amino]pyrrolidine

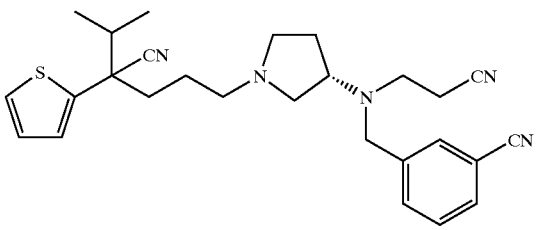

The title compound was synthesized in accordance with Example 75 from the iodide D and (3S)-3-[N-(2-cyanoethyl)-N-(3-cyanobenzyl)amino]pyrrolidine synthesized in accordance with the production method of "Synthetic method A" (1) of

Example 175

The Physico-chemical Data of, the Compound was as Velow.

Yield; 82%.

$^1$H-NMR (400 MHz, CDCl$_3$) δ 0.90 (d, J=6.4 Hz, 3H), 1.16 (d, J=6.8 Hz, 3H), 1.22–1.34 (m, 1H), 1.54–1.67 (m, 1H), 1.67–1.80 (m, 2H), 1.93–2.09 ([. 2H), 2.16–2.27 (m, 2H), 2.27–2.43 (m, 5H), 2.59–2.72 (m, 2H), 2.88 (t, J=6.8 Hz, 2H), 3.34–3.43 (m, 1H), 3.68 (d, J=15 Hz, 110, 3.74 (d, J=15 Hz, 1H), 6.96 (dd, J=3.6 Hz, 5.2 Hz, 1H), 7.11 (dd, J=1.2 Hz, 3.6 Hz, 1H), 7.27 (dd, J=1.2 Hz, 5.2 Hz, 1H), 7.41–7.48 (m, 1H), 7.54–7.58 (m, 1H), 7.62–7.66 (m, 2H)

Example 178 1-[1-cyano-4-(2-thienyl)-5-methylhexyl]-4-[{3-methoxy-(2R)-2-(2-]pyridyloxy)propyl]piperazine

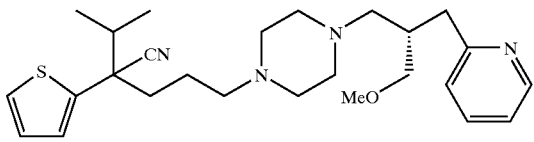

The title compound was synthesized in accordance with Example 75 from the iodide D and 1-[(3-methoxy-(2R)-2-(2-pyridyloxy))propyl]piperazine. The physico-chemical data of the target compound obtained is indicated below. The values of the physical properties of the title, compound obtained are indeicated below.

$^1$H-NMR (400 MHz, CDCl$_3$) δ 0.89 (d, J=6.8 Hz, 3H), 1.17 (d, J=6.4 Hz, 3H), 1.21–1.35 (m, 1H), 1.55–1.69 (m, 1H), 1.70–1.80 (m, 1H), 2.00–2.18 (m, 2H), 2.20–2.62 (m, 10H), 2.62–2.72 (m, 2H), 3.38 (s, 3H), 3.60–3.70 (m, 2H), 5.47–5.55 (m, 1H), 6.71–6.78 (m, 1H), 6.81–6.87 (m, 1H), 6.94 (dd, 1=3.6 Hz, 52 Hz, 1H), 7.10 (dd, J=1.6 Hz, 3.6 Hz, 1H), 7.25 (dd, J=1.6 Hz, 5.2 Hz, 1H), 7.50–7.58 (m, 1H), 8.09–8.13 (m, 1H)

Example 179 1-(6-bromo-2-pyridyl)-(3R)-3-{N-[4-cyano-4-(2-thienyl)-5-methylhexyl]Amino}Pyrrolidine

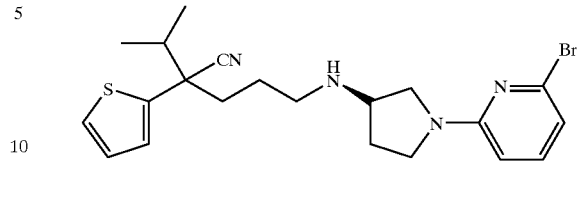

The title compound was synthesized in accordance with Example 75 from the iodide C (optically active compound) and (3R)-3-{N-[4-cyano-4-(2-thienyl)-5-methylhexyl]amino}pyrrolidine. The physico-chemical data of the compound was as below.

$^1$H-NMR (400 MHz, CDCl$_3$) δ 0.90 (d, J=6.8 Hz, 3H), 1.18 (d, J=6.8 Hz, 3H), 1.23–1.36 (m, 1H), 1.57–1.70 (m, 1H), 1.73–1.83 (m, 0.2H), 2.00–2.10 (m, 1H), 2.10–2.24 (m 2H), 2.56–2.71 (m, 2H), 3.14–3.22 (m, 1H), 3.34–3.44 (m, 211, 3.49–3.58 (m, 1H), 3.59–3.66 (m, 1H), 6.21 (d, J=8.0 Hz, 1H), 6.65 (d, J=7.2 Hz, 1H), 6.94 (dd, J=3.6 Hz, 5.2 Hz, 1H), 7.11 (dd, J=1.2 Hz, 3.6 Hz, 1H), 7.22 (dd, J=7.2 Hz, 8.0 Hz, 1H), 7.26 (dd, J=1.2 Hz, 5.2 Hz, 1H)

Example 180 1-[4-Cyano-4-(5-cyano-2-thienyl)-5-methylhexyl]-4-[2-(5-chlorobenzoxazoyl)methyl]piperazine

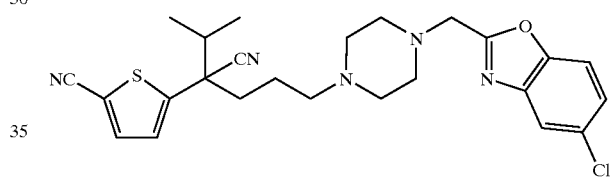

The title compound was synthesized in accordance with Example 77 from 1-[4-cyano-4-(5-cyano-2-thienyl)-5-methylhexyl]piperazine and 2-chloromethyl-5-chlorobenzoxazole synthesized in accordance with Example 83. The physico-chemical data of the compound was as below.

$^1$HNR (400 MHz, CDCl$_3$) δ 0.91 (d, J=6.88 Hz, 3H), 1.20 (d, J=6.4 Hz, 3H), 1.20–1.30 (m, 1H), 1.58–1.71 (m, 1H), 1.71–1.81 (m, 1H), 2.00–2.10 (m, 1H), 2.16–2.26 (m, 1H), 2.34 (t, J=6.8 Hz, 2H), 2.37–2.54 (m, 4H), 2.54–2.73 (D. 4H), 3.86 (s, 21), 7.14 (d, J=4.0 Hz, 1H), 7.31 (dd, J=2.0 Hz, 8.4 Hz, 1H), 7.45 (d, J=8.4 Hz, 1H), 7.51 (d, J=4.0 Hz, 1H), 7.68 (d, J=2.0 Hz, 1H)

Example 181 1-[4-Cyano-4-(5-cyano-2-thienyl)-5-methylhexyl]-4-[2-(5-methylbenzoxazoyl)methyl]piperazine

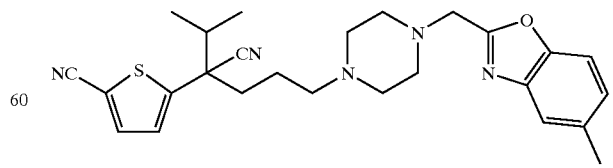

According to Example 180, from 1-[4-cyano-4-(5-cyano-2-thienyl)-5-methylhexyl]piperazine and 2-chloromethyl-5-methylbenzoxazole synthesized in accordance with Example 83, the title compound was synthesized in accordance with Example 77. The physico-chemical data of the compound was as below.
¹H-NMR (400 MHz, CDCl₃) δ 0.91 (d, J=6.8 Hz, 3H), 1.20 (d, 1=6.4 Hz, 3H), 1.20–1.30 (m, 1H), 1.58–1.70 (m, 1H), 1.70–1.81 (m, 1H), 2.00–2.10 (m, 1H), 2.16–2.26 (m, 1H), 2.33 (t, J=6.8 Hz, 2H), 2.46 (s, 3H), 2.37–2.54 (m, 4H), 2.55–2.73 (m, 4H), 3.85 (s, 2H), 7.12–7.16 (m, 1H), 7.14 (d, J=4.0 Hz, 1H), 7.39 (d, J=8.4 Hz, 1H), 7.47–7.49 (m, 1H), 7.51 (d, J=4.0 Hz, 1H)

Example 182 1-[4-Cyano-4-(5-cyano-2-thienyl)-5-methylhexyl]-4-[2-benzothiazoylmethyl]piperazine

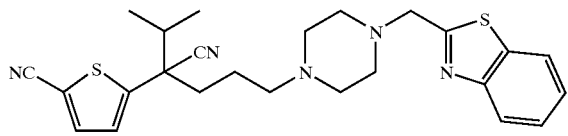

According to Example 180, the title compound was synthesized in accordance with Example 77 from 1-[4-cyano-4-(5-cyano-2-thienyl)-5-methylhexyl]piperazine in accordance with Example 180 and 2-chloromethylbenzothiazole which was synthesized in accordance with Example 83. The physico-chemical data of the compound was as below.
¹H-NMR (400 MHz, CDCl₃), 6.0.92 (d, J=6.8 Hz, 3H), 1.21. (d, J=6.8 Hz, 3H). 1.20–1.32 (m, 1H), 1.59–1.72 (m, 1H), 1.72–1.83 (m, 1H), 2.01–2.10 (m, 1H), 2.18–2.28 (m, 1H), 2.35 (t, J=7.4 Hz, 2H), 2.35–2.52 (m, 4H), 2.54–2.74 (m, 4H), 3.95 (s, 2H), 7.14 (d, J=3.6 Hz, 1H), 7.33–7.39 (m, 1H), 7.42–7.48 (m, 1H), 7.51 (d, J=3.6 Hz, 1H), 7.84–7.88 (m, 1H), 7.94–7.99 (m, 1H)

Example 183 1-[4-Cyano-4-(2-thienyl)-5-methylhexyl]-4-[2-(5-trifluoromethyl-2-pyridyloxy)ethyl]piperazine

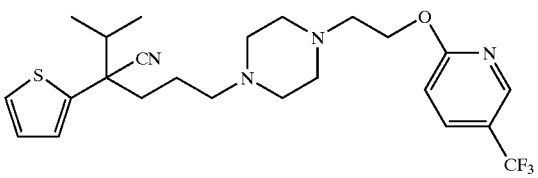

The target compound was synthesized in accordance with Example 75 from 4-cyano-4-(2-thienyl)-5-methylhexyl iodide and 1-[2-(5-trifluoromethyl-2-pyridyloxy)ethyl]piperazine. The physico-chemical data of the compound was as below.
¹H-NMR (400 MHz, CDCl₃) δ 0.90 (d, J=6.4 Hz, 3H), 1.18 (d, J=6.4 Hz, 3H), 1.20–1.38 (m, 1H), 1.55–1.70 (, 1H), 1.71–1.82 (m, 1H), 2.00–2.10 (m, 1H), 2.10–2.20 (m, 1H), 2.31 (t, J=7.4 Hz, 2H), 2.30–2.48 (m, 4H), 2.48–2.65 (m, 4H), 2.78 (t, J=6.0 Hz, 2H), 4.48 (t, J=6.0 Hz, 2H), 6.83 (d, J=8.8 Hz, 1H), 6.94 (dd, J=3.6 Hz, 5.2 Hz, 1H), 7.11 (dd, J=1.2 Hz, 3.6 Hz, 1H), 7.75 (dd, J=2.4 Hz, 8.8 Hz, 1H), 8.39–8.44 (m, 1H)

Example 184 1-[4-Cyano-4-(5-cyano-2-thienyl)-5-methylhexyl]-4-[2-(5-trifluoromethyl-2-pyridyloxy)ethyl]piperazine

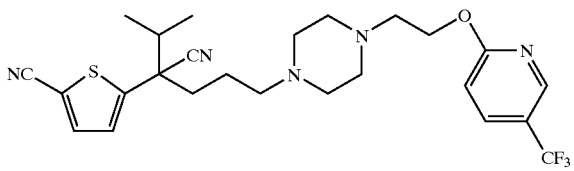

The title compound was synthesized in accordance with Example 77 from 4-cyano-4-(5-cyano-2-thienyl)-5-methylhexyl iodide and 1-[2-(5-trifluoromethyl-2-pyridyloxy)ethyl]piperazine. The physico-chemical data of the compound was as below.
¹H-NMR (400 MHz, CDCl₃) δ 0.92 (d, J=6.4 Hz, 3H), 1.21 (d, J=6.4 Hz, 3H), 1.20–1.31 (m, 1H), 1.60–1.82 (m, 2H), 2.00–2.10 (m, 1H), 2.17–2.28 (m, 1H), 2.28–2.48 (m, 6H), 2.48–2.65 (m, 4H), 2.79 (t, J=6.0 Hz, 2H), 4.49 (t, J=6.0 Hz, 2H), 6.83 (d, J=8.8 Hz, 1H), 7.15 (d, J=4.0 Hz, 1H), 7.51 (d, J=4.0 Hz, 1H), 7.76 (dd, J=2.4 Hz, 8.8 Hz, 1H), 8.40–8.44 (m, 1H)

Example 185 1-[4-Cyano-4-(2-thienyl)-5-methylhexyl]-4-[2-(5-chloro-3-pyridyloxy)ethyl]piperazine

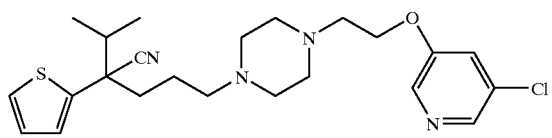

The title compound was synthesized in accordance with Example 75 from 4-cyano-4-(2-thienyl)-5-methylhexyl iodide and 1-[2-(5-chloro-3-pyridyloxy)ethyl]piperazine. The physico-chemical data of the compound was as below.
¹H-NMR (400 MHz, CDCL₃) δ 0.90 (d, J=6.8 Hz, 3H), 1.18 (d, J=6.4 Hz, 3H), 1.20–1.37 (m, 1H), 1.55–1.71), (m, 1H), 1.71–1.82 (m, 1H), 2.00–2.10 (m, 1H), 2.10–2.21 (m, 1H), 2.25–2.49 (m, 6H), 2.49–2.65 (m, 4H), 2.80 (t, J=5.6 Hz, 2H), 4.12 (t, 3=5.6 Hz, 21), 6.94 (dd, J=3.6 Hz, 5.2 Hz, 1H), 7.11 (dd, J=1.2 Hz, 3.6 Hz, 1H), 7.22 (t, J=2.0 Hz, 1H), 7.24–7.28 (m, 1H), 8.18 (d, J=2.0 Hz, 1H), 8.20 (d, J=2.0 Hz, 1H)

Example 186 1-[4-Cyano-4-(5-cyano-2-thienyl)-5-methylhexyl]-4-[2-(5-chloro-3-pyridyloxy)ethyl]piperazine

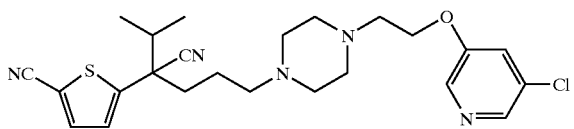

The title compound was synthesized in accordance with Example 77 from 4-cyano-4-(5-cyano-2-thienyl)-5-methylhexyl iodide and 1-[2-(5-chloro-3-pyridyloxy)ethyl]piperazine. The physico-chemical data of the compound was as below.
¹H-NMR (400 MHz, CDCL₃) 60.92 (d, J=6.4 Hz, 3H), 1.21 (d, J=6.4 Hz, 3H), 1.20–1.30 (m, 1H), 1.60–1.72 (m, 1H), 1.72–1.82 (m, 1H), 2.00–2.11 (m, 1), 2.17–2.28 (m, 1H), 2.28–2.48 (m, 6H), 2.49–2.65 (m, 4H), 2.81 (t, J=5.6 Hz, 2H), 4.13 (t, J=5.66 Hz, 210, 7.15 (d, J=4.0 Hz, 1H), 7.21–7.23 (m, 1H, 7.51 (d, J=4.0 Hz, 1H), 8.19 (d, J=1.6 Hz, 1H), 8.20 (d, 1=2.8 Hz, 1H)

Example 187 1-[4-cyano-4-(2-thienyl)-5-methylhexyl]-4-[2-(5-chloro-3-pyridyloxy)ethyl]piperidine

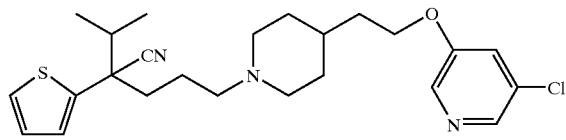

The title compound was synthesized in accordance with Example 75 from 4-cyano-4-(2-thienyl)-5-methylhexyl iodide and 4-[2-(5-chloro-3-pyridyloxy)ethyl]piperidine. The physico-chemical data of the compound was as below.
$^1$H-NMR (400 MHz, CDCL$_3$) δ 0.90 (d, J=6.8 Hz, 3H), 1.18 (d, J=6.8 Hz, 3H), 1.20–1.38 (m, 2H), 1.40–1.56 (m, 1H), 1.60–1.93 (m, 9H), 2.00–2.20 (m, 2H), 2.25–2.35 (m, 2H), 2.77–2.87 (m, 2H), 4.02 (t, J=6.4 Hz, 2H), 6.95 (dd, J=3.6 Hz, 5.2 Hz, 1H), 7.11 (dd, J=1.2 Hz, 3.6 Hz, 1H), 7.17–7.20 (m, 1) 7.24–7.28 (m, 1H), 8.16–8.20 (m 2H)

Example 188 1-[4-Cyano-4-(2-thienyl)-5-methylhexyl]-4-(3-pyridylamino)piperidine

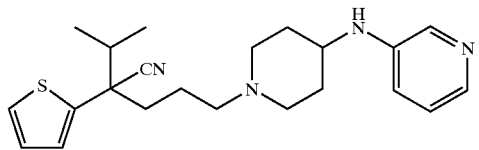

The title compound was synthesized in accordance with Example 75 from 4-cyano-4-(2-thienyl)-5-methylhexyl iodide and 4-(3-pyridylamino)piperidine. The physico-chemical data of the compound was as below.
$^1$H-NMR (400 MHz, CDCl$_3$) δ 0.90 (d, J=6.8 Hz, 3H), 1.18 (d, J=6.8 Hz, 3H), 1.24–1.38 (m, 1H), 1.38–1.50 (m, 2H), 1.58–1.71 (m, 1H), 1.73–1.83 (m, 1H) 1.95–2.21 (m, 5H), 2.29–2.36 (m, 2H), 2.72–2.81 (m, 2H), 3.20–3.31 (m, 1H), 3.48–3.56 (m, 1H), 6.81–6.86 (m, 2H), 6.94 (dd, J=3.6 Hz, 5.2 Hz, 1H), 7.05 (dd, J=4.8 Hz, 12.8 Hz, 1H), 7.11 (dd, J=1.2 Hz, 3.6 Hz, 1H), 7.26 (dd, J=1.2 Hz, 5.2 Hz, 1H), 7.92 (dd, J=1.6 Hz, 4.8 Hz, 1H), 7.99 (d, J=2.1 Hz, 1H)

Example 189 1-[4-cyano-4-(2-thienyl)-5-methylhexyl]-4-[2-{N-isopropyl-N-(2-pyridyl)amino]ethyl}Piperazine

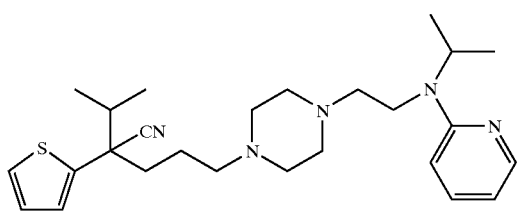

The title compound was synthesized in accordance with Example 75 from 4-cyano-4-(2-thienyl)-5-methylhexyl iodide and 1-[2-(N-isopropyl-N-(2-pyridyl)amino ethyl]piperazine. The physico-chemical data of the compound was as below.
$^1$H-NMR (400 MHz, CDCl$_3$) δ 0.90 (d, J=6.8 Hz, 3H), 1.14–1.21 (m, 9H), 1.24–1.38 (m, 1H), 1.58–1.70 (m, 1H), 1.72–1.82 (m, 1H), 2.00–2.10 (m, 1H). 2.10–2.21 (m, 1H), 2.28–2.66 (m, 12H), 3.41 (t, 1=8.0 Hz, 2H), 4.74–4.84 (m, 1H), 6.47–6.53 (m, 2H), 6.94 (dd, J=3.6 Hz, 5.2 Hz, 1H), 7.11 (dd, J=1.2 Hz, 3.6 Hz, 1H), 7.24–7.29 (m, 1H), 7.37–7.44 (m, 1H) 8.12–8.16 (m, 1H)

Example 190 1-[4-Cyano-4-(2-thienyl)-5-methylhexyl]-4-[2-(6-methoxymethyl-2-pyridyloxy)ethyl]piperazine

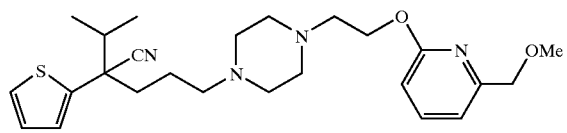

The titile compound was synthesized in accordance with Example 75 from 4-cyano-4-(2-thienyl)-5-methylhexyl iodide and 1-(2-(6-methoxymethyl-2-pyridyloxy)ethyl) piperazine. The physico-chemical data of the compound was as below.
ESI-MS; 457(M+H)$^+$ Example 191 1-[4-Cyano-4-(2-thienyl)-5-methylhexyl]-4-[2-(6-fluoromethyl-2-pyridyloxy)ethyl]piperazine

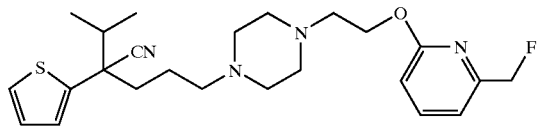

The title compound was synthesized in accordance with Example 75 from 4-cyano-4-(2-thienyl)-5-methylhexyl iodide and 1-[2-(6-fluoromethyl-2-pyridyloxy)ethyl]piperazine. The physico-chemical data of the compound was as below.

The values of the physical properties of the target compound obtained are indicated below.
ESI-MS; 445(M+H)$^+$ Example 192 1-[4-cyano-4-(2-thienyl)-5-methylhexyl]-4-[2-(6-bromo-2-pyridyloxy)ethyl]piperazine

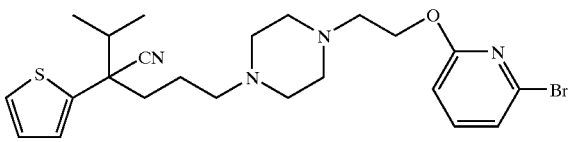

The title compound was synthesized in accordance with Example 75 from 4-cyano-4-(2-thienyl)-5-methylhexyl iodide and 1-[2-(6-bromo-2-pyridyloxy)ethyl]piperazine. The physico-chemical data of the compound was as below.
$^1$H-NMR (400 MHz, CDCl$_3$) δ 0.90 (d, J=6.4 Hz, 3H), 1.18 (d, J=6.4 Hz, 3H), 1.22–1.38 (m, 1H), 1.58–1.70 (m, 1H), 1.71–1.82 (m, 1H), 2.00–2.10 (m, 1H), 2.10–2.20 (m, 1H), 2.25–2.65 (m, 10H), 2.76 (t, J=6.0 Hz, 2H), 4.42 (t, J=6.0 Hz, 2H), 6.69 (d, J=8.0 Hz, 1H), 6.94 (dd, J=3.6 Hz, 5.2 Hz, 1H), 7.04 (d, J=8.0 Hz, 1H), 7.11 (dd, J=1.6 Hz, 3.6 Hz, 1H), 7.24–7.28 (m, 1H), 7.40 (t, J=8.0 Hz, 1H)

Example 193 1-[4-cyano-4-(2-thienyl)-5-methylhexyl]-4-[2-(6-fluoro-2-pyridyloxy)ethyl]piperazine

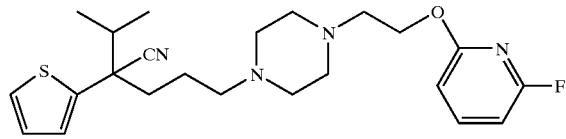

The title compound was synthesized in accordance with Example 75 from 4-cyano-4-(2-thienyl)-5-methylhexyl iodide and 1-[2-(6-fluoro-2-pyridyloxy)ethyl]piperazine. The physico-chemical data of the compound was as below.
ESI-MS; 431(M+H)⁺

Example 194 1-[4-cyano-4-(2-thienyl)-5-methylhexyl]-4-[2-(2-pyridyloxy)ethyl]piperazine

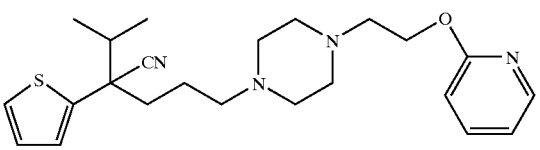

The title compound was synthesized in accordance with Example 75 from 4-cyano-4-(2-thienyl)-5-methylhexyl iodide and 1-[2-(2-pyridyloxy)ethyl]piperazine. The physico-chemical data of the compound was as below.
ESI-MS; 413(M+H)⁺

Example 195 1-[4-cyano-4-(2-thienyl)-5-methylhexyl]-4-[2-(6-methyl-2-pyridyloxy)ethyl]piperazine

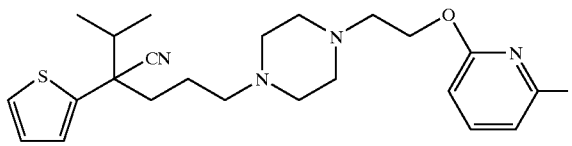

The title compound was synthesized in accordance with Example 75 from 4-cyano-4-(2-thienyl)-5-methylhexyl iodide and 1-[2-(6-methyl-2-pyridyloxy)ethyl]piperazine. The physico-chemical data of the compound was as below.
¹H-NMR (400 MHz, CDCl₃) δ 0.90 (d, J=6.8 Hz, 3H), 1.18 (d, J=6.8 Hz, 3H). 1.22–1.38 (m, 1H), 1.58–1.70 (m, 1H), 1.71–1.82 (m, 1H), 2.00–2.10 (m, 1H), 2.10–2.21 (m, 1H), 2.27–2.70 (m, 10H), 2.42 (s, 3H), 2.77 (t, J=6.0 Hz, 21), 4.41 (t, J=6.0 Hz, 2H), 6.51–6.55 (m, 1H), 6.67–6.72 (m, 1H), 6.94 (dd, J=3.6 Hz, 5.2 Hz, 1H), 7.11 (dd, J=1.6 Hz, 3.6 Hz, 1H), 7.25 (dd, J=1.6 Hz, 5.2 Hz, 1H), 7.43 (dd, J=7.2 Hz, 8.4 Hz, 1H)

Example 196 1-[4-cyano-4-(2-thienyl)-5-methylhexyl]-4-(2-(6-cyano-2-]pyridyloxy)ethyl]piperazine

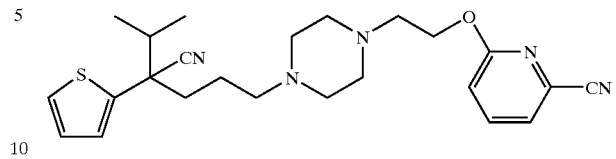

The title compound was synthesized in accordance with Example 75 from 4-cyano-4-(2-thienyl)-5-methylhexyl iodide and 1-[2-(6-cyano-2-pyridyloxy)ethyl]piperazine. The physico-chemical data of the compound was as below.

ESI-MS; 438(M+H)⁺

Example 197 1-[4-cyano-4-(5-cyano-2-thienyl)-5-methylhexyl]-4-[2-(6-cyano-2-pyridvloxy)ethyl]piperazine

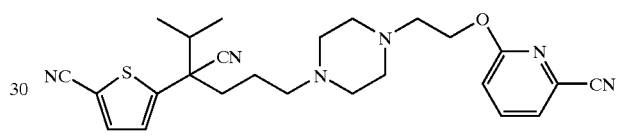

The title compound was synthesized in accordance with Example 75 from 4-cyano-4-(5-cyano-2-thienyl)-5-methylhexyl iodide and 1-[2-(6-cyano-2-pyridyloxy)ethyl]piperazine. The physico-chemical data of the compound was as below.

ESI-MS; 463(M+H)⁺

Example 198 1-[(4-cyano-5-methyl-4-phenyl)hexyl]-4-[N-[2-(4-fluorophenoxy)ethyl]-N-2-cyanoethyl]Aminopiperidine

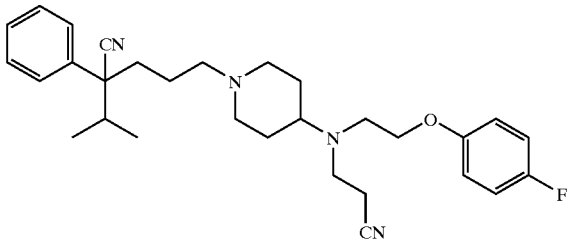

The title compound was synthesized in accordance with the production method of Example 35.

Hydrochloride: ESI-Mass; 491(MH⁺)

Example 199 1-[(4-cyano-5-methyl-4-phenyl)hexyl]-4-(2-hydroxybenzyl)piperazine

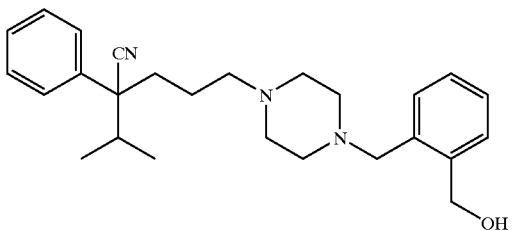

The title compound was obtained in accordance with the production method of Example 3.
Hydrochloride: ESI-Mass; 406(MH⁺)

Example 200 1-[[4-cyano-5-methyl-4-(2-thienyl)]hexyl]-4-[3(1-(4-fluorophenyl)cyclohexyl]propyl]piperazine

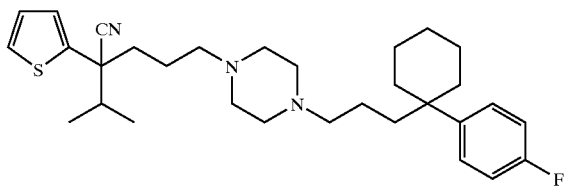

The title compound was obtained in accordance with the production method of Example 70 by using the above-mentioned 4-[3-[1-(4-fluorophenyl)cyclohexyl]propyl]piperazine.
Hydrochloride: ESI-Mass; 510(MH⁺)

Example 201 1-[[4-cyano-5-methyl-4-(3-benzothienyl)]hexyl]-4-[2-(3-cyanophenoxy)ethyl]piperazine

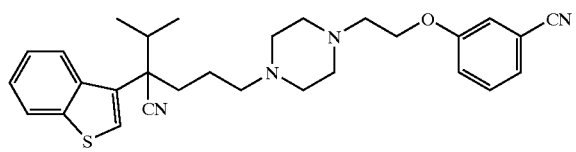

The title compound was obtained in accordance with the production method of Example 70.
Hydrochloride: ESI-Mass; 487(MH⁺)

Example 202 1-[[4-cyano-5-methyl-4-(3-benzothienyl)]hexyl]-4-benzylpiperazine

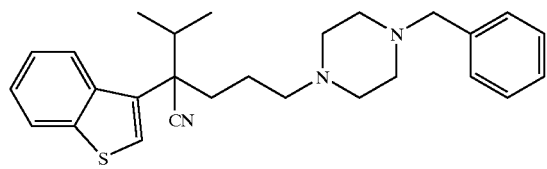

The title compound was obtained in accordance with the production method of Example 70.
Hydrochloride: ESI-Mass; 432(MH⁺)

Example 203 1-[[4-cyano-5-methyl-4-(3-benzothienyl)]hexyl]-4-(3-cyanobenzyl)piperazine

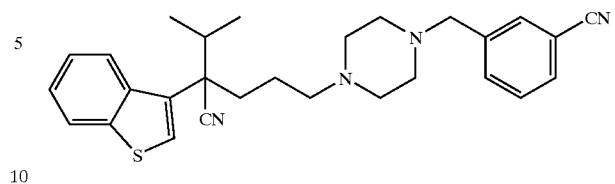

The title compound was obtained in accordance with the production method of Example 3.
Hydrochloride: ESI-Mass; 457(MH⁺)

Example 204 1-[[4-cyano-5-methyl-4-(3-benzothienyl)]hexyl]-4-[(2-thienyl)methyl]piperazine

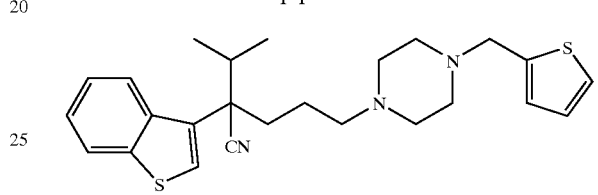

The title compound was obtained in accordance with the production method of Example 3.
Hydrochloride: ESI-Mass; 438(MH⁺)

Example 205 1-[[4-cyano-5-methyl-4-(3-benzothienyl)]hexyl]-4-[(4-cyano-2-thienyl)methyl]piperazine

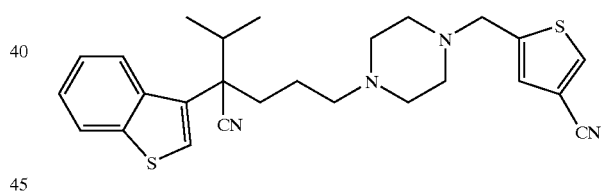

The title compound was obtained in accordance with the production method of Example 3.
Hydrochloride: ESI-Mass; 463(MH⁺)

Example 206 1-[[4-cyano-5-methyl-4-(3-benzothienyl)]hexyl]-4-(6-methyl-2-picolyl)piperazine

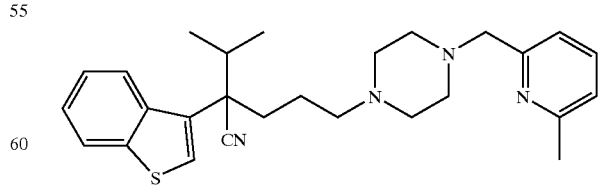

The title compound was obtained in accordance with the production method of Example 3.
Hydrochloride: ESI-Mass; 447(MH⁺)

Example 207 1-[[4-cyano-5-methyl-4-(1-methyl-2-pyrrolyl)]hexyl]-4-[2-(3-cyanophenoxy)ethyl]piperazine

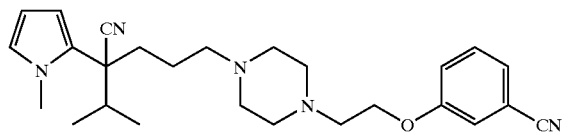

The title compound was obtained in accordance with the production method of Example 70.
Oxalate: ESI-Mass; 434(MH$^+$)

Example 208 1-[[4-cyano-5-methyl-4-(5-methyl-2-thienyl]hexyl]-4-[N-[2-(4-fluorophenoxy)ethyl]-N-2-cyanoethyl]Aminopiperidine

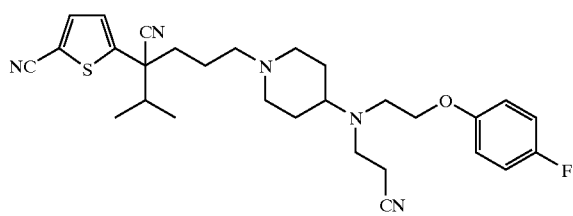

The title compound was obtained in accordance with the production method of Example 35.
Hydrochloride: ESI-Mass; 522(MH$^+$)

Example 209 1-[[4-cyano-5-methyl-4-(2-thienyl)]hexyl]-4-[N-[2-(4-fluorophenoxy)ethyl]-N-2-cyanoethyl]Aminopiperidine

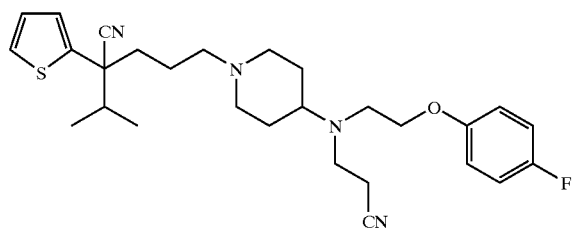

The title compound was obtained in accordance with the production method of Example 35.
Hydrochloride: ESI-Mass; 497(MH$^+$)

Example 210 1-[[4-cyano-5-methyl-4-(2-thienyl)]hexyl]-4-[(2-benzoxazolyl)amino]piperidine

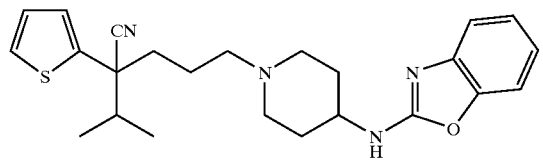

The title compound was obtained in accordance with the production method of Example 17.
Hydrochloride: ESI-Mass; 423(MH$^+$)

Example 211 1-[[4-cyano-5-methyl-4-(5-cyano-2-thienyl)]hexyl]-4-[(2-benzoxazolyl)aminopiperidine

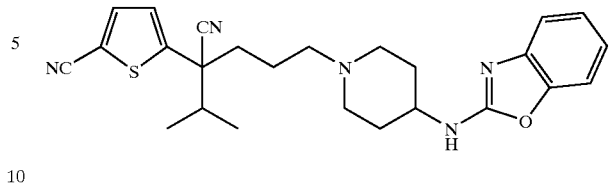

The title compound was obtained in accordance with the production method of Example 17.
Hydrochloride: ESI-Mass; 448(MH$^+$)

Example 212 1-[[4-cyano-5-methyl-4-(2-furyl)hexyl]-4-[2-(3-cyanophenoxy)ethyl]piperazine

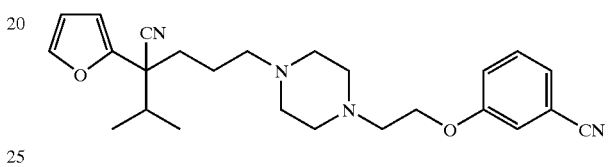

The title compound was obtained in accordance with the production method of Example 70.
Hydrochloride: ESI-Mass; 421(MH$^+$)

Example 213 1-[[4-cyano-5-methyl-4-(2-furyl)[hexyl]-4-[(2-benzoxazolyl)amino]piperidine

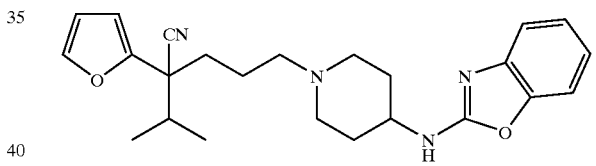

The title compound was obtained in accordance with the production method of Example 17.
Oxalate: ESI-Mass; 407(MH$^+$)

Example 214 1-[[4-cyano-5-methyl-4-(2-thienyl)hexyl]-4-[N-(2-benzoxazolyl)-N-(2-cyanoethyl)amino]piperidine

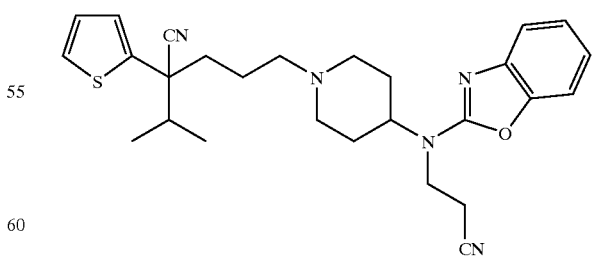

The title compound was obtained in accordance with the production method of Example 35.
Hydrochloride: ESI-Mass; 476(MH$^+$)

Example 215 1-[[4-cyano-5-methyl-4-(2-furyl)]hexyl]-4-[N-(2-benzoxazolyl)-N-(2-cyanoethyl)amino]piperidine

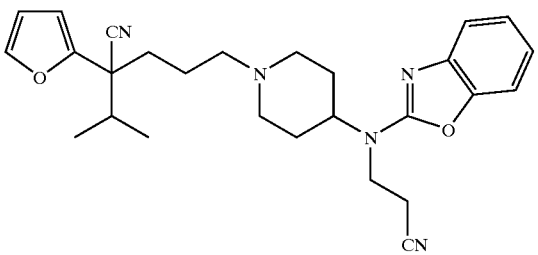

The title compound was obtained in accordance with the production method of Example 35.
Oxalate: ESI-Mass; 460(MH⁺)

Example 216 1-[[(4-cyano-5-methyl-4-phenyl)]hexyl]-4-(2-pyridyl)piperazine

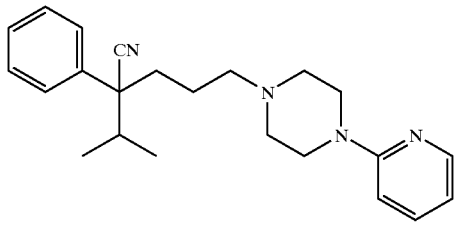

The title compound was obtained in accordance with the production method of Example 70.
Hydrochloride: ESI-Mass; 363(MH⁺)

Example 217 1-[[4-cyano-5-methyl-4-(2-thienyl)]hexyl]-4-(2-pyridyl)piperazine

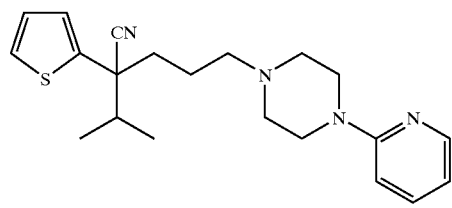

The title compound was obtained in accordance with the production method of Example 70.
Hydrochloride: ESI-Mass; 369(MH⁺)

Example 218 1-[(2-oxo-1.2-dihydro-3-quinolyl)methyl]-4-[(4-cyano-5-methyl-4-phenyl)hexyl]piperazine

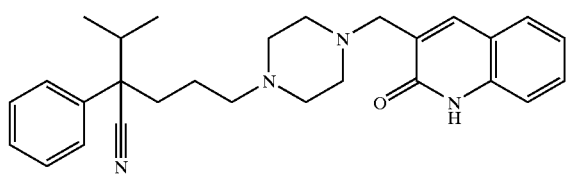

The oxalate of the title compound was obtained as a colorless solid in accordance with Example 3.
Oxalate:
$^1$H NMR (400 MHz, DMSO-d$_6$) δ 0.64 (d,]=6.8 Hz, 3H), 1.09 (d, J=6.4 Hz, 3H), 1.00–1.20 (m, 1H), 1.40–1.60 (m, 1H), 1.95–2.15 (m, 1H), 2.10–2.25 (m, 1H), 2.60–3.05 (m, 1H), 3.59 (s, 2H), 7.17 (t, J=7.2 Hz, 1H), 7.29 (d, J=8.4 Hz, 1H), 7.30–7.38 (m, 1H), 7.35–7.50 (m, 5H), 7.62 (dd, J=8.0 Hz, 1.2 Hz, 1H). 7.89 (s, 1H), 11.88 (s, 1H).

Example 219 1-[(2-oxo-1,2-dihydro-3-quinolyl)methyl]-4-[(4-cyano-5-methyl-4-phenyl)hexyl]piperidine

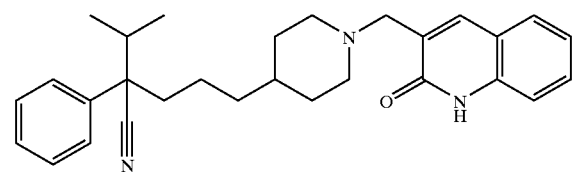

The oxalate of the title compound was obtained as a colorless solid in accordance with Example 3.
Oxalate:
$^1$H NMR (400 MHz, DMSO-d$_6$) δ 0.63 (d, J=6.8 Hz, 3H), 0.70–0.85 (m, 1H), 1.00–1.45 (m, 6H), 1.09 (d, J=6.8 Hz, 3H), 1.60 (br d, J=12.8 Hz, 2H), 1.87–2.08 (m, 2H), 2.10–2.23 (m, 1H), 2.75–2.95 (m, 21), 3.20–3.35 (m, 2H), 4.08 (s, 2H), 7.19–7.25 (m, 111, 7.28–7.44 (m, 6H), 7.53–7.58 (m, 1H). 7.65–7.70 (m, 1H), 8.13 (s, 1H), 12.13 (s, 1H).

Example 220 1-[(2-oxo-1,2-dihydro-3-pyridinyl)methyl]-4-[(4-cyano-5-methyl-4-phenyl)hexyl]piperidine

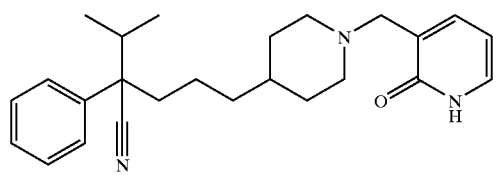

The oxalate of the title compound was obtained as a colorless solid in accordance with Example 3.
Oxalate:
$^1$H NMR (400 MHz, DMSO-d$_6$) δ 0.63 (d, J=6.8 Hz, 3H), 0.70–0.85 (s 1H), 1.00–1.45 ([. 6H), 1.09 (d, J=6.8 Hz, 3H), 1.59 (br d, J=13.2 Hz, 2H), 1.87–2.08 (m, 2H), 2.10–2.23 (m, 1H), 2.73–2.95 (m, 2H), 3.15–3.33 (m, 2H), 3.98 (s, 2H), 2.26 (d, J=6.8 Hz, 1H), 7.28–7.35 (m, 1H), 7.36–7.44 (m, 4H), 7.50 (dd, J=6.4 Hz, 2.0 Hz, 1H), 7.62–7.68 (m 1H).

Example 221 1-[(5-chloro-2-oxo-1.2-dihydro-3-pyridinyl)methyl]-4-[(4-cyano-5-methyl-4-phenyl)hexyl]piperidine

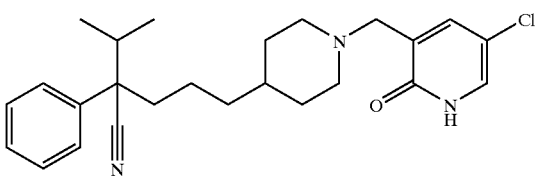

The oxalate of the title compound was obtained as a colorless solid in accordance with Example 3.

Oxalate:

¹H NMR (400 MHz, DMSO-dd₆) δ 0.63 (d, J=6.8 Hz, 3H), 0.70–0.85 (m, 1H), 1.00–1.40 (m, 6H), 1.09 (d, J=6.4 Hz, 3H), 1.53 (brd, J=13.2 Hz, 2H), 1.87–2.08 (m, 2H), 2.10–2.23 (m, 1H), 2.40–2.60 (m, 2H), 3.04 (brd, J=11.6 Hz, 2H), 3.68 (s, 2H), 7.25–7.35 (m, 1H), 7.36–7.44 (m, 4H), 7.59 (d, J=2.8 Hz, 1H), 7.66, (d, J=2.4 Hz, 1H).

Example 222 4-[(4-cyano-5-methyl-4-phenyl)hexyl]-1-{[1-(methanesulfonylamino}Phenyl]methyl]piperazine

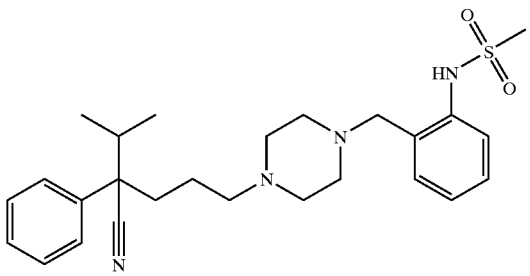

The oxalate of the title compound was obtained as a colorless solid in accordance with Example 3.

Oxalate:

¹H NMR (400 MHz, DMSO-d₆) δ 0.64 (d, J=6.4 Hz, 3H), 0.80–1.20 (m, 1H), 1.09 (d, J=6.8 Hz, 3H), 1.40–1.60 (m, 1H), 1.90–2.15 (m, 1H), 2.10–2.25 (m, 1H), 2.60–3.10 (m, 1H), 3.03 (s, 3H), 3.65 (s, 2[D, 7.13 (t, J=7.2 Hz, 1H), 7.26–7.47 (m, 8H).

Example 223 4-[(4-cyano-5-methyl-4-phenyl)hexyl]-1-{[2-(p-toluenesulfonylamino)phenyl]Methyl}Piperazine

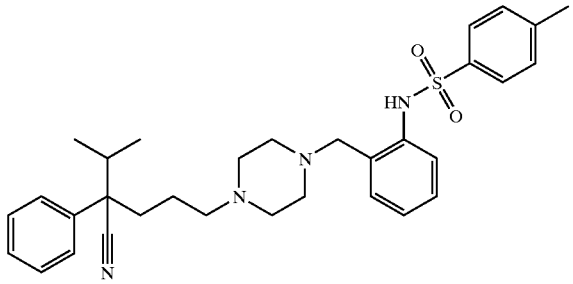

The oxalate of the title compound was obtained as a colorless solid in accordance with Example 3.

Oxalate:

¹H NMR (400 MHz, DMSO-d₆) δ 0.65 (d, J=6.4 Hz, 3H), 0.80–1.20 (m, 1H), 1.09 (d, J=6.8 Hz, 3H), 1.45–1.60 (m, 1H 1.95–2.15 (m, 1H), 2.10–2.25 (m, 1H), 2.33 (s, 3H), 2.60–3.05 (m, 1H), 3.34 (s, 2H), 7.05–7.12 (m, 2H), 7.16–7.24 (m, 2H), 7.32 (d, J=7.6 Hz, 2H), 7.29–7.37 (m, 1H), 7.37–7.46 (m 9H), 7.58 (d, J=8.0 Hz, 2H).

Example 224 4-[(4-cyano-5-methyl-4-phenyl)hexyl]-1-f-{[2-(methanesulfonylamino)phenyl]methyl}Piperidine

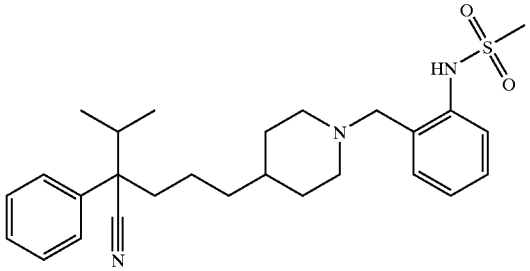

The title compound was obtained as a colorless oil in accordance with Example 3.

¹H NMR (400 MHz, CDCl₃) δ 0.80 (d, J=6.8 Hz, 3H), 0.85–1.05 (m, 1H), 1.05–1.45 (m, 6H), 1.22 (d, J=6.4 Hz, 3H), 1.50–1.68 (m, 21), 1.73–1.88 (m, 1H), 1.90–2.05 (m, 2H), 2.00–2.20 (m, 2H), 2.75–2.90 (m, 2H), 3.04 (s, 3H), 3.60 (s, 2H), 6.96–7.11 (m, 2H), 7.24–7.36 (m, 2H), 7.34–7.44 (m, 4H), 7.46–7.52 (m, 1H).

Example 225 4-(4-cyano-5-methyl-4-phenyl)hexyl]-1-{[2-(p-toluenesulfonylamino)phenyl]Methyl]piperidine

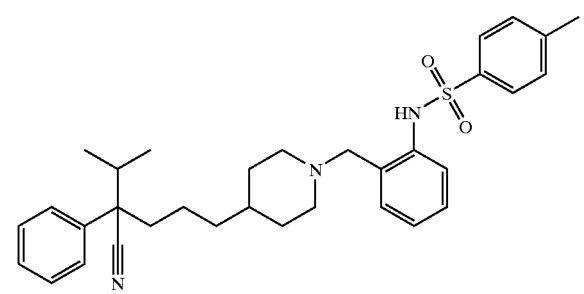

The title compound was obtained as a colorless oil in accordance with Example 3.

¹H NMR (400 MHz, CDCl₃) δ 0.77 (d, J=6.8 Hz, 3H), 0.85–1.02 (m, 1H), 1.08–1.30 (m, 5H), 1.25–1.44 (m, 1H), 1.19 (d, J=6.4 Hz, 3H), 1.57 (br t, J=13.6 Hz, 2H), 1.76–1.90 (m, 3H), 2.06–2.16 (m, 2H), 2.37 (s, 3H), 2.68 (br d, J=11.2 Hz, 2H), 3.13 (s, 2H), 6.91 (d, J=7.2 Hz, 1H), 6.95 (t, J=7.6 Hz, 1H), 7.19 (d, J=8.4 Hz, 2H), 7.16–7.22 (m, 1H), 7.26–7.41 (m, 51), 7.46 (d, J=8.0 Hz, 1H), 7.63 (d, J=8.4 Hz, 2H).

Example 226 1-[4-cyano-5-methyl-4-(2-chlorophenyl)hexyl]-4-[2-(4-fluorophenoxy)ethyl]piperazine

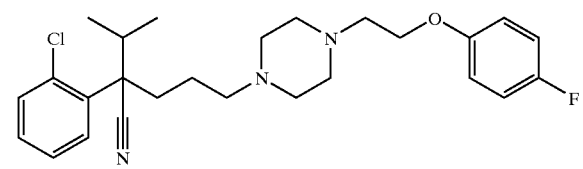

The oxalate of the title compound was obtained as a colorless solid in accordance with Example 48.
Oxalate:
¹H NMR (400 MHz, DMSO-d₆) δ 0.72 (d, J=6.8 Hz, 3H), 1.10 (d, J=6.8 Hz, 3H), 1.00–1.25 (m, 1H), 1.42–1.60 (m, 1H), 1.95–2.10 (m, 11), 2.45–2.65 (m, 11), 2.60–3.10 (m, 13H), 4.09 (t, J=5.2 Hz, 2H), 6.89–6.99 (m, 2H), 7.10 (t, J=8.8 Hz, 2H), 7.37–7.46 (m, 2H), 7.51 (dd, J=7.6 Hz, 1.6 Hz, 1H), 7.62 (dd, J=. 6 Hz, 1.6 Hz, 1H).

Example 227 1-[4-cyano-5-methyl-4-(O-tolyl)hexyl]-4-[2-(4-fluorophenoxy)ethyl]piperazine

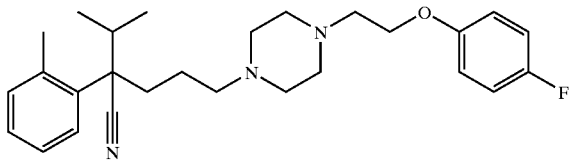

The oxalate of the title compound was obtained as a colorless solid in accordance with Example 48.
Oxalate:
¹H NMR (400 MHz, DMSO-d₆) δ 0.76 (d, J=6.4 Hz, 3H), 1.05 (d, J=6.4 Hz, 3H), 1.10–1.30 (m, 1H), 1.43–1.60 (m, 1H), 1.93–2.07 (m, 1H), 2.15–2.30 (m, 1H), 2.38–2.53 (m, 1H), 2.45 (s, 3H), 2.65–3.05 (m, 1H), 4.07 (t, J=5.2 Hz, 2H), 6.89–6.96 (m, 2H), 7.10 (t, J=8.0 Hz, 2H), 7.18–7.27 (m, 3H), 7.38–7.44 (m, 1H).

Example 228 1-[4-cyano-5-methyl-4-(2-methoxyphenyl)hexyl]-4-[2-(4-fluorophenoxy)ethyl]piperazine

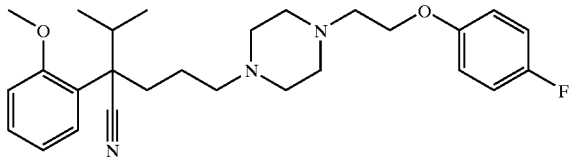

The oxalate of the title compound was obtained as a colorless solid in accordance with Example 48.
Oxalate:
¹H NMR (400 MHz, DMSO-d₆) δ 0.66 (d, J=6.8 Hz, 3H), 1.07 (d, J=6.4 Hz, 31), 1.00–1.20 (m, 1H), 1.40–1.55 (m, 11), 1.85–2.00 (m, 1H), 2.30–2.43 (m, 1H), 2.55–2.70 (m, 1H), 2.60–3.05 (m, 2H), 3.79 (s, 3H), 4.07 (t, J=5.2 Hz, 2H), 6.88–6.96 (m, 2H), 6.99 (t, J=7.6 Hz, 1H), 7.05–7.14 (m, 3H), 7.32–7.42 (m, 2H).

Example 229 N-[1-[(4-cyano-5-methyl-4-phenyl)hexyl]piperidine-4-yl]p-toluenesulfonamide

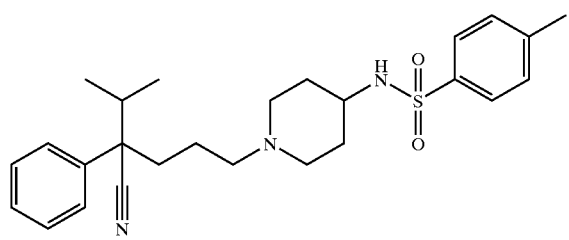

The title compound was obtained as a pale brown oil in accordance with Example 15.

¹H NMR (400 MHz, CDCL₃) δ 0.76 (d, J=6.8 Hz, 3H), 0.95–1.15 (m, 1H), 1.18 (d, J=6.8 Hz, 3H), 1.30–1.45 (m, 2H), 1.35–1.55 (m, 1H), 1.63–1.75 (m, 2H), 1.75–1.95 (m, 5H), 2.00–2.15 (m, 2H), 2.15–2.25 (m, 2H), 2.45–2.65 (m, 2H), 3.00–3.15 (m, 1H), 7.29 (d, J=8.0 Hz, 2H), 7.31–7.40 (m, 5H), 7.75 (d, J=7.6 Hz, 2H).

Example 230 1-[(4-cyano-5-methyl-4-phenyl)hexyl]-4-[3-hydroxy-1-(4-fluorophenoxy)propane-2-yl]piperazine

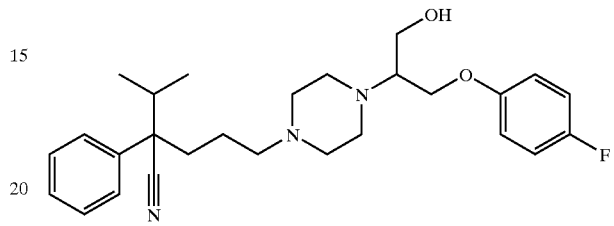

The oxalate of the title compound was obtained as a colorless solid in accordance with Example 15.

Oxalate:

¹H NMR (400 MHz, DMSO-d₆) δ 0.64 (d, J=6.8 Hz, 3H), 1.09 (d, J=6.8 Hz, 3H), 1.00–1.40 (m, 1H), 1.43–1.60 (m, 1H), 1.93–2.15 (m, 2H), 2.10–2.25 (m, 1H), 2.60–3.20 (m, 1H), 3.45–3.60 (m, 2H), 4.04 (d, J=5.6 Hz, 2H), 6.88–6.96 (m, 3H), 7.26 (t, J=7.6 Hz, 1H), 7.30–7.38 (m, 1H), 7.36–7.46 (m, 4H).

Example 231 1-[(4-cyano-5-methyl-4-phenyl)hexyl]-4-(3-cyanobenzyloxy)piperidine

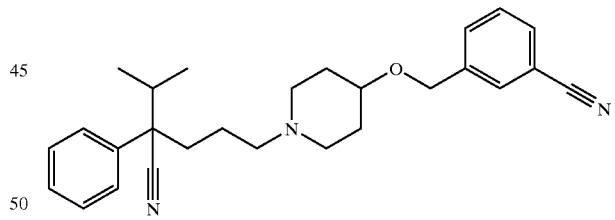

The oxalate of the title compound was obtained as a colorless solid in accordance with Example 15.

Oxalate:

¹H NMR (400 MHz, DMSO-d₆) δ 0.64 (d, J6.8 Hz, 3H), 1.11 (d, J=6.4 Hz, 3H1), 1.63–1.80 (m, 2H), 1.85–2.00 (m, 2H), 2.13–2.27 (m, 1H), 2.30–2.45 (m, 1H), 2.35–2.55 (m, 1H9), 2.75–3.00 (m, 4H), 3.00–3.20 (m, 2H), 3.50–3.60 (m, 1H)1, 4.52 (s, 2H), 7.33–7.40 (m, 1H), 7.40–7.48 (m, 4H), 7.54 (t, J=8.0 Hz, 1H). 7.66 (d, J=8.0 Hz, 1H), 7.74 (d, J=8.0 Hz, 1H), 7.77 (m, 1H).

Example 232 4-((3-cyano-4-methyl-3-phenyl)
pentyl]-1-{2-[3-(p-toluenesulfonylamino)phenoxy]
ethyl]piperazine

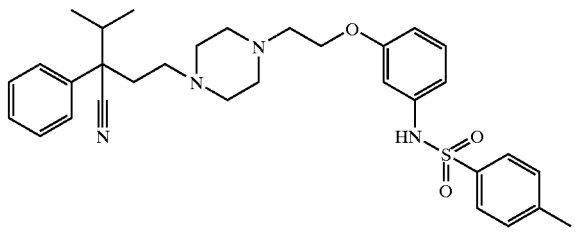

The oxalate of the title compound was obtained as a colorless solid in accordance with Example 3.
Oxalate:
$^1$H NMR (400 MHz, DMSO-d$_6$) δ 0.64 (d, J=6.8 Hz, 3H), 1.11 (d: J=6.4 Hz, 3H), 2.13–2.50 (m, 1H), 2.20–2.50 (m, 2H), 2.37 (s, 3H), 2.45–2.50 (m, 2H). 2.50–2.60 (m, 2H), 2.60–2.80 (m, 4H), 2.70–3.00 (m, 4H), 3.63 (t, J=6.4 Hz, 2H), 6.41 (dd, J=8.0 Hz, 2.0 Hz, 1H), 6.47 (d, J=2.0 Hz, 1H), 6.70 (dd, J=8.0 Hz, 2.4 Hz, 1H), 7.09 (t, J=8.0 Hz, 1H), 7.36 (d, J=8.4 Hz, 2H), 7.32–7.40 (m, 1H), 7.38–7.48 (m, 4H), 7.46 (d, J=8.0 Hz, 2H).

Example 233 4-[(4-cyano-5-methyl-4-phenyl)
hexyl]-1-{2-[3-(p-toluenesulfanylamino)phenoxy]
ethyl]piperazine

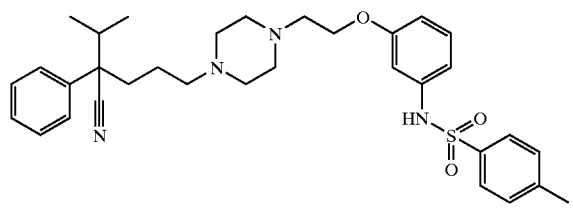

The oxalate of the title compound was obtained as a pale brown solid in accordance with Example 15.
Oxalate:
$^1$H NMR (400 MHz, DMSO-d$_6$) δ 0.64 (d, J=6.4 Hz, 3H), 1.09 (d, J=6.4 Hz, 3H), 1.00–1.20 (m, 1H), 1.43–1.60 (m, 1H), 1.90–2.13 (m, 2H), 2.15–2.25 (m, 1H), 2.37 (s, 31), 2.25–2.50 (m, 4H), 2.80–3.00 (m, 8H), 3.57 (t, J=6.8 Hz, 2H), 6.38–6.43 (m, 1H), 6.46 (s, 1H), 6.68 (dd, J=8.0 Hz, 2.0 Hz, 1H), 7.08 (t, J=7.6 Hz, 1H), 7.36 (d, J=8.4 Hz, 2H), 7.30–7.40 (m, 1H), 7.36–7.48 (m, 4H), 7.45 (d, J=8.4 Hz, 2H).

Example 234 1-[(4-cyano-5-methyl-4-phenyl)
hexyl]-4-[[3-(p-toluenesulfonylamino)phenoxy]
Methyl]piperidine

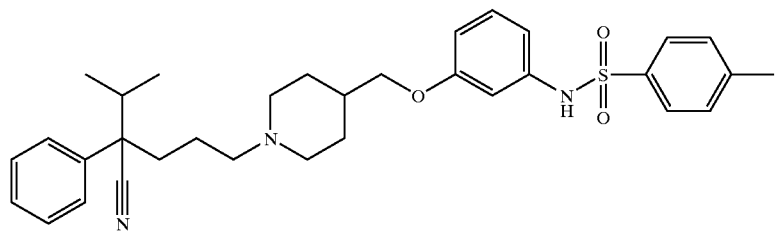

The title compound was obtained as yellow amorphous in accordance with Example 15.
$^1$H NMR (400 MHz, CDCL$_3$) δ 0.75 (d, J=6.8 Hz, 3H), 1.15 (d, J=6.4 Hz, 3H). 1.05–1.30 (m, 3H), 1.30–1.45 (m, 1H), 1.45–1.65 (m, 1H), 1.65 (br d. J=12.4 Hz, 2H), 1.65–1.80 (m, 1H), 1.75–1.95 (m, 2H), 2.00–2.18 (m, 2H), 2.26 (t, J=7.2 Hz, 2H), 2.40 (s, 3H), 2.67–2.80 (m, 2H), 3.31 (d, J=7.6 Hz, 2H), 6.43 (d, J=8.0 Hz, 1H), 6.56 (d, J=2.0 Hz, 1H), 6.67–6.76 (m, 1H), 7.08 (t, J=8.0 Hz, 1H), 7.22 (d, J=6.8 Hz, 2H), 7.20–7.40 (m, 5H), 7.45 (d, J=8.0 Hz, 2H).

Example 235 1-[(3-cyano-4-methyl-3-phenyl)
pentyl]-4-{[3-(p-toluenesulfonylamino)phenoxy]
Methyl]piperidine

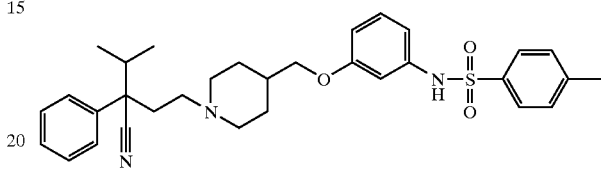

The title compound was obtained as pale brown amorphous in accordance with Example 3.6
$^1$H NMR (400 MHz, CDCl$_3$) δ 0.73 (d, J=6.8 Hz, 3H), 1.14 (d, J=6.4 Hz, 3H), 1.15–1.30 (m, 2H), 1.35–1.52 (m, 1H), 1.68 (br d, J=12.4 Hz, 2H), 1.73–2.05 (m, 31), 2.00–2.18 (m, 2H), 2.30–2.43 (m, 2H), 2.40 (s, 3H), 2.70–2.90 (m, 2H), 3.20–3.38 (m, 2H), 6.38 (dd, J=8.0 Hz, 2.0 Hz, 1H), 6.58 (d, J=1.6 Hz, 1H), 7.00 (dd, J=8.0 Hz, 2.0 Hz, 1H), 7.07 (t, J=8.0 Hz, 1H), 7.22 (d, J=7.6 Hz, 2H), 7.25–7.40 (m, 5H), 7.43 (d, J=8.4 Hz, 2H).

Example 236 1-(3-cyanobenzyl)-4-[(4-cyano-5-
methyl-4-phenyl)hexyl]piperidine

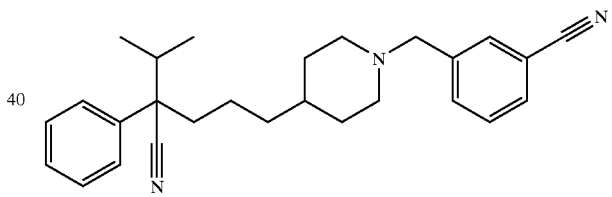

The oxalate of the title compound was obtained as a colorless solid in accordance with Example 48.
Oxalate:
$^1$H NMR (400 MHz, DMSO-d$_6$) δ 0.63 (d, J=6.8 Hz, 3H), 0.70–0.85 (m, 1H), 1.00–1.30 (m, 5H), 1.08 (d, J=6.4 Hz, 31), 1.20–1.35 (m, 1H), 1.58 (br d, J=12.8 Hz, 2H), 1.87–2.08 (m, 2H), 2.10–2.23 (m1H), 2.61 (br t, J=11.2 Hz, 2H), 3.11 (br d, J=10.8 Hz, 2H), 4.10 (s, 2H), 7.28–7.33 (m, 1H), 7.34–7.44 (m, 4H), 7.61 (t, J=7.6 Hz, 1H), 7.76 (d, J=7.6 Hz, 1H), 7.84–7.90 (m, 2H)).

Example 237 1-[(5-phenyl-2-oxo-1.2-dihydro-3-pyridinyl)methyl]-4-[(4-cyano-5-methyl-4-phenyl)hexyl]piperidine

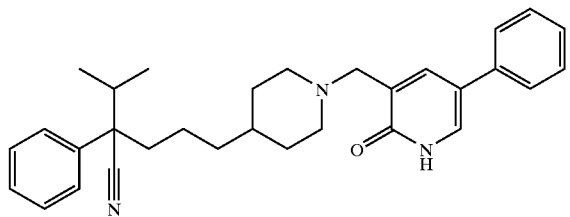

The title compound was obtained as a pale yellow oil in accordance with Example 3.
¹H NMR (400 MHz, CDCl₆) 0.77 (d, J=6.8 Hz, 3H), 0.85–1.00 (m, 1H), 1.10–1.45 (m, 4H), 1.19 (d, J=6.8 Hz, 3H), 1.50–1.65 (m, 2H), 1.60–2.20 (m, 5H), 2.80–3.00 (m, 2H), 3.54 (s, 2H), 7.24–7.48 (m, 10H), 7.64–7.70 (m, 1H), 7.78–7.84 (m, 1H).

Example 238 Ethyl 1-benzyl-4-(4-cyano-5-methyl-4-phenylhexyl)-2-piperazinecarboxylate

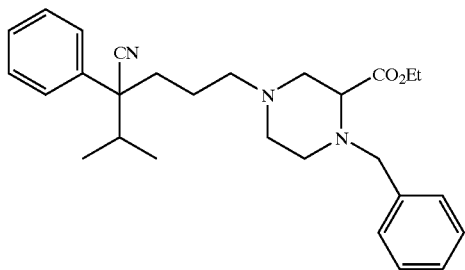

The title compound was synthesized by using 1-benzyl-2-(ethoxycarbonyl)piperazine (Synthesis 318, 1991) in accordance with Example 15.
Free Body:
¹H NMR (400 MHz, CDCl₃) δ 0.76 (d, J=6.6 Hz, 3H), 1.05–1.10 (m, 1H), 1.18–1.31 (m, 6H), 1.50–1.63 (m, 1H), 1.86–1.94 (m, 1H), 2.04–2.15 (m, 2H), 2.21–2.54(m, 7H), 2.96(m, 1H), 3.22–3.27 (m, 1H), 3.51 (m, 1H), 3.86–3.90(m, 1H), 4.12–4.23 (m, 2H); 7.21–7.37 (m, 10H).

Example 239 Ethyl 4-(4-cyano-5-methyl-4-phenylhexyl)-1-[2-(4-fluoronhenoxy)ethyl]-2-piperazinecarboxylate

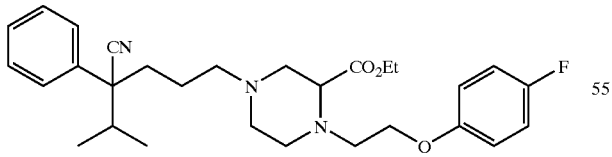

The title compound was synthesized by using ethyl 4-(4-cyano-5-methyl-4-phenylhexyl)-2-piperazinecarboxylate in accordance with Example 48.
Free Body:
¹H NMR (400 MHz, CDCl₃) δ 0.77 (d, J=6.8 Hz, 3H), 1.06–1.11 (m, 1H), 1.17–1.29(m, 6H), 1.51–1.62 (m, 1H), 1.86–1.91 (m, 1H), 2.05–2.11 (m, 2H). 2.22–2.36 (m, 4H), 2.52–2.55 (m, 3H), 2.94–3.01 (m, 2H), 3.13–3.16 (m, 1H), 3.38–3.39 (m, 1H), 4.01–4.03 (m, 2H), 4.14–4.22 (m, 2H), 6.78–6.82 (m, 2H), 6.92–6.97 (m, 2H), 7.26–7.31 (m, 1H), 7.36–7.37 (m, 4H).

Example 240 1-(4-cyano-5-methyl-4-phenylhexyl)-3-hydroxymethyl-4-[2-(4-fluorophenoxy)ethyl]piperazine

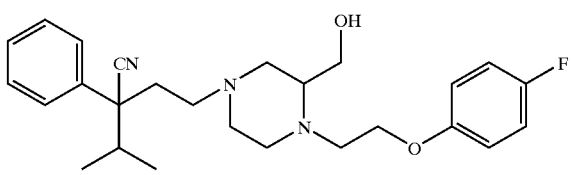

Into a diethyl ether solution (5.0 ml) of lithium aluminum hydride (20 mg) was added dropwise a diethyl ether solution (3.0 ml) of 213 mg of ethyl 4-(4-cyano-5-methyl-4-phenylhexyl)-1-[2-(4-fluorophenoxy)ethyl]-2-piperazinecarboxylate under ice-cooling. After stirring under ice-cooling for one hour, water (0.1 ml), a 1N aqueous sodium hydroxide (0.1 ml) and water (0.2 ml) were successively added to the reaction solution. Anhydrous magnesium sulfate was added to the reaction solution, and the unnecessary product was filtered. The solvent was evaporated, to give the title compound (194 mg).

Free Body:

¹H NMR (400 MHz, CDCl₃) δ 0.77 (d, J=6.6 Hz, 3H), 1.09–1.16 (m, 1H), 1.20(dd, J=6.8 Hz, 1.8 Hz, 3H), 1.53–1.60 (m, 1H), 1.86–1.91 (m, 1H), 2.04–2.27 (m, 5H), 2.35–2.61 (X, 5H), 2.74–2.78((m, 1H), 3.02–3.06 (m, 1H), 3.12–3.18 (m, 1H), 3.51–3.54(m, 1H), 3.97–4.02 (m, 3H), 6.80–6.85 (m, 2H), 6.94–6.98 (m, 2H), 7.26–7.33 (m, 1H), 7.35–7.39 (m, 4H).

Example 241 Ethyl 1-benzyl-4-[2-(4-fluorophenoxy)ethyl]-2-piperazinecarboxylate

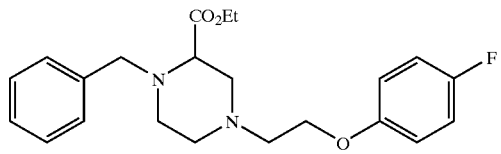

The title compound was synthesized by using 1-benzyl-2-(ethoxycarbonyl)piperazine (Synthesis 318, 1991) in accordance with Example 48. Free body:

¹H NMR (400 MHz, CDCl₃) δ 1.24–1.28(m, 3H, 2.36–2.12 (m, 1H), 2.54–2.61 (m, 2H), 2.71–2.83(m, 4H), 3.02 (m, 1H), 3.31–3.34 (m, 1H), 3.53–3.56(m, 1H), 3.89–3.92 (d, J=16.6 Hz, 1H), 3.99–4.05 (m, 2H), 4.11–4.24 (m, 2H), 6.79–6.83 (m, 2H), 6.93–6.98 (m, 2H), 7.23–7.34 (m, 5H).

Example 242 Ethyl 1-(4-cyano-5-methyl-4-phenylhexyl)-4-[2-(4-fluorophenoxy)ethyl]-2-piperazinecarboxyalte

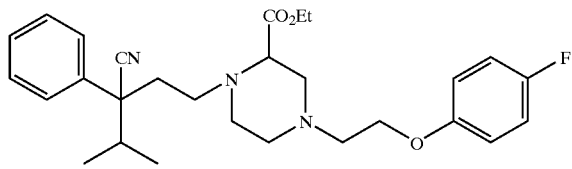

The title compound was synthesized by using ethyl 4-[2-(4-fluorophenoxy)ethyl]-2-piperazinecarboxylate in accordance with Example 15.
Free Body:
ESI-MS (m/e); 496(M+H)
The ethyl 4-[2-(4-fluorophenoxy)ethyl]-2-piperazinecarboxylate:

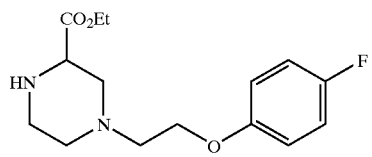

was obtained as a crude product (752 mg, 100%) by dissolving ethyl 1-benzyl-4-[2-(4-fluorophenoxy)ethyl)-2-piperazinecarboxylate (977 mg) synthesized in accordance with Example 241 in ethanol (15 ml), adding 210 mg of 10% Pd-C thereto, replacing the atmosphere of the reaction solution with hydrogen, stirring it, and evaporating it after completion of the reaction.
Free Body:
$^1$H NMR (400 MHz, $CDCL_3$) δ 1.24–1.28 (m, 3H), 2.33–2.34 (m, 1H), 2.48–2.50 (m, 1H), 2.72–2.91 (m, 4H), 3.04–3.10 (m, 2H), 3.56–3.59 (m, 1H), 4.04–4.08 (m, 2H), 4.16–4.22 (m, 2H), 6.82–6.86 (m, 2H), 6.94–6.99 (m, 2H).

Example 243 1-(4-cyano-5-methyl-4-phenylhexyl)-2-hydroxymethyl-4-[2-(4-fluorophenoxy)ethyl] piperazine

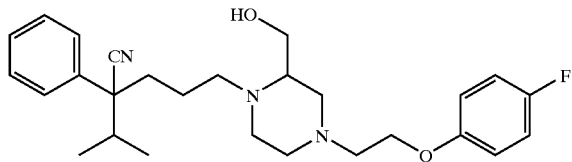

By using ethyl 1-(4-cyano-5-methyl-4-phenylhexyl)-4-[2-(4-fluorophenoxy)ethyl]-2-piperazinecarboxylate, the title compound was, synthesized in accordance with Example 240.
Free Body:
$^1$H NMR (400 MHz, $CDCl_3$) δ 0.77 (d, J=6.8 Hz, 3H), 1.07–1.14 (m, 1H), 1.20 (d, J=6.6 Hz, 3H), 1.43–1.56 (m, 1H), 1.79–1.90 (m, 1H), 2.04–2.83 (m, 1H), 3.47–3.51 (m, 1H), 3.83–3.91 (m, 1H), 4.01–4.10 (m, 2H), 6.80–6.84 (m, 2H), 6.94–6.98 (m, 2H), 7.26–7.40 (m, 5H).

Test Examples

The calcium inhibitory action (Test Example 1) in vitro was evaluated for the compound according to the present invention, and the shrinking action of infarction nidus (Test Example 2) in rat middle cerebral artery emphraxis model in vivo and the analgesic action (Test Example 3) in a formalin test using a mouse were evaluated. The respective test methods and results are as described below.

Test Example 1 Measurement of Potential Dependent Calcium Channel Activity Using Fluorescent Dye (fura2)

The most importance is attached to a "glutamic acid-Ca assumption" as the mechanism of brain infarction (neural cell death by ischemia). Namely, when cerebral blood flow is lowered, anaerobic glycolysis is carried out, and the ATP of brain tissue is exhausted. Ion concentration gradient in the inside and outside of the cell is not kept by this energy exhaustion, and depolarization occurs. The potential dependent calcium channel is activated by depolarization in pre synapse, and the excess release of glutamic acid is induced. In post synapse, the potential dependent calcium channel is activated by depolarization to increase the $Ca^{2+}$ concentration in the cell, and glutamic acid which was excessively released stimulates a glutamic acid receptor and increases the $ca^{2+}$ concentration in the cell. As a result of these, various kinds of enzymes, such as carpaine and phospholipase, depending on the $Ca^{2+}$ concentration are activated, and induce neural cell death. The present experiment system can evaluate the $Ca^{2+}$ influx in the pre synapse among these flow charts.

Further, it is known that 10 μM of nifedipine being an L-type inhibitor, 1 μM of n-conotoxin GVIA being an N-type inhibitor and 1 μM of w-Agatoxin-IVA being a P/Q type inhibitor exhibit inhibitions of 16%, 18% and 64% against the $Ca^{2+}$ influx, respectively (refer to the following reference literature). Accordingly, it is considered that the system is suitable for evaluating the N-type and P/Q type inhibitions.

REFERENCE LITERATURE

D. Bowman, S. Alexander and D. Lodge, Pharmacological characterization of the calcium channels coupled to the plateau phase of KCl-induced intracellular free $Ca^{2+}$ elevation in chicken and rat synaptosomes, Neuropharmacology, 32 (11) 1195–1202 (1993)

(1) Preparation of cerebral cortex synaptosome:

Cerebral cortex synaptosome was prepared as described below in accordance with the method described in "Neuropharmacology, 32(11), 1195–1202, 1993". Namely, cerebral cortex was taken out from a rat decapitated brain, and crushed with scissors coarsely. It was charged in a homogenizer, homogenized in 3 M sucrose, and centrifuged (1,500 g×10 min.) at 4° C. The supernatant obtained was further centrifuged (10,000 g×20 min.) at 4° C. 0.3 M of sucrose was added to the precipitate obtained and the mixture was suspended. The suspension was stratified in 0.8 M sucrose, and centrifuged (10,000 g×30 min.). The precipitate obtained was suspended in a "solution A" (118 mM-NaCl, 4.6 mM-KCl, 1 mM-$CaCl_2$, 1 mM-$MgCl_2$, 1.2 mM-$Na_2HPO_4$, 10 mM-D-glucose, 20 mM-HEPES-NaOH, pH 7.4, 0.1%-BSA), to prepare cerebral cortex synaptosome.

(2) Calcium channel inhibiting action:

4 mM-fura2/AM (Doujin) was suspended in the forementioned solution A to prepare a solution for loading. The solution for loading in an equal amount was added to the synaptosome solution prepared according to the method described above, and the mixture was incubated for 40 minutes at a room temperature. After completion of the incubation, the solution for loading was removed by centrifuge, and further washed 2 times with the solution A. The solution A containing the present compound was added to this solution, and the mixture was incubated for 10 minutes at a room temperature. The calcium channel was stimulated by adding 1/10 volume of a "solution B" (122.6 mM-KCl, 1 mM-CaCl$_2$, 1 mM-Mgcl$_2$, 1.2 mM-Na$_2$HPO$_4$, 10 mM-D-glucose, 20 mM-HEPES-NaOH, pH 7.4, 0.1%-BSA) to this solution. The calcium ion concentration in the cell was measured according to specific measurement by two wave lengths of 340 nm and 380 nm with ARUGUS-FDSS (HAMAMATSU PHOTONICS Co.), and IC50 values of the respective test compounds were determined. Further, verapamil hydrochloride was used as a control compound for comparison.
Result:

TABLE 1

| Ex. No. | IC$_{50}$ (μM) | Ex. No. | IC$_{50}$ (μM) | Ex. No. | IC$_{50}$ (μM) | Ex. No. | IC$_{50}$ (μM) |
|---|---|---|---|---|---|---|---|
| 1 | 8.4 | 70 | 13 | 144 | 12 | 191 | 6.4 |
| 3 | 5.4 | 75 | 9 | 145 | 15 | 193 | 11 |
| 5 | 7.6 | 76 | 13 | 146 | 7.4 | 195 | 10 |
| 6 | 9 | 78 | 8.9 | 147 | 13 | 196 | 12 |
| 7 | 5.8 | 85 | 10 | 148 | 14 | 197 | 9.8 |
| 8 | 6.8 | 92 | 3.1 | 149 | 10 | 200 | 3.7 |
| 9 | 4.5 | 93 | 6.9 | 150 | 11 | 201 | 8.1 |
| 11 | 5.1 | 94 | 0.7 | 151 | 9 | 202 | 7.2 |
| 12 | 8.2 | 95 | < | 152 | 6.1 | 203 | 9.2 |
| 13 | 6.6 | 96 | 1.9 | 153 | 7.4 | 204 | 14 |
| 14 | 6.5 | 97 | 2.1 | 154 | 9.8 | 205 | 11 |
| 17 | 8 | 98 | < | 155 | 7.9 | 206 | 14 |
| 18 | 5.6 | 99 | 0.8 | 156 | 10 | 207 | 16 |
| 22 | 8.7 | 100 | < | 157 | 9.9 | 208 | 6.3 |
| 24 | 3 | 101 | 0.8 | 158 | 14 | 209 | 5.2 |
| 25 | 4.9 | 102 | 1.9 | 159 | 12 | 210 | 4.6 |
| 26 | 5.2 | 104 | < | 160 | 8.0 | 211 | 7.8 |
| 30 | 7.7 | 105 | < | 161 | 12 | 212 | 7.3 |
| 31 | 4.5 | 106 | 1.3 | 162 | 20 | 213 | 17 |
| 32 | 5.1 | 107 | 1.6 | 163 | 14 | 214 | 11 |
| 33 | 2.6 | 108 | 0.6 | 164 | 21 | 215 | 13 |
| 34 | 4.4 | 109 | 0.5 | 165 | 24 | 218 | 18 |
| 37 | 8.3 | 110 | 5.6 | 166 | 16 | 219 | 9.8 |
| 38 | 5.8 | 112 | 5.9 | 167 | 13 | 220 | 32 < |
| 39 | 6.2 | 113 | 4.2 | 168 | 20 | 221 | 18 |
| 40 | 3.5 | 114 | 10 | 169 | 15 | 222 | 16 |
| 45 | 7.4 | 115 | 8.2 | 170 | 10 | 223 | 19 |
| 46 | 4.9 | 116 | 9.4 | 171 | 12 | 224 | 10 |
| 48 | 3.5 | 117 | 11 | 172 | 10 | 225 | 16 |
| 49 | 5.9 | 118 | 12 | 173 | 7.2 | 226 | 9.4 |
| 50 | 4.8 | 119 | 5.4 | 174 | 9.3 | 227 | 10 |
| 51 | 5.2 | 121 | 14 | 175 | 3.9 | 228 | 9.3 |
| 52 | 5.1 | 123 | 8.5 | 176 | 2.8 | 229 | 14 |
| 53 | 2.8 | 124 | 3.6 | 177 | 3.4 | 230 | 14 |
| 55 | 3.5 | 125 | 5.0 | 178 | 5.2 | 232 | 18 |
| 56 | 3.7 | 126 | 8.4 | 179 | 19 | 233 | 15 |
| 57 | 5.5 | 127 | 11 | 180 | 9.3 | 234 | 12 |
| 58 | 5.6 | 128 | 5.2 | 181 | 8.6 | 236 | 8.7 |
| 59 | 8.2 | 136 | 19 | 182 | 7.8 | 237 | 6.6 |
| 60 | 7.4 | 137 | 19 | 183 | 5.5 | 238 | 20 |
| 61 | 7.7 | 138 | 19 | 184 | 5.4 | 239 | 11 |
| 62 | 5.3 | 139 | 32 < | 185 | 13 | 240 | 9.0 |
| 64 | 6.2 | 140 | 11 | 186 | 18 | 242 | 12 |
| 65 | 2.7 | 141 | 15 | 187 | 6.9 | 243 | 9.9 |
| 66 | 4.4 | 142 | 8.9 | 189 | 5.8 | Control | >16 |
| 67 | 7.1 | 143 | 9.8 | 190 | 11 | — | — |

Control: verapamil hydrochloride

Test Example 2

Shrinking Effect of Infarction nidus in rat Middle Cerebral Artery Emphraxis Model (I)

A calcium ion in the cell plays an important role in the expression of various cell functions. But when the calcium ion concentration in the cell rises excessively, cell affection is induced (refer to literatures 1) and 2), hereinafter, the same as this.). For example, neural cell affection induced by excitatory amino-acid occurring in the case of cerebral ischemia provokes excessive rise of the calcium ion concentration in the cell (3) and 4)). The maintenance mechanism of membrane potential fails by excitatory amino-acid which rose in the case of local cerebral ischemia (3)), the depolarization of membrane is induced (5)), and the influx of the calcium ion into the cell through the potential dependent calcium channel is increased (6) and 7)). In light of these fact, it is suggested that an assumption that neural cell death is based on excitation toxicity by excitatory amino-acid is correlated with an assumption that neural cell death is based on the rise of the calcium ion concentration in the cell, and that the activation of potential dependent calcium channel contributes to the induction of neural cell death (8)). The potential dependent calcium channels existing in the neural cell are classified in 6 kinds of sub-types based on the electro-physiological and pharmacological investigation (T, L, N, P, Q and R types) (9)). Among these, N, P and Q types play an important role in the liberation of glutamic acid from rat cerebral cortex synaptosome (10) and 11)). Therefore, the protection effect for neural cell affection induced after local cerebral ischemia and possessed by the typical examples of the present compound in rat middle cerebral artery emphraxis model was evaluated.

(1) Preparation of specimen

The compound represented by the above formula (I) according to the present invention was dissolved in a physiological saline, and appropriately prepared so as to be in doses of 1.5, 5 and 15 mg/kg/h. The concentration of the specimen was calculated based on the average body weight of an animal. Further, the average body weight was calculated by measuring the body weight of all animals which are intended to be used for experiment. For example, in the case of 5 mg/kg/h, it was calculated as: concentration of specimen=5 mg×average body weight (kg)/administration volume (0.616 ml) per hour.

(2) Manufacture of nylon embolus

The embolus made from nylon stitch (Ethicon, Inc., Somerville, N.J., USA) of 4-0 monofilament was used for emphraxis of middle cerebral artery. As the nylon embolus, that prepared by previously rounding its tip with flame, fragmenting it in a length of 25 mm, and marking at a position of 17 mm from the tip with an oily felt pen was used.

(3) Implantation of catheter for intravenous administration

The implantation of catheter for intravenous administration (Atom Vein Catheter 3Fr, manufactured by ATOM MEDICAL Co., Ltd., Tokyo) was carried out under 70% laughing gas-2% halothane anaesthesia. Catheter which was filled up with a physiological saline solution was inserted from the femoral vein of left foot.

(4) Emphraxis of middle cerebral artery

The emphraxis of middle cerebral artery was carried out in accordance with the method of Longa et al (12)). The operation was carried out under 70% laughing gas-2% halothane anaesthesia just after implanting the catheter. A rat was laid in facing upward under the stereoscopic microscope for operation, the neck was cut open, and the portion where the whole carotid arteries of the right side are diverged to the external carotid artery and the internal carotid artery was confirmed. The external carotid artery was cut off at the periphery side, and the nylon embolus was inserted from the terminal of the external carotid artery which was cut off into the internal carotid artery. The embolus was inserted up to the position where the position of 17 mm from the tip of the embolus is duplicated with a branch point of the external carotid artery and the internal carotid artery, and was fixed. The nylon embolus was pulled back after 2 hours from the emphraxis of middle cerebral artery, in order to restart blood flow.

(5) Selection of animals which exhibit ischemia symptom

The rat was caught and lifted with the cauda after 30 minutes from the emphraxis of middle cerebral artery, an indivisual which expresses clearly the one side paralysis of a fore-leg (the paralysis of a fore-leg of the opponent side which loaded infarct) was provided for experiment as an example in which middle cerebral artery was occluded and was able to make an ischemia condition.

(6) Administration of medium and specimen

A rat which expressed the one side paralysis after 30 minutes from middle cerebral artery emphraxis was put in a cage of a body temperature control apparatus, and a probe for monitoring a body temperature was fixed in the rectum. Then, a syringe in which a medium or a specimen was charged was put in the catheter for intravenous administration, and the intravenous administration of the half amount (0.34 ml) of the dose which would be infused for 1 hour was carried out for one minute. Then, administration was carried out at a rate of 0.682 ml/h for 24 hours using a syringe pump for infusion (Razel Scientific Instruments, Inc., Stamford, Conn., USA). During the administration and for 2 hours after the administration, the temperature of the rectal was controlled in a range of from 37.0° C. to 38.5° C. under the body temperature control system.

(7) Measurement of infarction nidus size (TTC staining of brain slice)

After 24 hours from the emphraxis of middle cerebral artery, the rat was decapitated, the brain was taken out, and the blood attached was rinsed with physiological saline solution which was ice-cooled. Using the brain from which olfactory bulb was removed, it was sliced at an interval of 2 mm from the tip (6 slices in total), and they were immersed in a 2%-TTC solution so that the rear face of the brain is faced upward. The TTC was appropriately dissolved in physiological saline solution. After being left as it was at room temperature for one hour or more in the TTC solution, it was used for area determination of infarction nidus.

(8) Calculation of infarction nidus volume

The top of each slice (the rear face of brain) was used for calculation of infarction nidus area. As for the brain slices, images were taken in a computer (PM7500/100, Apple Japan, Tokyo) using an image taking device (CCD Color Camera, SANKEI Inc., Tokyo). The areas of infarction nidus of brain cortex in the images were measured using an image analysis software (NIH image ver. 1.60, National Institutes of Health, USA). The volume of the infarction nidus of one individual was calculated as the total sum (unit=$mm^3$) of 6 slices by multiplying the area (unit=$mm^2$) of the infarction nidus of the respective slices measured, by 2 (unit=mm) which is the thickness of the slice.

(9) Data analysis method

The volume (unit=$mm^3$) of the infarction nidus of brain cortex was indicated by average value±standard error. Statistical significance between the medium control group and the respective specimen groups was analyzed by multiplex comparative assay of Dunnett, and the level of significance was defined as 5% of both sides. Dose reactivity was analyzed by regression analysis, and the level of significance was defined as 5% of one side.

(10) Result:

After the middle cerebral artery was occluded by the nylon embolus for 2 hours, blood flow was restarted by removing the nylon embolus, and the volume of the infarction nidus was measured after 24 hours from the empphraxis of middle cerebral artery. As a result, the compound according to the present invention significantly suppressed the volume of the infarction nidus of cerebral cortex, and the dose dependency was confirmed in the shrinking effect of the infarction nidus by the compound according to the present invention as a result of regression analysis. For example, the compound of Example 70 reduced the volume of the infarction nidus of cerebral cortex by 4% (128.9±12.5 $mm^3$, n=16), 20% (108.0±14.9 $mm^3$, n=15) and 44% (75.7±11.2 $mm^3$, n=12: $p<0.01$), respectively, by carrying out intravenous administration in doses of 1.5, 5 and 15 mg/kg/h after 30 minutes from the emphraxis of middle cerebral artery, as compared with the volume of the infarction nidus of cerebral cortex of 134.3±12.3 $mm^3$ (n=19) for a control group. Further, the compound of Example 75 reduced the volume of the infarction nidus of cerebral cortex by 26% (119.9±12.6 $mm^3$, n=16), 37% (102.0±14.1 $mm^3$, n=14: $p<0.01$) and 49% (83.7±21.3 $mm^3$, n=11: $p<0.001$), respectively, by carrying out intravenous administration in doses of 1.5, 5 and 15 mg/kg/h after 30 minutes from the emphraxis of middle cerebral artery, as compared with the volume of the infarction nidus of cerebral cortex of 162.9±8.4 $mm^3$ (n=15) for control group.

Namely, the compound according to the present invention inhibits the calcium ion influx into rat cerebral cortex synaptosome which is induced by high concentration of KCl, and inhibits the disengagement of glutamic acid from rat cerebral cortex slice. Further, the present compound has a protecting action for neural cell affection caused by local cerebral ischemia in the present experiment, and exhibits a significant shrinking effect of the infarction nidus by administration carried after 30 minutes from ischemia development. Accordingly, the compound according to the present invention can exhibit the effectiveness by post administration even in apoplectic ictus of human.

Further, these results are supported by reports in which SNX-111 (CAS Registration No. 107452-89-1) being an N-type calcium channel inhibiting peptide protected the liberation of glutamic acid from cerebral cortex and subsequent neural cell affection in rat local cerebral ischemia model (13) and 14)), and also a report in which ω-agatoxin IVA being P/Q type channel inhibiting peptide exhibited a protective action for neural cell in rat local cerebral ischemia model (15)).

REFERENCE LITERATURE

1) Schanne, F.A.X., Kane, A. B., Young, E. E., Farber, J. L. Calcium dependence of toxic cell death: a final common pathway. Science 206: 700–702 (1979).
2) Kristian, T., Siesjo, B. K. Calcium in ischemic cell death. Stroke 29: 705–718 (1998).
3) Graham, S. H., Shiraisi, K., Panter, S. S., Simon, R. P., Faden, A. I. Changes in extracellular amino acid neurotransmitters produced by focal cerebral ischemia. Neurosci. Lett. 110: 124–130 (1990).
4) Rothman, S. M., Olney, J. W. Glutamate and the pathophysiology of hypoxic-ischemic brain damage. Ann. Neurol. 19: 105–111(1986).
5) Siesjo, B. K., Bengtsson, F. Calcium influxes, calcium antagonists, and calcium-related pathology in brain ischemia, hypoglycemia, and spreading depression: A unifying hypothesis. J. Cereb. Blood Flow Metab. 9: 127–140 (1989).

6) Mayer, M. L., Miller, R. J. Excitatory amino acid receptors, second messengers and regulation of intracellular Ca2+ in mammalian neurons. Trends Pharmacol. Sci. 11: 254–260 (1990).
7) Osuga, H., Hakim, A. M. Relationship between extracellular glutamate concentration and voltage-sensitive calcium channel function in focal cerebral ischemia in the rat. J. Cereb. Blood Flow Metab. 16: 629–636 (1996).
8) Choi, D. W. Calcium-mediated neurotoxicity: Relationship to specific channel types and role in ischemic damage. Trends Neurosci. 11: 465–469 (1988).
9) Randall, A. D., Tsien, R. W. Pharmacological dessection of multiple types of $Ca^{2+}$ channel currents in rat cerebellar granule neurons. J. Neurosci. 15: 2995–3012 (1995).
10) Turner, T.J., Dunlap, K. Pharmacological characterization of presynaptic calcium channels using subsecond biochemical measurements of synaptosomal neurosecretion. Neuropharmacology 34: 1469–1478 (1995).
11) Maubecin, V. A., Sanchez, V. N., Rosato Siri, M. D., Cherksey, B. D., Sugimori, K., Llinas, R., Uchitel, O. D. Pharmacological characterization of the voltage-dependent Ca2+ channels present in synaptosomes from rat and chicken central nervous system. J. Neurochem. 64: 2544–2551 (1995).
12) Longa, E. Z., Weinstein, P. R., Carlson, S., Cummins, R. Reversible middle cerebral artery occlusion without craniectomy in rats. Stroke 20: 84–91 (1989).
13) Bowersox, S. S., Singh, T., Luther, R. R. Selective blockade of N-type voltage-sensitive calcium channels protects against brain injury after transient focal ischemia in rats, Brain Res. 747: 343–347 (1997).
14) Takizawa, S., Matsushima, K., Fujita, H., Nanri, K., Ogawa, S., Shinohara, Y. A selective N-type calcium channel antagonist reduces extracellular glutamate release and infarct volume in focal cerebral ischemia. J. Cereb. Blood flow Metab. 15: 611–618 (1995).
15) Asakura, K., Matsuo, Y., Kanemasa, T., Ninomiya, M. P/Q-type $Ca^{2+}$ channel blocker ω-agatoxin IVA protect against brain injury after focal ischemia in rats. Brain Res. 7760: 140–145 (1997).

Test Example 3

Analgesic Effect (I) in Formalin Test Using Mouse

N-type calcium channel which is one of neuron specific calcium channels is selectively inhibited by SNX-111 of a low molecular polypeptide. Further, it is reported that SNX-111 exhibits an analgesic action by administration in spinal cord, in the formalin test which is one of analgesic tests (1) and 2)). Therefore, the analgesic effect obtained in the case where the intravenous administration of the present compound was carried out was studied in the formalin test (3)) using a mouse.

(1) Experimental animal

Ddy mice (male, 4 to 7 weeks age) purchased from Japan SLC Co, were used for experiment. Preliminary feeding of 4 days or more was carried out for mice (breeding condition: a room temperature 23±1° C., air humidity 55±5%, lighting cycle of every 12 hours). The mice were accommodated by a group of approximately 20 in a cage made of polycarbonate for 20 mice in which floor cloth (White Flake, Charles River Co., Ltd., Tokyo) was spread, and were bred. At the morning of the day tested, they were moved to a laboratory. They were freely fed MF (Oriental Yeast Co., Tokyo) as a feed. Further, they drunk city water freely.

(2) Test compound

Examples 7, 20, 47, 49, 58, 63, 64, 198, 199, 209, 189, 123, 124, 219 and 221 were used as test compounds. Further, as known analgesics, the morphine which is a narcotic strong analgesic and an indomethacin which is an antiphlogistic analgesic were used, and these were used as control drugs.

(3) Preparation of test compound

The compound according to the present invention was dissolved in 5.28% Mannitol so as to be 1 mg/ml (10 mg/kg). The test compounds were weighed on the experimental day to be prepared. On the other hand, morphine was dissolved in physiological saline so as to be 3 mg/ml (30 mg/kg), and the indomethacin was suspended in 0.5% methyl cellulose so as to be 1 mg/ml (10 mg/kg). The test compounds were weighed on the experimental day to be prepared.

(4) Preparation of reagent

30 µL of a commercially available 35.0–38.0% formaldehyde solution was sampled and added to 970 µa physiological saline. This was used as 3% formalin. Further, formalin is a 37% formaldehyde solution, and since the purity of the formaldehyde solution used is indicated as 35.0–38.0%, the 3% formalin which is prepared for the experiment to be used is accurately 2.84–3.08% formalin.

(5) Dose, administration route, number of examples 10 mg/kg of the present compound was intravenously administered (0.1 ml of 1 mg/ml solution was administered per a body weight of 10 g), 30 mg/kg of morphine was orally administered (0.1 ml of 3 mg/ml solution was administered per a body weight of 10 g), 10 mg/kg of indomethacin was orally administered (0.1 ml of 1 mg/ml suspension solution was administered per a body weight of 10 g), 0.1 ml of the respective solvents were intravenously or orally administered per a body weight of 10 g as controls. Five examples for every group were tested.

(6) Test method 10 mg/kg of the present compound was intravenously administered via tail vein, 30 mg/kg of morphine was orally administered and 10 mg/kg of indomethacin was orally administered. After 5, 30 and 90 minutes of the respective administrations, 20 µL of 3% formalin was subcutaneously administered to the planta of the mouse left hind leg, and the mouse was stored in an observation cage made of a transparent plastic. Just after the administration of formalin, the licking time of an action in which a mouse licked his left hind leg was measured for 5 minutes, and it was made as an index of pain. The respective solvents were similarly administered as the control. Setting the licking time of the control as 100%, the suppression rate (%) of the present compound was calculated by the following calculation formula.

Formula:

Depression rate (%)=(licking time of control-licking time of test compound)/(licking time of control)×100

(7) Result:

The compound according to the present invention statistically and significantly suppressed the licking time as compared with the control group, and the suppression rate was within a range of 33 to 88%. In particular, Example 189 showed the analgesic action by a suppression rate of 59%. On the other hand, the morphine showed the analgesic action by a suppression rate of 54%, and the suppression rate of indomethacin was—38% and no analgesic action was confirmed.

Namely, as a neuron specific calcium channel inhibitor, the compound according to the present invention exhibits the analgesic action similar as SNX-111 which is an N-type calcium channel inhibitor, exhibits the similar analgesic action as the morphine which is a narcotic strong analgesic even in comparison with known analgesics, and further exhibits more superior analgesic action to indomethacin which is an antiphlogistic analgesic. Accordingly, the compound according to the present invention is extremely useful for therapy and amelioration of a pain.

REFERENCE LITERATURE

1) Annika B. Malmberg, and Tony L. Yaksh (1994) Voltage-Sensitive Calcium Channels in Spinal Nociceptive Processing: Blockade of N- and P-Type Channels Inhibits Formalin-Induced Nociception. The Journal of Neuroscience 14(8): 4882–4890.
2) S. Scott Bowersox, Theresa Gadbois, Tejinder Singh, Mark Pettus, Yong-Xiang Wang and Robert R. Luther (1996) Selective N-type Neuronal Voltage-Sensitive Calcium Channel Blocker, SNX-111, Produces Spinal Antinociception in Rat Models of Acute, Persistent and Neuropathic Pain. The Journal of pharmacology and Experimental Therapeutics 279(3): 1243–1249.
3) Hunskaar S, Fasmer OB and Hole K (1985) Formalin test in mice, a useful technique for evaluating mild analgesics. Journal of Neuroscience Methods 14(1): 69–76.

What is claimed is:

1. A compound represented by the following formula (I), a salt thereof or a hydrate of them:

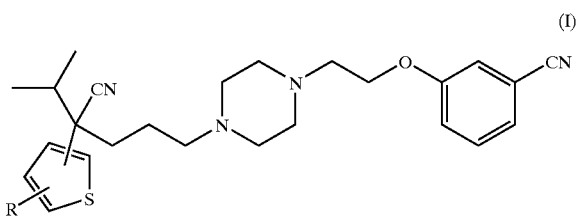

wherein R is a hydrogen atom or a nitrile.

2. The compound according to claim 1, a salt thereof or a hydrate of them, wherein R is the hydrogen atom.

3. The compound according to claim 1, a salt thereof or a hydrate of them, wherein R is the nitrile.

4. The compound according to claim 1, a salt thereof or a hydrate of them, wherein the compound is selected from the group consisting of:

1-[4-cyano-5-methyl-4-(5-cyano-2-thienyl)hexyl]-4-[2-(3-cyanophenoxy)ethyl]piperazine;

1-[4-cyano-5-methyl-4-(2-thienyl)hexyl]-4-[2-(3-cyanophenoxy)ethyl]piperazine;

1-(4-cyano-5-methyl-4-(3-cyano-2-thienyl)hexyl]-4-[2-(3-cyanophenoxy)ethyl]piperazine; and 1-[4-cyano-4-(3-cyano-5-thienyl)-5-methylhexyl]-4-[2-(3-cyanophenoxy)ethyl]piperazine.

5. The compound according to claim 1, a salt thereof or a hydrate of them, wherein the compound is selected from the group consisting of:

1-[4-cyano-5-methyl-4-(5-cyano-2-thienyl)hexyl]-4-[2-(3-cyanophenoxy)ethyl]piperazine;

1-[4-cyano-5-methyl-4-(3-cyano-2-thienyl)hexyl]-4-[2-(3-cyanophenoxy)ethyl]piperazine; and 1-[4-cyano-4-(3-cyano-5-thienyl)-5-methylhexyl]-4-[2-(3-cyanophenoxy)ethyl]piperazine.

6. The compound according to claim 1, a salt thereof or a hydrate of them, wherein the compound is 1-[4-cyano-5-methyl-4-(5-cyano-2-thienyl)hexyl]-4-[2-(3-cyanophenoxy)ethyl]piperazine.

7. The compound according to claim 1, a salt thereof or a hydrate of them, wherein the compound is 1-[4-cyano-5-methyl-4-(2-thienyl)hexyl]-4-[2-(3-cyanophenoxy) ethyl]piperazine.

8. The compound according to claim 1, a salt thereof or a hydrate of them, wherein the compound is 1-[4-cyano-5-methyl-4-(3-cyano-2-thienyl)hexyl]-4-[2-(3-cyanophenoxy)ethyl]piperazine.

9. The compound according to claim 1, a salt thereof or a hydrate of them, wherein the compound is 1-[4-cyano-4-(3-cyano-5-thienyl)-5-methylhexyl]-4-[2-(3-cyanophenoxy)ethyl]piperazine.

10. A pharmaceutical composition comprising:

the compound of claim 1, or the salt thereof or the hydrate of them; and a pharmaceutically acceptable carrier.

11. The pharmaceutical composition of claim 10, wherein said pharmaceutical composition further comprises at least one ingredient selected from the group consisting of an excipient, binder, disintegrant, lubricant, colorant, flavoring agent, stabilizer, emulsifier, absorption accelerator, surfactant, pH regulator, antiseptic and antioxidant.

12. A method for suppressing a neural cell death or protecting cerebral neural cell, said method comprising: administering a pharmacologically effective amount of the compound according to claim 1, a salt thereof, or a hydrate of them.

13. A method for treating or improving cerebral ischemia, or for treating pain, wherein said method comprises: applying an effective amount of the compound according to claim 1 to a patient in need thereof.

14. A method for treating pain, wherein said method comprises: applying pharmacologically effective amount of the compound according to claim 1, a salt thereof, or a hydrate of them to a patient in need thereof.

15. A method for inhibiting the death of neural cells or for protecting cerebral neural cells, wherein said method comprises:

applying an effective amount of the composition of claim 10 to a patient in need thereof.

16. A method for treating or improving cerebral ischemia, or for treating pain, wherein said method comprises: applying an effective amount of the composition of claim 10 to a patient in need thereof.

* * * * *

UNITED STATES PATENT AND TRADEMARK OFFICE
CERTIFICATE OF CORRECTION

PATENT NO.     : 6,906,072 B1
DATED          : June 14, 2005
INVENTOR(S)    : Noboru Yamamoto et al.

It is certified that error appears in the above-identified patent and that said Letters Patent is hereby corrected as shown below:

Column 113,
Line 49, "evaporated, to give a pale yellow oil. The resulting oil was" should read
-- evaporated to give a pale yellow oil. The resulting oil was --.
Line 62, "(d, J = 6.8Hz, 3H), 1.21-1.31 (m, 1H), 1.60-1.73 (x. 1H)," should read
-- (d, J = 6.8Hz, 3H), 1.21-1.31 (m, 1H), 1.60-1.73 (m, 1H), --.
Line 66, "Hz, 2H), 6.95 (d, J = 8.8 Hz, 2H1), 7.28 (d, J = 1.2 Hz, 1H)," should read
-- Hz, 2H), 6.95 (d, J = 8.8Hz, 2H), 7.28 (d, J = 1.2 Hz, 1H), --.

Column 114,
Line 25, "1.79 (dt, J = 4 Hz, J = 12.4 Hz, 1H, 2.07 (qui, J = 6.8 Hz, 1H)," should read
-- 1.79 (dt, J = 4 Hz, J = 12.4 Hz, 1H), 2.07 (qui, J = 6.8 Hz, 1H), --.
Line 54, "The solvent was evaporated, to give a crude product. The" should read
-- The solvent was evaporated to give a crude product. The --.
Line 58, "i11 mg (0.81 mmol) of potassium carbonate and 243 mg (1.05" should read
-- 111 mg (0.81 mmol) of potassium carbonate and 243 mg (1.05 --.

Column 115,
Line 2, "(d, J = 6.40 Hz, 3H), 1.20-1.38 (m, 1H), 1.60-1.86 (m, 21)," should read
-- (d, J = 6.40 Hz, 1H), 1.20-1.38 (m, 1H), 1.60-1.86 (m, 2H), --.

Column 116,
Line 1, "1H), 2.17-2.27 (m, 1H), 2.27-2.70 (m, 12H), 2.81 (t, I=6.0" should read
-- 1H), 2.17-2.27 (m, 1H), 2.27-2.70 (m, 12H), 2.81 (t, J=6.0 --.
Line 65, "6.93-6.98 (m, 1"), 7.26-7.28 (m, 2H)" should read
-- 6.93-6.98 (m, 1H), 7.26-7.28 (m, 2H) --.

UNITED STATES PATENT AND TRADEMARK OFFICE
CERTIFICATE OF CORRECTION

PATENT NO. : 6,906,072 B1
DATED : June 14, 2005
INVENTOR(S) : Noboru Yamamoto et al.

It is certified that error appears in the above-identified patent and that said Letters Patent is hereby corrected as shown below:

<u>Column 117,</u>
Line 23, "2.28-2.35 (m, 20), 2.35-2.65 (m, 8H), 2.81 (t, J = 5.9Hz, 2H)," should read
-- 2.28-2.35 (m, 2H), 2.35-2.65 (m, 8H), 2.81 (t, J = 5.9Hz, 2H), --.

Signed and Sealed this

Thirtieth Day of May, 2006

JON W. DUDAS
*Director of the United States Patent and Trademark Office*